(12) United States Patent
Anderson et al.

(10) Patent No.: US 9,180,244 B2
(45) Date of Patent: Nov. 10, 2015

(54) WEARABLE AUTOMATIC INJECTION DEVICE FOR CONTROLLED DELIVERY OF THERAPEUTIC AGENTS

(75) Inventors: Philip D. Anderson, Libertyville, IL (US); Joseph F. Julian, Libertyville, IL (US); Linas P. Laurusonis, Gurnee, IL (US); Timothy Parmer, Brooklyn Park, MN (US); Travis Yoch, Woodbury, MN (US); Samuel M. Jang, Woodbury, MN (US); Sean Corrigan, Chicago, IL (US); Tomas Matusaitis, Chicago, IL (US); William Fienup, St. Louis, MO (US); Chris Strahm, Deforest, WI (US)

(73) Assignee: AbbVie Biotechnology Ltd, Hamilton (BM)

( * ) Notice: Subject to any disclaimer, the term of this patent is extended or adjusted under 35 U.S.C. 154(b) by 507 days.

(21) Appl. No.: 13/092,102

(22) Filed: Apr. 21, 2011

(65) Prior Publication Data
US 2012/0022499 A1    Jan. 26, 2012

Related U.S. Application Data

(60) Provisional application No. 61/326,637, filed on Apr. 21, 2010.

(51) Int. Cl.
*A61M 31/00* (2006.01)
*A61M 5/142* (2006.01)
(Continued)

(52) U.S. Cl.
CPC .......... *A61M 5/14248* (2013.01); *A61M 5/141* (2013.01); *A61M 5/1413* (2013.01);
(Continued)

(58) Field of Classification Search
CPC ............... A61M 5/14248; A61M 2005/14268; A61M 5/1413
USPC ......... 604/500–506, 131, 151–155, 134–139, 604/890.1–892.1
See application file for complete search history.

(56) References Cited

U.S. PATENT DOCUMENTS

| | | |
|---|---|---|
| 2,398,544 A | 4/1946 | Lockhart |
| 2,459,875 A | 1/1949 | Folkman |

(Continued)

FOREIGN PATENT DOCUMENTS

| | | |
|---|---|---|
| DE | 2019296 | 11/1971 |
| DE | 19821933 | 11/1999 |

(Continued)

OTHER PUBLICATIONS

Communication pursuant to Article 94(3) EPC issued by the European Patent Office in European Application No. 05758156.3-2320, dated Jan. 18, 2011.

(Continued)

*Primary Examiner* — Phillip Gray
(74) *Attorney, Agent, or Firm* — McCarter & English, LLP; David R. Burns

(57) ABSTRACT

Exemplary embodiments provide wearable automatic injection devices for subcutaneously injecting a therapeutic agent into a patient's body at controlled rates, for example, in a single bolus. Exemplary embodiments provide methods for assembling wearable automatic injection devices for subcutaneously injecting a therapeutic agent into a patient's body at controlled rates. Exemplary embodiments provide methods for using wearable automatic injection devices for subcutaneously injecting a therapeutic agent into a patient's body at controlled rates.

43 Claims, 62 Drawing Sheets

(51) Int. Cl.
  *A61M 5/14*      (2006.01)
  *A61M 5/145*     (2006.01)
  *A61M 5/32*      (2006.01)
  *A61M 5/48*      (2006.01)
  *A61M 5/50*      (2006.01)
  *A61M 5/158*     (2006.01)
  *A61M 5/31*      (2006.01)
  *A61M 5/315*     (2006.01)
  *A61M 5/34*      (2006.01)

(52) U.S. Cl.
  CPC .......... *A61M5/1454* (2013.01); *A61M 5/14526* (2013.01); *A61M 5/14566* (2013.01); *A61M 5/326* (2013.01); *A61M 5/484* (2013.01); *A61M 5/488* (2013.01); *A61M 5/50* (2013.01); *A61M 2005/14252* (2013.01); *A61M 2005/14506* (2013.01); *A61M 2005/14513* (2013.01); *A61M 2005/1581* (2013.01); *A61M 2005/1583* (2013.01); *A61M 2005/3143* (2013.01); *A61M 2005/31518* (2013.01); *A61M 2005/341* (2013.01); *A61M 2205/13* (2013.01); *A61M 2207/00* (2013.01)

(56) References Cited

U.S. PATENT DOCUMENTS

| | | | |
|---|---|---|---|
| 2,565,081 | A | 8/1951 | Maynes |
| 2,591,457 | A | 4/1952 | Maynes |
| 2,701,566 | A | 2/1955 | Krug |
| 2,752,918 | A | 7/1956 | Uytenbogaart |
| 2,832,339 | A | 4/1958 | Sarnoff et al. |
| 2,888,924 | A | 6/1959 | Dunmire |
| 2,960,087 | A | 11/1960 | Uytenbogaart |
| 3,051,173 | A | 8/1962 | Johnson et al. |
| 3,055,362 | A | 9/1962 | Uytenbogaart |
| 3,066,670 | A | 12/1962 | Stauffer |
| 3,136,313 | A | 6/1964 | Enstrom et al. |
| 3,314,428 | A | 4/1967 | Johnson et al. |
| 3,330,279 | A | 7/1967 | Sarnoff et al. |
| 3,403,680 | A | 10/1968 | Sinclair et al. |
| 3,543,603 | A | 12/1970 | Gley |
| 3,605,743 | A | 9/1971 | Arce |
| 3,618,603 | A | 11/1971 | Levenson |
| 3,702,609 | A | 11/1972 | Steiner |
| 3,712,301 | A | 1/1973 | Sarnoff |
| 3,742,948 | A | 7/1973 | Post |
| 3,797,488 | A | 3/1974 | Hurschman et al. |
| 3,797,489 | A | 3/1974 | Sarnoff |
| 3,882,863 | A | 5/1975 | Sarnoff et al. |
| 3,892,237 | A | 7/1975 | Steiner |
| 3,910,260 | A | 10/1975 | Sarnoff et al. |
| 3,941,130 | A | 3/1976 | Tibbs |
| 4,004,577 | A | 1/1977 | Sarnoff |
| 4,031,893 | A | 6/1977 | Kaplan et al. |
| 4,106,770 | A | 8/1978 | Gray |
| 4,178,928 | A | 12/1979 | Tischlinger |
| 4,202,314 | A | 5/1980 | Smirnov et al. |
| 4,214,584 | A | 7/1980 | Smirnov et al. |
| 4,226,235 | A | 10/1980 | Sarnoff et al. |
| 4,258,713 | A | 3/1981 | Wardlow |
| 4,261,358 | A | 4/1981 | Vargas et al. |
| 4,275,729 | A | 6/1981 | Silver et al. |
| 4,394,863 | A | 7/1983 | Bartner |
| 4,425,120 | A | 1/1984 | Sampson et al. |
| 4,437,859 | A | 3/1984 | Whitehouse et al. |
| 4,447,231 | A | 5/1984 | Bekkering |
| 4,530,695 | A | 7/1985 | Phillips et al. |
| 4,565,543 | A | 1/1986 | Bekkering et al. |
| 4,573,976 | A | 3/1986 | Sampson et al. |
| 4,578,064 | A | 3/1986 | Sarnoff et al. |
| 4,624,660 | A | 11/1986 | Mijers et al. |
| 4,637,403 | A | 1/1987 | Garcia et al. |
| 4,664,653 | A | 5/1987 | Sagstetter et al. |
| 4,678,461 | A | 7/1987 | Mesa |
| 4,689,042 | A | 8/1987 | Sarnoff et al. |
| 4,723,937 | A | 2/1988 | Sarnoff et al. |
| 4,755,169 | A | 7/1988 | Sarnoff et al. |
| 4,795,432 | A | 1/1989 | Karczmer |
| 4,795,433 | A | 1/1989 | Sarnoff |
| 4,820,286 | A | 4/1989 | van der Wal |
| 4,822,340 | A | 4/1989 | Kamstra |
| 4,850,994 | A | 7/1989 | Zerbst |
| 4,852,768 | A | 8/1989 | Bartsch |
| 4,902,279 | A | 2/1990 | Schmidtz et al. |
| 4,923,447 | A | 5/1990 | Morgan |
| 4,927,416 | A | 5/1990 | Tomkiel |
| 4,929,237 | A | 5/1990 | Medway |
| 4,955,868 | A | 9/1990 | Klein |
| 4,966,592 | A | 10/1990 | Burns et al. |
| 4,994,034 | A | 2/1991 | Botich et al. |
| 5,041,088 | A | 8/1991 | Ritson et al. |
| 5,042,977 | A | 8/1991 | Bechtold et al. |
| 5,049,133 | A | 9/1991 | Villen Pascual |
| D322,479 | S | 12/1991 | Miyaguchi |
| 5,085,641 | A | 2/1992 | Sarnoff et al. |
| 5,085,642 | A | 2/1992 | Sarnoff et al. |
| 5,092,842 | A | 3/1992 | Bechtold et al. |
| 5,092,843 | A | 3/1992 | Monroe et al. |
| 5,102,393 | A | 4/1992 | Sarnoff et al. |
| 5,104,380 | A | 4/1992 | Holman et al. |
| 5,114,406 | A | 5/1992 | Gabriel et al. |
| 5,114,410 | A | 5/1992 | Caralt Battle |
| 5,137,516 | A | 8/1992 | Rand et al. |
| 5,163,918 | A | 11/1992 | Righi |
| 5,181,524 | A * | 1/1993 | Wanderer et al. ............. 600/577 |
| 5,201,708 | A | 4/1993 | Martin |
| 5,224,936 | A | 7/1993 | Gallagher |
| 5,242,240 | A | 9/1993 | Gorham |
| 5,244,465 | A | 9/1993 | Michel |
| 5,259,840 | A | 11/1993 | Boris |
| 5,263,934 | A | 11/1993 | Haak |
| 5,267,963 | A | 12/1993 | Bachynsky |
| 5,267,972 | A | 12/1993 | Anderson |
| 5,267,976 | A | 12/1993 | Guerineau et al. |
| 5,273,544 | A | 12/1993 | van der Wal |
| D343,897 | S | 2/1994 | Rand et al. |
| 5,295,965 | A | 3/1994 | Wilmot |
| 5,295,975 | A | 3/1994 | Lockwood |
| 5,298,024 | A | 3/1994 | Richmond |
| D346,219 | S | 4/1994 | Fardigh |
| 5,300,030 | A | 4/1994 | Crossman |
| 5,318,538 | A | 6/1994 | Martin |
| 5,320,609 | A | 6/1994 | Haber et al. |
| 5,334,144 | A | 8/1994 | Alchas et al. |
| 5,342,308 | A | 8/1994 | Boschetti |
| 5,346,480 | A | 9/1994 | Hess |
| 5,358,489 | A | 10/1994 | Wyrick |
| 5,376,080 | A | 12/1994 | Petrussa |
| 5,378,233 | A | 1/1995 | Haber et al. |
| 5,383,865 | A | 1/1995 | Michel |
| 5,391,151 | A | 2/1995 | Wilmot |
| 5,425,715 | A | 6/1995 | Dalling et al. |
| 5,433,712 | A | 7/1995 | Stiles |
| 5,478,316 | A | 12/1995 | Bitdinger et al. |
| 5,480,387 | A | 1/1996 | Gabriel et al. |
| 5,531,705 | A | 7/1996 | Alter et al. |
| 5,569,192 | A | 10/1996 | van der Wal |
| 5,591,138 | A | 1/1997 | Vaillancourt |
| 5,599,309 | A | 2/1997 | Marshall et al. |
| 5,616,128 | A | 4/1997 | Meyer |
| 5,616,132 | A | 4/1997 | Newman |
| 5,620,421 | A | 4/1997 | Schmitz |
| 5,634,906 | A | 6/1997 | Haber et al. |
| 5,637,094 | A | 6/1997 | Stewart, Jr. et al. |
| 5,645,534 | A | 7/1997 | Chanoch |
| 5,658,259 | A | 8/1997 | Pearson et al. |
| 5,681,291 | A | 10/1997 | Galli |
| 5,744,360 | A | 4/1998 | Hu et al. |
| 5,779,677 | A | 7/1998 | Frezza |
| 5,807,335 | A | 9/1998 | Kriesel et al. |
| 5,807,346 | A | 9/1998 | Frezza |
| 5,817,111 | A | 10/1998 | Riza |

(56) References Cited

U.S. PATENT DOCUMENTS

| | | | |
|---|---|---|---|
| 5,843,036 A | 12/1998 | Olive et al. |
| 5,860,957 A | 1/1999 | Jacobsen et al. |
| 5,885,250 A | 3/1999 | Kriesel et al. |
| 5,931,817 A | 8/1999 | Nguyen et al. |
| 5,957,886 A | 9/1999 | Weston |
| 5,957,897 A | 9/1999 | Jeffrey |
| 5,984,900 A | 11/1999 | Mikkelsen |
| 5,993,421 A | 11/1999 | Kriesel |
| 6,048,336 A | 4/2000 | Gabriel |
| 6,056,728 A | 5/2000 | von Schuckmann |
| 6,077,247 A | 6/2000 | Marshall et al. |
| 6,090,070 A | 7/2000 | Hager et al. |
| 6,090,080 A | 7/2000 | Jost et al. |
| 6,090,382 A | 7/2000 | Salfeld et al. |
| 6,099,503 A | 8/2000 | Stradella |
| 6,102,896 A | 8/2000 | Roser |
| 6,110,147 A | 8/2000 | Perouse |
| 6,149,626 A | 11/2000 | Bachynsky et al. |
| 6,159,181 A | 12/2000 | Crossman et al. |
| 6,171,285 B1 | 1/2001 | Johnson |
| 6,203,530 B1 | 3/2001 | Stewart, Sr. |
| 6,210,369 B1 | 4/2001 | Wilmot et al. |
| 6,213,987 B1 | 4/2001 | Hirsch |
| 6,221,044 B1 | 4/2001 | Greco |
| 6,241,709 B1 | 6/2001 | Bechtold et al. |
| 6,258,068 B1 | 7/2001 | Kirchofer et al. |
| 6,258,562 B1 | 7/2001 | Salfeld et al. |
| 6,270,479 B1 | 8/2001 | Bergens et al. |
| 6,277,097 B1 | 8/2001 | Mikkelsen et al. |
| 6,277,098 B1 | 8/2001 | Klitmose et al. |
| 6,277,099 B1 | 8/2001 | Strowe et al. |
| 6,280,421 B1 | 8/2001 | Kirchofer et al. |
| 6,312,412 B1 | 11/2001 | Saied et al. |
| 6,319,233 B1 | 11/2001 | Jansen et al. |
| 6,319,234 B1 | 11/2001 | Resfelli et al. |
| 6,322,540 B1 | 11/2001 | Grabis |
| 6,371,939 B2 | 4/2002 | Bergens et al. |
| 6,387,074 B1 | 5/2002 | Horppu et al. |
| 6,387,078 B1 | 5/2002 | Gillespie, III |
| 6,413,237 B1 | 7/2002 | Caizza et al. |
| 6,419,658 B1 | 7/2002 | Resfelli et al. |
| D461,555 S | 8/2002 | Binet et al. |
| 6,475,194 B2 | 11/2002 | Domici |
| 6,509,015 B1 | 1/2003 | Salfeld et al. |
| 6,517,517 B1 | 2/2003 | Farrugia et al. |
| 6,544,234 B1 | 4/2003 | Gabriel |
| 6,575,939 B1 | 6/2003 | Brunel |
| 6,589,210 B1 | 7/2003 | Rolfe |
| 6,595,956 B1 * | 7/2003 | Gross et al. .............. 604/141 |
| 6,656,163 B1 | 12/2003 | Marshall et al. |
| 6,656,164 B1 | 12/2003 | Smith |
| 6,673,035 B1 | 1/2004 | Rice et al. |
| 6,692,469 B1 | 2/2004 | Weekes et al. |
| 6,712,788 B2 | 3/2004 | Righi |
| 6,743,203 B1 | 6/2004 | Pickhard |
| 6,752,798 B2 | 6/2004 | McWethy |
| 6,767,336 B1 | 7/2004 | Kaplan |
| D494,270 S | 8/2004 | Reschke |
| 6,773,415 B2 | 8/2004 | Heiniger |
| 6,796,967 B2 | 9/2004 | Jensen |
| 6,802,827 B2 | 10/2004 | Andersson |
| 6,805,686 B1 | 10/2004 | Fathallah et al. |
| 6,808,507 B2 | 10/2004 | Roser |
| 6,817,989 B2 | 11/2004 | Svendsen |
| 6,872,194 B2 | 3/2005 | Doyle et al. |
| 6,926,697 B2 | 8/2005 | Malenchek |
| 6,932,793 B1 | 8/2005 | Marshall et al. |
| 6,945,960 B2 | 9/2005 | Barker |
| 6,976,976 B2 | 12/2005 | Doyle |
| 6,986,760 B2 | 1/2006 | Giambattista |
| 7,004,929 B2 | 2/2006 | McWethy |
| D518,175 S | 3/2006 | Hardin et al. |
| 7,056,306 B1 | 6/2006 | Halseth |
| 7,223,394 B2 | 5/2007 | Salfeld et al. |
| 7,320,682 B2 | 1/2008 | Cocker |
| 7,361,160 B2 | 4/2008 | Hommann et al. |
| 7,497,847 B2 | 3/2009 | Crawford |
| 7,541,031 B2 | 6/2009 | Salfeld et al. |
| 7,588,761 B2 | 9/2009 | Salfeld et al. |
| 7,694,828 B2 | 4/2010 | Swift et al. |
| 7,736,333 B2 | 6/2010 | Gillespie, III |
| D622,374 S | 8/2010 | Julian et al. |
| D629,509 S | 12/2010 | Julian et al. |
| 7,863,426 B2 | 1/2011 | Wan et al. |
| 7,919,264 B2 | 4/2011 | Maksymowych et al. |
| 7,938,802 B2 | 5/2011 | Bicknell et al. |
| 8,162,887 B2 | 4/2012 | Bicknell et al. |
| D677,380 S | 3/2013 | Julian et al. |
| 2001/0005781 A1 | 6/2001 | Bergens |
| 2001/0025168 A1 | 9/2001 | Gross et al. |
| 2001/0053894 A1 | 12/2001 | Steenfeldt-Jensen et al. |
| 2002/0002344 A1 | 1/2002 | Douglas et al. |
| 2002/0016563 A1 | 2/2002 | Hill et al. |
| 2002/0042592 A1 | 4/2002 | Wilmot et al. |
| 2002/0095120 A1 | 7/2002 | Larsen et al. |
| 2002/0111587 A1 | 8/2002 | Hommann et al. |
| 2002/0161337 A1 | 10/2002 | Shaw et al. |
| 2002/0169408 A1 | 11/2002 | Beretta et al. |
| 2002/0183690 A1 | 12/2002 | Arnisolle |
| 2003/0004466 A1 | 1/2003 | Bitdinger et al. |
| 2003/0004467 A1 | 1/2003 | Musick et al. |
| 2003/0023203 A1 | 1/2003 | Lavi et al. |
| 2003/0023205 A1 | 1/2003 | Botich et al. |
| 2003/0050606 A1 | 3/2003 | Brand et al. |
| 2003/0093036 A1 | 5/2003 | Crossman et al. |
| 2003/0105430 A1 | 6/2003 | Lavi et al. |
| 2003/0161744 A1 | 8/2003 | Vilks et al. |
| 2003/0187401 A1 | 10/2003 | Doyle |
| 2003/0212362 A1 | 11/2003 | Roser |
| 2003/0229308 A1 | 12/2003 | Tsals et al. |
| 2003/0236502 A1 | 12/2003 | De La Serna et al. |
| 2004/0019326 A1 | 1/2004 | Gilbert et al. |
| 2004/0024367 A1 | 2/2004 | Gilbert |
| 2004/0039336 A1 | 2/2004 | Amark et al. |
| 2004/0039337 A1 | 2/2004 | Letzing |
| 2004/0054327 A1 | 3/2004 | Gillespie |
| 2004/0147875 A1 | 7/2004 | Wallace et al. |
| 2004/0199117 A1 | 10/2004 | Giambattista et al. |
| 2004/0215151 A1 | 10/2004 | Marshall et al. |
| 2004/0225262 A1 | 11/2004 | Fathallah et al. |
| 2005/0020979 A1 | 1/2005 | Westbye et al. |
| 2005/0020984 A1 | 1/2005 | Lesch, Jr. |
| 2005/0027255 A1 | 2/2005 | Lavi et al. |
| 2005/0049550 A1 | 3/2005 | Kirchofer et al. |
| 2005/0049561 A1 | 3/2005 | Hommann et al. |
| 2005/0085776 A1 | 4/2005 | Hommann et al. |
| 2005/0096597 A1 | 5/2005 | Crawford |
| 2005/0101919 A1 | 5/2005 | Brunnberg |
| 2005/0124940 A1 | 6/2005 | Martin et al. |
| 2005/0137534 A1 | 6/2005 | Hommann |
| 2005/0137571 A1 | 6/2005 | Hommann |
| 2005/0165360 A1 | 7/2005 | Stamp |
| 2005/0165361 A1 | 7/2005 | Marshall et al. |
| 2005/0165362 A1 | 7/2005 | Slawson |
| 2005/0165363 A1 | 7/2005 | Judson et al. |
| 2005/0171476 A1 | 8/2005 | Judson et al. |
| 2005/0171477 A1 | 8/2005 | Rubin et al. |
| 2005/0209569 A1 | 9/2005 | Ishikawa et al. |
| 2005/0222539 A1 | 10/2005 | Gonzales et al. |
| 2005/0222540 A1 | 10/2005 | Kirchofer et al. |
| 2005/0261634 A1 | 11/2005 | Karlsson |
| 2005/0273054 A1 | 12/2005 | Asch |
| 2005/0273055 A1 | 12/2005 | Harrisson et al. |
| 2005/0273061 A1 | 12/2005 | Hommann et al. |
| 2005/0277885 A1 | 12/2005 | Scherer |
| 2005/0277886 A1 | 12/2005 | Hommann et al. |
| 2005/0277893 A1 | 12/2005 | Liversidge |
| 2005/0288633 A1 | 12/2005 | Jeffrey |
| 2006/0030819 A1 | 2/2006 | Young et al. |
| 2006/0036216 A1 | 2/2006 | Rimlinger et al. |
| 2006/0047250 A1 | 3/2006 | Hickinbotham et al. |
| 2006/0069350 A1 | 3/2006 | Buenger et al. |
| 2006/0069354 A1 | 3/2006 | Buenger et al. |
| 2006/0100588 A1 | 5/2006 | Brunnberg et al. |

(56) References Cited

U.S. PATENT DOCUMENTS

| | | | |
|---|---|---|---|
| 2006/0111666 A1 | 5/2006 | Hommann et al. |
| 2006/0111674 A1 | 5/2006 | Vedrine |
| 2006/0129122 A1 | 6/2006 | Wyrick |
| 2006/0167413 A1 | 7/2006 | Marshall et al. |
| 2006/0189933 A1 | 8/2006 | Alheidt |
| 2006/0253083 A1 | 11/2006 | Liu |
| 2007/0049865 A1 | 3/2007 | Radmer et al. |
| 2007/0129674 A1 | 6/2007 | Liversidge |
| 2007/0142776 A9 | 6/2007 | Kovelman et al. |
| 2007/0161960 A1 | 7/2007 | Chen et al. |
| 2007/0239117 A1 | 10/2007 | Chelak |
| 2008/0097337 A1 | 4/2008 | Judd |
| 2008/0208125 A1 | 8/2008 | Bicknell et al. |
| 2008/0208140 A1 | 8/2008 | Barrelle |
| 2008/0269692 A1 | 10/2008 | James |
| 2008/0300549 A1 | 12/2008 | Verespej |
| 2009/0024076 A1 | 1/2009 | Babaev |
| 2009/0024093 A1 | 1/2009 | Carrel |
| 2009/0036870 A1 | 2/2009 | Mounce et al. |
| 2009/0093792 A1 | 4/2009 | Gross et al. |
| 2009/0157012 A1 | 6/2009 | Magne |
| 2009/0240210 A1 | 9/2009 | Walton |
| 2009/0299328 A1 | 12/2009 | Mudd et al. |
| 2010/0160869 A1 | 6/2010 | Liversidge |
| 2010/0160894 A1 | 6/2010 | Julian et al. |
| 2010/0168683 A1 | 7/2010 | Cabiri |
| 2011/0054414 A1 | 3/2011 | Shang et al. |
| 2011/0178500 A1 | 7/2011 | Shang et al. |
| 2012/0022499 A1 | 1/2012 | Anderson et al. |
| 2012/0107783 A1 | 5/2012 | Julian et al. |
| 2012/0197209 A1 | 8/2012 | Bicknell et al. |
| 2012/0233834 A1 | 9/2012 | Szechinski et al. |
| 2012/0238961 A1 | 9/2012 | Julian et al. |
| 2012/0289905 A1 | 11/2012 | Julian et al. |

FOREIGN PATENT DOCUMENTS

| | | |
|---|---|---|
| DE | 60207576 | 6/2006 |
| EP | 0068864 | 1/1983 |
| EP | 1334740 | 8/2003 |
| EP | 1364667 | 11/2003 |
| EP | 1523360 | 4/2005 |
| EP | 2067496 | 6/2009 |
| EP | 2085104 | 8/2009 |
| GB | 2243552 | 11/1991 |
| GB | 2388033 | 11/2003 |
| JP | 50-14835 | 5/1975 |
| JP | 5-161712 | 6/1993 |
| JP | 2001-512038 | 8/2001 |
| JP | 2002507459 A | 3/2002 |
| JP | 2005538773 A | 12/2005 |
| JP | 2006507060 | 3/2006 |
| RU | 2004256 | 12/1993 |
| RU | 2131748 | 6/1999 |
| RU | 2169584 | 6/2001 |
| WO | 8912473 A1 | 12/1989 |
| WO | WO 93/13819 A1 | 7/1993 |
| WO | WO 94/09839 A1 | 5/1994 |
| WO | WO 94/13342 A1 | 6/1994 |
| WO | WO 94/26333 A1 | 11/1994 |
| WO | WO 99/22789 A1 | 5/1999 |
| WO | WO 99/22792 A1 | 5/1999 |
| WO | WO 01/37908 A1 | 5/2001 |
| WO | WO 01/62319 A2 | 8/2001 |
| WO | 02/02165 A2 | 1/2002 |
| WO | 03/039433 A1 | 5/2003 |
| WO | WO 03/039633 A2 | 5/2003 |
| WO | WO 03/077968 A2 | 9/2003 |
| WO | WO 03/097133 A1 | 11/2003 |
| WO | WO 03/099358 | 12/2003 |
| WO | WO 2004/000397 | 12/2003 |
| WO | 2004/024211 A2 | 3/2004 |
| WO | WO 2004/047892 | 6/2004 |
| WO | WO 2004/060451 A1 | 7/2004 |
| WO | WO 2004/067068 A1 | 8/2004 |
| WO | WO 2005/002653 | 1/2005 |
| WO | 2005/037350 A2 | 4/2005 |
| WO | WO 2005/046765 A2 | 5/2005 |
| WO | WO 2005/079889 A1 | 9/2005 |
| WO | WO 2005/090836 | 9/2005 |
| WO | WO 2005/113039 A1 | 12/2005 |
| WO | WO 2005/115508 A1 | 12/2005 |
| WO | WO 2005/115509 A1 | 12/2005 |
| WO | WO 2005/115510 A1 | 12/2005 |
| WO | WO 2005/115511 A1 | 12/2005 |
| WO | WO 2005/115512 A1 | 12/2005 |
| WO | WO 2005/115513 A1 | 12/2005 |
| WO | WO 2005/115516 A1 | 12/2005 |
| WO | WO 2006/000785 | 1/2006 |
| WO | WO 2006/058061 A1 | 6/2006 |
| WO | WO 2008/005315 | 1/2008 |
| WO | 2010/029054 A1 | 3/2010 |
| WO | 2011/014514 A1 | 2/2011 |
| WO | 2011/014704 A2 | 2/2011 |
| WO | 2012/145752 A2 | 10/2012 |
| ZA | 9805195 A | 1/1999 |

OTHER PUBLICATIONS

Communication of a Notice of Opposition issued in European Application No. 04822031.3-1526, dated Jan. 6, 2010.
Communication pursuant to Article 96(2) EPC issued in European Application No. 04822031.3-1526, dated May 31, 2007.
Communication under Rule 112 EPC issued in European Application No. 04822031.3, dated Mar. 13, 2007.
International Search Report issued in International Application No. PCT/GB2005/002487, dated Aug. 19, 2005.
Written Opinion issued in International Application No. PCT/GB2005/002487, dated Dec. 23, 2006.
International Preliminary Report on Patentability issued in International Application No. PCT/GB2005/002487, dated Sep. 7, 2006.
International Search Report issued in International Application No. PCT/US2011/033504, dated Jul. 8, 2011.
Written Opinion issued in International Application No. PCT/US2011/033504, dated Jul. 8, 2011.
International Search Report issued in International Application No. PCT/US2007/015095, dated Sep. 11, 2008.
Written Opinion issued in International Application No. PCT/US2007/015095, dated Sep. 11, 2008.
International Preliminary Report on Patentability issued in International Application No. PCT/US2007/015095, dated Jun. 19, 2009.
International Search Report issued in International Application No. PCT/US2010/033012, dated Jul. 2, 2010.
Written Opinion issued in International Application No. PCT/US2010/033012, dated Jul. 2, 2010.
International Search Report issued in International Application No. PCT/US2010/060496, dated Feb. 16, 2011.
Written Opinion issued in International Application No. PCT/US2010/060496, dated Feb. 16, 2011.
International Search Report issued in International Application No. PCT/US2004/013278, dated May 30, 2005.
Written Opinion issued in International Application No. PCT/US2004/013278, dated Oct. 29, 2006.
International Preliminary Report on Patentability issued in International Application No. PCT/US2004/013278, dated Nov. 1, 2006.
Office Action issued in Russian Application No. 2006145501/14(049694), dated May 21, 2009.
Decision on Grant issued in Russian Application No. 2006145501/14(049694), dated Nov. 2, 2009.
Decision on Grant issued in Russian Application No. 2009102986/14(003862), dated Jun. 30, 2011.
Notice of Reasons for Rejection issued in Japanese Application No. 2007-517459, dated Aug. 24, 2010.
Notice of Reasons for Rejection issued in Japanese Application No. 2007-517459, dated Mar. 8, 2011.
Office Action issued in Mexican Application No. PA/a/2006/015056, dated Jul. 28, 2010.
Office Action issued in Mexican Application No. PA/a/2006/015056, dated Apr. 1, 2011.

(56) References Cited

OTHER PUBLICATIONS

Reexamination Decision issued in Chinese Application No. 200580020958.6, dated Jun. 13, 2011.
Notification of Reexamination issued in Chinese Application No. 200580020958.6, dated Aug. 17, 2010.
Rejection Decision issued in Chinese Application No. 200580020958.6, dated Jun. 5, 2009.
Office Action issued in Chinese Application No. 200580020958.6, dated Sep. 5, 2008.
Office Action issued in Australian Application No. 2005256832, dated Apr. 18, 2011.
Office Action issued in Australian Application No. 2005256832, dated Feb. 22, 2010.
Examination Report issued in New Zealand Application No. 552340, dated Apr. 27, 2009.
Examination Report issued in New Zealand Application No. 552340, dated Aug. 12, 2010.
Notification of Provisional Rejection issued in Korean Application No. 10-2006-7026814, dated Jul. 19, 2011.
BD Preventis, Shielding System for Prefilled Syringes, http://www.bd.com/pharmaceuticals/products/safety-engineered.asp, last accessed Aug. 26, 2010.
"Abbott Receives FDA Approval for New Humira Delivery Device," Press Release, dated Jun. 26, 2006 (color).
Correspondence from Dept. of Health & Human Services, Food and Drug Administration, to Robert Shaw/Owen Mumford, Inc. regarding Section 501(k) notification to market device, dated Nov. 10, 1999.
Correspondence from Dept. of Health & Human Services, Food and Drug Administration, to Robert Shaw/Owen Mumford, Inc. regarding Section 501(k) notification to market device, dated Mar. 6, 2000.
Owen Mumford drawing/schematic of the Abbott-Plunger AUTOject Mini, dated Mar. 25, 2002, Drawing No. P02 207.
Owen Mumford drawing/schematic of the Plunger-Miniject dated Mar. 30, 1993, Drawing No. P93.022.
Owen Mumford drawing/schematic of the Plunger-Miniject dated Mar. 30, 1993, Drawing No. AJ 358.
Owen Mumford drawing/schematic A of the Plunger-Miniject dated Sep 5, 1997, Drawing No. AJ 654.
Owen Mumford drawing/schematic B of the Plunger-Miniject dated Sep. 5, 1997, Drawing No. AJ 654.
Office Action issued in Canadian Application No. 2,571,571, dated Oct. 24, 2011.
Office Action issued in Chinese Application No. 201010576413.6, dated Nov. 2, 2011.
International Preliminary Report on Patentability issued in International Application No. PCT/US2010/033012, dated Nov. 1, 2011.
Decision of Final Rejection issued in Japanese Application No. 2007-517459, dated Jan. 10, 2012.
Summons to Attend Oral Proceedings pursuant to Rule 115(1) EPC, dated Apr. 20, 2012.
Notice of Rejection issued in Japanese Application No. 2009-518284, dated May 29, 2012.
International Search Report issued in International Application No. PCT/US2012/022433, dated Jul. 5, 2012.
Written Opinion issued in International Application No. PCT/US2012/022433, dated Jul. 5, 2012.
Examination Report issued in New Zealand Application No. 602782, dated May 21, 2013.
Extended European Search Report issued in European Application No. 11772739.6, dated Aug. 16, 2013.
International Preliminary Report on Patentability issued in International Application No. PCT/US2012/034683, dated Oct. 22, 2013.
Written Opinion issued in International Application No. PCT/US2012/034683, dated Oct. 21, 2013.
International Search Report issued in International Application No. PCT/US2012/034683, dated Mar. 6, 2013.
Communication pursuant to Article 94(3) EPC issued in European Application No. 11772739.6, dated May 19, 2014.
Examination Report issued in Australian Application No. 2011242602, dated Apr. 9, 2014.
Examination Report issued in New Zealand Application No. 702172, dated Jan. 12, 2015.
Final Examination Report issued in Singapore Application No. 201207754-1, dated Nov. 27, 2014.
Further Examination Report issued in New Zealand Application No. 602782, dated Nov. 28, 2014.
Notice of Reasons for Rejection issued in Japanese Application No. 2013-506316, mailed Jan. 13, 2015.
Office Action issued in Chinese Application No. 201180030497.6, dated May 9, 2014.
Written Opinion and Search Report issued in Singaporean Application No. 201207754-1, mailed Jan. 22, 2014.

\* cited by examiner

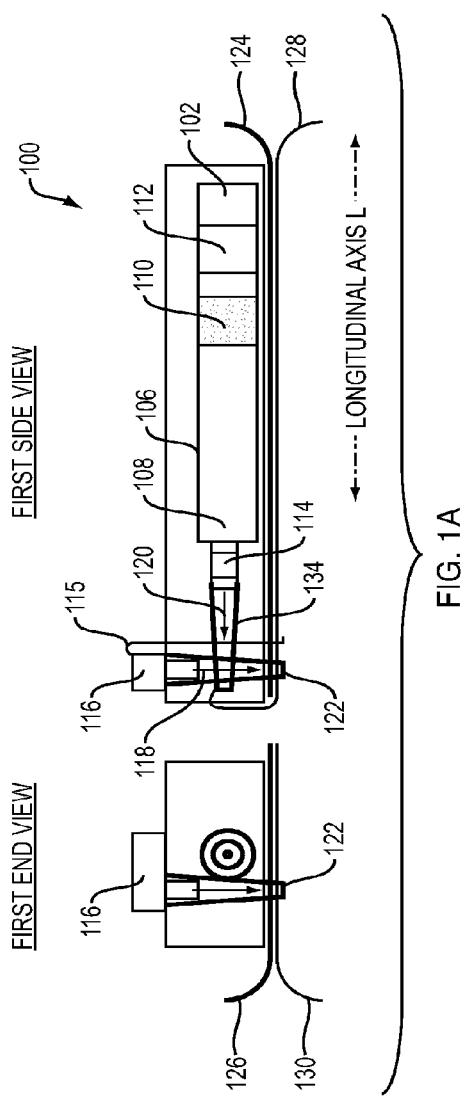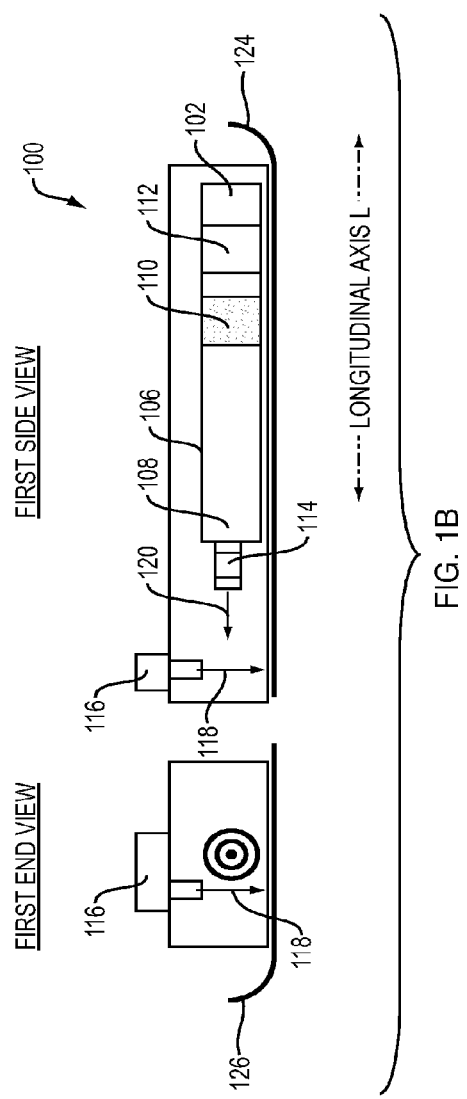

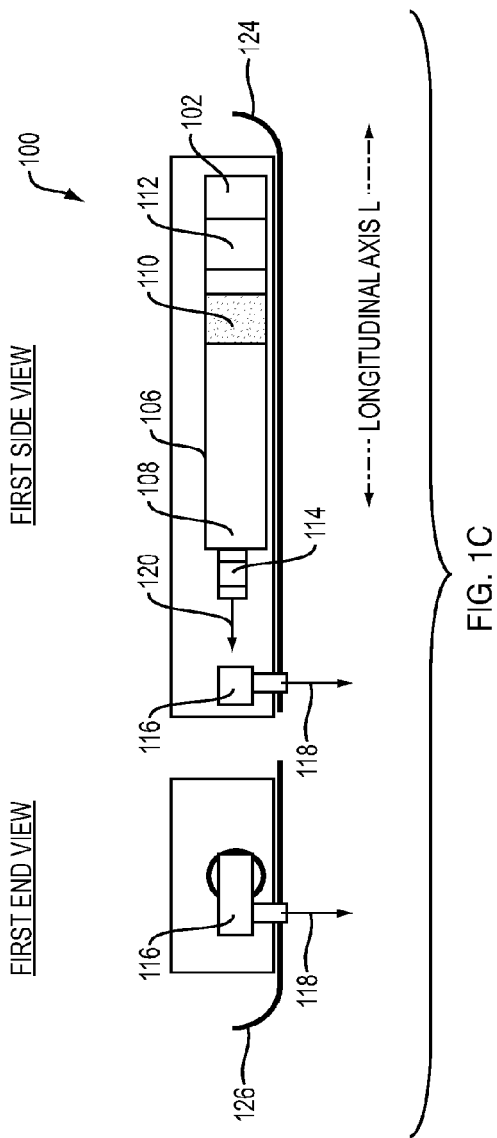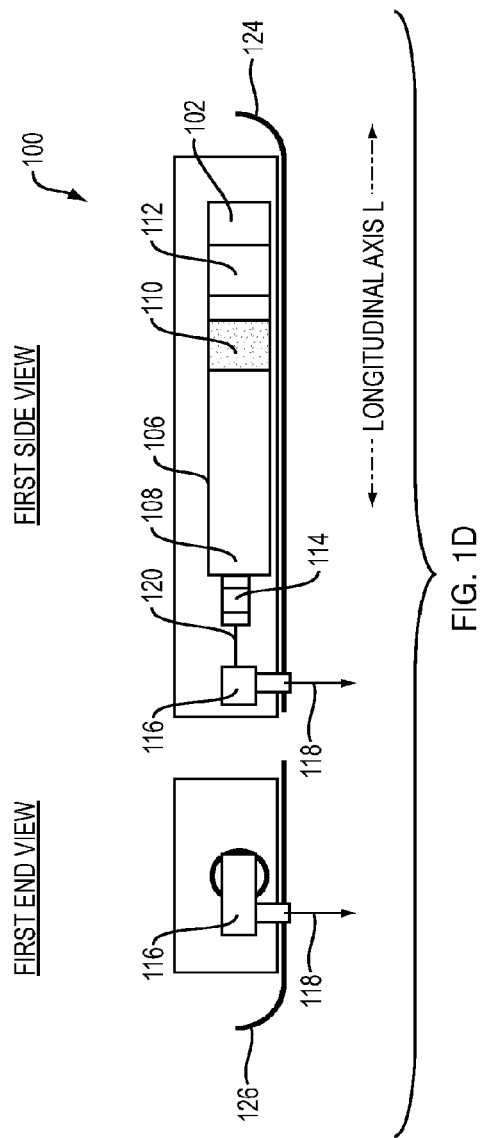

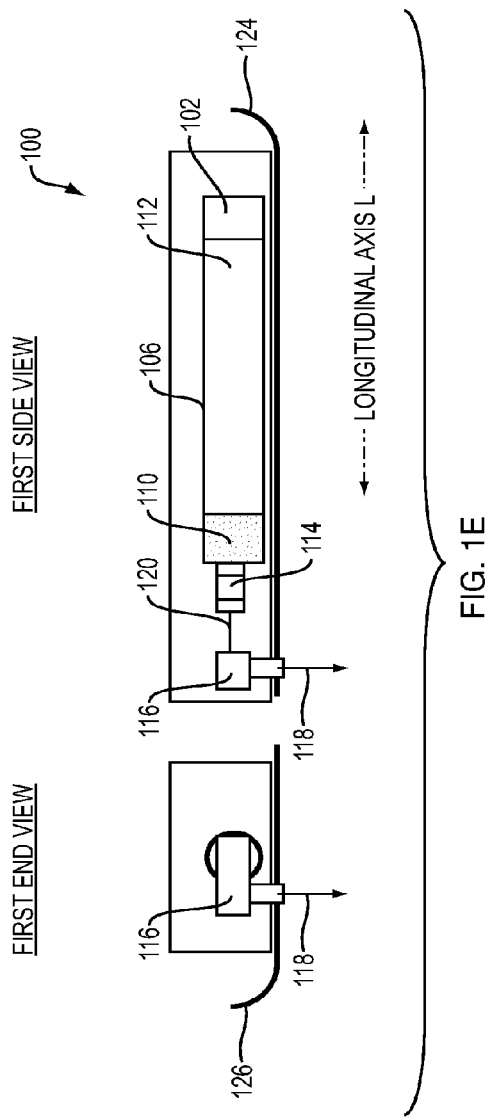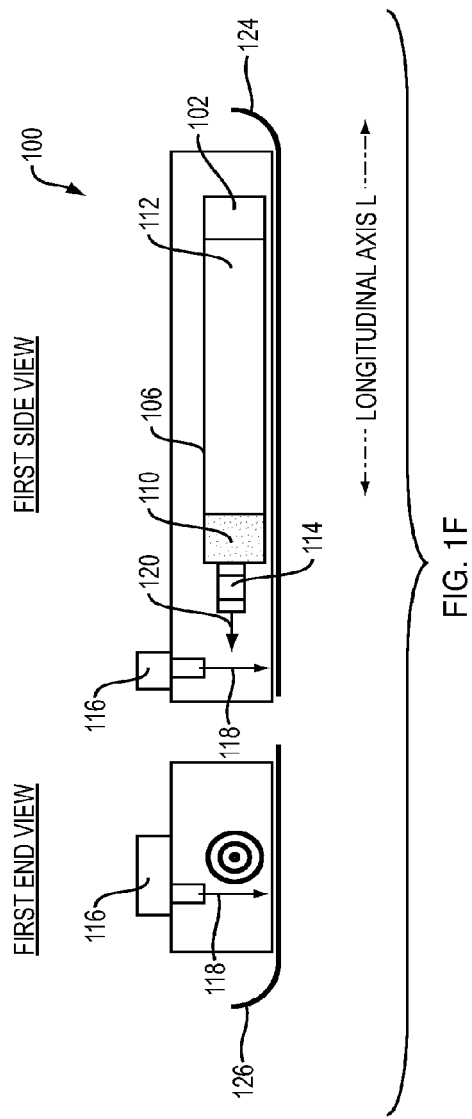

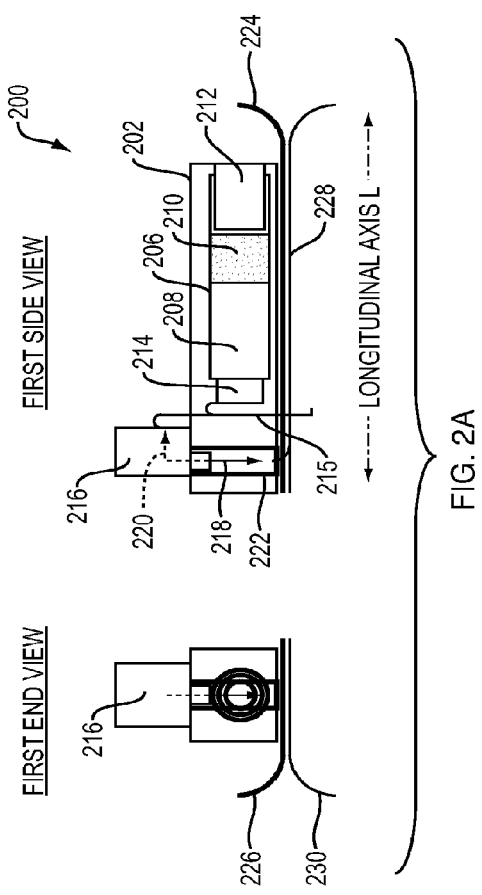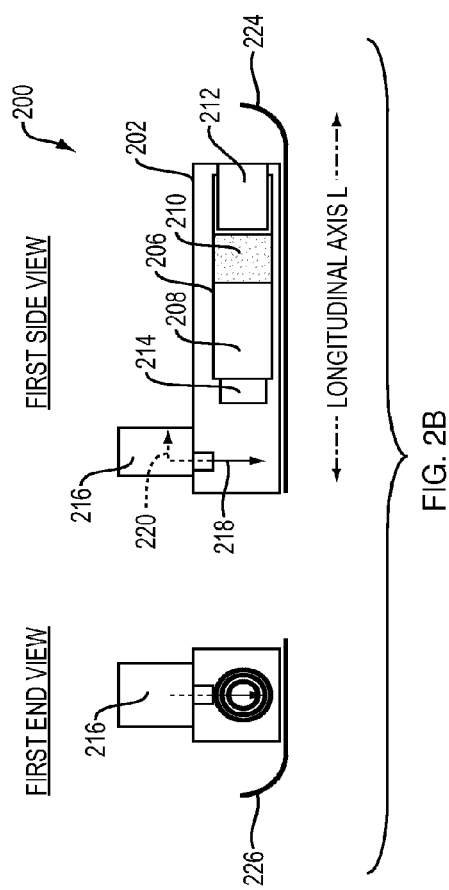

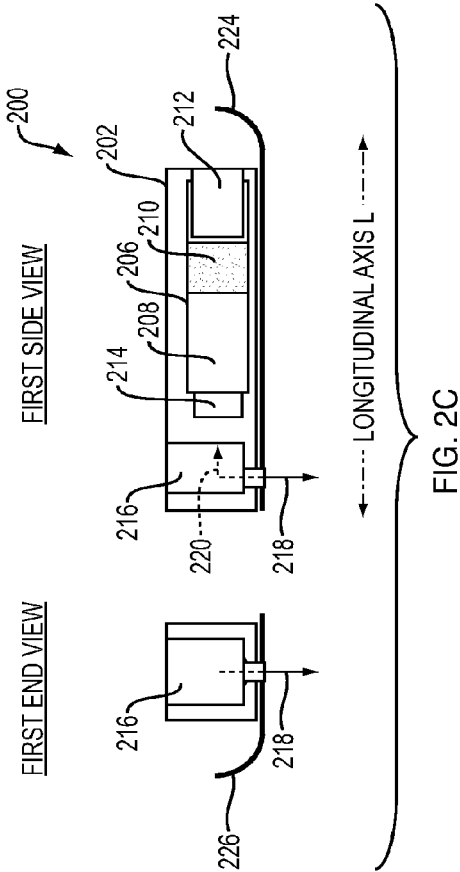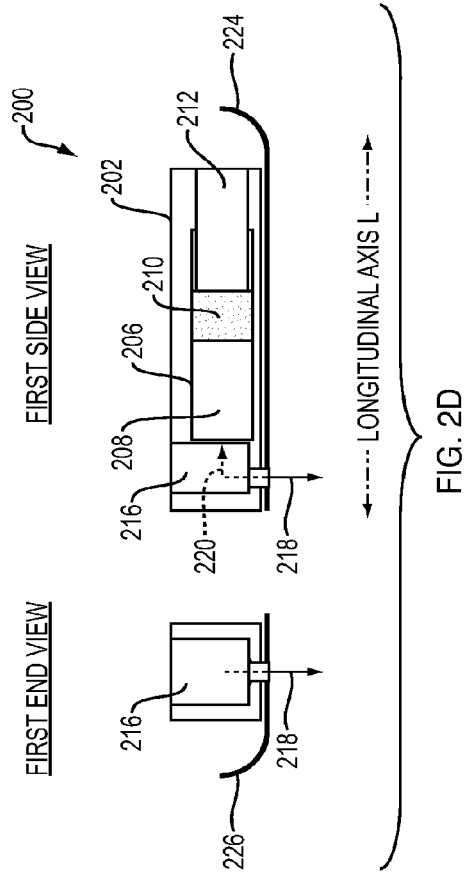

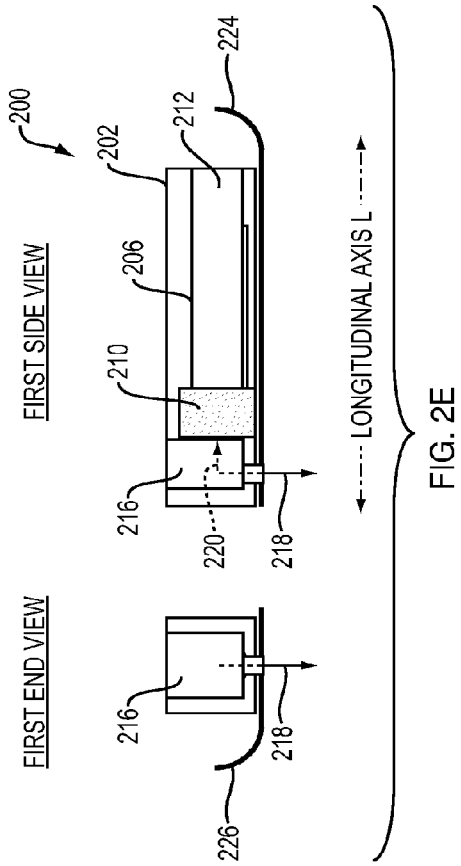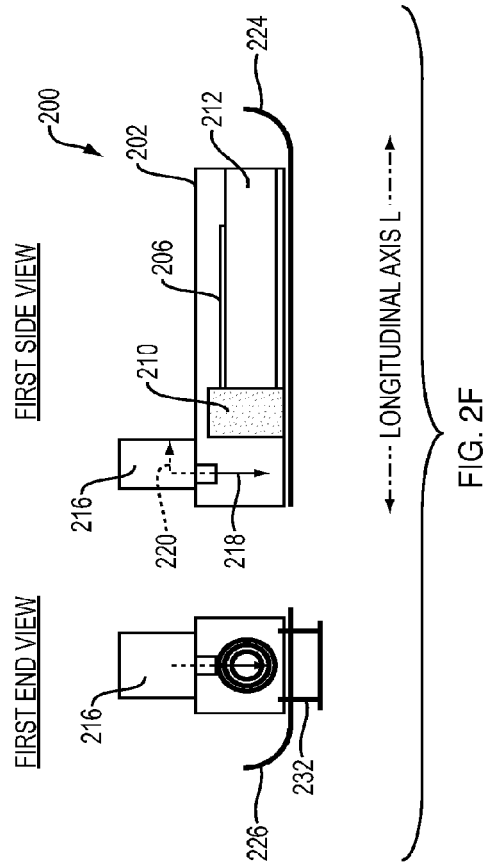

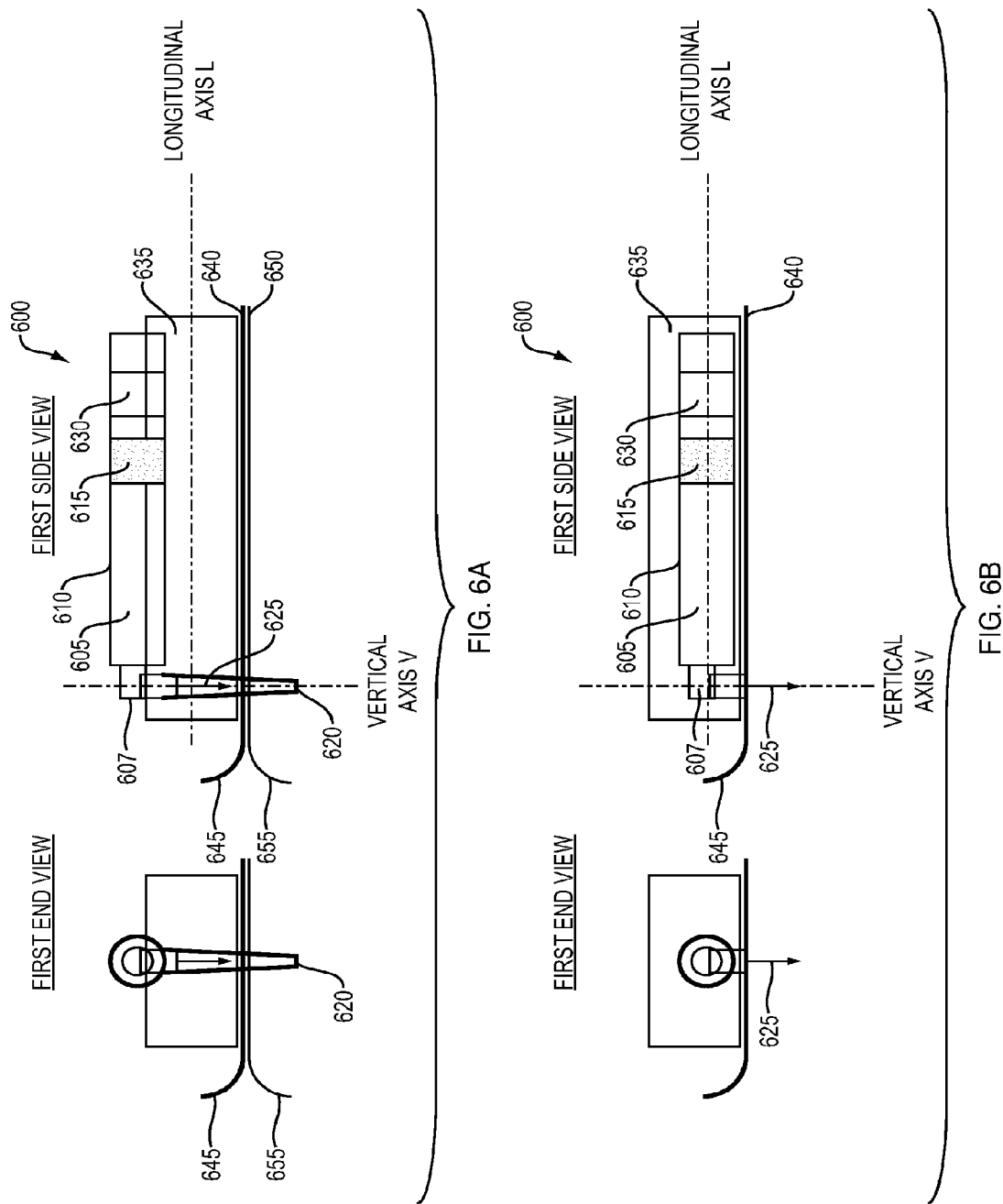

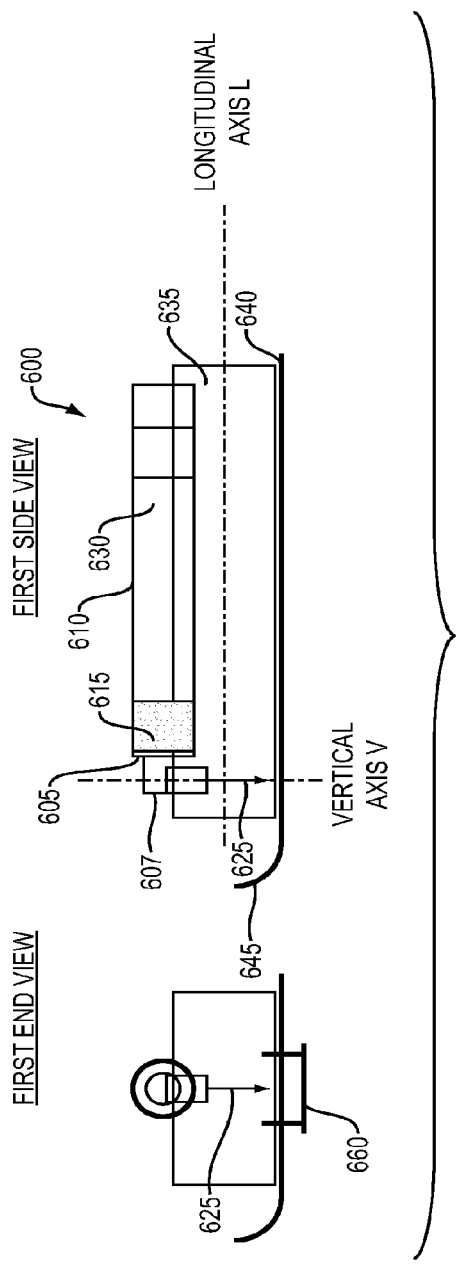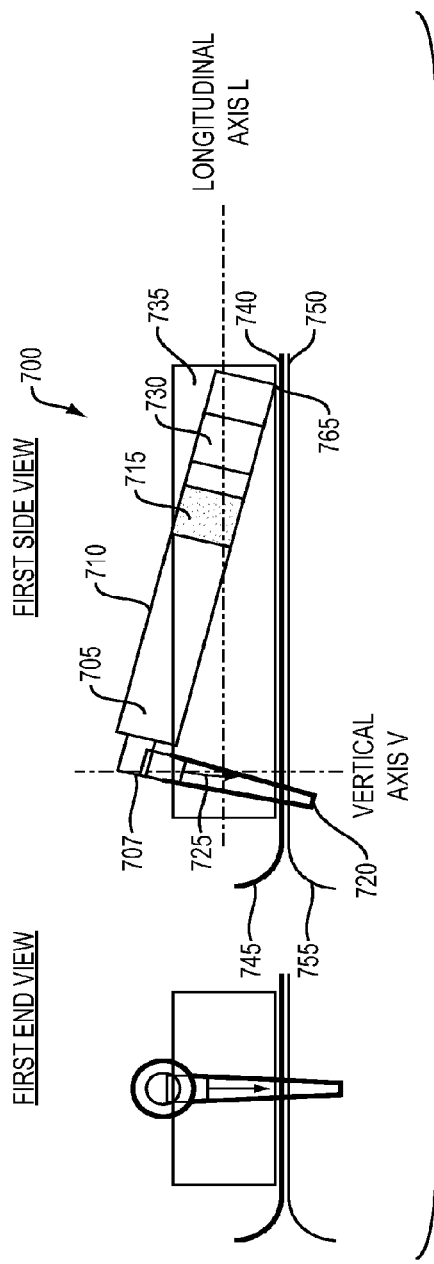

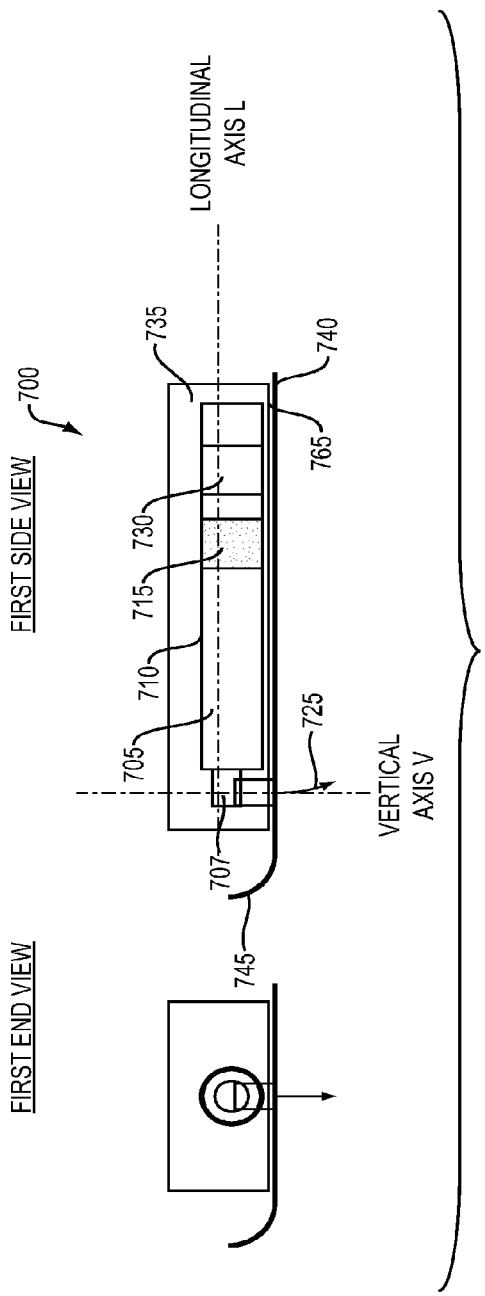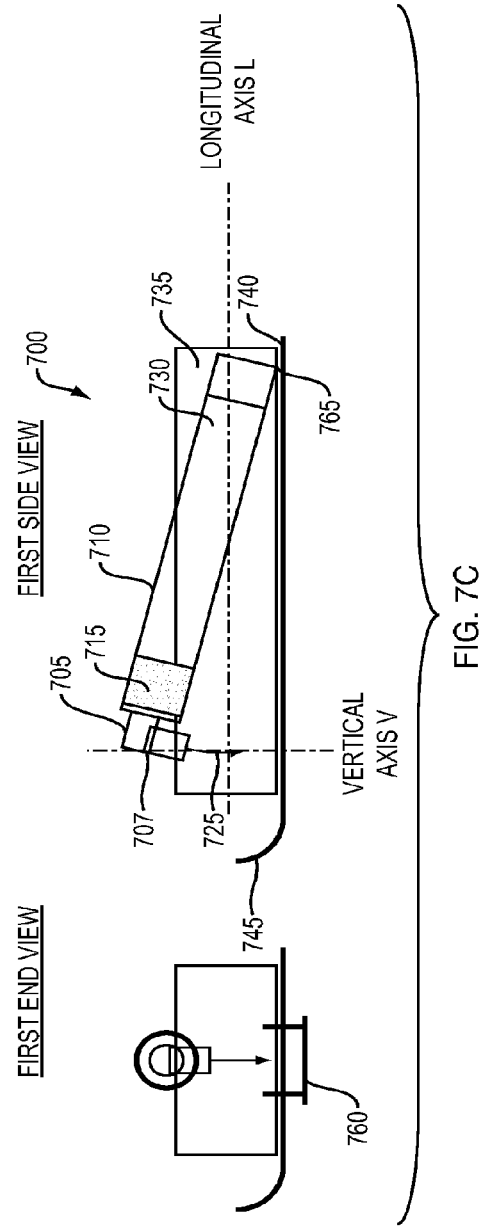

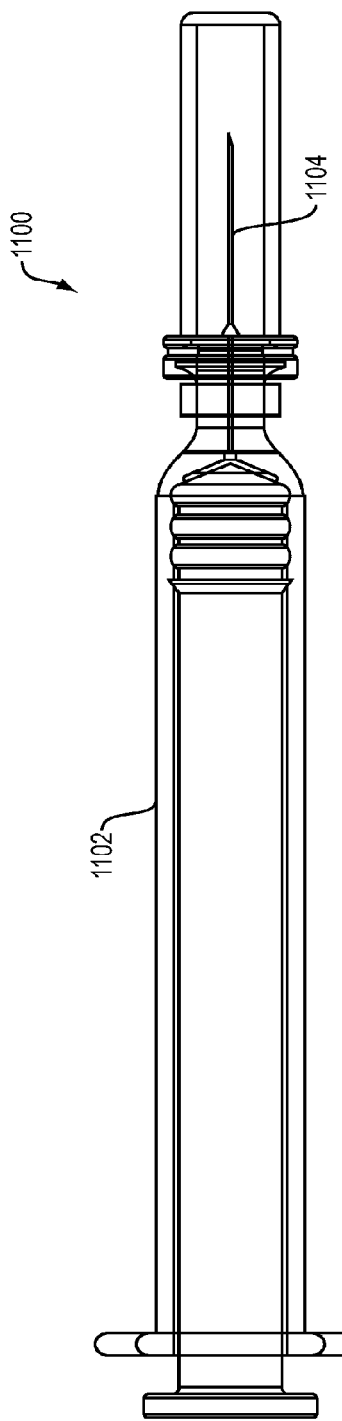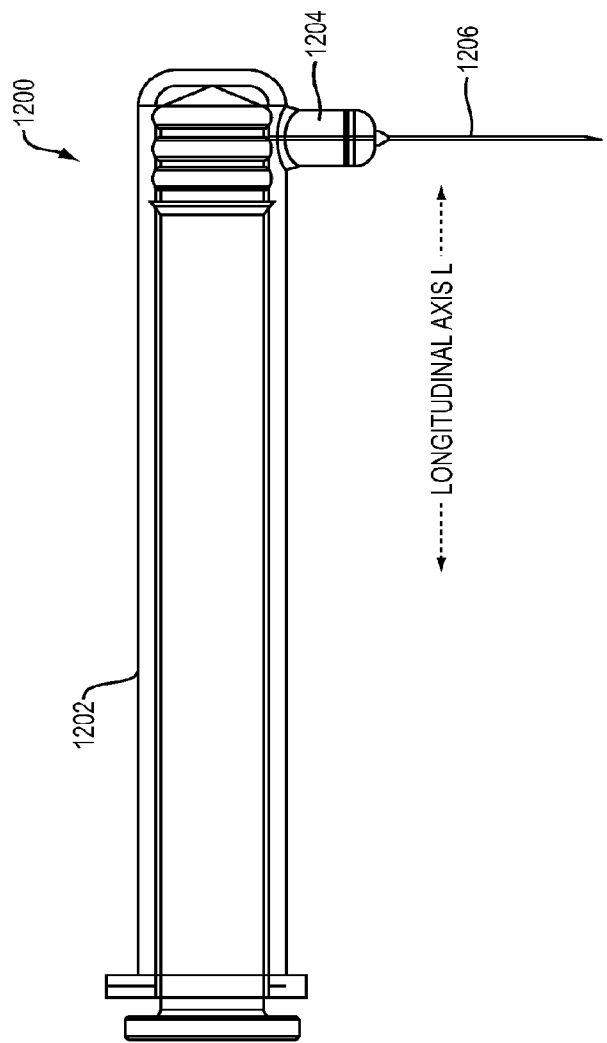

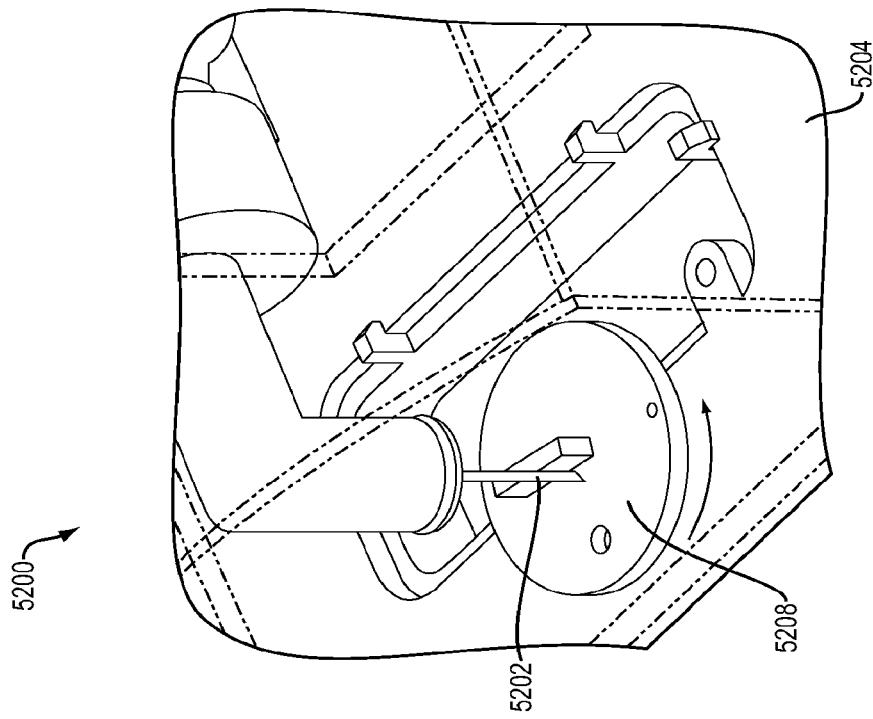
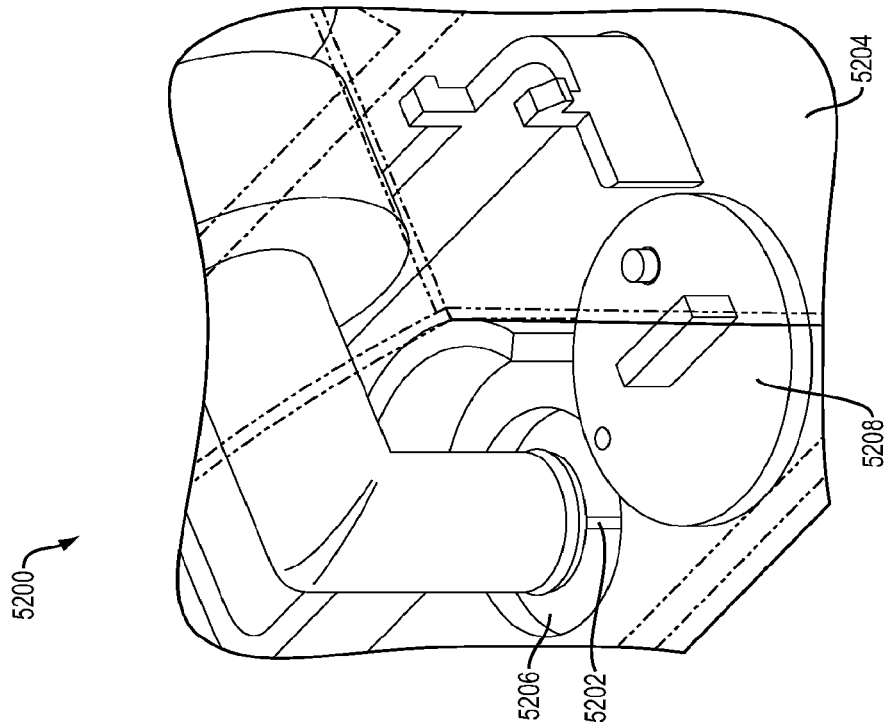
FIG. 52B
FIG. 52A

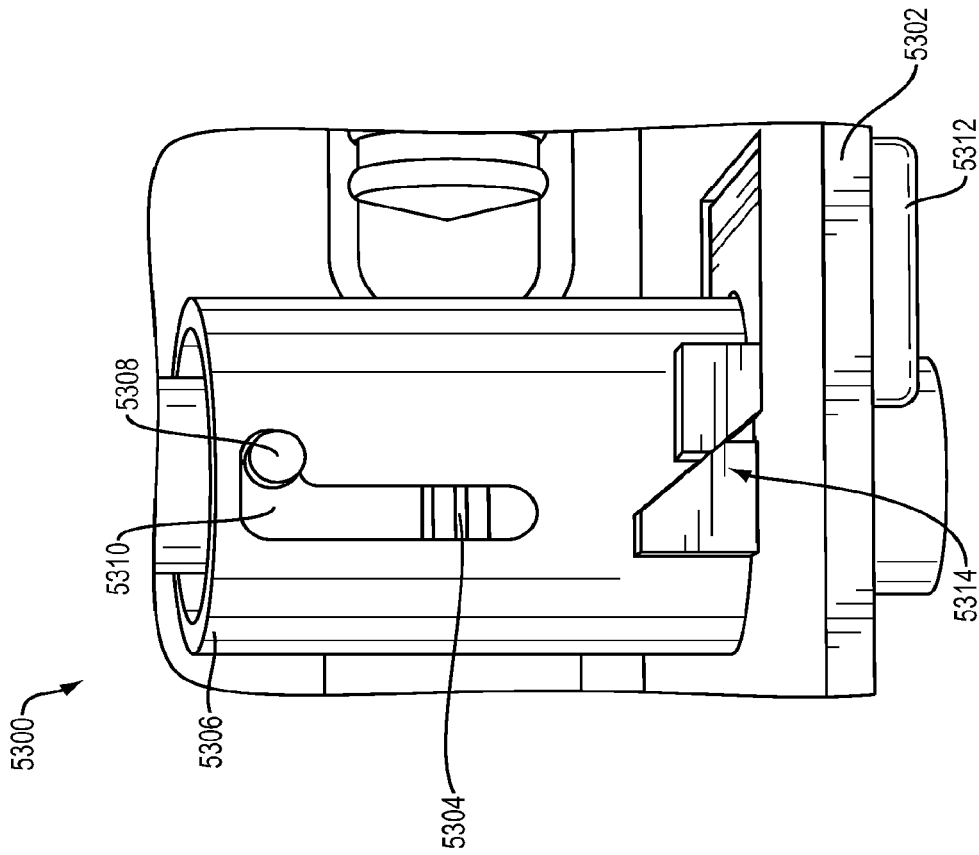
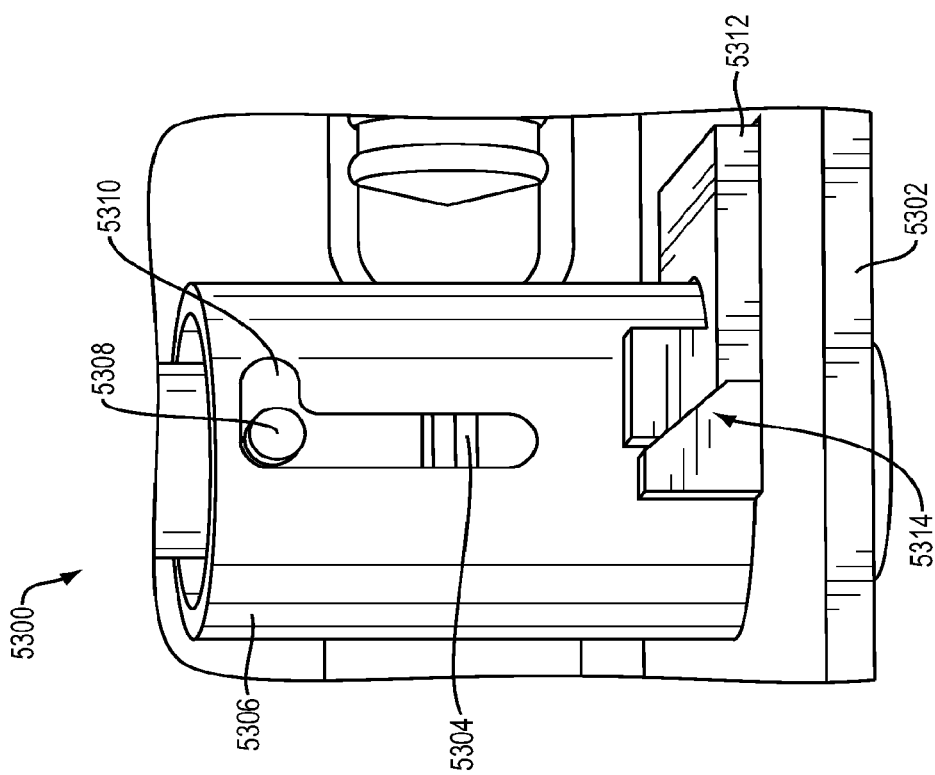

SEQUENCE LISTING

<160> NUMBER OF SEQ ID NOS: 37

<210> SEQ ID NO 1
<211> LENGTH: 107
<212> TYPE: PRT
<213> ORGANISM: Artificial

<220> FEATURE:
<223> OTHER INFORMATION: D2E7 light chain variable region

<400> SEQUENCE: 1

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys
            100                 105
```

<210> SEQ ID NO 2
<211> LENGTH: 121
<212> TYPE: PRT
<213> ORGANISM: Artificial
<220> FEATURE:
<223> OTHER INFORMATION: D2E7 heavy chain variable region

<400> SEQUENCE: 2

```
Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser
        115                 120
```

<210> SEQ ID NO 3
<211> LENGTH: 9
<212> TYPE: PRT
<213> ORGANISM: Artificial
<220> FEATURE:
<223> OTHER INFORMATION: D2E7 light chain variable region CDR3
<221> NAME/KEY: VARIANT
<222> LOCATION: 9
<223> OTHER INFORMATION: Xaa = Any Amino Acid

<400> SEQUENCE: 3

```
Gln Arg Tyr Asn Arg Ala Pro Tyr Xaa
 1               5
```

```
<210> SEQ ID NO 4
<211> LENGTH: 12
<212> TYPE: PRT
<213> ORGANISM: Artificial
<220> FEATURE:
<223> OTHER INFORMATION: D2E7 heavy chain variable region CDR3
<221> NAME/KEY: VARIANT
<222> LOCATION: 12
<223> OTHER INFORMATION: Xaa = Any Amino Acid

<400> SEQUENCE: 4

Val Ser Tyr Leu Ser Thr Ala Ser Ser Leu Asp Xaa
 1               5                  10

<210> SEQ ID NO 5
<211> LENGTH: 7
<212> TYPE: PRT
<213> ORGANISM: Artificial
<220> FEATURE:
<223> OTHER INFORMATION: D2E7 light chain variable region CDR2

<400> SEQUENCE: 5

Ala Ala Ser Thr Leu Gln Ser
 1               5

<210> SEQ ID NO 6
<211> LENGTH: 17
<212> TYPE: PRT
<213> ORGANISM: Artificial
<220> FEATURE:
<223> OTHER INFORMATION: D2E7 heavy chain variable region CDR2

<400> SEQUENCE: 6

Ala Ile Thr Trp Asn Ser Gly His Ile Asp Tyr Ala Asp Ser Val Glu
 1               5                  10                  15

Gly

<210> SEQ ID NO 7
<211> LENGTH: 11
<212> TYPE: PRT
<213> ORGANISM: Artificial
<220> FEATURE:
<223> OTHER INFORMATION: D2E7 light chain variable region CDR1

<400> SEQUENCE: 7

Arg Ala Ser Gln Gly Ile Arg Asn Tyr Leu Ala
 1               5                  10

<210> SEQ ID NO 8
<211> LENGTH: 5
<212> TYPE: PRT
<213> ORGANISM: Artificial
<220> FEATURE:
<223> OTHER INFORMATION: D2E7 heavy chain variable region CDR1

<400> SEQUENCE: 8

Asp Tyr Ala Met His
 1               5

<210> SEQ ID NO 9
<211> LENGTH: 107
<212> TYPE: PRT
<213> ORGANISM: Artificial
<220> FEATURE:
<223> OTHER INFORMATION: 2SD4 light chain variable region
```

<400> SEQUENCE: 9

Asp Ile Gln Met Thr Gln Ser Pro Ser Ser Leu Ser Ala Ser Ile Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Tyr
                85                  90                  95

Ala Phe Gly Gln Gly Thr Lys Val Glu Ile Lys
            100                 105

<210> SEQ ID NO 10
<211> LENGTH: 121
<212> TYPE: PRT
<213> ORGANISM: Artificial
<220> FEATURE:
<223> OTHER INFORMATION: 2SD4 heavy chain variable region

<400> SEQUENCE: 10

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Asp Trp Val
        35                  40                  45

Ser Ala Ile Thr Trp Asn Ser Gly His Ile Asp Tyr Ala Asp Ser Val
50                  55                  60

Glu Gly Arg Phe Ala Val Ser Arg Asp Asn Ala Lys Asn Ala Leu Tyr
65                  70                  75                  80

Leu Gln Met Asn Ser Leu Arg Pro Glu Asp Thr Ala Val Tyr Tyr Cys
                85                  90                  95

Thr Lys Ala Ser Tyr Leu Ser Thr Ser Ser Ser Leu Asp Asn Trp Gly
            100                 105                 110

Gln Gly Thr Leu Val Thr Val Ser Ser
        115                 120

<210> SEQ ID NO 11
<211> LENGTH: 9
<212> TYPE: PRT
<213> ORGANISM: Artificial
<220> FEATURE:
<223> OTHER INFORMATION: 2SD4 light chain variable region CDR3

<400> SEQUENCE: 11

Gln Lys Tyr Asn Ser Ala Pro Tyr Ala
1               5

<210> SEQ ID NO 12
<211> LENGTH: 9
<212> TYPE: PRT
<213> ORGANISM: Artificial
<220> FEATURE:
<223> OTHER INFORMATION: EP B12  light chain variable region CDR3

```
<400> SEQUENCE: 12

Gln Lys Tyr Asn Arg Ala Pro Tyr Ala
 1               5

<210> SEQ ID NO 13
<211> LENGTH: 9
<212> TYPE: PRT
<213> ORGANISM: Artificial
<220> FEATURE:
<223> OTHER INFORMATION: VL10E4 light chain variable region CDR3

<400> SEQUENCE: 13

Gln Lys Tyr Gln Arg Ala Pro Tyr Thr
 1               5

<210> SEQ ID NO 14
<211> LENGTH: 9
<212> TYPE: PRT
<213> ORGANISM: Artificial
<220> FEATURE:
<223> OTHER INFORMATION: VL100A9 light chain variable region CDR3

<400> SEQUENCE: 14

Gln Lys Tyr Ser Ser Ala Pro Tyr Thr
 1               5

<210> SEQ ID NO 15
<211> LENGTH: 9
<212> TYPE: PRT
<213> ORGANISM: Artificial
<220> FEATURE:
<223> OTHER INFORMATION: VLL100D2 light chain variable region CDR3

<400> SEQUENCE: 15

Gln Lys Tyr Asn Ser Ala Pro Tyr Thr
 1               5

<210> SEQ ID NO 16
<211> LENGTH: 9
<212> TYPE: PRT
<213> ORGANISM: Artificial
<220> FEATURE:
<223> OTHER INFORMATION: VLL0F4 light chain variable region CDR3

<400> SEQUENCE: 16

Gln Lys Tyr Asn Arg Ala Pro Tyr Thr
 1               5

<210> SEQ ID NO 17
<211> LENGTH: 9
<212> TYPE: PRT
<213> ORGANISM: Artificial
<220> FEATURE:
<223> OTHER INFORMATION: LOE5 light chain variable region CDR3

<400> SEQUENCE: 17

Gln Lys Tyr Asn Ser Ala Pro Tyr Tyr
 1               5

<210> SEQ ID NO 18
<211> LENGTH: 9
<212> TYPE: PRT
<213> ORGANISM: Artificial
<220> FEATURE:
<223> OTHER INFORMATION: VLL0G7 light chain variable region CDR3
```

```
<400> SEQUENCE: 18

Gln Lys Tyr Asn Ser Ala Pro Tyr Asn
 1               5

<210> SEQ ID NO 19
<211> LENGTH: 9
<212> TYPE: PRT
<213> ORGANISM: Artificial
<220> FEATURE:
<223> OTHER INFORMATION: VLLOG9 light chain variable region CDR3

<400> SEQUENCE: 19

Gln Lys Tyr Thr Ser Ala Pro Tyr Thr
 1               5

<210> SEQ ID NO 20
<211> LENGTH: 9
<212> TYPE: PRT
<213> ORGANISM: Artificial
<220> FEATURE:
<223> OTHER INFORMATION: VLLOH1 light chain variable region CDR3

<400> SEQUENCE: 20

Gln Lys Tyr Asn Arg Ala Pro Tyr Asn
 1               5

<210> SEQ ID NO 21
<211> LENGTH: 9
<212> TYPE: PRT
<213> ORGANISM: Artificial
<220> FEATURE:
<223> OTHER INFORMATION: VLLOH10 light chain variable region CDR3

<400> SEQUENCE: 21

Gln Lys Tyr Asn Ser Ala Ala Tyr Ser
 1               5

<210> SEQ ID NO 22
<211> LENGTH: 9
<212> TYPE: PRT
<213> ORGANISM: Artificial
<220> FEATURE:
<223> OTHER INFORMATION: VL1B7 light chain variable region CDR3

<400> SEQUENCE: 22

Gln Gln Tyr Asn Ser Ala Pro Asp Thr
 1               5

<210> SEQ ID NO 23
<211> LENGTH: 9
<212> TYPE: PRT
<213> ORGANISM: Artificial
<220> FEATURE:
<223> OTHER INFORMATION: VL1C1 light chain variable region CDR3

<400> SEQUENCE: 23

Gln Lys Tyr Asn Ser Asp Pro Tyr Thr
 1               5

<210> SEQ ID NO 24
<211> LENGTH: 9
<212> TYPE: PRT
<213> ORGANISM: Artificial
<220> FEATURE:
<223> OTHER INFORMATION: VL0.1F4 light chain variable region CDR3
```

-continued

```
<400> SEQUENCE: 24

Gln Lys Tyr Ile Ser Ala Pro Tyr Thr
1               5

<210> SEQ ID NO 25
<211> LENGTH: 9
<212> TYPE: PRT
<213> ORGANISM: Artificial
<220> FEATURE:
<223> OTHER INFORMATION: VL0.1H8 light chain variable region CDR3

<400> SEQUENCE: 25

Gln Lys Tyr Asn Arg Pro Pro Tyr Thr
1               5

<210> SEQ ID NO 26
<211> LENGTH: 9
<212> TYPE: PRT
<213> ORGANISM: Artificial
<220> FEATURE:
<223> OTHER INFORMATION: LOE7.A light chain variable region CDR3

<400> SEQUENCE: 26

Gln Arg Tyr Asn Arg Ala Pro Tyr Ala
1               5

<210> SEQ ID NO 27
<211> LENGTH: 12
<212> TYPE: PRT
<213> ORGANISM: Artificial
<220> FEATURE:
<223> OTHER INFORMATION: 2SD4 heavy chain variable region CDR3

<400> SEQUENCE: 27

Ala Ser Tyr Leu Ser Thr Ser Ser Ser Leu Asp Asn
1               5                   10

<210> SEQ ID NO 28
<211> LENGTH: 12
<212> TYPE: PRT
<213> ORGANISM: Artificial
<220> FEATURE:
<223> OTHER INFORMATION: VH1B11 heavy chain variable region CDR3

<400> SEQUENCE: 28

Ala Ser Tyr Leu Ser Thr Ser Ser Ser Leu Asp Lys
1               5                   10

<210> SEQ ID NO 29
<211> LENGTH: 12
<212> TYPE: PRT
<213> ORGANISM: Artificial
<220> FEATURE:
<223> OTHER INFORMATION: VH1D8 heavy chain variable region CDR3

<400> SEQUENCE: 29

Ala Ser Tyr Leu Ser Thr Ser Ser Ser Leu Asp Tyr
1               5                   10

<210> SEQ ID NO 30
<211> LENGTH: 12
<212> TYPE: PRT
<213> ORGANISM: Artificial
<220> FEATURE:
<223> OTHER INFORMATION: VH1A11 heavy chain variable region CDR3
```

```
<400> SEQUENCE: 30

Ala Ser Tyr Leu Ser Thr Ser Ser Ser Leu Asp Asp
1               5                   10

<210> SEQ ID NO 31
<211> LENGTH: 12
<212> TYPE: PRT
<213> ORGANISM: Artificial
<220> FEATURE:
<223> OTHER INFORMATION: VH1B12 heavy chain variable region CDR3

<400> SEQUENCE: 31

Ala Ser Tyr Leu Ser Thr Ser Phe Ser Leu Asp Tyr
1               5                   10

<210> SEQ ID NO 32
<211> LENGTH: 12
<212> TYPE: PRT
<213> ORGANISM: Artificial
<220> FEATURE:
<223> OTHER INFORMATION: VH1E4 heavy chain variable region CDR3

<400> SEQUENCE: 32

Ala Ser Tyr Leu Ser Thr Ser Ser Ser Leu His Tyr
1               5                   10

<210> SEQ ID NO 33
<211> LENGTH: 12
<212> TYPE: PRT
<213> ORGANISM: Artificial
<220> FEATURE:
<223> OTHER INFORMATION: VH1F6 heavy chain variable region CDR3

<400> SEQUENCE: 33

Ala Ser Phe Leu Ser Thr Ser Ser Ser Leu Glu Tyr
1               5                   10

<210> SEQ ID NO 34
<211> LENGTH: 12
<212> TYPE: PRT
<213> ORGANISM: Artificial
<220> FEATURE:
<223> OTHER INFORMATION: 3C-H2 heavy chain variable region CDR3

<400> SEQUENCE: 34

Ala Ser Tyr Leu Ser Thr Ala Ser Ser Leu Glu Tyr
1               5                   10

<210> SEQ ID NO 35
<211> LENGTH: 12
<212> TYPE: PRT
<213> ORGANISM: Artificial
<220> FEATURE:
<223> OTHER INFORMATION: VH1-D2.N heavy chain variable region CDR3

<400> SEQUENCE: 35

Val Ser Tyr Leu Ser Thr Ala Ser Ser Leu Asp Asn
1               5                   10

<210> SEQ ID NO 36
<211> LENGTH: 321
<212> TYPE: DNA
<213> ORGANISM: Artificial
<220> FEATURE:
<223> OTHER INFORMATION: D2E7 light chain variable region
```

```
<400> SEQUENCE: 36
gacatccaga tgacccagtc tccatcctcc ctgtctgcat ctgtagggga cagagtcacc      60
atcacttgtc gggcaagtca gggcatcaga aattacttag cctggtatca gcaaaaacca     120
gggaaagccc ctaagctcct gatctatgct gcatccactt tgcaatcagg ggtcccatct     180
cggttcagtg gcagtggatc tgggacagat ttcactctca ccatcagcag cctacagcct     240
gaagatgttg caacttatta ctgtcaaagg tataaccgtg caccgtatac ttttggccag     300
gggaccaagg tggaaatcaa a                                               321

<210> SEQ ID NO 37
<211> LENGTH: 363
<212> TYPE: DNA
<213> ORGANISM: Artificial
<220> FEATURE:
<223> OTHER INFORMATION: D2E7 heavy chain variable region

<400> SEQUENCE: 37
gaggtgcagc tggtggagtc tgggggaggc ttggtacagc ccggcaggtc cctgagactc      60
tcctgtgcgg cctctggatt cacctttgat gattatgcca tgcactgggt ccggcaagct    120
ccagggaagg gcctggaatg ggtctcagct atcacttgga atagtggtca catagactat    180
gcggactctg tggagggccg attcaccatc tccagagaca acgccaagaa ctccctgtat    240
ctgcaaatga acagtctgag agctgaggat acggccgtat attactgtgc gaaagtctcg    300
taccttagca ccgcgtcctc ccttgactat tggggccaag gtaccctggt caccgtctcg    360
agt                                                                  363
```

WEARABLE AUTOMATIC INJECTION DEVICE FOR CONTROLLED DELIVERY OF THERAPEUTIC AGENTS

RELATED APPLICATIONS

This application is related to and claims priority to U.S. Provisional Application Ser. No. 61/326,637, filed Apr. 21, 2010, the entire contents of which are expressly incorporated herein by reference in their entirety.

BACKGROUND

Automatic injection devices offer an alternative to manually-operated syringes for delivering therapeutic agents into patients' bodies and allowing patients to self-administer injections. Automatic injection devices have been used to deliver medications under emergency conditions, for example, to administer epinephrine to counteract the effects of a severe allergic reaction. Automatic injection devices have also been described for use in administering anti-arrhythmic medications and selective thrombolytic agents during a heart attack (See, e.g., U.S. Pat. Nos. 3,910,260; 4,004,577; 4,689,042; 4,755,169; and 4,795,433). Various types of automatic injection devices are also described in, for example, U.S. Pat. Nos. 3,941,130; 4,261,358; 5,085,642; 5,092,843; 5,102,393; 5,267,963; 6,149,626; 6,270,479; and 6,371,939; and International Patent Publication No. WO/2008/005315.

Conventionally, an automatic injection device houses a syringe and, when operated, causes the syringe to move forwardly and a needle to project from the housing so that a therapeutic agent contained in the syringe is ejected into a patient's skin. An automatic injection device typically includes a bung disposed within the syringe that, when actuated, moves within the syringe to expel the therapeutic agent from the syringe and into the patient's skin.

SUMMARY

Exemplary embodiments provide wearable automatic injection devices that may adhere to the skin or clothing of a patient and deliver a therapeutic agent into the patient's body by subcutaneous injection at slow, controlled injection rates, e.g., in a single slow bolus. Exemplary embodiments provide methods of assembling exemplary wearable automatic injection devices. Exemplary embodiments also provide methods of using wearable automatic injection devices worn by a patient for slow, controlled therapeutic agent delivery. Exemplary wearable automatic injection devices reduce or eliminate a burning sensation often felt or perceived by patients who use a conventional automatic injection device. Exemplary wearable automatic injection devices maintain the sterility of the therapeutic agent container (e.g., syringe), are easy to use, pre-fill capable, easy to manufacture, and/or do not require aseptic assembly. The wearable automatic injection devices provided by exemplary embodiments may adhere to the skin or clothing of the patient to deliver any therapeutic agent subcutaneously including, but not limited to, a biologic drug, such as, for example, an antibody, insulin, etc.

In accordance with an exemplary embodiment, a wearable automatic injection device is provided for providing a subcutaneous injection of a therapeutic agent into a patient. The device includes a housing comprising a patient contact portion securable to the patient. The device also includes an injection assembly moveably disposed in the housing holding a hypodermic injection needle for insertion into the patient, the injection assembly moveable between a retracted position in which the injection needle does not protrude outside the housing and an extended position in which the injection needle protrudes outside the housing. The device also includes a vessel provided in the housing for holding the therapeutic agent, a plunger moveably disposed in the vessel for ejecting the therapeutic agent from the vessel into the injection assembly, and a plunger actuation mechanism for actuating the plunger within the vessel. The device also includes a retraction trigger responsive to a change of state of the wearable automatic injection device from an injection state to a post-injection state, and a retraction mechanism for automatically retracting the injection assembly from the extended position in the injection state to the retracted position in the post-injection state upon triggering by the retraction trigger.

In accordance with another exemplary embodiment, a method is provided for subcutaneously injecting a therapeutic agent into a patient. The method includes providing a wearable automatic injection device including a housing comprising a patient contact portion securable to the patient. The device also includes an injection assembly moveably disposed in the housing holding a hypodermic injection needle for insertion into the patient, the injection assembly moveable between a retracted position in which the injection needle does not protrude outside the housing and an extended position in which the injection needle protrudes outside the housing. The device also includes a vessel provided in the housing for holding the therapeutic agent, a plunger moveably disposed in the vessel for ejecting the therapeutic agent from the vessel into the injection assembly, and a plunger actuation mechanism for actuating the plunger within the vessel. The device also includes a retraction trigger responsive to a change of state of the wearable automatic injection device from an injection state to a post-injection state, and a retraction mechanism for automatically retracting the injection assembly from the extended position in the injection state to the retracted position in the post-injection state upon triggering by the retraction trigger. The method includes securing the wearable automatic injection device to the skin of the patient or an article of clothing on the patient using the patient contact of the housing. The method also includes administering the therapeutic agent into the skin of the patient using the wearable automatic injection device.

In accordance with another exemplary embodiment, a wearable automatic injection device is provided for subcutaneously injecting a therapeutic agent into a patient. The device includes a housing and a cartridge assembly movably disposed within the housing. The cartridge includes a barrel portion for holding the therapeutic agent, and a hollow needle in fluid communication with the barrel portion for ejecting the therapeutic agent from the barrel portion. The cartridge also includes a bung for sealing the barrel portion and selectively applying pressure to the therapeutic agent to force the therapeutic agent through the hollow needle. The cartridge further includes a plunger actuator for applying pressure to the bung, and a trigger mechanism that actuates the plunger actuator to apply pressure to the bung when the cartridge is depressed from a ready position (in a pre-injection state) to a depressed position (in an injection state) inside the housing. The trigger mechanism actuates the plunger actuator such that the therapeutic agent is ejected from the barrel portion and into the patient at a controlled, slow rate with little or no burning sensation felt or perceived by the patient. The device also includes a fastener layer disposed on a patient contact surface to fasten the device to the skin or clothing of the patient or to an article of clothing of the patient. The fastener layer may include an adhesive for temporarily securing the wearable automatic injection device to the patient at least during the controlled injection of the therapeutic agent.

The wearable automatic injection device includes a retraction mechanism that retracts the cartridge from the depressed position to a retracted position (in a post-injection state). The wearable automatic injection device also includes a retraction trigger that activates the retraction mechanism, the retraction trigger trips when delivery of the therapeutic agent completes, or times out due an elapsed period of time, or when the wearable automatic injection device is removed from the patient, for example, before delivery of the therapeutic agent is completed. The wearable automatic injection device operates and functions entirely on mechanical principles or in combination with a controlled reaction to transition from any state (i.e., a pre-injection state, an injection state, a post-injection state), and controls the injection rate of the therapeutic agent over a time period that is selected for patient comfort, convenience or preference, or exceeds a time period for injection by a conventional automatic handheld device. In an exemplary embodiment, the time period of the injection by an exemplary wearable automatic injection device may range between about ten seconds and about twelve hours. In a preferred embodiment, the time period may range between about five minutes and about thirty minutes.

In another exemplary embodiment, a method is provided for subcutaneously injecting a therapeutic agent into a patient. The method includes providing a wearable automatic injection device comprising a housing and a cartridge assembly movably disposed within the housing. The cartridge includes a barrel portion for holding a therapeutic agent, and a hollow needle in fluid communication with the barrel portion for ejecting the therapeutic agent from the barrel portion. The cartridge also includes a bung for sealing the barrel portion and selectively applying pressure to the therapeutic agent to force the therapeutic agent through the hollow needle. The cartridge further includes a plunger actuator for applying pressure to the bung, and a trigger mechanism that actuates the plunger actuator to apply pressure to the bung when the cartridge is depressed from a ready position (in a pre-injection state) to a depressed position (in an injection state) inside the housing. The trigger mechanism actuates the plunger actuator such that the therapeutic agent is ejected from the barrel portion and into the patient at a controlled, slow rate and substantially free of any burning sensation.

The method also includes depressing the cartridge from the ready position to a depressed position within the housing. Depressing the cartridge automatically causes the injection needle that is used to pierce the patient's skin to project from an opening in the housing to penetrate the skin of the patient, and actuates the plunger actuator to apply pressure to the bung such that the therapeutic agent is delivered into the patient at a controlled, slow rate and substantially free of any burning sensation.

The method further includes automatically retracting the cartridge from the depressed to a retracted position (in a post-injection state) in the housing when delivery of the therapeutic agent is completed, or times out due to an elapsed period of time, or when the wearable automatic injection device is removed from the skin or clothing of the patient, for example, before delivery of the therapeutic agent is completed.

In an exemplary embodiment, a wearable automatic injection device is provided. The wearable automatic injection device provides a subcutaneous injection of a therapeutic agent into a patient. The wearable automatic injection device includes a housing having a patient contact portion securable to the patient and an interior portion defined by a plurality of walls and defining at least one open end opposing the patient contact portion. The wearable automatic injection device also includes a cartridge assembly movably disposed within the interior portion of the housing and movable from any of a ready position, an injection position, and a retraction position. The wearable automatic injection device further includes a trigger mechanism responsive to a change in state of the wearable automatic injection device from a pre-injection state to an injection state to actuate a plunger actuator disposed in the cartridge assembly to begin ejection of a therapeutic agent from the cartridge assembly, and a retraction trigger responsive to a change of state of the wearable automatic injection device from the injection state to a post-injection state. The wearable automatic injection device also includes a retraction mechanism responsive to the retraction trigger to automatically retract the cartridge assembly from the patient when the automatic injection device enters the post-injection state.

In another exemplary embodiment, a method of subcutaneously injecting a therapeutic agent into a patient is provided. The method includes securing to a patient a wearable automatic injection device comprising a housing having a patient contact portion securable to the patient and an interior portion defined by a plurality of walls and defining at least one open end opposing the patient contact portion and a cartridge assembly movably disposed within the interior portion of the housing and movable from any of a ready position, an injection position, and a retraction position, the cartridge assembly holding the therapeutic agent in a pre-fillable and/or pre-filled sterile manner. The method also includes depressing the cartridge assembly downwardly towards the patient contact portion to cause the wearable automatic injection device to enter an injection state from a pre-injection state to automatically project a needle from a needle aperture in the housing and penetrate the skin of the patient and expel the therapeutic agent into the patient at a controlled rate.

BRIEF DESCRIPTION OF THE DRAWINGS

The foregoing and other objects, aspects, features, and advantages of exemplary embodiments will become more apparent and may be better understood by referring to the following description taken in conjunction with the accompanying drawings, in which:

FIG. 1A illustrates a first end view and a first side view of an exemplary wearable device including a cartridge assembly in a packaged pre-injection state.

FIG. 1B illustrates the first end view and the first side view of the exemplary device of FIG. 1A before an injection in a pre-injection state in which a needle cover covering the injection needle is removed in preparation for an injection.

FIG. 1C illustrates the first end view and the first side view of the exemplary device of FIG. 1A during an injection in an injection state in which the patient's skin is pierced by the injection needle.

FIG. 1D illustrates the first end view and the first side view of the exemplary device of FIG. 1A during an injection in an injection state in which a barrel portion of the device containing a dose of the therapeutic agent is deployed forwardly within the housing of the device.

FIG. 1E illustrates the first end view and the first side view of the exemplary device of FIG. 1A during an injection in an injection state in which a bung of the device is actuated by a plunger actuator to expel the dose of the therapeutic agent from the barrel portion.

FIG. 1F illustrates the first end view and the first side view of the exemplary device of FIG. 1A after an injection in a post-injection state in which the injection needle is retracted within the housing of the device.

FIG. 2A illustrates a first end view and a first side view of an exemplary wearable device including a syringe assembly in a packaged pre-injection state.

FIG. 2B illustrates the first end view and the first side view of the exemplary device of FIG. 2A before an injection in a pre-injection state in which a needle cover covering the injection needle is removed in preparation for an injection.

FIG. 2C illustrates the first end view and the first side view of the exemplary device of FIG. 2A during an injection in an injection state in which the patient's skin is pierced by the injection needle.

FIG. 2D illustrates the first end view and the first side view of the exemplary device of FIG. 2A during an injection in an injection state in which a barrel portion of the device containing a dose of the therapeutic agent is deployed forwardly within the housing of the device.

FIG. 2E illustrates the first end view and the first side view of the exemplary device of FIG. 2A during an injection in an injection state in which a bung of the device is actuated by a plunger actuator to expel the dose of the therapeutic agent from the barrel portion.

FIG. 2F illustrates the first end view and the first side view of the exemplary device of FIG. 2A after an injection in a post-injection state in which the injection needle is retracted within the housing of the device.

FIG. 6A illustrates an exemplary wearable automatic injection device suitable for linear insertion into a patient in a pre-injection state.

FIG. 6B illustrates the exemplary device of FIG. 6A in an injection state ready to inject or injecting a dose of a therapeutic agent into a patient.

FIG. 6C illustrates the exemplary device of FIGS. 6A and 6B in a post injection state after it has completed injecting the therapeutic agent into the patient or removed from the patient prior to completion of the injecting of the therapeutic agent.

FIG. 7A illustrates an exemplary wearable automatic injection device suitable for rotary insertion in a pre-injection state ready for use by a patient.

FIG. 7B illustrates the exemplary device of FIG. 7A in an injection state ready to inject or injecting a dose of a therapeutic agent into a patient.

FIG. 7C illustrates the exemplary device of FIGS. 7A and 7B in a post-injection state after it has completed injecting the therapeutic agent into the patient or removed from the patient prior to completion of the injecting of the therapeutic agent.

FIG. 11 illustrates an exemplary barrel portion in which a distal end of the barrel portion bears an injection needle that extends substantially along the longitudinal axis of the barrel portion.

FIG. 12 illustrates an exemplary barrel portion in which a distal end of the barrel portion bears an injection needle that extends at about 90 degrees relative to the longitudinal axis of the barrel portion.

FIGS. 52A and 52B illustrate an exemplary needle protection system that maintains an injection needle in a retracted position within a housing of an exemplary automatic injection system.

FIGS. 53A and 53B illustrate another exemplary needle protection system provided in an exemplary automatic injection system.

DETAILED DESCRIPTION

Figure 3:
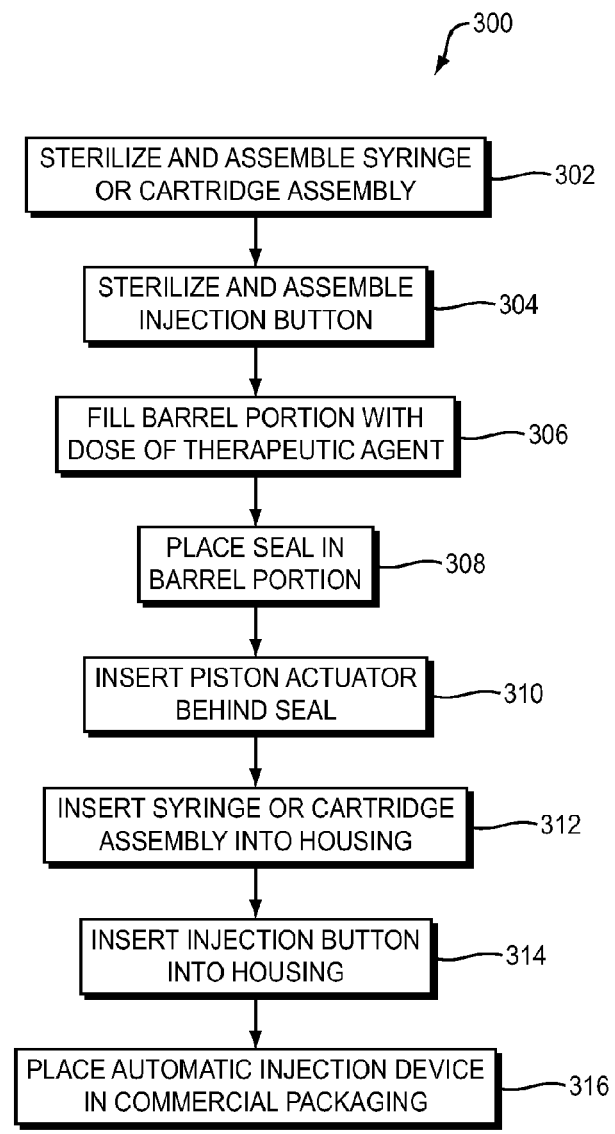
FIG. 3 is a flow chart of an exemplary method of assembling an exemplary wearable automatic injection device.

Subcutaneous injection is a primary mode of therapeutic agent delivery and involves administering a bolus of a therapeutic agent into a patient. Subcutaneous injections are highly effective in administering various therapeutic agents including insulin, vaccines, and drugs such as morphine. Automatic injection devices offer an alternative to a syringe for delivering a therapeutic agent and allow patients to self-administer subcutaneous injections of therapeutic agents. Conventional automatic injection devices include hand held automatic injection devices and patch pumps, which are self-adhesive, patient-mounted auto-injectors. In use, a patch pump containing a therapeutic agent is mounted onto the skin or clothing of a patient and triggered to inject the therapeutic agent into the patient. Conventional patch pumps are typically filled by a patient prior to use. In addition, certain conventional patch pumps have an exposed needle inside the pump, and thus require secondary sterile packaging to maintain sterility.

Studies have shown that there is a direct correlation between the injection rate of certain therapeutic agents and the pain perceived by a patient upon injection of the therapeutic agents or agents. Some therapeutic agents cause pain, e.g., a burning or stinging sensation when injected rapidly into the patient. The pain sensation may be the result of a physiological response of the patient's skin to the subcutaneous injection of a therapeutic agent. Large volumes of any therapeutic agent, greater than one milliliter, may also cause pain when injected into the skin. Antibodies, and portions thereof, are exemplary therapeutic agents that are least painful when delivered at slow injection rates. Currently, there are no commercially viable conventional patch pumps that effectively address the discomfort associated with fast injection rates of hand held automatic injection devices.

Exemplary embodiments are described below with reference to certain illustrative embodiments. While exemplary embodiments are described with respect to using a wearable automatic injection device to provide an injection of a dose of a liquid medication, one of ordinary skill in the art will recognize that exemplary embodiments are not limited to the illustrative embodiments and that exemplary automatic injection devices may be used to inject any suitable substance into a patient. In addition, components of exemplary automatic injection devices and methods of making and using exemplary automatic injection devices are not limited to the illustrative embodiments described below.

A syringe assembly of exemplary automatic injections devices may contain a dose of a TNFα inhibitor. In an exemplary embodiment, the TNFa inhibitor may be a human TNFa antibody or antigen-biding portion thereof. In an exemplary embodiment, the human TNFa antibody or antigen-binding portion thereof may be adalimumab or golimumab.

Exemplary embodiments provide wearable automatic injection devices that may adhere to the skin or clothing of the patient and deliver a therapeutic agent into patient by subcutaneous injection at slow, controlled injection rates, e.g., in a single slow bolus. The slow, controlled injection rates achieved by exemplary devices minimize the pain sensation associated with a volume of a therapeutic agent entering into the patient's tissue. Exemplary time durations for slow delivery achieved by exemplary devices may range from about 5 minutes to about 30 minutes, but are not limited to this exemplary range. Exemplary volumes of therapeutic agent deliverable by exemplary devices may range from about 0.8 milliliters to about 1 milliliter, but are not limited to this exemplary range. In addition, exemplary devices may advantageously minimize inflections in the delivery profile against time of the therapeutic agent.

Exemplary embodiments minimize the size envelope of exemplary automatic injection devices, and provide scalable solutions with configurable delivery times and delivery profiles that may be used for a range of therapeutic agent viscosities.

Exemplary embodiments provide wearable automatic injection devices that deliver a therapeutic agent into a patient by subcutaneous injection at slow, controlled injection rates, e.g., in a single slow bolus without battery power or other components requiring electrical current or charge to operate. Exemplary embodiments also provide methods of using the wearable automatic injection devices for slow, controlled therapeutic agent delivery. The wearable automatic injection devices provided by exemplary embodiments are pre fillable prior to delivery to the patient, maintain sterility of the therapeutic agent and all subcutaneous contact surfaces (i.e., a hypodermic needle and one or more septums) to avoid the need for aseptic assembly and address the perceived patient discomfort due to injection by conventional hand held automatic injection devices. Exemplary wearable automatic injection devices include a primary therapeutic barrel portion that maintains sterility and therefore requires no aseptic assembly. Exemplary wearable automatic injection devices are disposable, easy to use, pre-fill capable, and may substantially or completely eliminate the burning sensation often experienced by a patient that uses a wearable automatic injection device. The wearable automatic injection devices provided by exemplary embodiments can be used to deliver any therapeutic agent that may be delivered subcutaneously including, but not limited to, an antibody or insulin, etc.

I. DEFINITIONS

Certain terms are defined in this section to facilitate understanding of exemplary embodiments.

The wearable automatic injection device of exemplary embodiments may include a "therapeutically effective amount" or a "prophylactically effective amount" of an antibody or antibody portion of the invention. A "therapeutically effective amount" refers to an amount effective, at dosages and for periods of time necessary, to achieve the desired therapeutic result. A therapeutically effective amount of the antibody, antibody portion, or other TNFα inhibitor may vary according to factors such as the disease state, age, sex, and weight of the patient, and the ability of the antibody, antibody portion, or other TNFα inhibitor to elicit a desired response in the patient. A therapeutically effective amount is also one in which any toxic or detrimental effects of the antibody, antibody portion, or other TNFα inhibitor are outweighed by the therapeutically beneficial effects. A "prophylactically effective amount" refers to an amount effective, at dosages and for periods of time necessary, to achieve the desired prophylactic result. Typically, since a prophylactic dose is used in patients prior to or at an earlier stage of disease, the prophylactically effective amount will be less than the therapeutically effective amount.

The terms "substance" and "therapeutic agent" refer to any type of drug, biologically active agent, biological substance, chemical substance or biochemical substance that is capable of being administered in a therapeutically effective amount to a patient employing exemplary automatic injection devices. Exemplary substances include, but are not limited to, agents in a liquid state. Such agents may include, but are not limited to, adalimumab (HUMIRA®) and proteins that are in a liquid solution, e.g., fusion proteins and enzymes. Examples of proteins in solution include, but are not limited to, Pulmozyme (Dornase alfa), Regranex (Becaplermin), Activase (Alteplase), Aldurazyme (Laronidase), Amevive (Alefacept), Aranesp (Darbepoetin alfa), Becaplermin Concentrate, Betaseron (Interferon beta-1b), BOTOX (Botulinum Toxin Type A), Elitek (Rasburicase), Elspar (Asparaginase), Epogen (Epoetin alfa), Enbrel (Etanercept), Fabrazyme (Agalsidase beta), Infergen (Interferon alfacon-1), Intron A (Interferon alfa-2a), Kineret (Anakinra), MYOBLOC (Botulinum Toxin Type B), Neulasta (Pegfilgrastim), Neumega (Oprelvekin), Neupogen (Filgrastim), Ontak (Denileukin diftitox), PEGASYS (Peginterferon alfa-2a), Proleukin (Aldesleukin), Pulmozyme (Dornase alfa), Rebif (Interferon beta-1a), Regranex (Becaplermin), Retavase (Reteplase), Roferon-A (Interferon alfa-2), TNKase (Tenecteplase), and Xigris (Drotrecogin alfa), Arcalyst (Rilonacept), NPlate (Romiplostim), Mircera (methoxypolyethylene glycol-epoetin beta), Cinryze (C1 esterase inhibitor), Elaprase (idursulfase), Myozyme (alglucosidase alfa), Orencia (abatacept), Naglazyme (galsulfase), Kepivance (palifermin) and Actimmune (interferon gamma-1b).

A protein in solution may also be an immunoglobulin or antigen-binding fragment thereof, such as an antibody or antigen-binding portion thereof. Examples of antibodies that may be used in an exemplary automatic injection device include, but are not limited to, chimeric antibodies, non-human antibodies, human antibodies, humanized antibodies, and domain antibodies (dAbs). In an exemplary embodiment, the immunoglobulin or antigen-binding fragment thereof, is an anti-TNFa and/or an anti-IL-12 antibody (e.g., it may be a dual variable domain immunoglobulin (DVD) IgTM). Other examples of immunoglobulins or antigen-binding fragments thereof that may be used in the methods and compositions of exemplary embodiments include, but are not limited to, 1D4.7 (anti-IL-12/IL-23 antibody; Abbott Laboratories); 2.5 (E)mg1 (anti-IL-18; Abbott Laboratories); 13C5.5 (anti-IL-13 antibody; Abbott Laboratories); J695 (anti-IL-12; Abbott Laboratories); Afelimomab (Fab 2 anti-TNF; Abbott Laboratories); HUMIRA (adalimumab) Abbott Laboratories); Campath (Alemtuzumab); CEA-Scan Arcitumomab (fab fragment); Erbitux (Cetuximab); Herceptin (Trastuzumab); Myoscint (Imciromab Pentetate); ProstaScint (Capromab Pendetide); Remicade (Infliximab); ReoPro (Abciximab); Rituxan (Rituximab); Simulect (Basiliximab); Synagis (Palivizumab); Verluma (Nofetumomab); Xolair (Omalizumab); Zenapax (Daclizumab); Zevalin (Ibritumomab Tiuxetan); Orthoclone OKT3 (Muromonab-CD3); Panorex (Edrecolomab); Mylotarg (Gemtuzumab ozogamicin); golimumab (Centocor); Cimzia (Certolizumab pegol); Soliris (Eculizumab); CNTO 1275 (ustekinumab); Vectibix (panitumumab); Bexxar (tositumomab and I131 tositumomab); and Avastin (bevacizumab).

Additional examples of immunoglobulins, or antigen-binding fragments thereof, that may be used in the methods and compositions of exemplary embodiments include, but are not limited to, proteins comprising one or more of the following: the D2E7 light chain variable region (SEQ ID NO: 1), the D2E7 heavy chain variable region (SEQ ID NO: 2), the D2E7 light chain variable region CDR3 (SEQ ID NO: 3), the D2E7 heavy chain variable region CDR3 (SEQ ID NO:4), the D2E7 light chain variable region CDR2 (SEQ ID NO: 5), the D2E7 heavy chain variable region CDR2 (SEQ ID NO: 6), the D2E7 light chain variable region CDR1 (SEQ ID NO: 7), the D2E7 heavy chain variable region CDR1 (SEQ ID NO: 8), the 2SD4 light chain variable region (SEQ ID NO: 9), the 2SD4 heavy chain variable region (SEQ ID NO: 10), the 2SD4 light chain variable CDR3 (SEQ ID NO: 11), the EP B12 light chain variable CDR3 (SEQ ID NO: 12), the VL10E4 light chain variable CDR3 (SEQ ID NO: 13), the VL100A9 light chain variable CDR3 (SEQ ID NO: 14), the VLL100D2 light chain variable CDR3 (SEQ ID NO: 15), the VLLOF4 light chain variable CDR3 (SEQ ID NO: 16), the LOE5 light chain variable CDR3 (SEQ ID NO: 17), the VLLOG7 light chain variable CDR3 (SEQ ID NO: 18), the VLLOG9 light chain variable CDR3 (SEQ ID NO: 19), the VLLOH1 light chain variable CDR3 (SEQ ID NO: 20), the VLLOH10 light chain variable CDR3 (SEQ ID NO: 21), the VL1B7 light chain variable CDR3 (SEQ ID NO: 22), the VL1C1 light chain variable CDR3 (SEQ ID NO: 23), the VL0.1F4 light chain variable CDR3 (SEQ ID NO: 24), the VL0.1H8 light chain variable CDR3 (SEQ ID NO: 25), the LOE7.A light chain variable CDR3 (SEQ ID NO: 26), the 2SD4 heavy chain variable region CDR (SEQ ID NO: 27), the VH1B11 heavy chain variable region CDR (SEQ ID NO: 28), the VH1D8 heavy chain variable region CDR (SEQ ID NO: 29), the VH1A11 heavy chain variable region CDR (SEQ ID NO: 30), the VH1B12 heavy chain variable region CDR (SEQ ID NO: 31), the VH1E4 heavy chain variable region CDR (SEQ ID NO: 32), the VH1F6 heavy chain variable region CDR (SEQ ID NO: 33), the 3C-H2 heavy chain variable region CDR (SEQ ID NO: 34), and the VH1-D2.N heavy chain variable region CDR (SEQ ID NO: 35).

The term "human TNFα" (abbreviated herein as hTNFα, or simply hTNF) refers to a human cytokine that exists as a 17 kD secreted form and a 26 kD membrane associated form, the biologically active form of which is composed of a trimer of noncovalently bound 17 kD molecules. The structure of hTNFα is described further in, for example, Pennica, D., et al. (1984) Nature 312:724-729; Davis, J. M., et al. (1987) Biochem. 26:1322-1326; and Jones, E. Y., et al. (1989) Nature 338:225-228. The term human TNFα is intended to include recombinant human TNFα (rhTNFα), which can be prepared by standard recombinant expression methods or purchased commercially (R & D Systems, Catalog No. 210-TA, Minneapolis, Minn.). TNFα is also referred to as TNF.

The term "TNFα inhibitor" refers to an agent that interferes with TNFα activity. The term also includes each of the anti-TNFα human antibodies (used interchangeably herein with TNFα antibodies) and antibody portions described herein as well as those described in U.S. Pat. Nos. 6,090,382; 6,258,562; 6,509,015; 7,223,394; and 6,509,015. In one embodiment, the TNFα inhibitor used in the invention is an anti-TNFα antibody, or a fragment thereof, including infliximab (Remicade®, Johnson and Johnson; described in U.S. Pat. No. 5,656,272); CDP571 (a humanized monoclonal anti-TNF-alpha IgG4 antibody); CDP 870 (a humanized monoclonal anti-TNF-alpha antibody fragment); an anti-TNF dAb (Peptech); CNTO 148 (golimumab; Centocor, See WO 02/12502 and U.S. Pat. No. 7,521,206 and U.S. Pat. No. 7,250,165); and adalimumab (HUMIRA® Abbott Laboratories, a human anti-TNF mAb, described in U.S. Pat. No. 6,090,382 as D2E7). Additional TNF antibodies that may be used in the invention are described in U.S. Pat. Nos. 6,593,458; 6,498,237; 6,451,983; and 6,448,380. In another embodiment, the TNFα inhibitor is a TNF fusion protein, e.g., etanercept (Enbrel®, Amgen; described in WO 91/03553 and WO 09/406,476). In another embodiment, the TNFα inhibitor is a recombinant TNF binding protein (r-TBP-I) (Serono).

In one embodiment, the term "TNFα inhibitor" excludes infliximab. In one embodiment, the term "TNFα inhibitor" excludes adalimumab. In another embodiment, the term "TNFα inhibitor" excludes adalimumab and infliximab.

In one embodiment, the term "TNFα inhibitor" excludes etanercept, and, optionally, adalimumab, infliximab, and adalimumab and infliximab.

In one embodiment, the term "TNFα antibody" excludes infliximab. In one embodiment, the term "TNFα antibody"

excludes adalimumab. In another embodiment, the term "TNFα antibody" excludes adalimumab and infliximab.

The term "antibody" refers to immunoglobulin molecules generally comprised of four polypeptide chains, two heavy (H) chains and two light (L) chains inter-connected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The antibodies of the invention are described in further detail in U.S. Pat. Nos. 6,090,382; 6,258,562; and 6,509,015.

The term "antigen-binding portion" of an antibody (or simply "antibody portion") refers to one or more fragments of an antibody that retain the ability to specifically bind to an antigen (e.g., hTNFα). Fragments of a full-length antibody can perform the antigen-binding function of an antibody. Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. (1989) Nature 341:544-546), which consists of a VH or VL domain; (vi) an isolated complementarity determining region (CDR); and (vii) a dual variable domain immunoglobulin (DVD-Ig). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); See e.g., Bird et al. (1988) Science 242:423-426; and Huston et al. (1988) Proc. Natl. Acad. Sci. USA 85:5879-5883). Such single chain antibodies are also encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (See e.g., Holliger et al. (1993) Proc. Natl. Acad. Sci. USA 90:6444-6448; Poljak et al. (1994) Structure 2:1121-1123). The antibody portions of the invention are described in further detail in U.S. Pat. Nos. 6,090,382; 6,258,562; and 6,509,015.

The term "recombinant human antibody" refers to all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (See e.g., Taylor et al. (1992) Nucl. Acids Res. 20:6287) or antibodies prepared, expressed, created or isolated by any other means that involves splicing of human immunoglobulin gene sequences to other DNA sequences. Such recombinant human antibodies have variable and constant regions derived from human germ line immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germ line VH and VL sequences, may not naturally exist within the human antibody germ line repertoire in vivo.

Such chimeric, humanized, human, and dual specific antibodies can be produced by recombinant DNA techniques known in the art, for example using methods described in PCT International Application No. PCT/US86/02269; European Patent Application No. 184,187; European Patent Application No. 171,496; European Patent Application No. 173,494; PCT International Publication No. WO 86/01533; U.S. Pat. No. 4,816,567; European Patent Application No. 125,023; Better et al. (1988) Science 240:1041-1043; Liu et al. (1987) Proc. Natl. Acad. Sci. USA 84:3439-3443; Liu et al. (1987) J. Immunol. 139:3521-3526; Sun et al. (1987) Proc. Natl. Acad. Sci. USA 84:214-218; Nishimura et al. (1987) Cancer Res. 47:999-1005; Wood et al. (1985) Nature 314: 446-449; Shaw et al. (1988) J. Natl. Cancer Inst. 80:1553-1559; Morrison (1985) Science 229:1202-1207; Oi et al. (1986) BioTechniques 4:214; U.S. Pat. No. 5,225,539; Jones et al. (1986) Nature 321:552-525; Verhoeyan et al. (1988) Science 239:1534; and Beidler et al. (1988) J. Immunol. 141:4053-4060, Queen et al. (1989) Proc. Natl. Acad. Sci. USA 86:10029-10033 (1989); U.S. Pat. No. 5,530,101; U.S. Pat. No. 5,585,089; U.S. Pat. No. 5,693,761; U.S. Pat. No. 5,693,762; WO 90/07861; and U.S. Pat. No. 5,225,539.

The term "isolated antibody" refers to an antibody that is substantially free of other antibodies having different antigenic specificities (e.g., an isolated antibody that specifically binds hTNFα and is substantially free of antibodies that specifically bind antigens other than hTNFα). An isolated antibody that specifically binds hTNFα may have cross-reactivity to other antigens, such as TNFα molecules from other species. Moreover, an isolated antibody may be substantially free of other cellular material and/or chemicals.

The term "neutralizing antibody" (or an "antibody that neutralized hTNFα activity") refers to an antibody whose binding to hTNFα results in inhibition of the biological activity of hTNFα. This inhibition of the biological activity of hTNFα can be assessed by measuring one or more indicators of hTNFα biological activity, such as hTNFα-induced cytotoxicity (either in vitro or in vivo), hTNFα-induced cellular activation and hTNFα binding to hTNFα receptors. These indicators of hTNFα biological activity can be assessed by one or more of several standard in vitro or in vivo assays known in the art (See U.S. Pat. No. 6,090,382). Preferably, the ability of an antibody to neutralize hTNFα activity is assessed by inhibition of hTNFα-induced cytotoxicity of L929 cells. As an additional or alternative parameter of hTNFα activity, the ability of an antibody to inhibit hTNFα-induced expression of ELAM-1 on HUVEC, as a measure of hTNFα-induced cellular activation, can be assessed.

The term "surface plasmon resonance" refers to an optical phenomenon that allows for the analysis of real-time biospecific interactions by detection of alterations in protein concentrations within a biosensor matrix, for example using the BiAcore system (Pharmacia Biosensor AB, Uppsala, Sweden and Piscataway, N.J.). For further descriptions, see Example 1 of U.S. Pat. No. 6,258,562 and Jönsson et al. (1993) Ann. Biol. Clin. 51:19; Jönsson et al. (1991) Biotechniques 11:620-627; Johnsson et al. (1995) J. Mol. Recognit. 8:125; and Johnnson et al. (1991) Anal. Biochem. 198:268.

The term "Koff" refers to the off rate constant for dissociation of an antibody from the antibody/antigen complex.

The term "Kd" refers to the dissociation constant of a particular antibody-antigen interaction.

The term "IC50" refers to the concentration of the inhibitor required to inhibit the biological endpoint of interest, e.g., neutralize cytotoxicity activity.

The term "dose" or "dosage" refers to an amount of a substance, such as a TNFα inhibitor, which is administered to a patient preferably using the wearable automatic injection device of the invention. In one embodiment, the dose comprises an effective amount, for example, including, but not limited to, 20 mg, 30 mg, 40 mg, 50 mg, 60 mg, 70 mg, 80 mg, 90 mg, 100 mg, 110 mg, 120 mg, 130 mg, 140 mg, 150 mg, and 160 mg, of the TNFα inhibitor adalimumab.

The term "dosing" refers to the administration of a substance (e.g., an anti-TNFα antibody) to achieve a therapeutic objective (e.g., treatment of rheumatoid arthritis).

The term "dosing regimen" describes a treatment schedule for a substance, such as a TNFα inhibitor, e.g., a treatment schedule over a prolonged period of time and/or throughout the course of treatment, e.g. administering a first dose of a TNFα inhibitor at week 0 followed by a second dose of a TNFα inhibitor on a biweekly dosing regimen.

The term "biweekly dosing regimen", "biweekly dosing", and "biweekly administration" refer to the time course of administering a substance (e.g., an anti-TNFα antibody) to a patient to achieve a therapeutic objective, e.g., throughout the course of treatment. The biweekly dosing regimen is not intended to include a weekly dosing regimen. Preferably, the substance is administered every 9 to 19 days, more preferably, every 11 to 17 days, even more preferably, every 13 to 15 days, and most preferably, every 14 days. In one embodiment, the biweekly dosing regimen is initiated in a patient at week 0 of treatment. In another embodiment, a maintenance dose is administered on a biweekly dosing regimen. In one embodiment, both the loading and maintenance doses are administered according to a biweekly dosing regimen. In one embodiment, biweekly dosing includes a dosing regimen wherein doses of a TNFα inhibitor are administered to a patient every other week beginning at week 0. In one embodiment, biweekly dosing includes a dosing regimen where doses of a TNFα inhibitor are administered to a patient every other week consecutively for a given time period, e.g., 4 weeks, 8 weeks, 16, weeks, 24 weeks, 26 weeks, 32 weeks, 36 weeks, 42 weeks, 48 weeks, 52 weeks, 56 weeks, etc. Biweekly dosing methods are also described in U.S. 2003/0235585.

The term "combination" as in the phrase "a first agent in combination with a second agent" includes co-administration of a first agent and a second agent, which for example may be dissolved or intermixed in the same pharmaceutically acceptable carrier, or administration of a first agent, followed by the second agent, or administration of the second agent, followed by the first agent.

The term "concomitant" as in the phrase "concomitant therapeutic treatment" includes administering an agent in the presence of a second agent. A concomitant therapeutic treatment method includes methods in which the first, second, third, or additional substances are co-administered. A concomitant therapeutic treatment method also includes methods in which the first or additional agents are administered in the presence of a second substance or additional substances, wherein the second or additional agents, for example, may have been previously administered. A concomitant therapeutic treatment method may be executed step-wise by different patients. For example, one subject may administer to a patient a first agent and a second subject may to administered to the patient a second substance, and the administering steps may be executed at the same time, or nearly the same time, or at distant times, so long as the first substance (and additional substances) are after administration in the presence of the second substance (and additional substances). The actor and the patient may be the same entity (e.g., human).

The term "combination therapy" refers to the administration of two or more therapeutic substances, e.g., an anti-TNFα antibody and another drug. The other drug(s) may be administered concomitant with, prior to, or following the administration of an anti-TNFα antibody.

The term "treatment" refers to therapeutic treatment, as well as prophylactic or suppressive measures, for the treatment of a disorder, such as a disorder in which TNFα is detrimental, e.g., rheumatoid arthritis.

The term "patient" or "user" refers to any type of animal, human or non-human, that may be injected a substance using exemplary automatic injection devices.

The terms "wearable automatic injection device" and "wearable autoinjector" refer to a device worn by a patient that enables the patient to self-administer a therapeutically effective dose of a therapeutic agent by either fastening the wearable device directly to his or her skin or fastening the wearable device to an article of clothing that allows penetration of a hypodermic needle, wherein the wearable device differs from a conventional syringe by the inclusion of a mechanism for automatically delivering the therapeutic agent to the patient by injection when the mechanism is engaged.

The terms "syringe" and "cartridge" encompass a sterile barrel portion that is filled with a dose of a therapeutic agent prior to distribution or sale to a patient or other non-medical professional for administration of the therapeutic agent to a patient. In an exemplary embodiment, a distal end of the barrel portion of a syringe may be coupled to a sterile hypodermic needle. In an exemplary embodiment, a distal end of the barrel portion of a cartridge may not be coupled to a needle. That is, in exemplary embodiments, a syringe may be a cartridge with a pre-attached hollow needle coupled to its barrel portion.

Exemplary embodiments described herein with reference to a syringe assembly may also be implemented using a cartridge assembly. Similarly, exemplary embodiments described herein with reference to a cartridge assembly may also be implemented using a syringe assembly.

The term "vessel" refers to either a syringe or cartridge that may be used in an exemplary wearable automatic injection device for holding a dose of a therapeutic agent.

The term "injection needle" refers to a needle in a wearable automatic injection device that is inserted into a patient's body to deliver a dose of a therapeutic agent into the patient's body. In an exemplary embodiment, the injection needle may be directly coupled to or in contact with a syringe or a cartridge assembly that holds the dose of the therapeutic agent. In another exemplary embodiment, the injection needle may be indirectly coupled to the syringe or cartridge assembly, for example, via a syringe needle and/or a transfer mechanism that provides fluid communication between the syringe or cartridge and the injection needle.

The term "syringe needle" refers to a needle in a wearable automatic injection device that is coupled to or in contact with a syringe or a cartridge assembly for conveying a dose of a therapeutic agent from the syringe or cartridge assembly to an injection needle which, in turn, delivers the therapeutic agent into a patient's body. In an exemplary embodiment, the syringe needle is not inserted into the patient's body. In another exemplary embodiment, the syringe needle may be inserted into the patient's body.

In an exemplary wearable automatic injection device including a syringe assembly, the syringe needle may be coupled directly to the barrel portion of the syringe and may be in fluid communication with the barrel portion. In an exemplary wearable automatic injection device including a cartridge assembly, the syringe needle may be provided separately from the barrel portion of the cartridge, for example, within an injection button or a transfer mechanism. During an injection stage, the syringe needle may be inserted into a distal end of the barrel portion of the cartridge to establish fluid communication between the syringe needle and the barrel portion.

The term "pre-injection state" refers to a state of a wearable automatic injection device prior to the start of delivery of a therapeutic agent contained in the device.

The term "injection state" refers to one or more states of a wearable automatic injection device during the delivery of a therapeutic agent contained in the device.

The term "post-injection state" refers to completion of delivery of a therapeutically effective dose of a therapeutic agent contained in the device and to removal of the device from the patient prior to completion of delivery of a therapeutically effective dose of the therapeutic agent.

The term "slow" refers to a delivery rate of a volume of a therapeutic agent. In an exemplary embodiment, a volume of about 0.1 milliliters to about 1 milliliter or more may be delivered in a delivery time period of about ten seconds to about twelve hours. In a preferred embodiment, the delivery time period may range from about five minutes to about thirty minutes.

The term "clothing" refers to any suitable covering on a patient's body to which an exemplary wearable automatic injection device may be coupled or attached. The article of clothing may thus form an intermediate layer between the device and the patient's skin and may be used to indirectly couple the device to the patient's skin. In an exemplary embodiment, the article of clothing may be snug clothing on the patient's body, for example, nylon stockings. In another exemplary embodiment, the article of clothing may be a covering on the patient's skin including, but not limited to, a medical tape, a bandage, and the like. In another exemplary embodiment, the article of clothing may be a coupling mechanism that adheres the device in the proximity of the patient's skin including, but not limited to, a sleeve that may fit round a portion of the patient's body, a belt, a strap (e.g., a Velcro strap), and the like.

II. EXEMPLARY EMBODIMENTS

Certain exemplary wearable automatic injection devices are described with reference to FIGS. 1-10. Certain exemplary needle systems that may be used in exemplary wearable automatic injection devices to convey a therapeutic agent are described with reference to FIGS. 11-23. Certain exemplary plunger actuation systems that may be used in exemplary wearable automatic injection devices to expel a therapeutic agent from a syringe or cartridge are described with reference to FIGS. 24-51. Certain exemplary needle protection systems that may be used in exemplary wearable automatic injection devices to maintain an injection needle in a retracted position in a post-injection state are described with reference to FIGS. 52-55.

Exemplary wearable automatic injection devices may employ a syringe assembly (as illustrated in FIGS. 1A-1F) or a cartridge assembly (as illustrated in FIGS. 2A-2F) for holding a dose of a therapeutic agent that may be delivered into a patient's body through an injection needle.

FIGS. 1A-1F illustrate an exemplary embodiment of a wearable automatic injection device 100 including a syringe assembly that may be used to inject a dose of a therapeutic agent into the body of a patient. FIG. 1A illustrates a first end view and a first side view of the exemplary wearable device 100 in a packaged pre-injection state. FIG. 1B illustrates the first end view and the first side view of the exemplary device 100 in a pre-injection state in which a needle shield covering the injection needle is removed in preparation for an injection. FIG. 1C illustrates the first end view and the first side view of the exemplary device 100 during an injection in an injection state in which the patient's skin is pierced by the injection needle. FIG. 1D illustrates the first end view and the first side view of the exemplary device 100 during an injection in an injection state in which the barrel portion containing the dose of the therapeutic agent is deployed forwardly within the housing of the device 100. FIG. 1E illustrates the first end view and the first side view of the exemplary device 100 during an injection in an injection state in which the bung is actuated by a plunger actuator to expel the dose of the therapeutic agent from the barrel portion. FIG. 1F illustrates the first end view and the first side view of the exemplary device 100 after an injection in a post-injection state in which the injection needle is retracted within the housing of the device 100.

The wearable automatic injection device 100 may include a housing 102. In an exemplary embodiment, the housing 102 may have an elongated configuration, although one of ordinary skill in the art will recognize that the housing 102 may have any suitable size, shape and configuration for housing a barrel portion containing a dose of a therapeutic agent to be injected. In an exemplary embodiment, the housing 102 may be formed of any suitable material including, but not limited to, plastic and other known materials.

The housing 102 of the wearable automatic injection device 100 may include an adhesive layer 124 disposed along a patient contact portion at the bottom of the housing 102 that is placed proximal to the skin of the patient or an article of clothing of the patient. In some exemplary embodiments, the adhesive layer 124 may be configured to be placed on the skin of the patient in order to attach the housing 102 to the patient to deliver the dose of the therapeutic agent. The adhesive layer 124 may include a non-adhesive tab 126 that is not adhesive. The non-adhesive tab 126 may be gripped by the patient and pulled to remove the wearable automatic injection device 100 from the skin or clothing of the patient.

Before the wearable automatic injection device 100 is put to use, e.g., in the package state illustrated in FIG. 1A, the adhesive layer 124 may be covered by a protective film 128 which preserves the adhesive nature of the adhesive layer 124. The protective film 128 may include a tab 130 which may be gripped by the patient and pulled to remove the protective film 128 from the adhesive layer 124. This exposes the adhesive layer 124, allowing the patient to attach the housing 102 to his or her skin or article of clothing by placing the side with the adhesive layer 124 on the skin or the article of clothing.

The housing 102 may house a syringe assembly extending substantially along a longitudinal axis L between a proximal end (farthest from the injection needle) and a distal end (nearest to the injection needle). The syringe assembly may include a barrel portion 106 for holding a dose 108 of a therapeutic agent to be injected into a patient's skin. The barrel portion 106 may extend substantially along the longitudinal axis between a proximal end (farthest from the injection needle) and a distal end (nearest to the injection needle). In an exemplary embodiment, the barrel portion 106 may be a substantially cylindrical member having a circular cross-section, although one of ordinary skill in the art will recognize that the barrel portion 106 may have any suitable shape or configuration.

In an exemplary embodiment, the barrel portion 106 may be stationary within the housing 102 so that the injection process does not result in the movement of the barrel portion 106 within and relative to the housing 102. In another exemplary embodiment, the barrel portion 106 may initially, i.e., before an injection in a pre-injection state, be in a retracted position toward the proximal end of the device 100 (as illustrated in FIGS. 1A-1C), and may be actuated during an injection in an injection state to an extended position toward the distal end of the device 100.

A bung 110 may be provided at the proximal end of the barrel portion 106 to seal the dose of the therapeutic agent within the barrel portion 106 and to apply a force to the dose to expel the dose from the barrel portion 106. The bung 110 may be moveable within the barrel portion 106 toward the distal end of the barrel portion 106 in order to expel the dose from the barrel portion 106 during an injection in an injection state. In an exemplary embodiment, the bung 110 may be configured to perform both functions of sealing the dose and squeezing the dose out of the barrel portion 106. In another exemplary embodiment, a bung may be provided to seal the dose within the barrel portion 106 and a separate piston or plunger rod may be provided to impart a force to the bung in order to squeeze the dose out of the barrel portion 106.

The syringe assembly may include, at or near its distal end, a syringe stopper or a distal portion of the syringe 114 that may include a syringe needle 120 and a needle cover 134 for covering the syringe needle 120. The needle cover 134 may include a soft needle shield, a rigid needle shield, or both. In an exemplary embodiment, the syringe needle 120 may be aligned parallel to the longitudinal axis L of the device 100. The syringe needle 120 may have any suitable size, shape and configuration suitable for piercing a septum, and is not limited to the illustrative embodiment.

The syringe assembly may include, at or near its proximal end, a plunger actuator 112 for selectively actuating the bung 110 forwardly within the barrel portion 106 toward the distal end in order to inject the therapeutically effective dose contained in the barrel portion 106 into a patient's skin. The plunger actuator 112 may employ an energy storage and controlled energy release mechanism to actuate the bung 110. In exemplary embodiments, the plunger actuator 112 may be located outside the barrel portion 106 or partly or fully within the barrel portion 106. In an exemplary embodiments, the plunger actuator 112 may drive the bung 110 directly or indirectly though the use of a plunger disposed between the bung 110 and the plunger actuator 112.

In an exemplary embodiment, the plunger actuator 112 may include a biasing mechanism, e.g., a spring, that is retracted before injection and that is released during injection to actuate the bung 110 forwardly within the barrel portion 106. In another exemplary embodiment, the plunger actuator 112 may include a chemical gas generator, e.g., an expanding foam, that is in a non-expanded phase before injection and that expands during injection to actuate the bung 110 forwardly within the barrel portion 106. In other exemplary embodiments, the plunger actuator 112 may employ hydraulic pressure of working fluids, gas pressure of compressed gases, osmotic pressure, hydrogel expansion, and the like.

In an exemplary embodiment, the plunger actuator 112 may be moved forwardly within the barrel portion 106 in a substantially linear manner, i.e., substantially constant speed. This may allow the dose to be delivered to the patient at a substantially constant delivery rate. The plunger actuator 112 may include or may be coupled to a damping mechanism that may be used to absorb energy, for example, an initial release of energy, and to provide a more controlled release of energy during energy release by the plunger actuator 112. The controlled release of energy may result in a substantially linear delivery profile, i.e., a substantially constant rate of delivery of the dose over time, and may prevent abrupt changes in the speed of the delivery. In an exemplary embodiment, a plunger actuator 112 may employ the hydraulic pressure of a working fluid and a damping mechanism may employ a flow restrictor placed in a fluid pathway between the working fluid and the bung 110. In another exemplary embodiment, a plunger actuator 112 may employ a biasing mechanism and a damping mechanism may employ a viscous damper, a swiss lever escapement, a runaway escapement, and the like. In another exemplary embodiment, a plunger actuator 112 may employ a stepper motor connected to a gear drive system to provide a constant linear delivery profile.

The housing 102 of the wearable automatic injection device 100 may also house an injection button 116 bearing a hollow hypodermic injection needle 118 that is configured to pierce the patient's skin. In an exemplary embodiment, the injection needle 118 may be aligned orthogonally to the longitudinal axis L of the device 100. In an exemplary embodiment, the injection needle 118 may be held in place by an injection needle carrier (not pictured) provided in the injection button 116 or separately from the injection button 116. The injection needle 118 may have any suitable size, shape and configuration suitable for piercing the skin of the patient to deliver the therapeutic agent, and is not limited to the illustrative embodiment. Suitable needles may have a length configured or selected to provide an injection depth suitable for the desired therapy. Subcutaneous injections typically penetrate about six to ten millimeters into the skin. In an exemplary embodiment, the injection needle 118 may have a length of about twelve mm and may be injected to a depth of about seven mm into the skin. In other exemplary embodiments, the injection needle 118 may have lengths suitable for intradermal, other subcutaneous, or intramuscular therapies. Suitable injection needles may have a wall thickness suitable to provide sufficient mechanism strength, a diameter suitable to allow a desired flow rate of the injected substance while minimizing patient sensation, and a tip geometry suitable for the desired therapy while minimizing patient sensation. Suitable injection needles may be coated as needed to minimize patient sensation as allowed by therapy. The injection needle 118 may be covered and maintained in aseptic condition, i.e., sterile condition, by a needle cover 122, for example, a rigid needle shield, a soft needle shield, or both.

The injection button 116 may also include a pierceable septum disposed in the vicinity of the syringe needle 120. In a pre-injection state, the syringe needle 120 does not pierce the septum, thus prevent fluid communication between the barrel portion 106 and the syringe needle 120. In an injection state, when pierced by a needle, for example, the syringe needle 120, the septum may allow the dose to leave the barrel portion 106 and enter the syringe needle 120. In an exemplary embodiment, one or more covers 115 may enclose the septum in a sterility barrier. The covers 115 may be pierced when the syringe needle 120 pierces the septum.

In an exemplary embodiment, the injection needle 118 and the syringe needle 120 may be coupled to and in fluid communication with each other via the body of the injection button 116. In another exemplary embodiment, the injection needle 118 and the syringe needle 120 may be coupled to and in fluid communication with each other via one or more fluid conduits (not pictured). In another exemplary embodiment, the injection needle 118 and the syringe needle 120 may be directly coupled to and in fluid communication with each other.

In an exemplary embodiment, before an injection in a pre-injection state, the injection button 116 may be in a vertically raised position relative to the housing 102 such that the injection button 116 protrudes from the top of the housing 102, as illustrated in FIGS. 1A and 1B. In this position, the injection needle 118 may be retracted within the housing 102 and may not be inserted into the patient's skin. In this position, the syringe needle 120 may be aligned vertically below the septum in the syringe stopper 114 and may not pierce the septum. At the beginning of the injection process, the injection button 116 may be pressed downward, for example, by a user of the device or automatically. This may push the injection button 116 to a vertically depressed position relative to the housing 102 closer to the patient's skin such that the injection button 116 no longer protrudes from the top of the housing 102, as illustrated in FIGS. 1C-1E. In this position, the injection needle 118 may protrude from the bottom of the housing 102 and may be inserted into the patient's skin. In this position, the syringe needle 120 may be aligned with the septum in the syringe stopper 114 and may pierce the septum.

In an exemplary embodiment, the septum may initially be spaced from the injection button 116. In this embodiment, the syringe needle 120 may pierce the septum when the syringe stopper 114 bearing the syringe needle 120 is advanced within the housing 102 toward the septum. That is, before an injection in a pre-injection state, the syringe needle 120 may be spaced from the septum such that there is no fluid communication between the barrel portion 106 and the injection needle 118 coupled to the injection button 116. In an injection state, the barrel portion 106 may advance within the housing 102 toward the distal end of the device 100 such that that the syringe needle 120 may pierce the septum and establish fluid communication between the barrel portion 106 and the injection needle 118 coupled to the injection button 116. This fluid communication may allow the dose of the therapeutic agent to flow from the barrel portion 106 into the patient's skin through the syringe needle 120 and the injection needle 118 when pressure is applied to the dose by the bung 110 during an injection in an injection state.

Referring now to FIG. 1F, in an exemplary embodiment, the housing 102 of the wearable automatic injection device 100 may include a skin sensor foot 132, which is a structure housed under or in the portion of the housing 102 proximal to the injection site. Prior to injection of the therapeutic agent and during injection, the skin sensor foot 132 is retained within or forms a portion of the underside of the housing 102. When the wearable automatic injection device 100 is attached to the injection site and activated, the skin sensor foot 132 may be free to move but may be constrained by the injection site. When the wearable automatic injection device 100 is removed from the injection site, regardless of whether the drug delivery was completed, the skin sensor foot 132 is no longer constrained, and extends and projects outside the periphery of the housing 102. This, in turn, trips a retraction trigger. When the retraction trigger is activated, a retraction mechanism retracts the injection needle 120 which may also raise the injection button 116 from the vertically lowered position to the vertically raised position, so that the injection button 116 protrudes from the top of the housing 102 and the injection needle 118 is retracted within the housing 102.

FIG. 1A illustrates the wearable automatic injection device 100 in a pre-injection state, for example, as packaged, in which the barrel portion 106 may be pre-fillable and/or pre-filled with the dose 108 of the therapeutic agent and in a retracted position ready for use. The barrel portion 106 may contain the dose 108 of the therapeutic agent in the interior space defined between the wall or walls of the barrel portion 106 and the bung 110. In an embodiment, the plunger actuator 112 may store energy that, when released, may actuate the bung 110. The injection button 116 may be partially disposed within the housing 102 at the vertically raised position above the injection site, and the injection needle 118 may be retracted within the housing 102. The protrusion of the injection button 116 out of the top of the housing 102 may provide a visual indication to the patient that the wearable automatic injection device 100 is not in operation.

FIG. 1B illustrates the wearable automatic injection device 100 in a pre-injection state in which the needle cover 122 and the septum cover are removed. In exemplary embodiments, the protective film 128 may include a linking member that is connected to the needle cover 122, the septum and syringe needle covers in the syringe stopper 114. The linking member may include a tether or other linkage mechanism. When the protective film 128 is removed, the linking member of the protective film 128 may remove the needle cover 122 and the septum and syringe needle covers in the syringe stopper 114.

FIG. 1C illustrates the wearable automatic injection device 100 during an injection in an injection state in which the injection button 116 is in the vertically lowered position within the housing 102. In the vertically lowered position, the injection button 116 may be disposed within the housing 102 at a depressed or vertically lowered location above the injection site, and the injection needle 118 may project from the bottom of the housing 102 through an aperture in the housing 102 so that it can penetrate the skin at the injection site. In the vertically lowered state, the injection button 116 may not protrude from the top of the housing 102, which may provide a visual indication to the patient that the wearable automatic injection device 100 is in operation.

FIG. 1D illustrates the wearable automatic injection device 100 during an injection in an injection state in which the barrel portion 106 containing the dose 108 of the therapeutic agent is deployed forwardly from a retracted position to an extended position within the housing of the device 100. The advancement of the barrel portion 106 may bring the distal end of the barrel portion 106 or the syringe stopper 114 in the vicinity of or in contact with the injection button 116. In an exemplary embodiment, the syringe needle 120 may pierce the septum held in the syringe stopper 114 in order to establish fluid communication between the barrel portion 106 and the injection needle 118.

FIG. 1E illustrates the wearable automatic injection device 100 during an injection in an injection state in which the plunger actuator 112 is triggered to move the bung 110. Triggering of the plunger actuator 112 may release stored energy in the plunger actuator 112 in order to move the bung 110 within the barrel portion 106 toward the distal end of the device 100. The movement of the bung 110 may eject the dose of the therapeutic agent from the barrel portion 106 through the distal end of the barrel portion 106. Any suitable mechanism may be used to trigger the plunger actuator 112 including, but not limited to, a linking member that is coupled to and activated by the depression of the injection button 116 or by the removal of the needle cover 122, a trigger button that may be used by the user, and the like.

FIG. 1F illustrates the wearable automatic injection device 100 after an injection in a post-injection state, for example, after injecting a therapeutically effective dose of the therapeutic agent or removal of the wearable automatic injection device 100 from the patient before delivery of a therapeutically effective dose of the therapeutic agent, in which the injection button 116 is in the vertically raised position. In the vertically raised position, the injection button 116 may be disposed partly within the housing 102 at an elevated or vertically raised location above the injection site, and the injection needle 118 may be retracted within the housing 102. A portion of the injection button 116 may project from the top of the housing 102 to provide a visual indication to the patient that the wearable automatic injection device assembly 100 is not in operation (i.e., in a post-injection state). The barrel portion 106 may be empty of the therapeutic agent and the plunger actuator 112 may no longer store energy. A skin sensor foot 132 may extend from the bottom of the housing 102 upon removal of the device 100 from the injection site.

The housing 102 may include a retraction mechanism that automatically raises the injection button 116 from the vertically lowered injection state (shown in FIGS. 1C-1E) to the vertically raised post-injection state (shown in FIG. 1F). In an exemplary embodiment, the retraction mechanism may include a biasing mechanism, e.g., a spring, that biases the syringe assembly away from the injection site when the retraction mechanism is triggered.

A retraction trigger, when activated, may trigger the retraction mechanism in order to raise the injection button 116 from the vertically lowered state to the vertically raised state. In an exemplary embodiment, the bung 110 and/or the plunger actuator 112 may include a linking member connected to the retraction trigger. The linking member may include a tether or other linkage mechanism. The linking member may be of a suitable length such that, when the bung 110 has been moved to the end of the barrel portion 106 (delivering a complete dose), the linking member triggers a latch that in turn trips the retraction trigger. In another exemplary embodiment, the extension of the skin sensor foot 132 from the bottom of the housing 102 may trip the retraction trigger.

In an exemplary embodiment, the retraction mechanism may include an end-of-dose retraction trigger that, when tripped, triggers the retraction mechanism. The end-of-dose retraction trigger may be tripped when the therapeutically effective dose of therapeutic agent in the wearable automatic injection device is delivered. In an exemplary embodiment, the end-of-dose retraction trigger may include a latch, e.g., a flexible plastic hook, that is released upon completed drug delivery. The retraction mechanism may also include an early-removal retraction trigger that, when tripped, triggers the retraction mechanism. The early-removal retraction trigger may be tripped when the wearable automatic injection device is removed from the injection site before the therapeutically effective dose of therapeutic agent is completely delivered. In an exemplary embodiment, the early-removal retraction trigger may include a latch, e.g., a flexible plastic hook, that is released upon removal of the wearable automatic injection device 100 from the injection site. The retraction mechanism is responsive to the end-of-dose retraction trigger and responsive to the early-removal retraction trigger to automatically retract the syringe assembly from the injection site.

In an exemplary embodiment, raising of the injection button 116 to the vertically raised position may cause the syringe needle 120 to bend upward, thus preventing undesirable reuse of the syringe needle and the wearable automatic injection device.

FIGS. 2A-2F illustrate an exemplary embodiment of a wearable automatic injection device 200 including a cartridge assembly that may be used to inject a dose of a therapeutic agent into the body of a patient. FIG. 2A illustrates a first end view and a first side view of the exemplary wearable device 200 in a packaged pre-injection state. FIG. 2B illustrates the first end view and the first side view of the exemplary device 200 in a pre-injection state in which a needle shield covering the injection needle is removed in preparation for an injection. FIG. 2C illustrates the first end view and the first side view of the exemplary device 200 during an injection in an injection state in which the patient's skin is pierced by the injection needle. FIG. 2D illustrates the first end view and the first side view of the exemplary device 200 during an injection in an injection state in which the barrel portion containing the dose of the therapeutic agent is deployed forwardly within the housing of the device 200. FIG. 2E illustrates the first end view and the first side view of the exemplary device 200 during an injection in an injection state in which the bung is actuated by a plunger actuator to expel the dose of the therapeutic agent from the barrel portion. FIG. 2F illustrates the first end view and the first side view of the exemplary device 200 after an injection in a post-injection state in which the injection needle is retracted within the housing of the device 200.

The wearable automatic injection device 200 may include a housing 202. In an exemplary embodiment, the housing 202 may have an elongated configuration, although one of ordinary skill in the art will recognize that the housing 202 may have any suitable size, shape and configuration for housing a barrel portion containing a dose of a therapeutic agent to be injected. In an exemplary embodiment, the housing 202 may be formed of any suitable material including, but not limited to, plastic and other known materials.

The housing 202 of the wearable automatic injection device 200 may include an adhesive layer 224 disposed along a patient contact portion at the bottom of the housing 202 that is placed proximal to the skin of the patient or an article of clothing of the patient. In some exemplary embodiments, the adhesive layer 224 may be configured to be placed on the skin of the patient in order to attach the housing 202 to the patient to deliver the dose of the therapeutic agent. The adhesive layer 224 may include a non-adhesive tab 226 that is not adhesive. The non-adhesive tab 226 may be gripped by the patient and pulled to remove the wearable automatic injection device 200 from the skin or clothing of the patient.

Before the wearable automatic injection device 200 is put to use, e.g., in the package state illustrated in FIG. 2A, the adhesive layer 224 may be covered by a protective film 228 which preserves the adhesive nature of the adhesive layer 124. The protective film 228 may include a tab 230 which may be gripped by the patient and pulled to remove the protective film 228 from the adhesive layer 224. This exposes the adhesive layer 224, allowing the patient to attach the housing 202 to his or her skin or article of clothing by placing the side with the adhesive layer 224 on the skin or the article of clothing.

The housing 202 may house a therapeutic agent cartridge assembly extending substantially along a longitudinal axis L between a proximal end (farthest from the injection needle) and a distal end (nearest to the injection needle). The cartridge assembly may include a barrel portion 206 for holding a dose 208 of a therapeutic agent to be injected into a patient's skin. The barrel portion 206 may extend substantially along the longitudinal axis between a proximal end (farthest from the injection needle) and a distal end (nearest to the injection needle). In an exemplary embodiment, the barrel portion 206 may be a substantially cylindrical member having a circular cross-section, although one of ordinary skill in the art will recognize that the barrel portion 206 may have any suitable shape or configuration.

In an exemplary embodiment, the barrel portion 206 may be stationary within the housing 202 so that the injection process does not result in the movement of the barrel portion 206 within and relative to the housing 202. In another exemplary embodiment, the barrel portion 206 may initially, i.e., before an injection in a pre-injection state, be in a retracted position toward the proximal end of the device 200 (as illustrated in FIGS. 2A-2C), and may be actuated during an injection in an injection state to an extended position toward the distal end of the device 200.

A bung 210 may be provided at the proximal end of the barrel portion 206 to seal the dose of the therapeutic agent within the barrel portion 206 and to apply a force to the dose to expel the dose from the barrel portion 206. The bung 210 may be moveable within the barrel portion 206 toward the distal end of the barrel portion 206 in order to expel the dose from the barrel portion 206 during an injection in an injection state. In an exemplary embodiment, the bung 210 may be configured to perform both functions of sealing the dose and squeezing the dose out of the barrel portion 206. In another exemplary embodiment, a bung may be provided to seal the dose within the barrel portion 206 and a separate piston may be provided to impart a force to the bung in order to squeeze the dose out of the barrel portion 206.

The cartridge assembly may include, at or near its proximal end, a plunger actuator 212 for selectively actuating the bung 210 forwardly within the barrel portion 206 toward the distal end in order to inject the therapeutically effective dose contained in the barrel portion 206 into a patient's skin. The plunger actuator 212 may employ an energy storage and controlled energy release mechanism to actuate the bung 210. In exemplary embodiments, the plunger actuator 212 may be located outside the barrel portion 206 or partly or fully within the barrel portion 206. In an exemplary embodiment, the plunger actuator 212 may drive the bung 210 directly or indirectly though the use of a plunger disposed between the bung 210 and the plunger actuator 212.

In an exemplary embodiment, the plunger actuator 212 may include a biasing mechanism, e.g., a spring, that is retracted before injection and that is released during injection to actuate the bung 210 forwardly within the barrel portion 206. In another exemplary embodiment, the plunger actuator 212 may include a chemical gas generator, e.g., an expanding foam, that is in a non-expanded phase before injection and that expands during injection to actuate the bung 210 forwardly within the barrel portion 206. In other exemplary embodiments, the plunger actuator 212 may employ hydraulic pressure of working fluids, gas pressure of compressed gases, osmotic pressure, hydrogel expansion, and the like.

In an exemplary embodiment, the plunger actuator 212 may be moved forwardly within the barrel portion 206 in a substantially linear manner, i.e., substantially constant speed. This may allow the dose to be delivered to the patient at a substantially constant delivery rate. The plunger actuator 212 may include or may be coupled to a damping mechanism that may be used to absorb energy, for example, an initial release of energy, and to provide a more controlled release of energy during energy release by the plunger actuator 212. The controlled release of energy may result in a substantially linear delivery profile, i.e., a substantially constant rate of delivery of the dose over time, and may prevent abrupt changes in the speed of the delivery.

In an exemplary embodiment, a plunger actuator 212 may employ one or more fluid circuits containing a working fluid in which the hydraulic pressure of the working fluid applies a force to the bung to move the bung within the barrel portion of the cartridge. A damping mechanism may employ a flow restrictor placed in the fluid circuit between a source of the working fluid and the bung.

In another exemplary embodiment, a plunger actuator 212 may employ a biasing mechanism, for example, a spiral spring or a helical compression spring. A damping mechanism may employ a viscous damper, a swiss lever escapement, a runaway escapement, and the like.

In another exemplary embodiment, a plunger actuator 212 may employ a stepper motor connected to a gear drive system to provide a constant linear delivery profile.

The cartridge assembly may include, at or near its distal end, a cartridge stopper 214 that may include a septum and a cover 215 for the septum. The septum may be a pierceable layer of material that is disposed adjacent to the distal end of the barrel portion 206 in order to seal the dose in the barrel portion 206. When intact, the septum may seal the dose within the barrel portion 206. When pierced by a needle, for example, a syringe needle, the septum may allow the dose to leave the barrel portion 206 and enter the syringe needle. The septum may be formed of a material that may be pierced by a syringe needle. A cover may be provided to protectively cover the septum from accidental piercing by the syringe needle when the device 200 is in the packaged pre-injection state as illustrated in FIG. 2A. In an exemplary embodiment, the cartridge stopper 214 may also include a cover to protectively cover a syringe needle provided in the vicinity of the cartridge stopper 214, thereby preventing accidental piercing of the septum by the syringe needle when the device 200 is in the packaged pre-injection state as illustrated in FIG. 2A.

The housing 202 of the wearable automatic injection device 200 may also house an injection button 216 bearing a hollow hypodermic injection needle 218 that is configured to pierce the patient's skin. In an exemplary embodiment, the injection needle 218 may be aligned orthogonally to the longitudinal axis L of the device 200. In an exemplary embodiment, the injection needle 218 may be held in place by an injection needle carrier (not pictured) provided in the injection button 216 or separately from the injection button 216. The injection needle 218 may have any suitable size, shape and configuration suitable for piercing the skin of the patient to deliver the therapeutic agent, and is not limited to the illustrative embodiment. Suitable needles may have a length configured or selected to provide an injection depth suitable for the desired therapy. Subcutaneous injections typically penetrate about six to ten millimeters into the skin. In an exemplary embodiment, the injection needle 218 may have a length of about twelve mm and may be injected to a depth of about seven mm into the skin. In other exemplary embodiments, the injection needle 218 may have lengths suitable for intradermal, other subcutaneous, or intramuscular therapies. Suitable injection needles may have a wall thickness suitable to provide sufficient mechanism strength, a diameter suitable to allow a desired flow rate of the injected substance while minimizing patient sensation, and a tip geometry suitable for the desired therapy while minimizing patient sensation. Suitable injection needles may be coated as needed to minimize patient sensation as allowed by therapy. The injection needle 218 may be covered and maintained in a septic condition by a needle cover 222, for example, a rigid needle shield, a soft needle shield, or both.

The injection button 216 may also bear a hollow syringe needle 220 configured to pierce the septum and establish fluid communication with the barrel portion 206. In an exemplary embodiment, the syringe needle 220 may be aligned parallel to the longitudinal axis L of the device 200. The syringe needle 220 may have any suitable size, shape and configuration suitable for piercing the septum and is not limited to the illustrative embodiment.

In an exemplary embodiment, the injection needle 218 and the syringe needle 220 may be coupled to and in fluid communication with each other via the body of the injection button 216. In another exemplary embodiment, the injection needle 218 and the syringe needle 220 may be coupled to and in fluid communication with each other via one or more fluid conduits (not pictured). In another exemplary embodiment, the injection needle 218 and the syringe needle 220 may be directly coupled to and in fluid communication with each other.

In an exemplary embodiment, before an injection in a pre-injection state, the injection button 216 may be in a vertically raised position relative to the housing 202 such that the injection button 216 protrudes from the top of the housing 202, as illustrated in FIGS. 2A and 2B. In this position, the injection needle 218 may be retracted within the housing 202 and may not be inserted into the patient's skin. In this position, the syringe needle 220 may be aligned vertically above the septum in the cartridge stopper 214 and may not pierce the septum. At the beginning of the injection process, the injection button 216 may be pressed downward, for example, by a user of the device or automatically. This may push the injection button 216 to a vertically depressed position relative to the housing 202 closer to the patient's skin such that the injection button 216 no longer protrudes from the top of the housing 202, as illustrated in FIGS. 2C-2E. In this position, the injection needle 218 may protrude from the bottom of the housing 202 and may be inserted into the patient's skin. In this position, the syringe needle 220 may be aligned with the septum in the cartridge stopper 214 and may pierce the septum.

In an exemplary embodiment, the septum may initially be spaced from the injection button 216. In this embodiment, the syringe needle 220 may pierce the septum when the cartridge stopper 214 bearing the septum is advanced within the housing 202 toward the injection button 216. That is, before an injection in a pre-injection state, the syringe needle 220 may be spaced from the septum such that there is no fluid communication between the barrel portion 206 and the injection needle 218 coupled to the injection button 216. In an injection state, the barrel portion 206 may advance within the housing 202 toward the distal end of the device 200 so that the syringe needle 220 may pierce the septum and establish fluid communication between the barrel portion 206 and the injection needle 218 coupled to the injection button 216. This fluid communication may allow the dose of the therapeutic agent to flow from the barrel portion 206 into the patient's skin through the syringe needle 220 and the injection needle 218 when pressure is applied to the dose by the bung 210 during an injection in an injection state.

Referring now to FIG. 2F, in an exemplary embodiment, the housing 202 of the wearable automatic injection device 200 may include a skin sensor foot 232, which is a structure housed under or in the portion of the housing 202 proximal to the injection site. Prior to injection of the therapeutic agent and during injection, the skin sensor foot 232 is retained within or forms a portion of the underside of the housing 202. When the wearable automatic injection device 200 is attached to the injection site and activated, the skin sensor foot 232 may be free to move but may be constrained by the injection site. When the wearable automatic injection device 200 is removed from the injection site, regardless of whether the drug delivery was completed, the skin sensor foot 232 is no longer constrained, and extends and projects outside the periphery of the housing 202. This, in turn, trips a retraction trigger. When the retraction trigger is activated, a retraction mechanism retracts the injection needle 220 which may also raise the injection button 216 from the vertically lowered position to the vertically raised position, so that the injection button 216 protrudes from the top of the housing 202 and the injection needle 218 is retracted within the housing 202.

FIG. 2A illustrates the wearable automatic injection device 200 in a pre-injection state, for example, as packaged, in which the barrel portion 206 may be pre-fillable and/or pre-filled with the dose 208 of the therapeutic agent and in a retracted position ready for use. The barrel portion 206 may contain the dose 208 of the therapeutic agent in the interior space defined between the wall or walls of the barrel portion 206 and the bung 210. In an embodiment, the plunger actuator 212 may store energy that, when released, may actuate the bung 210. The injection button 216 may be partially disposed within the housing 202 at the vertically raised position above the injection site, and the injection needle 218 may be retracted within the housing 202. The protrusion of the injection button 216 out of the top of the housing 202 may provide a visual indication to the patient that the wearable automatic injection device 200 is not in operation.

FIG. 2B illustrates the wearable automatic injection device 200 in a pre-injection state in which the needle cover 222 and the septum cover are removed. In exemplary embodiments, the protective film 228 may include a linking member that is connected to the needle cover 222 and the septum and syringe needle covers in the cartridge stopper 214. The linking member may include a tether or other linkage mechanism. When the protective film 228 is removed, the linking member of the protective film 228 may remove the needle cover 222 and the septum and syringe needle covers in the cartridge stopper 214.

FIG. 2C illustrates the wearable automatic injection device 200 during an injection in an injection state in which the injection button 216 is in the vertically lowered position within the housing 202. In the vertically lowered position, the injection button 216 may be disposed within the housing 202 at a depressed or vertically lowered location above the injection site, and the injection needle 218 may project from the bottom of the housing 202 through an aperture in the housing 202 so that it can penetrate the skin at the injection site. In the vertically lowered state, the injection button 216 may not protrude from the top of the housing 202, which may provide a visual indication to the patient that the wearable automatic injection device 200 is in operation.

FIG. 2D illustrates the wearable automatic injection device 200 during an injection in an injection state in which the barrel portion 206 containing the dose 208 of the therapeutic agent is deployed forwardly from a retracted position to an extended position within the housing of the device 200. The advancement of the barrel portion 206 may bring the distal end of the barrel portion 206 or the cartridge stopper 214 in the vicinity of or in contact with the injection button 216. In an exemplary embodiment, the syringe needle 220 may pierce the septum held in the cartridge stopper 214 in order to establish fluid communication between the barrel portion 206 and the injection needle 218.

FIG. 2E illustrates the wearable automatic injection device 200 during an injection in an injection state in which the plunger actuator 212 is triggered to move the bung 210. Triggering of the plunger actuator 212 may release stored energy in the plunger actuator 212 in order to move the bung 210 within the barrel portion 206 toward the distal end of the device 200. The movement of the bung 210 may eject the dose of the therapeutic agent from the barrel portion 206 through the distal end of the barrel portion 206. Any suitable mechanism may be used to trigger the plunger actuator 212 including, but not limited to, a linking member that is coupled to and activated by the depression of the injection button 216 or by the removal of the needle cover 222, a trigger button that may be used by the user, and the like.

FIG. 2F illustrates the wearable automatic injection device 200 after an injection in a post-injection state, for example, after injecting a therapeutically effective dose of the therapeutic agent or removal of the wearable automatic injection device 200 from the patient before delivery of a therapeutically effective dose of the therapeutic agent, in which the injection button 216 is in the vertically raised position. In the vertically raised position, the injection button 216 may be disposed partly within the housing 202 at an elevated or vertically raised location above the injection site, and the injection needle 218 may be retracted within the housing 202. A portion of the injection button 216 may project from the top of the housing 202 to provide a visual indication to the patient that the wearable automatic injection device assembly 200 is not in operation (i.e., in a post-injection state). The barrel portion 206 may be empty of the therapeutic agent and the plunger actuator 212 may no longer store energy. A skin sensor foot 232 may extend from the bottom of the housing 202 upon removal of the device 200 from the injection site.

The housing 202 may include a retraction mechanism that automatically raises the injection button 216 from the vertically lowered injection state (shown in FIGS. 2C-2E) to the vertically raised post-injection state (shown in FIG. 2F). In an exemplary embodiment, the retraction mechanism may include a biasing mechanism, e.g., a spring, that biases the cartridge assembly away from the injection site when the retraction mechanism is triggered.

A retraction trigger, when activated, may trigger the retraction mechanism in order to raise the injection button 216 from the vertically lowered state to the vertically raised state. In an exemplary embodiment, the bung 210 and/or the plunger actuator 212 may include a linking member connected to the retraction trigger. The linking member may include a tether or other linkage mechanism. The linking member may be of a suitable length such that, when the bung 210 has been moved to the end of the barrel portion 206 (delivering a complete dose), the linking member triggers a latch that in turn trips the retraction trigger. In another exemplary embodiment, the extension of the skin sensor foot 232 from the bottom of the housing 202 may trip the retraction trigger.

In an exemplary embodiment, the retraction mechanism may include an end-of-dose retraction trigger that, when tripped, triggers the retraction mechanism. The end-of-dose retraction trigger may be tripped when the therapeutically effective dose of therapeutic agent in the wearable automatic injection device is delivered. In an exemplary embodiment, the end-of-dose retraction trigger may include a latch, e.g., a flexible plastic hook, that is released upon completed drug delivery. The retraction mechanism may also include an early-removal retraction trigger that, when tripped, triggers the retraction mechanism. The early-removal retraction trigger may be tripped when the wearable automatic injection device is removed from the injection site before the therapeutically effective dose of therapeutic agent is completely delivered. In an exemplary embodiment, the early-removal retraction trigger may include a latch, e.g., a flexible plastic hook, that is released upon removal of the wearable automatic injection device 200 from the injection site. The retraction mechanism is responsive to the end-of-dose retraction trigger and responsive to the early-removal retraction trigger to automatically retract the cartridge assembly from the injection site.

In exemplary embodiments, the barrel portion of the wearable automatic injection device 100 (in FIG. 1)/200 (in FIG. 2) may be pre-fillable and/or pre-filled with any volume of a therapeutic agent, e.g., a therapeutic antibody, desired for intradermal, subcutaneous, or intramuscular injections. In an exemplary embodiment, the barrel portion 106 may be pre-fillable and/or pre-filled with a volume of between about 0.1 milliliters and about 1.0 milliliters, although exemplary devices are not limited to this exemplary range of therapeutic agent volumes.

In exemplary embodiments, the wearable automatic injection device 100 (in FIG. 1)/200 (in FIG. 2) may be used to inject a therapeutically effective amount of therapeutic agent over a period of time ranging from about ten seconds to about twelve hours. Certain other exemplary embodiments provide actuation devices and systems that cause actuation of the syringe plunger at a slow rate in order to deliver the therapeutic agent to a patient at a slow rate. Exemplary slow embodiments may deliver therapeutic agent volumes of about 0.1 milliliters to about 1 milliliter or more in about five minutes to about thirty minutes, although exemplary delivery rates are not limited to this exemplary range.

Exemplary embodiments may provide a linear delivery profile for the therapeutic agent so that the delivery rate is substantially constant over time. In some cases, a linear delivery profile may reduce discomfort experienced by the patient. In an exemplary embodiment, the therapeutic agent may be delivered in a single slow bolus.

The rate of delivery of the therapeutic agent may be dependent on the ambient temperature. At room temperature, i.e., about 72° F., the accuracy of the delivery time may range between about three percent and about ten percent.

Exemplary dimensions of exemplary devices are described with reference to Tables 1-6. However, one of ordinary skill in the art will recognize that the exemplary dimensions are provided for illustrative purposes, and that exemplary automatic injection devices are not limited to the illustrative dimensions.

In an exemplary embodiment, a wearable automatic injection device may have an exemplary length of about 4.37 inches, an exemplary width of about 2.12 inches, and an exemplary height of about 1.25 inches. In an exemplary embodiment, the diameter of the barrel portion is about 1.470 inches and the length of the barrel portion is about 2.520 inches. Tables 1-3 summarize the components of the length, width and height, respectively, for two exemplary types of the exemplary device.

TABLE 1

Summary of components of the length of an exemplary device (inch)

| Element | Type 1 | Type 2 |
|---|---|---|
| Wall thickness | 0.185 | 0.120 |
| Septum | 0.397 | 0.272 |
| Needle | 0.500 | 0.500 |
| Barrel portion | 2.520 | 2.520 |
| Advance spring | 0.470 | 0.322 |
| Hydraulic connection | 0.113 | 0.113 |
| Wall thickness | 0.185 | 0.120 |
| Total | 4.370 | 3.968 |

TABLE 2

Summary of components of the width of an exemplary device (inch)

| Element | Type 1 | Type 2 |
| --- | --- | --- |
| Wall thickness | 0.185 | 0.120 |
| Needle lock | 1.045 | 0.935 |
| Barrel portion width | 0.470 | 0.470 |
| Syringe lock | 0.235 | 0.235 |
| Wall thickness | 0.185 | 0.120 |
| Total | 2.120 | 1.880 |

TABLE 3

Summary of components of the height of an exemplary device (inch)

| Element | Type 1 | Type 2 |
| --- | --- | --- |
| Wall thickness | 0.100 | 0.120 |
| Needle cover | 0.431 | 0.431 |
| Septum | 0.400 | 0.350 |
| Spring solid height | 0.200 | 0.000 |
| Wall thickness | 0.185 | 0.125 |
| Total | 1.316 | 1.026 |

In an exemplary embodiment, the diameter of the barrel portion in production may be increased from about 1.470 inches by about 0.125 inches, and the length of the barrel portion may be decreased in production from about 2.520 inches by about 0.732 inches. Tables 4-6 summarize the components of the length, width and height, respectively, for two exemplary types of the exemplary device.

TABLE 4

Summary of components of the length of an exemplary device (inch)

| Element | Type 1 | Type 2 |
| --- | --- | --- |
| Wall thickness | 0.185 | 0.120 |
| Septum | 0.397 | 0.272 |
| Needle | 0.500 | 0.250 |
| Barrel portion | 2.520 | 1.788 |
| Advance spring | 0.470 | 0.322 |
| Hydraulic connection | 0.113 | 0.113 |
| Wall thickness | 0.185 | 0.120 |
| Total | 4.370 | 2.986 |

TABLE 5

Summary of components of the width of an exemplary device (inch)

| Element | Type 1 | Type 2 |
| --- | --- | --- |
| Wall thickness | 0.185 | 0..120 |
| Needle lock | 1.045 | 0.935 |
| Barrel portion width | 0.470 | 0.595 |
| Syringe lock | 0.235 | 0.235 |
| Wall thickness | 0.185 | 0.120 |
| Total | 2.120 | 2.005 |

TABLE 6

Summary of components of the height of an exemplary device (inch)

| Element | Type 1 | Type 2 |
| --- | --- | --- |
| Wall thickness | 0.100 | 0.120 |
| Needle cover | 0.431 | 0.493 |
| Septum | 0.400 | 0.350 |
| Spring solid height | 0.200 | 0.000 |
| Wall thickness | 0.185 | 0.125 |
| Total | 1.316 | 1.088 |

FIG. 3 is a flow chart of an exemplary method 300 of assembling an exemplary automatic injection device 100. In step 302, a syringe or a cartridge assembly may be sterilized and assembled. In step 304, an injection button may be sterilized and assembled. In step 306, the barrel portion of the syringe or cartridge assembly may be filled with a dose of a therapeutic agent that is to be administered to a patient. In step 308, a sterile bung may be placed in the barrel portion of the syringe or cartridge assembly to seal the therapeutic agent inside the barrel portion. The containment of the therapeutic agent inside the wearable automatic injection device by the sterile barrel portion and the sterile bung maintains sterility of the therapeutic agent. As such, in an exemplary embodiment, the remaining components of the wearable automatic injection device may be assembled in a non-sterile environment after the barrel portion is pre-fillable and/or pre-filled with the therapeutic agent. For example, in step 310, a non-sterile plunger actuator, for example, a biasing mechanism may be inserted behind the bung.

In step 312, the syringe or cartridge assembly may be inserted into a non-sterile housing. The housing may be pre-assembled with other non-sterile components, e.g., an adhesive layer, a protective film, a skin sensor foot, and the like. In step 314, the injection button (with an enclosed sterile fluid path and one or more needles) may be inserted into the non-sterile housing. In exemplary embodiments, the barrel portion, the enclosed hypodermic injection needle, the syringe needle, the needle cover, and the bung may provide the sterility barrier for the therapeutic agent and the fluid path. Thus, once the barrel portion is filled with the therapeutic agent and the bung is inserted into the barrel portion, assembly of the remaining portions of the device does not require aseptic conditions. No therapeutic agent transfer steps need to be performed by the user. In step 316, the assembled automatic injection device may be placed in an over-wrap, if necessary, and may then be commercially packaged for sale. FIG. 1A illustrates an exemplary embodiment of the assembled automatic injection device in the packaged pre-injection state.

Figure 4:
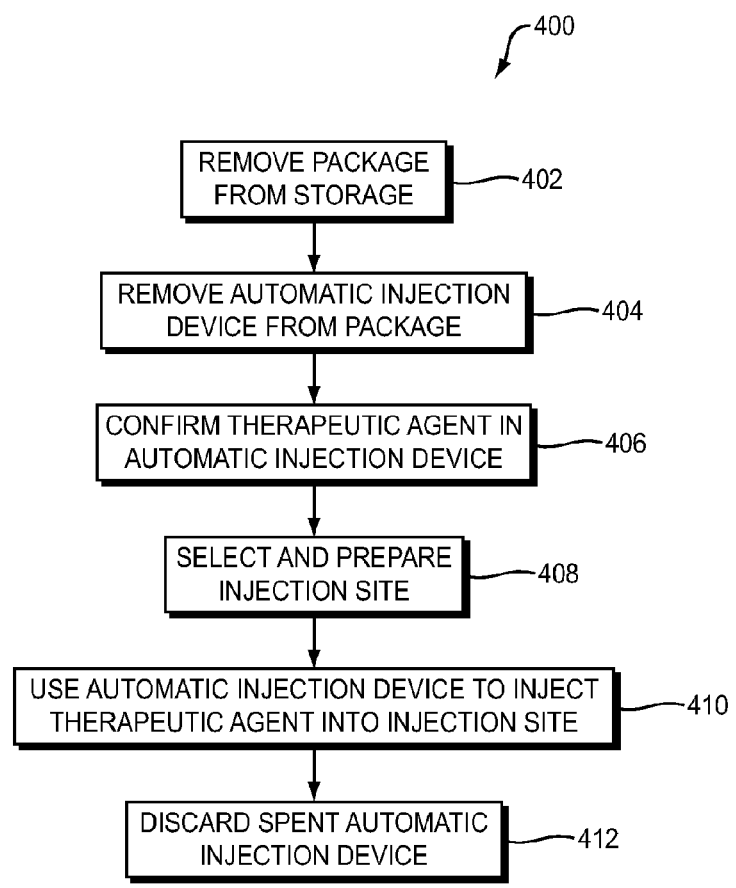
FIG. 4 is a flow chart of an exemplary method of using an exemplary automatic wearable injection device.

FIG. 4 is a flow chart of an exemplary method 400 of using an exemplary automatic injection device. The wearable automatic injection device packaged and pre-fillable and/or pre-filled with a therapeutic agent may be generally stored in refrigerated storage before use. In step 402, the packaged automatic injection device may be removed from storage. In step 404, the wearable automatic injection device may be removed from its packaging and any over-wrap, and warmed to room temperature, e.g., by leaving the wearable device outside the packaging at room temperature or by warming the wearable device. In step 406, the patient may confirm that the barrel portion contains a volume of the therapeutic agent through an therapeutic agent inspection window disposed in the device housing, and may also confirm the clarity of the therapeutic agent if necessary.

In step 408, the injection site on the skin of the patient may be selected and prepared for the delivery of the therapeutic agent. In step 410, the patient uses the wearable automatic injection device to inject the therapeutic agent into the injection site. The steps generally involved within step 410 are described below in connection with FIG. 5. In step 412, after performing the injection, the wearable automatic injection device may be removed from the patient and discarded in an appropriate manner.

Figure 5:
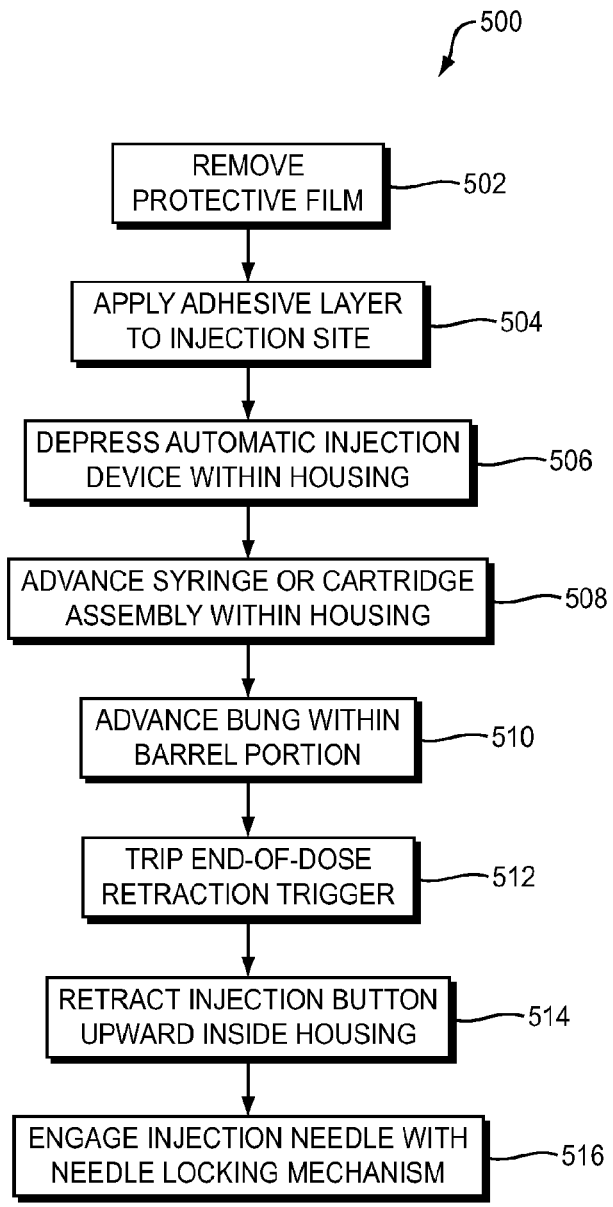
FIG. 5 is a flow chart of an exemplary method of using an exemplary wearable automatic injection device to inject a therapeutic agent into a patient.

FIG. 5 is a flow chart of an exemplary method 500 of using an exemplary automatic injection device to inject a therapeutically effective amount of a therapeutic agent into a patient. Exemplary method 500 is a detailed outline of step 410 in FIG. 4. In step 502, the patient removes the protective film that covers and protects the adhesive layer of the wearable automatic injection device. In some exemplary embodiments, removal of the protective film also removes the needle cover and the septum cover in the syringe or cartridge stopper.

In step 504, the patient applies the patient contact portion of the wearable automatic injection device with the adhesive layer to the injection site (or an article of clothing around the injections site) so that the device is reliably retained on the injection site during the injection of the therapeutically effective dose of therapeutic agent.

In step 506, once the wearable automatic injection device is attached to the injection site, the patient may depress the injection button from a vertically raised position in the pre-injection state to a vertically lowered position in the injection state within the housing. In the vertically raised position, the end of the injection button bearing the injection needle is retracted within the housing and is not exposed to the outside of the housing. When depressed, the end of the injection button bearing the injection needle is moved downward either linearly or rotationally within the housing so that the injection needle emerges from an aperture in the housing and is exposed. This allows the injection needle to penetrate the skin of the patient to an appropriate depth for injection of the therapeutic agent. The downward movement of the injection button in the housing may be linear (i.e., a vertical downward movement) or rotary (i.e., in a circular movement about a pivot point).

In an exemplary embodiment, the injection button is depressed into the housing by the patient manually pushing down the injection button. In another exemplary embodiment, the patient may activate an injection trigger, e.g., a trigger button located in a conveniently accessible location such as the top of the housing, which causes the injection trigger to automatically depress the injection button into the housing and in turn, cause the injection needle to pierce the skin of the patient. In an exemplary embodiment, pressing the injection trigger button may release a latch in the injection trigger that allows a spring to bias the injection button downwardly in the housing. The same motion of the injection button may cause the injection needle to be inserted into the injection site to an appropriate depth.

In step 508, depressing the injection button may trigger a syringe or cartridge actuator that moves the syringe or cartridge assembly, more specifically, the barrel portion, forwardly within and relative to the housing from a retracted position (in which the distal end of the syringe or cartridge assembly is spaced from the injection button) to an extended position (in which the distal end of the syringe or cartridge assembly is adjacent to and/or in contact with the injection button). In another exemplary embodiment, the syringe or cartridge actuator is triggered not by depressing the injection button, but by the user activating a trigger, e.g., in the form of a trigger button. In an exemplary embodiment, movement of the syringe or cartridge assembly toward the injection button may cause the syringe needle to pierce the septum.

In step 510, when the distal end of the barrel portion makes contact with the injection button, the plunger actuator may break the static friction (i.e., stiction) between the bung and the inside wall or walls of the barrel portion and cause the bung to move forwardly toward the syringe needle in the injection button to deliver the therapeutic agent via the injection needle. The plunger actuator may overcome the bung stiction in one step and actuate the bung in a subsequent step, or the plunger actuator may overcome the bung stiction and actuate the bung concurrently. Movement of the bung may cause the dose to be released through the syringe needle into the injection needle and thereby into the patient's skin.

In an exemplary embodiment, the forward advancement of the syringe or cartridge assembly within the housing and the forward advancement of the bung within the barrel portion may take place in separate steps. In another exemplary embodiment, the forward advancement of the syringe or cartridge assembly within the housing and the forward advancement of the bung within the barrel portion may take place in the same step, for example, simultaneously.

The rate of therapeutic agent delivery may depend on the characteristics of the plunger actuator. The plunger actuator may take the form of several exemplary embodiments. In some exemplary embodiments, the plunger actuator may employ means of energy storage and release, e.g., biasing mechanisms (including, but not limited to, one or more springs, for example, spiral springs or helical compression springs), compressed gases, chemical gas generators (such as expanding foams), osmotic pressure, hydrogel expansion, etc. A damping or control mechanism (including, but not limited to, a viscous damper or an escapement) may be used to absorb energy, for example, an initial release of energy, and to provide a more controlled release of energy during energy release by the plunger actuator. A flow restrictor placed in a fluid pathway between the needle and the bung may be used to further regulate the rate of therapeutic agent delivery, e.g., where the plunger actuator delivers an unconstrained spring force via a working fluid. Thus, an appropriate plunger actuator and an appropriate control mechanism may be selected to deliver the dose at a controlled rate, e.g., in a single slow bolus free of or substantially free of any burning sensation to the patient.

In an exemplary embodiment, depressing the injection button may arm the retraction mechanism which, when triggered, retracts the injection button into the housing 102 after an injection in a post-injection state.

In step 512, upon delivery of the therapeutically effective dose, the bung and/or the plunger actuator may trip the end-of-dose retraction trigger of the retraction mechanism. The bung and/or the plunger actuator may include a linking member connected to the end-of-dose retraction trigger. The linking member may include a tether or other linkage mechanism. The linking member may be of a suitable length such that, when the bung has been moved to the end of the syringe or cartridge assembly (delivering a complete dose), the linking member triggers a latch that in turn trips the retraction trigger.

In step 514, once the end-of-dose retraction trigger is tripped, the retraction mechanism may retract the injection button upward inside the housing and away from the patient contact portion so that the syringe or cartridge assembly enters a post-injection state. In an exemplary embodiment, the movement of the injection button from the injection state to the post-injection state creates an audible sound, e.g., a "click," which provides an aural indication of the completion of therapeutic agent delivery. Once retracted, the injection button protrudes outside the housing, which provides a visual indication of the state of the wearable automatic injection device, for example, completion of therapeutic agent delivery or a visual indication of the device in the post-injection state.

However, if the wearable device is removed from the skin of the patient before the completion of therapeutically effective dose of the therapeutic agent, the skin sensor foot may extend to the outside of the housing and trip the early-removal retraction trigger of the retraction mechanism. Once the early-removal retraction trigger is tripped, the retraction mechanism deploys the injection button upward in the housing away from the patient contact portion so that the syringe or cartridge assembly enters a post-injection state. In an exemplary embodiment, the plunger actuator may continue to move forwardly in the barrel portion toward the syringe needle when the device is removed from the patient before completion of delivery of a therapeutically effective dose of the therapeutic agent.

In step 516, upon retraction, a needle lock engages with the injection needle to prevent redeployment of the injection needle to provide needle-stick protection. The needle lock may be a member that prevents the injection needle from exiting the housing once engaged, and may be located in the housing near the injection needle. Exemplary needle locks may include, but are not limited to, a plastic plate, a metal plate, a clip, etc.

FIGS. 6A-6C illustrate an exemplary embodiment of a wearable automatic injection device 600 suitable for linear insertion of a needle into the skin of a patient. By linear insertion, the end of a cartridge assembly bearing a needle descends linearly within a housing of the wearable automatic injection device so that the needle is inserted into the patient. More specifically, FIG. 6A illustrates the exemplary wearable device in a Pre-Injection State, for example, as packaged; FIG. 6B illustrates the exemplary wearable device in an Injection State just before, while or just after it injects a therapeutic agent into a patient; and FIG. 6C illustrates the exemplary wearable device in a Post Injection State after it has completed delivery of the therapeutic agent into the patient or removed from the patient prior to completion of delivery of the therapeutic agent.

The wearable automatic injection device 600 includes a housing 635 for housing a therapeutic agent cartridge assembly 610, containing a dose of a therapeutic agent to be injected subcutaneously into a patient. In an exemplary embodiment, the outside of the therapeutic agent cartridge assembly 610 may be provided with one or more ridges, and the inside of the housing 635 may be provided with one or more grooves or channels that provide a smooth pathway for the ridges of the cartridge assembly 610 as the cartridge assembly moves within the housing 635. The one or more ridges on the outside of the cartridge assembly 610 may take the form of raised lines on the cartridge assembly 610. The one or more grooves or channels on the inside of the housing 635 may take the formed of U-shaped depressed or trough-like lines. The top portion of the grooves or channels may be open so that the ridges may slide in and out of the top portion of the grooves or channels. In the linear insertion embodiment illustrated in FIGS. 6A-6C, the ridges and grooves/channels may be straight lines. In the rotary insertion embodiment illustrated in FIGS. 7A-7C, the ridges and grooves/channels may be lines that are curved about the center of rotation, i.e., the pivot point of the cartridge assembly 610.

In another exemplary embodiment, the outside of the cartridge assembly 610 may not have any ridges, and the inside of the housing 635 may not have any grooves or channels.

The housing 635 preferably has an elongated configuration, though one of ordinary skill in the art will recognize that the housing 635 may have any suitable size, shape and configuration for housing a hypodermic needle couplable to a barrel portion of a therapeutic agent to be injected. The housing 635 may be formed of any suitable material including, but not limited to, plastic and other known materials. In another embodiment, the therapeutic agent cartridge 610 may be formed of any compatible material suitable for sterilization including, but not limited to, glass and other known materials.

The housing 635 includes an adhesive layer 640 disposed along a patient contact portion of the housing 635 that is placed proximal to the skin of the patient or an article of clothing of the patient. In some embodiments, the adhesive layer 640 is configured to be placed on the skin of the patient to attach the housing 635 to the patient to deliver a therapeutic agent. The adhesive layer 640 includes a non-adhesive tab 645 which is not adhesive. The non-adhesive tab 645 may be gripped by the patient and pulled to remove the adhesive layer 640 and thus the wearable automatic injection device 600 from the skin or clothing of the patient.

Before the wearable automatic injection device 600 is put to use, e.g., in the Pre-Injection state, the adhesive layer 640 is covered by a protective film 650 which preserves the adhesive nature of the adhesive layer 640. The protective film 650 may include a tab 655 which may be gripped by the patient and pulled to remove the protective film 650 from the adhesive layer 640. This exposes the adhesive layer 640, allowing the patient to attach the housing 635 to his or her skin or article of clothing by placing the side with the adhesive layer 640 on the skin or the article of clothing.

In exemplary embodiments, the protective film 650 (in FIG. 6A)/750 (in FIG. 7A) may include a linking member that is connected to the plunger actuator 630 (in FIG. 6A)/730 (in FIG. 7A). The linking member may include a tether or other linkage mechanism. When the protective film 650 (in FIG. 6A)/750 (in FIG. 7A) is removed, the linking member of the protective film 650 (in FIG. 6A)/750 (in FIG. 7A) relieves static friction between the bung 615 (in FIG. 6A)/715 (in FIG. 7A) and the interior wall of the barrel 605 (in FIG. 6A)/705 (in FIG. 7A), and triggers the plunger actuator 630 (in FIG. 6A)/730 (in FIG. 7A).

The therapeutic agent cartridge assembly 610 may include a hollow barrel portion 605 for holding a therapeutically effective dose of the therapeutic agent to be injected. The illustrative barrel portion 605 is substantially cylindrical in shape, although one of ordinary skill in the art will recognize that the barrel portion 605 may have any suitable shape or configuration. A bung 615 seals the dose of the therapeutic agent within the barrel portion 605.

The therapeutic agent cartridge assembly 610 may also include a hollow hypodermic needle 625 connectable to or connected to, and in fluid communication with, the barrel portion 605, through which the dose can be ejected by applying pressure to the bung 615. The needle 625 may have any suitable size, shape and configuration suitable for piercing the skin of the patient to deliver the therapeutic agent subcutaneously, and is not limited to the illustrative embodiment. Suitable needles may have a length configured or selected to provide an injection depth suitable for the desired therapy. Subcutaneous injections typically penetrate about six to ten millimeters into the skin. In an exemplary embodiment, needle 625 may have a length of about twelve mm and may be injected to a depth of about seven mm into the skin. In other exemplary embodiments, needle 625 may have lengths suitable for intradermal, other subcutaneous, or intramuscular therapies. Suitable needles may have a wall thickness suitable to provide sufficient mechanism strength, a diameter suitable to allow a desired flow rate of the injected substance while minimizing patient sensation, and a tip geometry suitable for the desired therapy while minimizing patient sensation. Suitable needles may be coated as needed to minimize patient sensation as allowed by therapy. Needle 625 may be covered and maintained in a septic condition by a soft and rigid needle shield assembly 620.

In the exemplary embodiment illustrated in FIGS. 6A-6C, the needle 625 projects substantially at a right angle to the longitudinal axis of the wearable device 600. In this exemplary embodiment, the barrel portion 605 includes an elbow 607 that extends substantially at a right angle to the longitudinal axis of the device 600. In this embodiment, the needle 625 is connected to the elbow 607.

The wearable automatic injection device 600 may include a plunger actuator 630 for selectively actuating the bung 615 forwardly toward the distal end of the therapeutic agent cartridge assembly 610 to inject the therapeutically effective dose contained in the barrel portion 605 into the patient. The plunger actuator 630 may employ an energy storage and controlled energy release mechanism to actuate the bung 615. In an exemplary embodiment, the plunger actuator 630 may include a biasing mechanism, e.g., a spring, that is retracted before injection and that is released during injection to actuate the bung 615 forwardly in the barrel portion 605. In another exemplary embodiment, the plunger actuator 630 may include a chemical gas generator, e.g., an expanding foam, that is in a non-expanded phase before injection and that expands during injection to actuate the bung 615 forwardly in the barrel portion 605 toward the distal end of the therapeutic agent cartridge assembly 610. In other exemplary embodiments, the plunger actuator 630 may employ compressed gases, osmotic pressure, hydrogel expansion, etc. A damping mechanism may be used to absorb energy, for example, an initial release of energy, and to provide a controlled release of energy during energy release by the plunger actuator 630 (in FIG. 6A)/730 (in FIG. 7A). A flow restrictor placed in a fluid pathway between the needle and the bung 615 (in FIG. 6A)/715 (in FIG. 7A) may be used to further regulate the rate of therapeutic agent delivery, e.g., where the plunger actuator 630 (in FIG. 6A)/730 (in FIG. 7A) delivers an unconstrained spring force.

In an exemplary embodiment, the plunger actuator 630 may be advanced forwardly inside the barrel portion 605 in a constant linear motion. Any number of mechanisms, internal or external to the wearable automatic injection device 600, may be used to provide a constant linear motion including, but not limited to, a stepper motor connected to a gear drive system. Other exemplary mechanisms for providing a substantially constant linear motion in a controlled fashion are described with reference to FIGS. 24-45.

The bung 615 (in FIG. 6A)/715 (in FIG. 7A) and/or the plunger actuator 630 (in FIG. 6A)/730 (in FIG. 7A) may include a linking member connected to the retraction trigger. The linking member may include a tether or other linkage mechanism. The linking member may be of a suitable length such that, when the bung 615 (in FIG. 6A)/715 (in FIG. 7A) has been moved to the end of the cartridge assembly 610 (in FIG. 6A)/710 (in FIG. 7A) (delivering a complete dose), the linking member triggers a latch that in turn trips the retraction trigger.

Referring now to FIG. 6C, in an exemplary embodiment, the housing 635 includes a skin sensor foot 660, which is a structure housed under or in the portion of the housing 635 proximal to the injection site. Prior to injection of the therapeutic agent and during injection, the skin sensor foot 660 is retained within or forms a portion of the underside of the housing 635. When the wearable automatic injection device 600 is attached to the injection site and activated, the skin sensor foot 660 may be free to move but may be constrained by the injection site. When the wearable automatic injection device 600 is removed from the injection site, regardless of whether the drug delivery was completed, the skin sensor foot 660 is no longer constrained, and extends and projects outside the periphery of the housing 635. This, in turn, trips the removal retraction trigger.

FIG. 6A illustrates the wearable automatic injection device 600 in a Pre-Injection State, for example, as packaged and ready for use or as ready for packaging. The device 600 may include a pre-fillable and/or pre-filled syringe or cartridge assembly. In an exemplary embodiment, in a pre-injection state, the syringe or cartridge assembly may be in a retracted position ready for use. In the Pre-Injection State, the therapeutic agent cartridge assembly 610 is partially disposed within the housing 635 at an elevated location distal from the injection site, and the needle 625 is retracted within the housing 635. Visual indications to the patient that the wearable automatic injection device 600 is not in operation may include a portion of the therapeutic agent cartridge assembly 610 projecting outside the housing 635 in the pre-injection state. The barrel portion 605 contains a dose of a therapeutic agent which is contained by the interior space defined between the wall or walls of the barrel portion 605 and the bung 615. In an embodiment, the plunger actuator 630 stores energy.

FIG. 6B illustrates the wearable automatic injection device 600 in an Injection State ready to inject, injecting or just after injecting a therapeutically effective dose of a therapeutic agent, in which the therapeutic agent cartridge assembly 610 is in a depressed position. In the depressed position, the therapeutic agent cartridge assembly 610 is disposed within the housing 635 at a depressed location proximal to the injection site, and the needle 625 projects outside the housing 635 through an aperture in the housing 635 so that it can penetrate the skin at the injection site. In the Injection State, the therapeutic agent cartridge assembly 610 does not project outside the housing 635 to provide a visual indication to the patient that the wearable automatic injection device 600 is in operation. The plunger actuator 630 releases its stored energy to actuate the bung 615. This cooperative movement of the plunger actuator 630 and the bung 615 ejects the therapeutic agent in the barrel portion 605 out through the needle 625.

FIG. 6C illustrates the wearable automatic injection device 600 in a Post Injection State, for example, after injecting a therapeutically effective dose of the therapeutic agent or removal of the wearable automatic injection device 600 from the patient before delivery of a therapeutically effective dose of the therapeutic agent, in which the therapeutic agent cartridge assembly 610 is in a retracted position. In the retracted position, the therapeutic agent cartridge assembly 610 is disposed within the housing 635 at an elevated location distal from the injection site, and the needle 625 is retracted within the housing 635. A portion of the therapeutic agent cartridge assembly 610 projects outside the housing 635 to provide a visual indication to the patient that the wearable automatic injection device assembly 600 is not in operation (i.e., in a Post-Injection state). The barrel portion 605 may be empty of the therapeutic agent, and the plunger actuator 630 may no longer store energy.

The housing 635 includes a retraction mechanism that automatically raises the therapeutic agent cartridge assembly 610 from the Injection State (depressed position shown in FIG. 6B) to the Post-Injection state (retracted position shown in FIG. 6C). In an exemplary embodiment, the retraction mechanism may include a biasing mechanism, e.g., a spring, that biases the cartridge assembly away from the injection site when the retraction mechanism is triggered.

The retraction mechanism includes an end-of-dose retraction trigger that, when tripped, triggers the retraction mechanism. The end-of-dose retraction trigger is tripped when the therapeutically effective dose of therapeutic agent in the wearable automatic injection device is delivered. In an exemplary embodiment, the end-of-dose retraction trigger may include a latch, e.g., a flexible plastic hook, that is released upon completed drug delivery. The retraction mechanism also includes an early-removal retraction trigger that, when tripped, triggers the retraction mechanism. The early-removal retraction trigger is tripped when the wearable automatic injection device is removed from the injection site before the therapeutically effective dose of therapeutic agent is completely delivered. In an exemplary embodiment, the early-removal retraction trigger may include a latch, e.g., a flexible plastic hook, that is released upon removal of the wearable automatic injection device 600 from the injection site. The retraction mechanism is responsive to the end-of-dose retraction trigger and responsive to the early-removal retraction trigger to automatically retract the cartridge assembly from the injection site.

FIGS. 7A-7C illustrate an exemplary embodiment of a wearable automatic injection device 700 suitable for rotary insertion of the needle into the skin of a patient. In rotary insertion, the end of a therapeutic agent cartridge assembly 710 bearing the needle 725 descends in a rotary fashion about a pivot point to insert the needle 725 into the skin of the patient. More specifically, FIG. 7A illustrates the exemplary wearable device in a Pre-Injection State, for example, as packaged with a pre-filled and curved sterile hypodermic needle and barrel portion holding a therapeutic agent; FIG. 7B illustrates the exemplary wearable device while in an Injection State just before, while or just after injecting a therapeutic agent into a patient; and FIG. 7C illustrates the exemplary wearable device in a Post Injection State after delivery of the therapeutic agent into the patient or removal of the wearable device from the patient prior to completing delivery of the therapeutic agent to the patient.

The therapeutic agent cartridge assembly 710 is rotatably movable within the housing 735 about a pivot point 765 in the housing. In an exemplary embodiment, the outside of the therapeutic agent cartridge assembly 710 may be provided with one or more ridges, and the inside of the housing 735 may be provided with one or more grooves or channels that provide a pathway for the ridges of the cartridge 710 as the cartridge moves within the housing 735 amongst the various states. In another exemplary embodiment, the outside of the cartridge assembly 710 is free of ridges, and the inside of the housing 735 is free of grooves or channels.

When the therapeutic agent cartridge assembly 710 is depressed into the housing 735, the therapeutic agent cartridge assembly 710 moves rotatably downward about the pivot point 765 such that the needle 725 becomes exposed and penetrates the skin of the patient. In this exemplary embodiment, the needle 725 penetrates the skin of the patient at an angle offset from 90°. Similarly, when the therapeutic agent cartridge assembly 710 is retracted, the therapeutic agent cartridge assembly 710 moves rotatably upward about the pivot point 765 such that the needle 725 retracts within the housing 735. The mechanism to implement this rotational motion of the therapeutic agent cartridge assembly 710 may be simpler and more robust than the mechanism required for the linear insertion of FIGS. 6A-6C.

The needle 725 is curved, with a radius defined by the pivot point 765 and the distance from the needle 715 to the pivot point 765 along the longitudinal axis of the housing 735. The curvature of the needle 725 increases the comfort of the patient during insertion of the needle. The needle 725 may be preferentially oriented with the sharp needle tip closest to the pivot point 765.

Features in FIGS. 7A-7C similar to those illustrated in FIGS. 6A-6C are described above in connection with FIGS. 6A-6C.

In exemplary embodiments, the therapeutic agent cartridge assembly 610 and 720 of FIGS. 6A-6C and 7A-7C, respectively, may be pre-fillable and/or pre-filled with any volume of a therapeutic agent, e.g., a therapeutic antibody, desired for intradermal, subcutaneous, or intramuscular injections. In an exemplary embodiment, the cartridge assembly 610 and 720 may be pre-fillable and/or pre-filled with a volume of about 0.8-0.85 milliliters, although exemplary cartridge assemblies are not limited to these exemplary volumes. In another exemplary embodiment, the cartridge assembly 610 and 720 may be pre-fillable and/or pre-filled with a volume of about 1 milliliter or more.

In exemplary embodiments, the wearable automatic injection device 600 (in FIG. 6A)/700 (in FIG. 7A) may be used to inject the therapeutically effective amount of therapeutic agent over a period of time ranging from about ten seconds to about twelve hours. In an exemplary embodiment, the therapeutic agent may be delivered at a fixed rate for a delivery time of between about five minutes and about thirty minutes. The wearable automatic injection device 600 (in FIG. 6A)/700 (in FIG. 7A) may be used to inject a volume of therapeutic agent in a single slow bolus.

The rate of delivery of the therapeutic agent may be dependent on the ambient temperature. At room temperature, i.e., about 72° F., the accuracy of the delivery time may range between about three percent and about ten percent.

Figure 8:
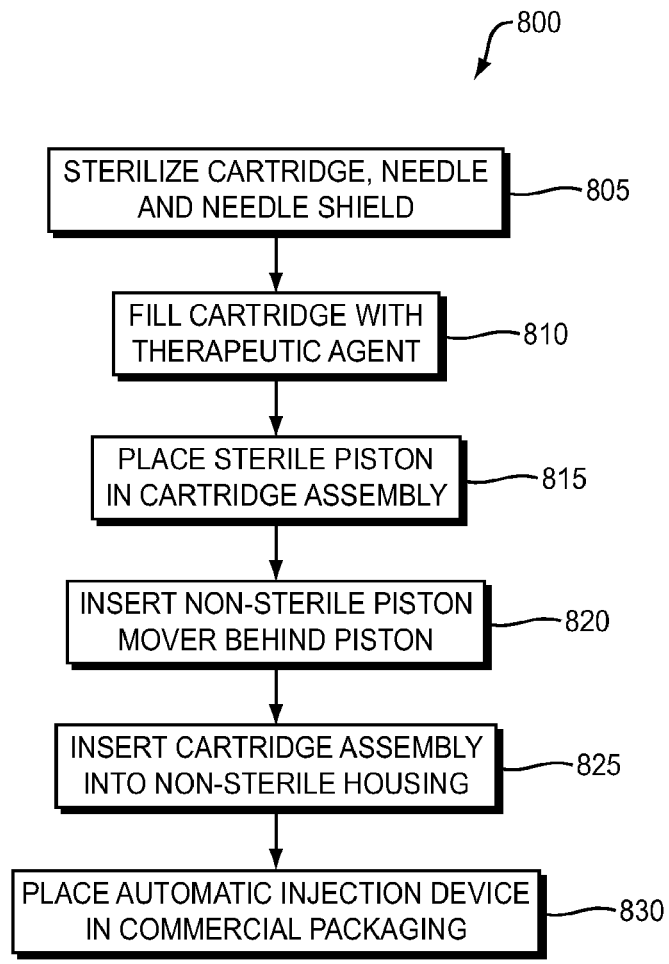
FIG. 8 is a flow chart of an exemplary method of assembling an exemplary wearable automatic injection device.

FIG. 8 is a flow chart of an exemplary method 800 of assembling an exemplary wearable automatic injection device 600 or 700. In step 805, the barrel portion 605/705, needle 625/725 and needle shield 620/720 are sterilized. In step 810, the barrel portion 605/705 is filled with a dose of the therapeutic agent that is to be administered to the patient. In step 815, a sterile bung 615/715 is placed in the barrel portion 605/705 to seal the therapeutic agent inside the barrel portion 605/705. The containment of the therapeutic agent inside the wearable automatic injection device 600 or 700 by the sterile barrel portion 605/705, the sterile bung 615/715 and the needle shroud 620/720 maintains sterility of the therapeutic agent and the needle 625/725. As such, the remaining components of the wearable automatic injection device may be assembled in a non-sterile environment after the barrel portion 605/705 is pre-filled with a therapeutic agent. For example, in step 820, a non-sterile plunger actuator 630/730 is inserted behind the bung 615/715 in the therapeutic agent cartridge assembly 610/710.

In step 825, the therapeutic agent cartridge assembly 610/710 is inserted into a non-sterile housing 635/735. The housing 635/735 may be pre-assembled with other non-sterile components, e.g., the adhesive layer 640/740, the protective film 650/750, the skin sensor foot 660/760. In exemplary embodiments, the barrel portion 605/705, the needle 625/725, the needle shield 620/720 and the bung 615/715 of the therapeutic agent cartridge assembly 610/710 provide the sterility barrier for the therapeutic agent and the subcutaneous contact surfaces. Thus, once the barrel portion 605/705 is filled with the therapeutic agent, the plunger 615/715 is inserted into the barrel portion 605/705 and the needle shroud 620/720 is in place: assembly of the remaining portions of the therapeutic agent cartridge assembly 610/710 and assembly of the housing 635/735 do not require aseptic conditions. No therapeutic agent transfer steps need to be performed by the user. FIGS. 6A and 7A illustrate exemplary embodiments of the wearable assembled automatic injection device 600/700 in a Pre-Injection state.

In step 830, the assembled wearable automatic injection device 600/700 may be placed in an over-wrap, if necessary, and is then commercially packaged for sale.

Figure 9:
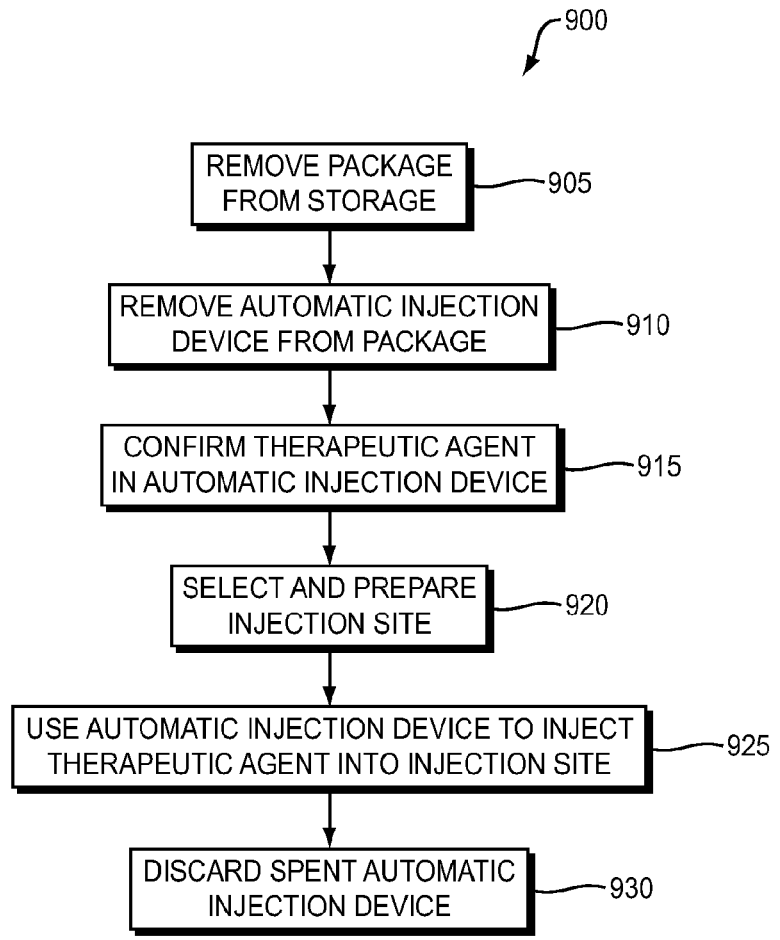
FIG. 9 is a flow chart of an exemplary method of using an exemplary wearable automatic injection device.

FIG. 9 is a flow chart of an exemplary method 900 of using an exemplary wearable automatic injection device 600 or 700. The wearable automatic injection device 600/700 packaged and pre-filled with a therapeutic agent is generally stored in refrigerated storage before use. In step 905, the packaged wearable automatic injection device 600/700 is removed from storage. In step 910, the wearable automatic injection device 600/700 is removed from its packaging and any over-wrap and warmed to room temperature, e.g., by leaving the wearable device outside the packaging at room temperature or by warming the wearable device. In step 915, the patient confirms the therapeutic agent cartridge assembly 610/710 includes a volume of the therapeutic agent in the wearable device 600/700 through an therapeutic agent inspection window disposed in the wearable device housing and may also confirm the clarity of the therapeutic agent, if necessary. In step 920, the injection site on the skin of the patient is selected and prepared for the delivery of the therapeutic agent. In step 925, the patient uses the wearable automatic injection device 600/700 to inject the therapeutic agent into the injection site. The steps generally involved within step 920 are described below in connection with FIG. 10. In step 930, after the wearable automatic injection device 600/700 is removed from the patient, the removed wearable automatic injection device 600/700 is discarded in an appropriate manner.

Figure 10:
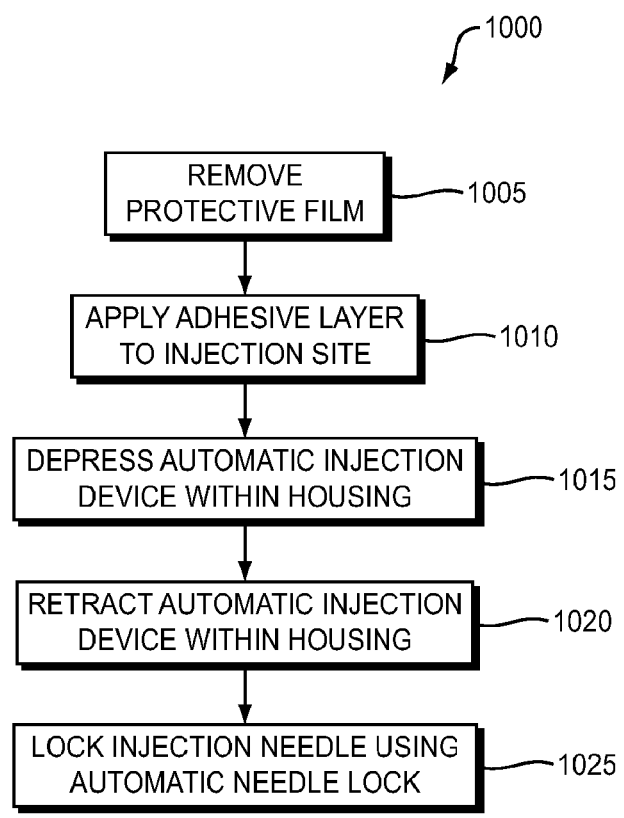
FIG. 10 is a flow chart of an exemplary method of using an exemplary wearable automatic injection device to inject a therapeutic agent into a patient.

FIG. 10 is a flow chart of an exemplary method 1000 of using an exemplary wearable automatic injection device 600 or 700 to inject a therapeutically effective amount of a therapeutic agent into a patient. Exemplary method 1000 is a detailed outline of step 920 in FIG. 9. In step 1005, the patient removes the protective film 650/750 that covers and protects the adhesive layer 640/740 of the wearable automatic injection device 600/700. In some exemplary embodiments, removal of the protective film 650/750 also removes the needle shield 620/720 and exposes the needle 625/725 for injection. In some exemplary embodiments, removal of protective film 650/750 also breaks static friction (i.e., stiction) between the bung 615/715 and the interior wall of the barrel 605/705 and triggers the plunger actuator 630/730. In exemplary embodiments, the protective film 650/750 may include a linking member that is connected to the plunger actuator 630/730. The linking member may include a tether or other linkage mechanism. When the protective film 650/750 is removed, the linking member of the protective film 650/750 relieves static friction between the bung 615/715 and the interior wall of the barrel 605/705, and triggers the plunger actuator 630/730.

In step 1010, the patient applies the patient contact portion of the wearable automatic injection device 600/700 with the adhesive layer 640/740 to the injection site (or an article of clothing around the injections site) so that the wearable device is reliably retained on the injection site during the injection of the therapeutically effective dose of therapeutic agent.

In step 1015, once the wearable automatic injection device 600/700 is attached to the injection site, the therapeutic agent cartridge assembly 610/710 is depressed from a ready position in the Pre-Injection State to a depressed position in the Injection State within the housing 635/735. In the ready position, the end of the therapeutic agent cartridge assembly 610/710 bearing the needle 625/725 is retracted within the housing 635/735 and is not exposed to the outside of the housing. When depressed, the end of the therapeutic agent cartridge assembly 610/710 bearing the needle 625/725 is moved downward either linearly or rotationally within the housing 635/735 so that the needle 625/725 emerges from an aperture in the housing 635/735 and is exposed. This allows the needle 625/725 to penetrate the skin of the patient to an appropriate depth for injection of the therapeutic agent. The downward movement of the therapeutic agent cartridge assembly 610/710 in the housing 635/735 may be linear (i.e., a vertical downward movement) or rotary (i.e., in a circular movement about a pivot point). FIGS. 6B and 7B illustrate exemplary embodiments of the wearable automatic injection device 600 and 700 in an Injection state with the therapeutic agent cartridge 610/710 depressed into the housing 635/735 after step 1015 is performed.

In an exemplary embodiment, the therapeutic agent cartridge assembly 610/710 is depressed into the housing 635/735 by the patient manually pushing down the therapeutic agent cartridge assembly 610/710. In another exemplary embodiment, the patient may activate an insertion trigger, e.g., an insertion trigger button located in a conveniently accessible location such as the top of the housing 635/735, which causes an insertion trigger to automatically depress the therapeutic agent cartridge assembly 610/710 into the housing 635/735 and in turn, cause the needle 625/725 to pierce the skin of the patient. In an exemplary embodiment, pressing the insertion trigger button may release a latch in the insertion trigger that allows a spring to bias the cartridge assembly 610/710 downwardly in the housing 635/735. The same motion of the cartridge assembly 610/710 may cause the needle 625/725 to be inserted into the injection site to an appropriate depth.

In an exemplary embodiment, depressing the therapeutic agent cartridge assembly 610/710 triggers the plunger actuator 630/730 to begin movement of the bung 615/715 to cooperatively inject the therapeutically effective dose into the patient. Depression of the therapeutic agent cartridge assembly 610/710 causes the plunger actuator 630/730 to break the static friction (i.e., stiction) between the bung 615/715 and the inside wall or walls of the barrel portion 605/705 and cause the bung 615/715 to move forwardly toward the needle 625/725 in the therapeutic agent cartridge assembly 610/710 to deliver the therapeutic agent via the needle 625/725. The plunger actuator 630/730 may overcome the bung stiction in one step and actuate the bung in a subsequent step, or the plunger actuator 630/730 may overcome the bung stiction and actuate the bung concurrently. In another exemplary embodiment, the plunger actuator 630/730 is triggered not by depressing the therapeutic agent cartridge, but by the user activating an injection trigger, e.g., in the form of an injection trigger button.

The rate of therapeutic agent delivery may depend on the characteristics of the plunger actuator 630/730. The plunger actuator 630/730 may take the form of several exemplary embodiments. In some exemplary embodiments, the plunger actuator 630/730 may employ means of energy storage and release, e.g., biasing mechanisms (such as springs), compressed gases, chemical gas generators (such as expanding foams), osmotic pressure, hydrogel expansion, etc. A damping mechanism may be used to absorb energy, for example, an initial release of energy, and to provide a more controlled release of energy during energy release by the plunger actuator 630/730. A flow restrictor placed in a fluid pathway between the needle and the bung 615/715 may be used to further regulate the rate of therapeutic agent delivery, e.g., where the plunger actuator 630/730 delivers an unconstrained spring force. Thus, an appropriate plunger actuator 630/730 and an appropriate flow restrictor may be selected to deliver the dose at a controlled rate, e.g., in a single slow bolus free of or substantially free of any burning sensation to the patient.

In an exemplary embodiment, depressing the therapeutic agent cartridge assembly 610/710 also arms the retraction mechanism which, when triggered, retracts the therapeutic agent cartridge assembly 610/710 into the housing 635/735.

In step 1020, the therapeutic agent cartridge assembly 610/710 is retracted from the depressed position to a retracted position in a Post-Injection State so that it protrudes outside the housing 635/735 and the needle 625/725 is retracted within the housing 635/735 or protected by the skin sensor foot 660/760 or both. FIGS. 6C and 7C illustrate exemplary embodiments of automatic injection device 600 and 700, respectively, in a retracted position after step 1020. Step 1020 is performed either when the therapeutically effective dose of therapeutic agent is delivered or when the wearable automatic injection device 600/700 is removed from the injection site before the therapeutically effective dose is completely delivered.

Upon delivery of the therapeutically effective dose, the bung 615/715 and/or the plunger actuator 630/730 trips the end-of-dose retraction trigger of the retraction mechanism. The bung 615/715 and/or the plunger actuator 630/730 may include a linking member connected to the retraction trigger. The linking member may include a tether or other linkage mechanism. The linking member may be of a suitable length such that, when the bung 615/715 has been moved to the end of the cartridge assembly 610/710 (delivering a complete dose), the linking member triggers a latch that in turn trips the retraction trigger.

Once the end-of-dose retraction trigger is tripped, the retraction mechanism deploys the therapeutic agent cartridge assembly 610/710 upward inside the housing 635/735 and away from the patient contact portion so that the therapeutic agent cartridge assembly 610/710 enters a Post-Injection State. In an exemplary embodiment, the movement of the therapeutic agent cartridge assembly 610/710 from the injection state to the post-injection state creates an audible sound, e.g., a "click," which provides an aural indication of the completion of therapeutic agent delivery. Once retracted, the therapeutic agent cartridge assembly 610/710 protrudes outside the housing 635/735 (as shown in FIGS. 6C and 7C), which provides a visual indication of the state of the wearable automatic injection device 600/700, for example, completion of therapeutic agent delivery or a visual indication of the device in the Post-Injection State.

However, if the wearable device 600/700 is removed from the skin of the patient before the completion of therapeutically effective dose of the therapeutic agent, the skin sensor foot 660/760 extends to the outside of the housing 635/735 and trips the early-removal retraction trigger of the retraction mechanism. Once the early-removal retraction trigger is tripped, the retraction mechanism deploys the therapeutic agent cartridge assembly 610/710 upward in the housing 635/735 away from the patient contact portion so that the therapeutic agent cartridge assembly 610/710 is returned to a retracted position. In an exemplary embodiment, the plunger actuator 630/730 may continue to move forwardly in the therapeutic agent cartridge 610/720 toward the needle 625/725 when the wearable device 600/700 is removed from the patient before completion of delivery of a therapeutically effective dose of the therapeutic agent.

In step 1025, upon retraction, an automatic needle lock engages with the injection needle 625/725 to prevent redeployment of the needle 625/725 to provide needle-stick protection. The needle lock may be a member that prevents the needle 625/725 from exiting the housing 635/735 once engaged, and may be located in the housing 635/735 near the needle 625/725. Exemplary needle locks may include, but are not limited to, a plastic plate, a metal plate, a clip, etc.

III. EXEMPLARY NEEDLE SYSTEMS

Exemplary embodiments provide different exemplary needle assemblies for injecting a dose of a therapeutic agent into a patient's skin. In some exemplary embodiments, an injection needle, coupled to a barrel portion of an exemplary automatic injection device containing the dose, may be inserted into the patient's skin to inject the dose into the patient's skin. In other exemplary embodiments, a syringe needle may be coupled to a barrel portion containing the dose to conduct the dose out of the barrel portion, and an injection needle coupled to the syringe needle may be inserted into the patient's skin to inject the dose into the patient's skin.

In some exemplary embodiments, as illustrated in FIGS. 11 and 12, a syringe may include a barrel portion and an injection needle coupled to a distal end of the barrel portion. The injection needle may be inserted into the patient's skin to deliver a therapeutic agent contained in the barrel portion of the syringe. The injection needle may be aligned at any suitable angle relative to the longitudinal axis of the barrel portion ranging from about 0 degrees to about 180 degrees.

FIG. 11 illustrates an exemplary syringe 1100 suitable for use in an exemplary automatic injection device. The syringe 1100 includes a barrel portion 1102 configured to hold a dose of a therapeutic agent and extending between a proximal end and a distal end along a longitudinal axis L. A distal end of the barrel portion 1102 is coupled to an injection needle 1104 that extends along the longitudinal axis L.

FIG. 12 illustrates an exemplary syringe 1200 suitable for use in an exemplary automatic injection device. The syringe 1200 includes a barrel portion 1202 configured to hold a dose of a therapeutic agent and extending between a proximal end and a distal end along a longitudinal axis L. A distal end of the barrel portion 1202 may include an elbow portion 1204 that extends substantially at 90 degrees from the longitudinal axis L. A distal end of the elbow portion 1204 is coupled to an injection needle 1206 that extends substantially at 90 degrees from the longitudinal axis L. One of ordinary skill in the art will recognize that exemplary automatic injection devices may include injection needles that extend along the longitudinal axis L of the syringe or that extend at any suitable angle relative to the longitudinal axis L of the syringe. Exemplary angles may include, but are not limited to, about 70 degrees to about 110 degrees.

Figure 13:
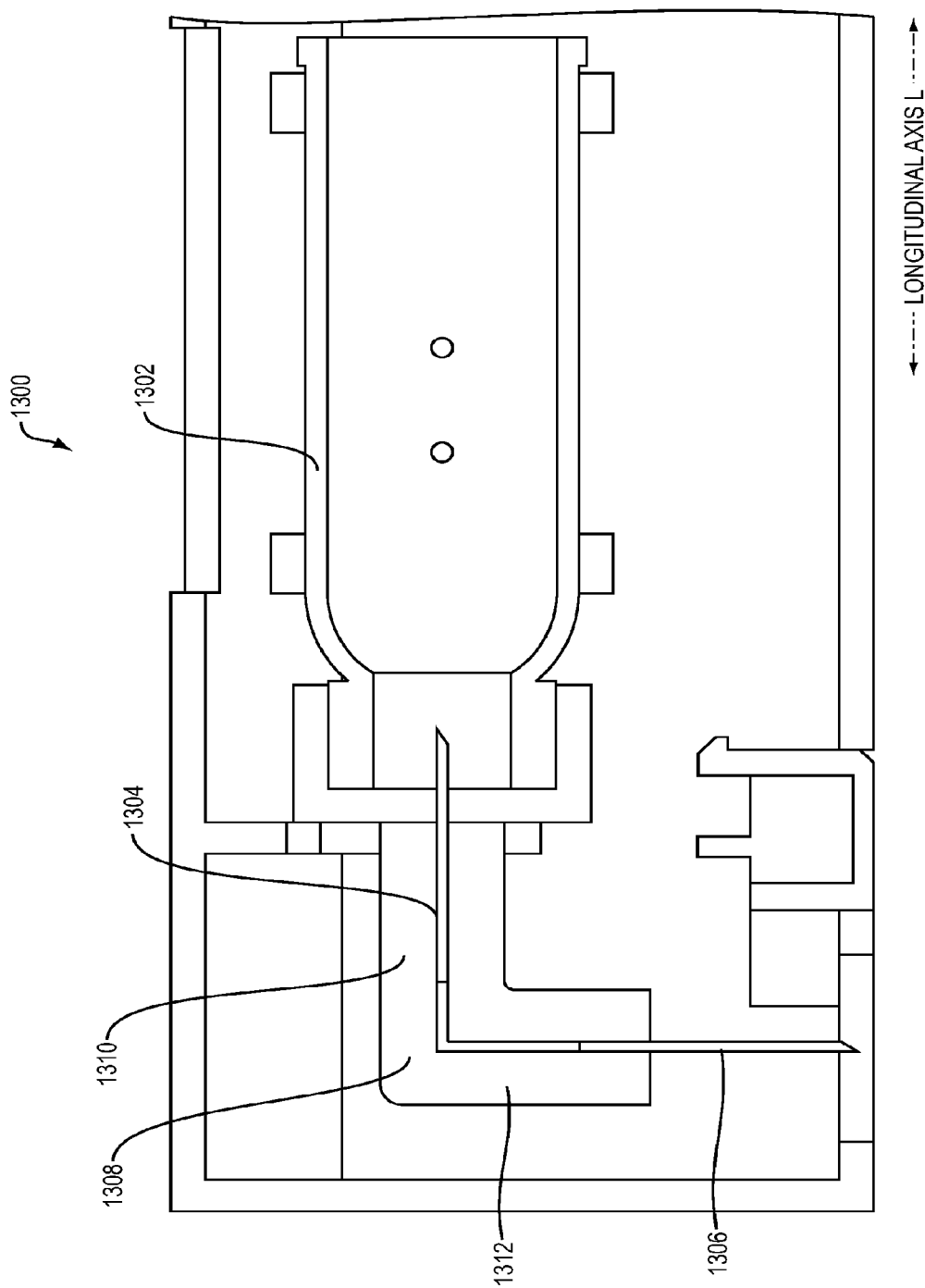
FIG. 13 illustrates an exemplary needle assembly in which an exemplary adapter couples a syringe needle to an injection needle.
Figure 14:
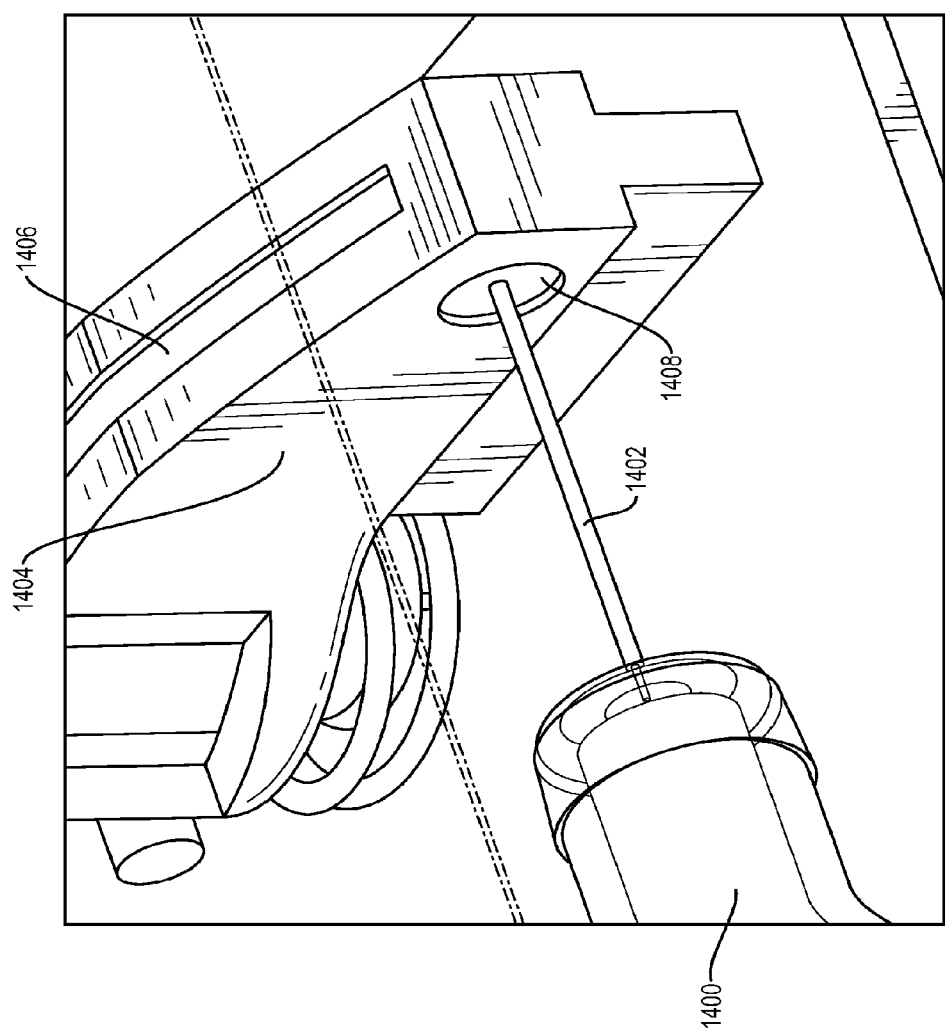
FIG. 14 illustrates an exemplary needle assembly in which a fluid conduit couples a syringe needle to an injection needle.

In some exemplary embodiments, as illustrated in FIGS. 13 and 14, a syringe may include a barrel portion and an injection needle coupled to a distal end of the barrel portion. The injection needle may be inserted into a patient's skin to deliver a therapeutic agent contained in the barrel portion of the syringe. The injection needle may be aligned at any suitable angle relative to the longitudinal axis of the barrel portion ranging from about 0 degrees to about 180 degrees.

In some exemplary embodiments, as illustrated in FIGS. 13 and 14, a syringe may include a barrel portion and an injection needle coupled directly or indirectly to a distal end of the barrel portion. The syringe needle may convey a therapeutic agent contained in the barrel portion of the syringe to the injection needle, and the injection needle may deliver the therapeutic agent into a patient's skin. A coupling between the syringe needle and the injection needle may be provided by one or more intermediate components. An exemplary coupling component may include, for example, an adapter, provided between the distal end of the barrel portion and the injection needle.

FIG. 13 illustrates an exemplary syringe 1300 suitable for use in an exemplary automatic injection device. The syringe 1300 includes a barrel portion 1302 configured to extend from a proximal end to a distal end along a longitudinal axis L and configured to hold a dose of a therapeutic agent. A distal end of the barrel portion 1302 is coupled to a hollow syringe needle 1304. The syringe needle 1304 is, in turn, coupled to a hypodermic injection needle 1306 through an exemplary intermediate adapter 1308. More specifically, a proximal portion of the adapter 1308 is coupled to the syringe needle 1304 and a distal portion of the adapter 1308 is coupled to the injection needle 1306. The adapter 1308 may establish a substantially 90 degree alignment between the longitudinal axis L of the barrel portion 1302 and the hypodermic injection needle 1306.

The exemplary adapter 1308 is a component that includes a first portion 1310 that extends from the barrel portion 1302 substantially parallel to the longitudinal axis L, and a second portion 1312 that extends from the first portion 1310 substantially perpendicular to the longitudinal axis L. More specifically, a proximal end of the first portion 1310 is coupled to a distal end of the barrel portion 1302. In an exemplary embodiment, the proximal end of the first portion 1310 may envelope the distal end of the barrel portion 1302. A distal end of the first portion 1310 is coupled to a proximal end of the second portion 1312. A distal end of the second portion 1312 is coupled to a proximal end of the injection needle 1306. In an exemplary embodiment, the first portion 1310 and the second portion 1312 of the adapter 1308 may be formed integrally.

Exemplary adapters may be formed of a rigid material including, but not limited to, plastic materials, steel, and the like. Exemplary adapters may alternatively be formed of a flexible material including, but not limited to, rubber and the like.

The configuration of the adapter 1308 coupled to the injection needle 1306 allows the injection needle 1306 to extend at about 90 degrees relative to the longitudinal axis L of the syringe. This configuration simplifies the manufacturing of the wearable automatic injection device as it eliminates the need for a bent injection needle. The exemplary injection needle 1306 maintains a low profile against the patient while allowing for proper insertion into the patient's skin during an injection in an injection state. One of ordinary skill in the art will recognize that exemplary injection needles may be bent from the longitudinal axis of the syringe to any suitable angle not limited to about 90 degrees, e.g., about 70 degrees to about 110 degrees.

In some exemplary embodiments, one or more fluid conduits may be disposed between the syringe needle and the injection needle to allow a flow of the therapeutic agent from the barrel portion to the injection needle through the syringe needle. Any suitable fluid conduit or fluid transfer mechanism may be used to establish the one or more fluid conduits between the syringe needle and the injection needle. In an exemplary embodiment, a pierceable septum in its intact state may separate the syringe needle from fluid communication from the injection needle. When the syringe needle pierces the septum during an injection in an injection state, fluid communication may be established between the syringe needle and the injection needle through the fluid conduit.

FIG. 14 illustrates a portion of an exemplary automatic injection device in which a fluid conduit couples a syringe needle and an injection needle. The device includes a syringe or cartridge assembly having a barrel portion 1400 holding a dose of a therapeutic agent. A distal end of the barrel portion 1400 is coupled to a syringe needle 1402. A transfer mechanism 1404 is provided in contact with or in the vicinity of the syringe needle 1402, and also in contact with or in the vicinity of an injection needle (not pictured). The transfer mechanism 1404 includes a fluid conduit or passageway 1406 that establishes fluid communication between the syringe needle 1402 and the injection needle.

In an exemplary embodiment, the transfer mechanism 1404 includes a pierceable septum 1408 that separates the syringe needle 1402 from the fluid conduit 1406 in the transfer mechanism 1404 before an injection in a pre-injection state. In an exemplary embodiment, during an injection in an injection state, the syringe or cartridge may be moved toward the transfer mechanism 1404 so that the syringe needle 1402 pierces the septum 1408 to create a fluid communication path among the barrel portion 1400, the fluid conduit 1406 of the transfer mechanism 1404, and the injection needle. The therapeutic agent may thereby flow out of the barrel portion 1400 through the syringe needle 1402 into the fluid conduit 1406. The therapeutic agent may then be transmitted through the fluid conduit 1406 into the injection needle for delivery of the therapeutic agent to a patient.

Figure 15:
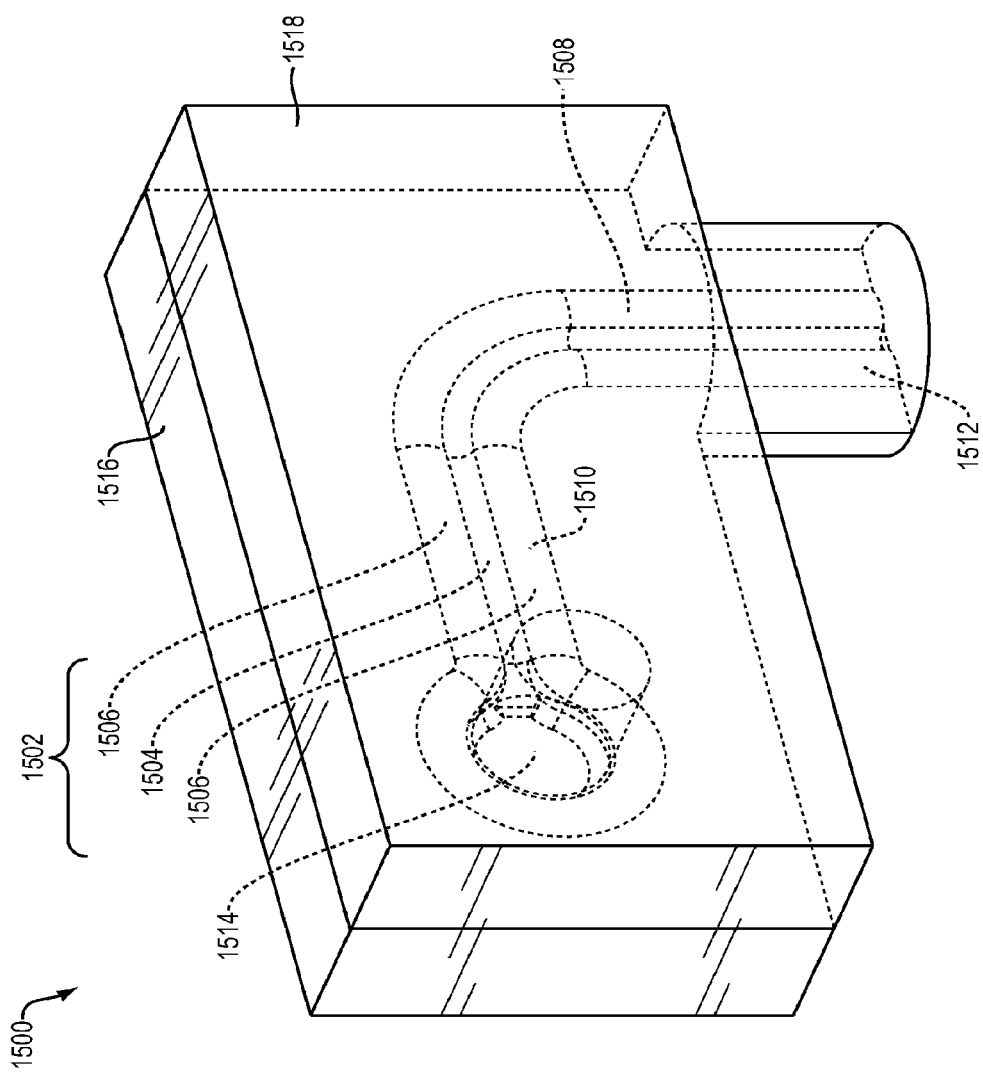
FIG. 15 illustrates an exemplary transfer mechanism for providing a fluid conduit between a syringe needle and an injection needle.

FIG. 15 illustrates an exemplary transfer mechanism 1500 for providing a fluid conduit 1502 between a syringe needle (not pictured) and an injection needle (not pictured). The fluid conduit 1502 may include a centrally extending channel 1504 through which the therapeutic agent flows from the syringe needle to the injection needle, and raised wall portions 1506 extending along the edges of the channel 1504 in order to constrain the fluid to the channel 1504. The fluid conduit 1502 may take any suitable form and dimension. In the illustrative embodiment, the fluid conduit 1502 has a first substantially straight portion 1508 aligned at about 90 degrees from a second substantially straight portion 1510.

The fluid conduit 1502 may include a fluid inlet 1512 for entry of the therapeutic agent from the syringe needle, and a fluid outlet 1514 for exit of the therapeutic agent into the injection needle. The fluid inlet 1512 may be coupled directly or indirectly to the proximal end of a syringe needle. In an exemplary embodiment, a pierceable septum (not pictured) may be provided at the fluid inlet 1512 to prevent fluid flow from the syringe needle when the septum is intact, and to allow fluid flow from the syringe needle when the septum is pierced by the syringe needle. The fluid outlet 1514 may be coupled directly or indirectly to the distal end of the injection needle in order to establish a fluid flow path between the fluid conduit 1502 and the injection needle.

Alternatively, 1512 may be used as the fluid outlet and 1514 may be used as the fluid inlet. In this exemplary embodiment, fluid inlet 1514 may be coupled directly or indirectly to a syringe needle, and fluid outlet 1512 may be coupled directly or indirectly to an injection needle.

The transfer mechanism 1500 may be formed of two housing portions 1516 and 1518 stacked together. In an exemplary embodiment, the fluid conduit 1502 may be formed on the surface of portion 1516, and portion 1518 may be stacked over the fluid conduit 1502 so as to seal the edges of the fluid conduit 1502 in order to prevent fluid leakage from the fluid conduit. Compression between the two housing portions 1516 and 1518 may be provided by one or more mechanical interlocking mechanism, for example, one or more fasteners, snaps, chemical bonding, ultrasonic welding, and others.

The fluid conduit 1502 may be formed on the surface of the housing portion 1516 using any suitable technology. In an exemplary embodiment, the raised wall portions 1506 of the fluid conduit 1502 may be formed of a low durometer material molded as a gasket to seal the flow path of the therapeutic agent. In another exemplary embodiment, laser welding may be used to trace a path around the perimeter of the channel 1504 in order to simultaneously create a seal around the channel 1504 and bond the two housing portions 1516 and 1518 together.

Figure 16:
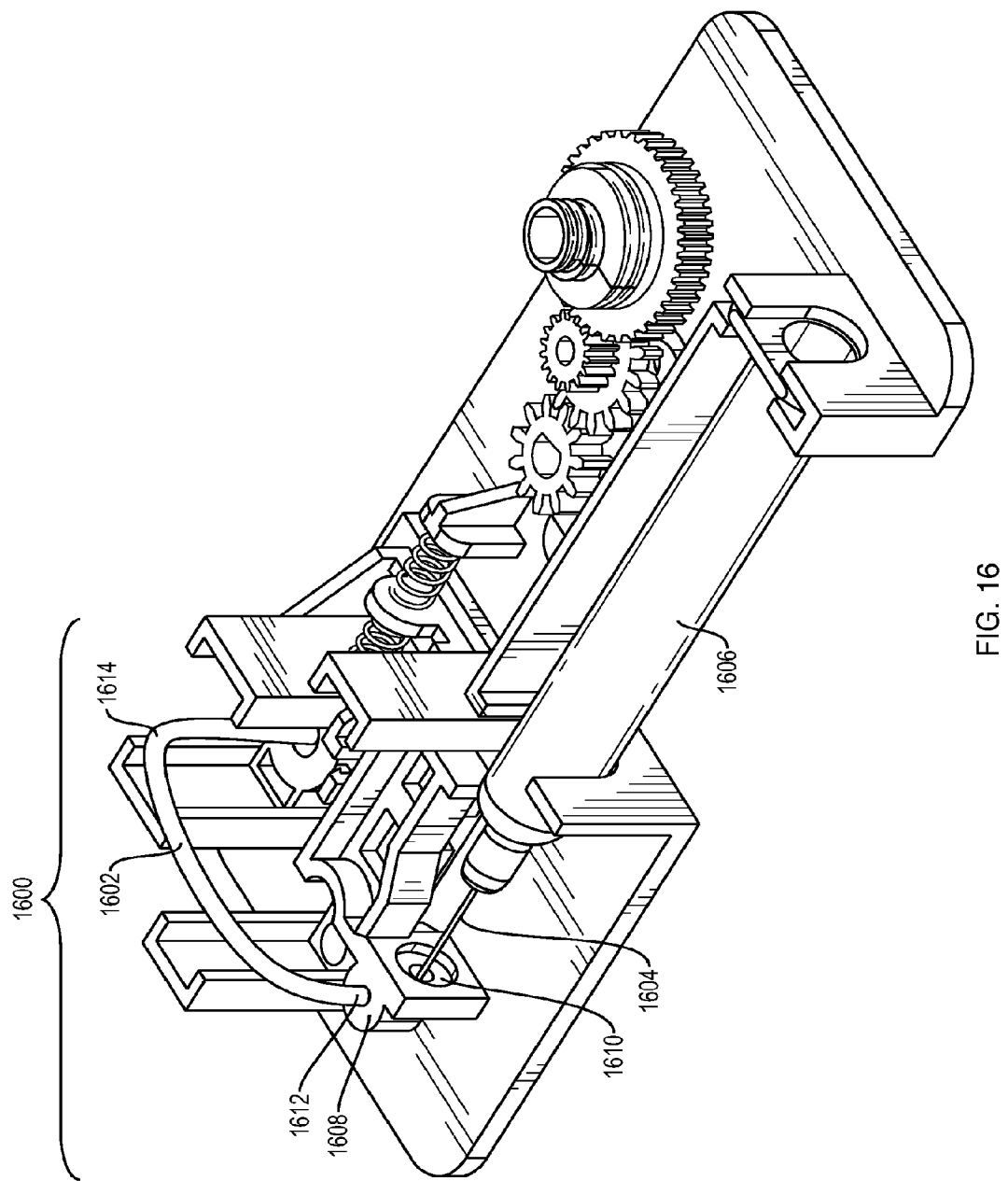
FIG. 16 illustrates an exemplary transfer mechanism for providing a fluid conduit between a syringe needle and an injection needle.

FIG. 16 illustrates an exemplary transfer mechanism 1600 for providing a fluid conduit 1602 between a syringe with a syringe needle 1604 coupled to a barrel portion 1606 and an injection needle (not pictured). The transfer mechanism 1600 may include a first portion 1608 having a septum 1610 provided in the vicinity of the syringe needle 1604.

The first portion 1608 of the transfer mechanism 1600 may include an internal hollow space for accommodating the therapeutic agent and an inlet port 1612 coupled to one end of a hollow tube 1614. Another end of the hollow tube 1614 is coupled directly or indirectly (for example, through a second portion similar to first portion 1608) to the injection needle. The hollow tube 1614 provides a fluid path from the syringe needle 1604 to the injection needle. The hollow tube 1614 may take any suitable form, alignment and dimension. In the illustrative embodiment, the hollow tube 1614 extends substantially at right angles to the longitudinal axis of the barrel portion 1606.

In an exemplary embodiment, the transfer mechanism 1600 may be moveable upward and/or downward along the vertical axis. In this embodiment, before an injection in a pre-injection state (for example, when the syringe needle is covered by a needle cover), the transfer mechanism 1600 may be in a vertically raised position above the syringe needle 1604 such that the syringe needle 1604 is not aligned with the septum 1610 in the transfer mechanism 1600, thereby preventing fluid communication between the syringe needle 1604 and the transfer mechanism 1600. At the beginning of an injection (for example, upon removal of the syringe cover from the syringe needle 1604), the transfer mechanism 1600 may be automatically lowered to a vertically lowered position such that the syringe needle 1604 becomes aligned with the septum 1610 in the transfer mechanism 1600, thus allowing the syringe needle 1604 to pierce the septum 1610. Exemplary embodiments may provide any suitable actuation mechanism for lowering the transfer mechanism 1600 from the vertically raised position to the vertically lowered position at the beginning of an injection.

In an exemplary embodiment, the syringe needle 1604 may be initially coupled to or provided immediately adjacent to the first portion 1608. In another embodiment, the syringe may be in a retraction position within the wearable automatic injection device and the syringe needle 1604 may be initially separated from the first portion 1608 of the transfer mechanism 1600. In this embodiment, before an injection in a pre-injection state, the syringe needle 1604 may be separated from the septum 1610 in the first portion 1608 and may not be in fluid communication with the transfer mechanism 1600. At the beginning of an injection, the syringe may be moved forwardly by a cartridge or syringe actuator to an extended position within the device, and the syringe needle 1604 may pierce the septum 1610, allowing the therapeutic agent to flow from the barrel portion 1606 to the transfer mechanism 1600. Exemplary embodiments may provide any suitable syringe or cartridge actuation mechanism for advancing the barrel portion and/or the cartridge assembly within the housing between the retracted position and the extended position in order to pierce the septum and convey the therapeutic agent to the patient's skin through the injection needle.

An advantage of the exemplary transfer mechanism 1600 is that the motions of the syringe needle 1604 and the injection needle are decoupled and independent from each other. For example, the mechanism coupling the syringe needle 1604 to the inlet port 1612 need not take into consideration how this coupling would affect the outlet of the transfer mechanism 1600 coupled to the injection needle.

Figure 17:
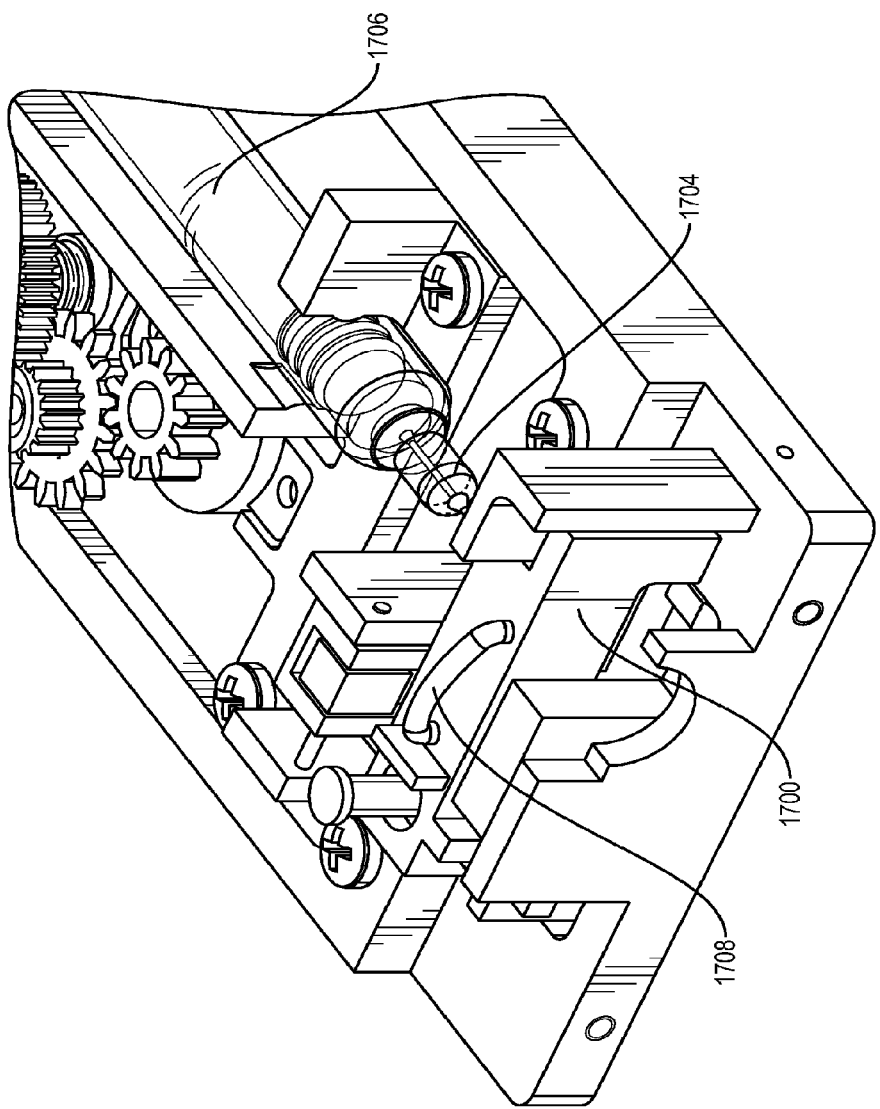
FIG. 17 illustrates an exemplary transfer mechanism for providing a fluid conduit between a syringe needle and an injection needle.

FIG. 17 illustrates an exemplary transfer mechanism 1700 for providing a fluid conduit between a syringe having a syringe needle 1704 coupled to a barrel portion 1706 and an injection needle (not pictured). The transfer mechanism 1700 may include an inlet portion (not pictured) couplable to the syringe needle 1704 and an outlet portion (not pictured) couplable to the injection needle. A hollow tube 1708, for example, a jumper tube, may be used to couple the inlet portion of the transfer mechanism to the outlet portion of the transfer mechanism. The hollow tube 1708 provides a fluid path from the syringe needle 1704 to the injection needle. The hollow tube 1708 may take any suitable form, alignment and dimension. In the illustrative embodiment, the hollow tube 1708 extends substantially at right angles to the longitudinal axis of the barrel portion 1706.

In an exemplary embodiment, the inlet portion of the transfer mechanism 1700 may include a septum (not pictured) provided in the vicinity of the syringe needle 1704. Piercing of the septum by the syringe needle 1704 may establish fluid communication between the barrel portion 1706 and the transfer mechanism 1700. In an exemplary embodiment, the outlet portion of the transfer mechanism may include a septum (not pictured) provided in the vicinity of the injection needle. Piercing of the septum by the injection needle may establish fluid communication between the transfer mechanism 1700 and the patient's skin.

In an exemplary embodiment, the transfer mechanism 1700 may be moveable upward and/or downward along the vertical axis. In this embodiment, before an injection in a pre-injection state (for example, when the syringe needle is covered by a needle cover), the transfer mechanism 1700 may be in a vertically raised position above the syringe needle 1704 such that the syringe needle 1704 is not aligned with the septum in the transfer mechanism 1700, thereby preventing fluid communication between the syringe needle 1704 and the transfer mechanism 1700. At the beginning of an injection (for example, upon removal of the syringe cover from the syringe needle 1704), the transfer mechanism 1700 may be automatically lowered to a vertically lowered position such that the syringe needle 1704 becomes aligned with the septum in the transfer mechanism 1700, thus allowing the syringe needle 1704 to pierce the septum. Exemplary embodiments may provide any suitable actuation mechanism for lowering the transfer mechanism 1700 from the vertically raised position to the vertically lowered position at the beginning of an injection.

In an exemplary embodiment, the syringe needle 1704 may be initially coupled to or provided immediately adjacent to the first portion 1708. In another embodiment, the syringe may be in a retraction position within the wearable automatic injection device and the syringe needle 1704 may be initially separated from the transfer mechanism 1700. In this embodiment, before an injection in a pre-injection state, the syringe needle 1704 may be separated from the septum and may not be in fluid communication with the transfer mechanism 1700. At the beginning of an injection, the syringe may be moved forwardly by a cartridge or syringe actuator to an extended position within the device, and the syringe needle 1704 may pierce the septum, allowing the therapeutic agent to flow from the barrel portion 1706 to the transfer mechanism 1700. Exemplary embodiments may provide any suitable syringe or cartridge actuation mechanism for advancing the barrel portion and/or the cartridge assembly within the housing between the retracted position and the extended position in order to pierce the septum and convey the therapeutic agent to the patient's skin through the injection needle.

In the exemplary embodiments illustrated in 15-17, a tight and reliable fluid path conveys the therapeutic agent from the barrel portion of a syringe or cartridge through a pierced septum and a tube or channel in a transfer mechanism and eventually into an injection needle. This configuration allows the syringe needle assembly and the injection needle assembly to move independently of each other, which facilitates retraction of the injection needle into the housing in a post-injection state after an injection has been performed, while leaving the syringe needle in a position in which it pierces the septum.

Figure 18A:
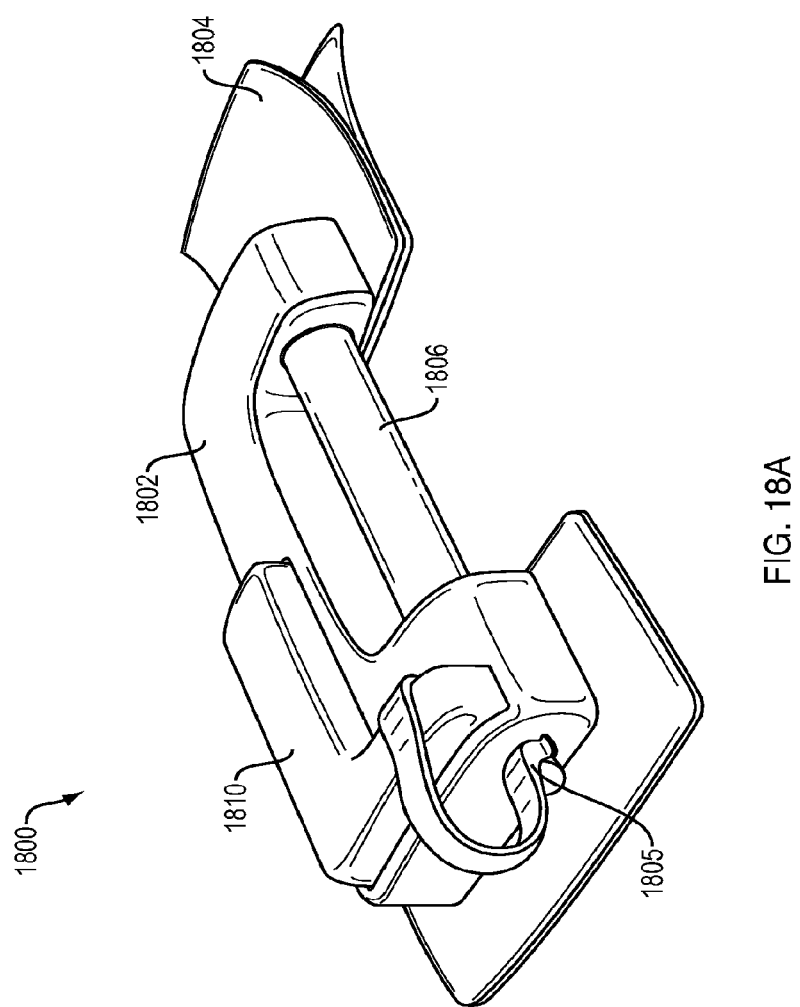
FIG. 18A illustrates a perspective view of an exemplary wearable automatic injection device.
Figure 18B:
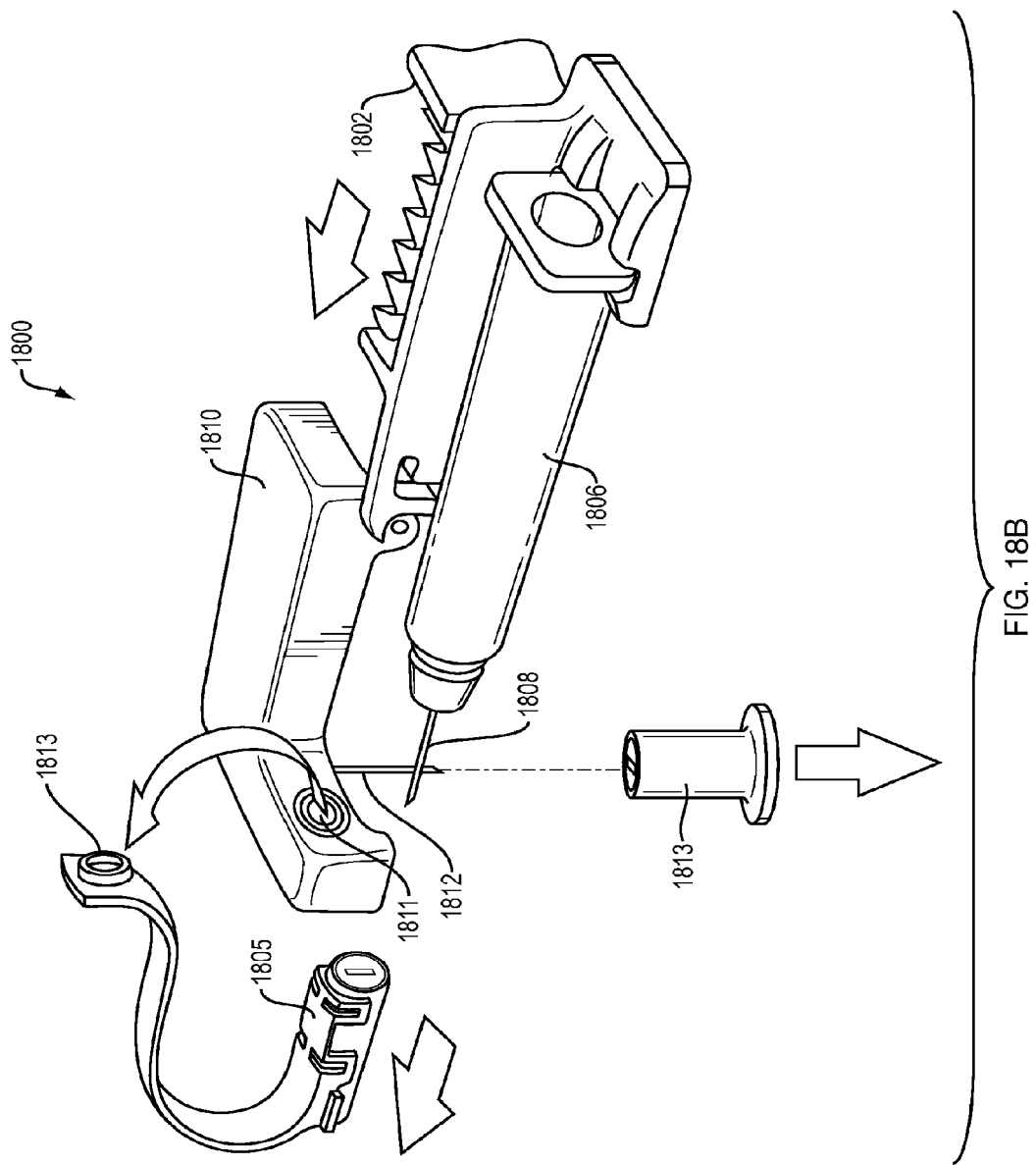
FIG. 18B illustrates a disassembled view showing the components of the exemplary device of FIG. 18A.

FIGS. 18A and 18B illustrate an exemplary wearable automatic injection device including a syringe and an exemplary transfer mechanism. FIG. 18A illustrates a perspective view of the device. FIG. 18B illustrates a disassembled view showing the components of the device. The automatic injection device 1800 includes a housing portion 1802 that includes an adhesive layer 1804 at a patient contact region that may be removed to attach the device to a patient's body or clothing.

The housing portion 1802 holds a syringe 1806 in a stationary or moveable manner in the device 1800. The syringe 1806 holds a dose of a therapeutic agent and that is coupled to a syringe needle 1808 at its distal end. The syringe needle 1808 may extend substantially along the longitudinal axis of the syringe 1806. In a packaged pre-injection state, the syringe needle 1808 may be covered by a syringe needle cover 1805, which may be removed by a patient before an injection. In an injection state, the syringe needle 1808 may be uncovered. In an exemplary embodiment, removal of the adhesive layer 1804 may also remove the syringe needle cover 1805.

An injection button 1810 is provided in the vicinity of the syringe needle 1808. The injection button 1810 includes holds an injection needle 1812 at substantially 90 degrees relative to the syringe needle 1808, and includes a transfer mechanism that provides a fluid conduit between the syringe needle 1808 and the injection needle 1812. In a packaged pre-injection state, the injection needle 1812 may be covered by an injection needle cover 1813, which may be removed by a patient before an injection. In an injection state, the injection needle 1812 may be uncovered. In an exemplary embodiment, removal of the adhesive layer 1804 may also remove the injection needle cover 1813.

The injection button 1810 also includes a septum 1811 that prevents the syringe needle 1808 from establishing fluid communication with the fluid conduit in the injection button 1810. A cover 1813 may be provided to cover the septum 1811 in a pre-injection state, which may be removed by a patient before an injection. In an exemplary embodiment, the septum cover 1813 and the syringe needle cover 1805 may be coupled so that removal of one also removes the other.

In an exemplary embodiment, in a pre and post-injection state, the syringe needle cover 1805 may cover the syringe needle 1808, and the injection button 1810 may be in a vertically raised position as displaced by the syringe needle cover 1805 such that the injection needle 1812 is retracted within the housing 1802. In this state, the septum 1811 of the injection button 1810 may be vertically above the syringe needle 1808. In addition, the syringe 1806 may be in a retracted position along the longitudinal axis of the assembly 1806 spaced from the septum 1811 of the injection button 1810.

When the syringe needle cover 1805 is removed from the syringe needle 1808, the injection button 1810 is lowered to a vertically lowered position such that the injection needle 1812 protrudes outside the housing 1802 into the patient contact region. In an exemplary embodiment, the injection button 1810 may be automatically lowered by the removal of the syringe needle cover 1805. In another exemplary embodiment, the injection button 1810 is lowered by the patient pushing downward on the injection button 1810.

In an exemplary embodiment, the lowering of the injection button 1810 aligns the syringe needle 1808 with the septum 1811 of the injection button 1810. The lowering of the injection button 1810 also triggers a syringe actuator that advances the syringe 1806 along its longitudinal axis toward the septum 1811 of the injection button 1810. This causes the syringe needle 1808 to pierce the septum 1811 and establish fluid communication with the injection needle 1812.

Figure 19A:
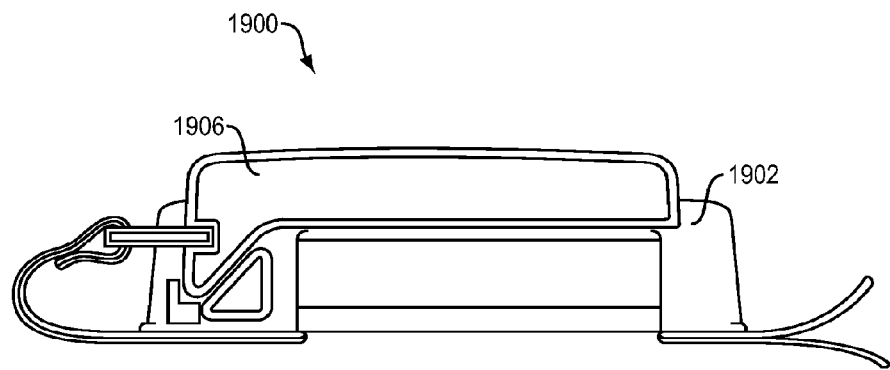
FIG. 19A illustrates a side view of an exemplary wearable automatic injection device.
Figure 19B:
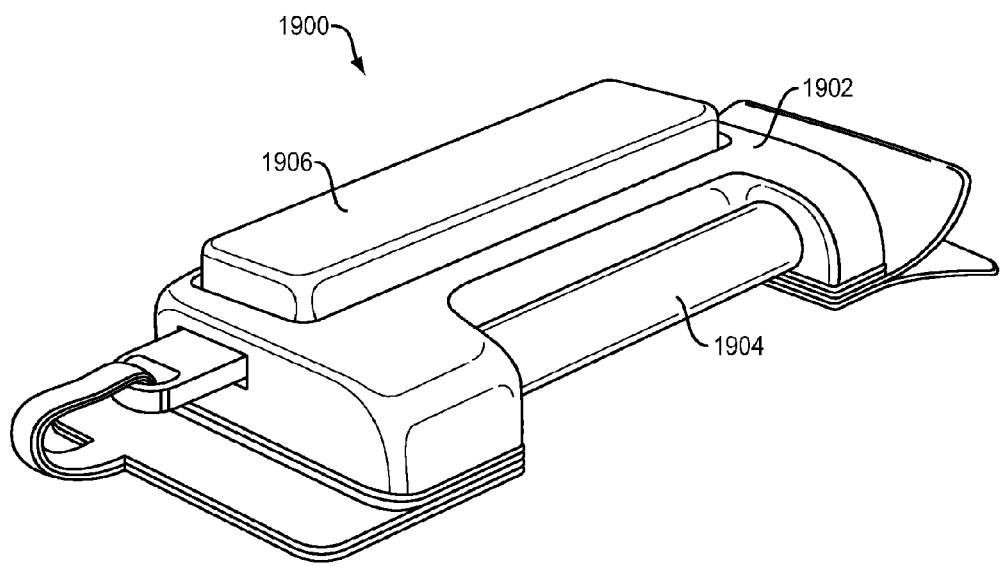
FIG. 19B illustrates a perspective view showing the components of the device of FIG. 19A.

FIGS. 19A and 19B illustrate an exemplary wearable automatic injection device including a syringe and an exemplary transfer mechanism. FIG. 19A illustrates a side view of the device. FIG. 19B illustrates a perspective view showing the components of the device. The automatic injection device 1900 includes a housing 1902 holding a syringe 1904 in a stationary of moveable manner relative to the housing 1902. An injection button 1906 is provided in the housing 1902 in the vicinity of the syringe 1904 and holds an injection needle (not pictured). The housing 1902 includes an adhesive layer 1908 for attachment at a patient contact region.

Other components in the device 1900 similar to the components in the device 1800 are described with reference to FIGS. 18A and 18B.

Figure 20A:
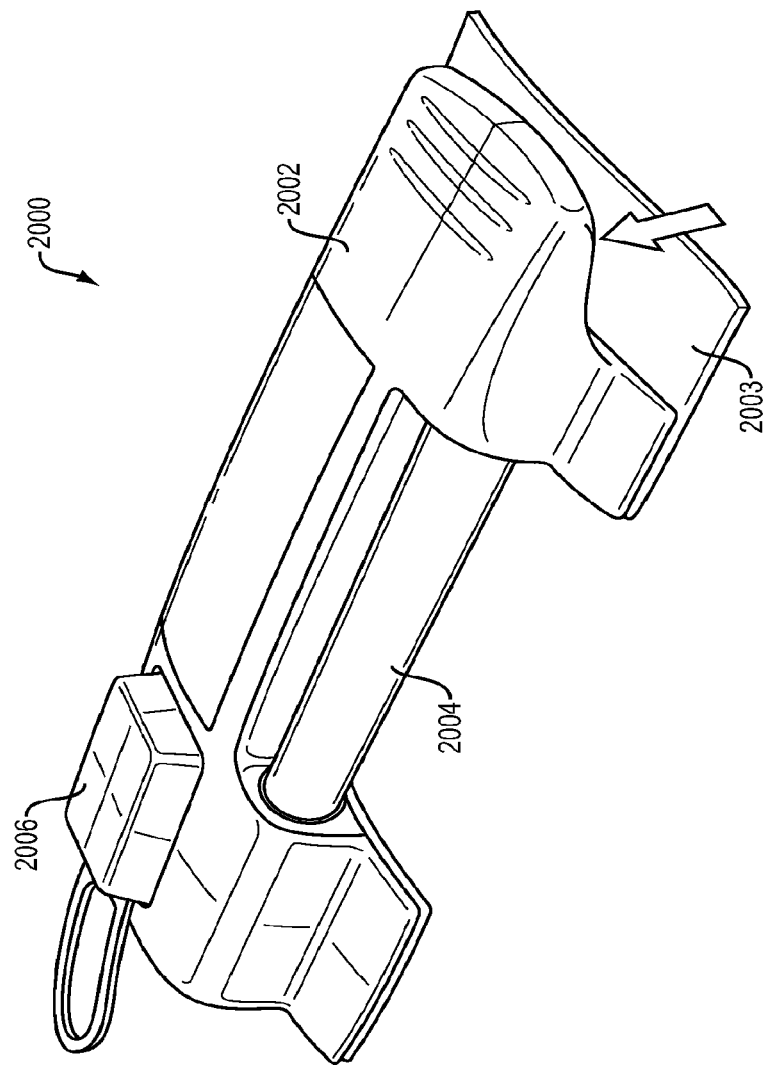
FIG. 20A illustrates a perspective view of an exemplary wearable automatic injection device.
Figure 20B:
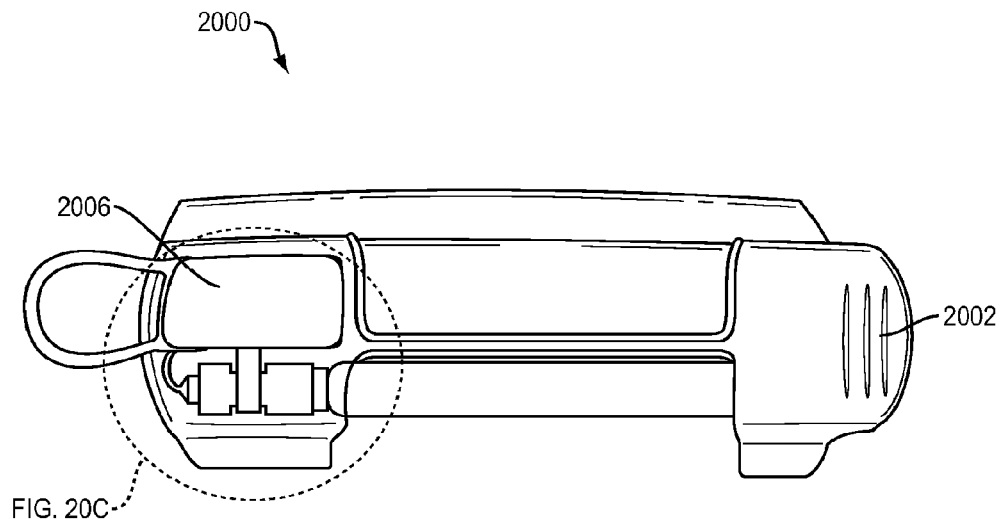
FIG. 20B illustrates a top view of the device of FIG. 20A.
Figure 20C:
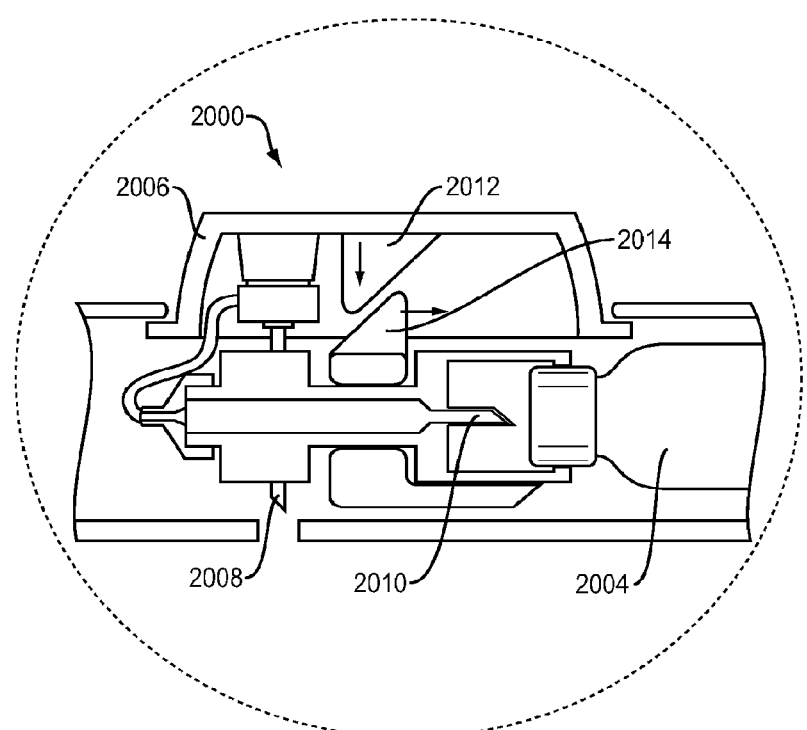
FIG. 20C illustrates a side view of the transfer mechanism of the device of FIG. 20A.

FIGS. 20A-20C illustrate an exemplary wearable automatic injection device including a cartridge assembly and an exemplary transfer mechanism. FIG. 20A illustrates a perspective view of the device. FIG. 20B illustrates a top view of the device. FIG. 20C illustrates a side view of the transfer mechanism of the device. The automatic injection device 2000 includes a housing 2002 having an adhesive layer 2003 for attachment at a patient contact region. The housing 2002 holds a cartridge 2004 in a stationary or moveable manner relative to the housing 2002. The cartridge 2004 is configured to hold a dose of a therapeutic agent.

An injection button 2006 is provided in the housing 2002 in the vicinity of the cartridge 2004. The injection button 2006 may hold or be coupled to an injection needle 2008 extending substantially at 90 degrees relative to the longitudinal axis of the cartridge 2004 and a syringe needle 2010 extending substantially parallel to the longitudinal axis of the cartridge 2004. The injection button 2006 may form or include a transfer mechanism that establishes fluid communication between the cartridge 2004 to the injection needle 2008 through the syringe needle 2010.

The injection button 2006 may include a housing engagement portion 2012 that engages with a housing portion 2014 when the injection button 2006 is pressed down during an injection in an injection state. In an exemplary embodiment illustrated in FIG. 20C, the engagement between the housing engagement portion 2012 and the housing portion 2014 causes the housing portion 2014 to move parallel to the longitudinal axis of the cartridge 2004 toward the distal end of the cartridge 2004, thus allowing the syringe needle 2010 to establish fluid communication with the barrel portion of the cartridge 2004. In another exemplary embodiment, the engagement between the housing engagement portion 2012 and the housing portion 2014 causes the cartridge 2004 to move parallel to the longitudinal axis of the cartridge 2004 toward the syringe needle 2010, thus allowing the syringe needle 2010 to establish fluid communication with the barrel portion of the cartridge 2004.

Other components in the device 2000 similar to the components in the device 1800 are described with reference to FIGS. 18A and 18B.

Figure 21A:
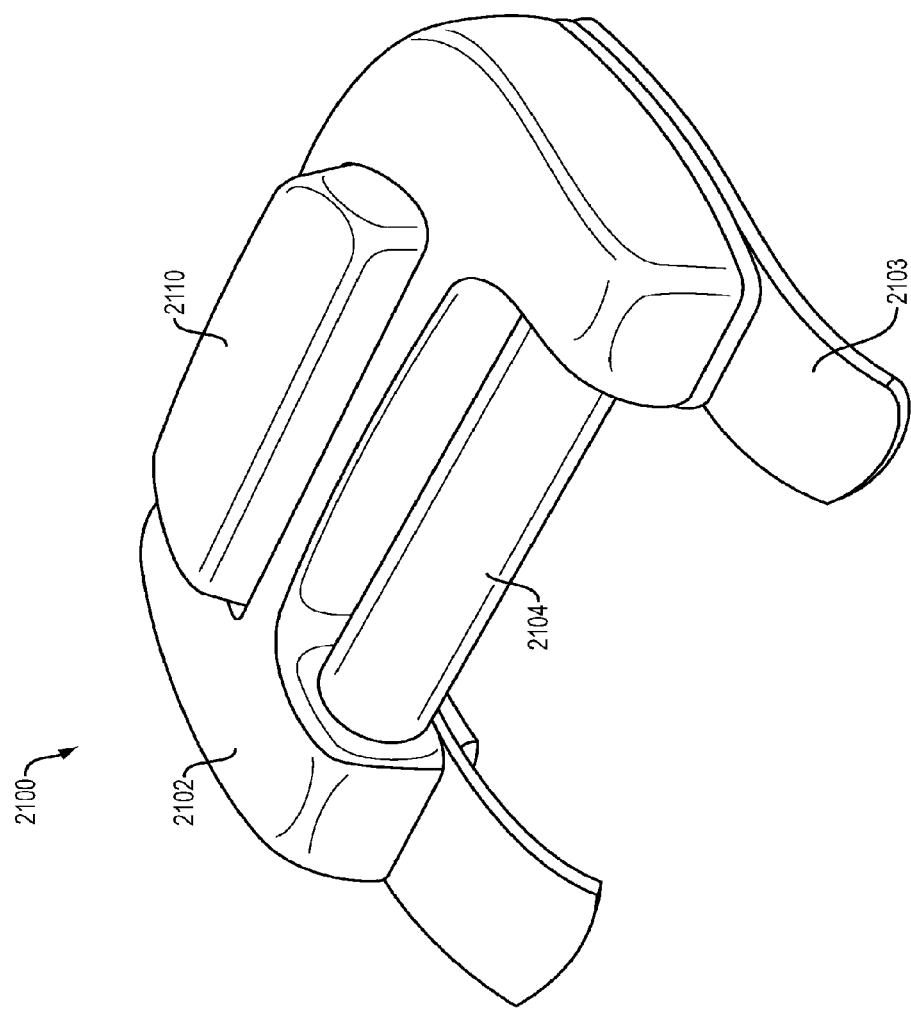
FIG. 21A illustrates a perspective view of an exemplary wearable automatic injection device including an exemplary cartridge assembly.
Figure 21B:
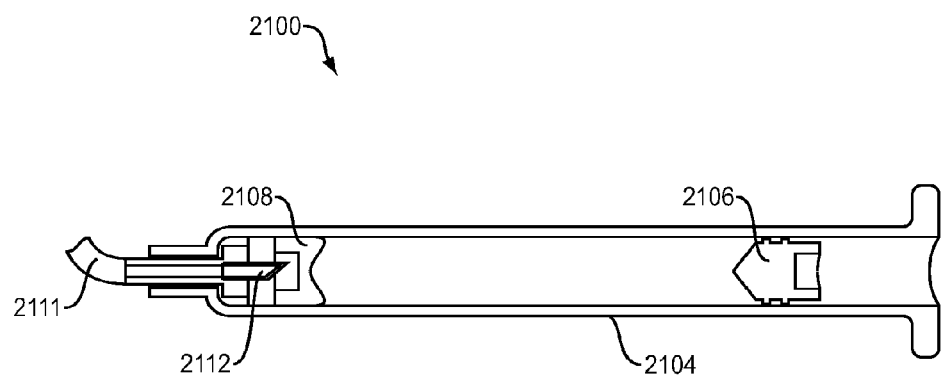
FIG. 21B illustrates a sectional view of the exemplary cartridge assembly of FIG. 21A taken along a longitudinal axis.
Figure 21C:
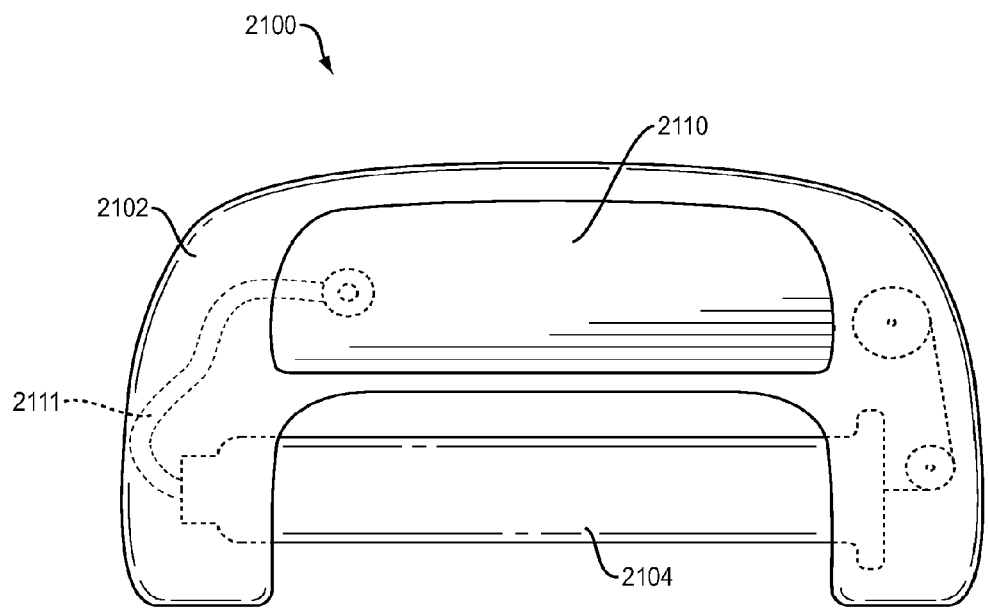
FIG. 21C illustrates a transparent top view of the exemplary device of FIG. 21A.

FIGS. 21A-21C illustrate an exemplary wearable automatic injection device including an exemplary cartridge assembly. FIG. 21A illustrates a perspective view of the exemplary wearable automatic injection device. FIG. 21B illustrates a sectional view of the cartridge assembly taken along a longitudinal axis. FIG. 21C illustrates a transparent top view of the transfer mechanism of the device. The automatic injection device 2100 includes a housing 2102 having an adhesive layer 2103 for attachment at a patient contact region. The housing 2102 holds a cartridge 2104 in a stationary or moveable manner relative to the housing 2102. The cartridge 2104 is configured to hold a dose of a therapeutic agent. A proximal end of the cartridge 2104 includes a bung 2106 and a distal end of the cartridge 2104 includes a septum 2108 that cooperatively seal the dose within the cartridge 2104.

An injection button 2110 is provided in the housing 2102 in the vicinity of the cartridge 2104. The injection button 2110 holds an injection needle at a proximal end that extends substantially at 90 degrees relative to the longitudinal axis of the cartridge 2104. The injection button 2110 is coupled to a transfer mechanism 2111 that holds a syringe needle 2112 in the vicinity of the cartridge 2104. The syringe needle 2112 extends substantially parallel to the longitudinal axis of the cartridge 2104. The transfer mechanism 2111 includes a fluid conduit to establish fluid communication between the cartridge 2104 to the injection needle 2108 through the syringe needle 2110. In a pre-injection state, the syringe needle 2112 may extend partly into a distal end of the cartridge 2104 but may be spaced from the septum 2108. In an injection state, the bung 2106 may be moved within the cartridge 2104 such that the fluid pressure in the cartridge 2104 moves the septum 2108 forward toward the syringe needle 2112. This causes the syringe needle 2112 to pierce the septum 2108 and establishes fluid communication between the cartridge 2104 and the injection needle through the syringe needle 2112.

Other components in the device 2100 similar to the components in the device 1800 are described with reference to FIGS. 18A and 18B.

Figure 22:
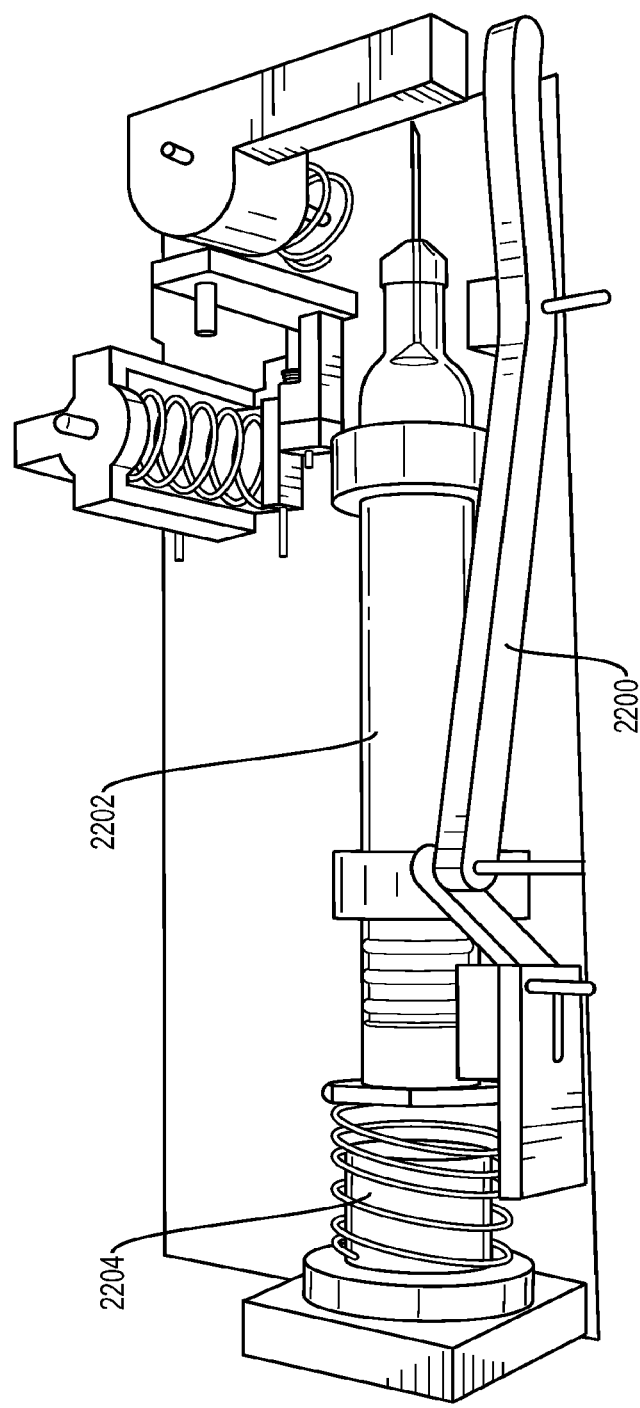
FIG. 22 illustrates an exemplary syringe or cartridge actuator that may be used to advance a barrel portion and/or the cartridge assembly from a retraction position to an extended position within the housing of a wearable automatic injection device.

FIG. 22 illustrates an exemplary syringe or cartridge actuator 2200 that may be used to advance a syringe 2202 or a cartridge assembly from a retraction position to an extended position within the housing of a wearable automatic injection device. A proximal end of the barrel portion and/or the cartridge assembly may be coupled to a biasing member 2204, for example, a drive spring, that applies a force on the barrel portion of the syringe and/or the cartridge assembly to move the barrel portion and/or the cartridge assembly toward a septum in a transfer mechanism (not pictured). The syringe or cartridge actuator 2200 may counter the biasing force of the biasing member, and may hold and lock the barrel portion and/or the cartridge assembly in a retracted position in a stable and reliable manner.

When triggered, the syringe or cartridge actuator 2200 may allow the barrel portion and/or the cartridge assembly to move forward toward the septum under the force of the biasing member. In an exemplary embodiment, the syringe or cartridge actuator 2200 may be configured and/or set to a certain distance to control the level of triggering force required to advance the barrel portion and/or the cartridge assembly from the retracted position to the extended position.

Any suitable trigger mechanism may be used to trigger the syringe or cartridge actuation systems. In an exemplary embodiment, the trigger mechanism may automatically trigger the syringe or cartridge actuation system when the wearable automatic injection device moves from a pre-injection state to an injection state. In an exemplary embodiment, the downward vertical movement of an injection button within the housing to provide a fluid path between the syringe or cartridge assembly and the injection needle may provide a trigger force to trigger the plunger actuation system. In another exemplary embodiment, the forward movement of the syringe or cartridge assembly within the housing to establish a fluid path between the syringe or cartridge assembly and the injection needle may provide a trigger force to trigger the syringe or cartridge system. In another exemplary embodiment, the syringe or cartridge system may be manually triggered by a user.

Before an injection in a pre-injection state, a needle cover, for example, a soft and rigid needle shield assembly (not pictured), provided at the distal end of the syringe may protectively cover the syringe needle. At this stage, since the syringe needle is covered with the needle cover, the distal end of the syringe has a first greater diameter. As such, the transfer mechanism including the septum is maintained in a vertically raised position above the needle cover, and the septum is not aligned with the syringe needle. When the needle cover is removed from the syringe in preparation for an injection (for example, manually by a user or by an automatic mechanism), the transfer mechanism is allowed to lower to a vertically lowered position since it is not longer kept displaced by the rigid needle shield, and the septum in the transfer mechanism is aligned with the syringe needle. The removal of the needle cover thus lowers the transfer mechanism from its raised position to its lowered position. The lowering of the transfer mechanism, in turn, applies a trigger force to the syringe or cartridge actuator 2200 and operates as the trigger mechanism for the syringe or cartridge actuator 2200.

Figure 23:
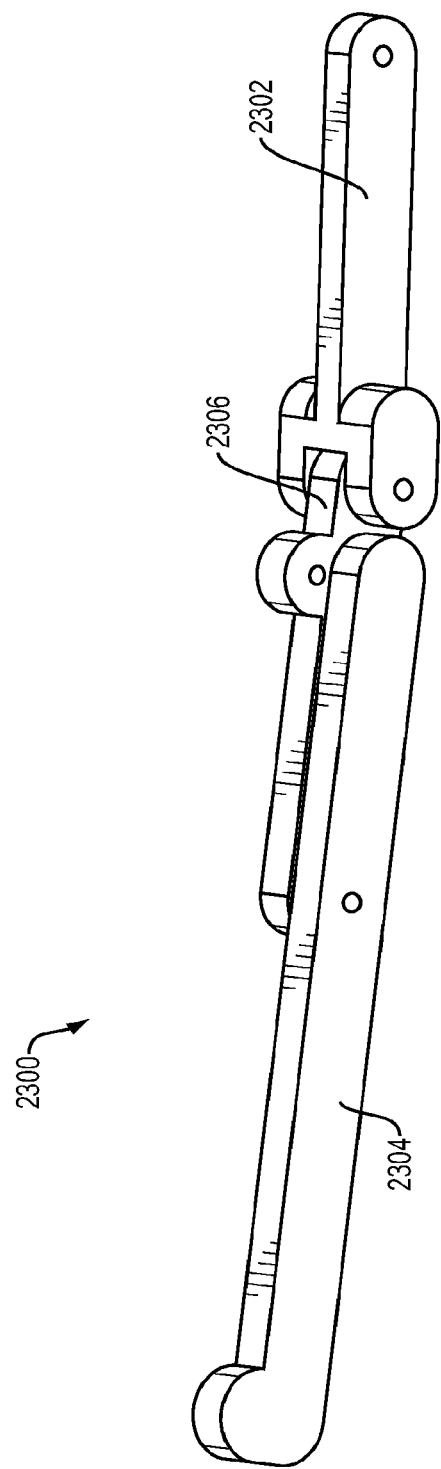
FIG. 23 illustrates an exemplary syringe or cartridge actuator including a first portion, a second portion and a hinge portion provided between the first and second portions.

FIG. 23 illustrates an exemplary syringe or cartridge actuator 2300 including a first portion 2302, a second portion 2304 and a hinge portion 2306 provided between the first and second portions. The hinge portion 2306 allows the first and second portions to rotate about the hinge relative to each other. In different rotational configurations, the first and second portions may have exemplary angles of between about 0 degrees and about 180 degrees between each other. The actuator 2300 may be coupled to the syringe and to the septum and/or the transfer mechanism. When the septum and/or transfer mechanism is in its first raised position, the actuator 2300 may hold the syringe in place in its retracted position. When the septum and/or transfer mechanism is in its second lowered position, the actuator 2300 may release the syringe so that the biasing member may push the syringe forward to its extended position in order to pierce the septum.

IV. EXEMPLARY PLUNGER ACTUATION SYSTEMS AND NEEDLE RETRACTION SYSTEMS

Exemplary embodiments provide plunger actuation systems for actuating a bung in a barrel portion of a wearable automatic injection device so that the bung moves forwardly within the barrel portion and expels a dose of a therapeutic agent contained in the barrel portion. Any suitable trigger mechanism may be used to trigger the plunger actuation systems. In an exemplary embodiment, the trigger mechanism may automatically trigger the plunger actuation system when the wearable automatic injection device moves from a pre-injection state to an injection state. In an exemplary embodiment, the downward vertical movement of an injection button within the housing to provide a fluid path between the syringe or cartridge assembly and the injection needle may provide a trigger force to trigger the plunger actuation system. In another exemplary embodiment, the forward movement of the syringe or cartridge assembly within the housing to establish a fluid path between the syringe or cartridge assembly and the injection needle may provide a trigger force to trigger the plunger actuation system. In another exemplary embodiment, the plunger actuation system may be manually triggered by a user.

Certain other exemplary embodiments provide plunger actuation devices and systems that cause actuation of the syringe plunger at a slow rate in order to deliver the therapeutic agent to a patient at a slow rate. Exemplary slow embodiments may deliver therapeutic agent volumes of about 0.1 milliliters to about 1 milliliter or more in about five minutes to about thirty minutes, although exemplary delivery rates are not limited to this exemplary range.

Exemplary embodiments may provide a linear delivery profile for the therapeutic agent so that the delivery rate is substantially constant over time. In some cases, a linear delivery profile may reduce discomfort experienced by the patient.

Figure 24:
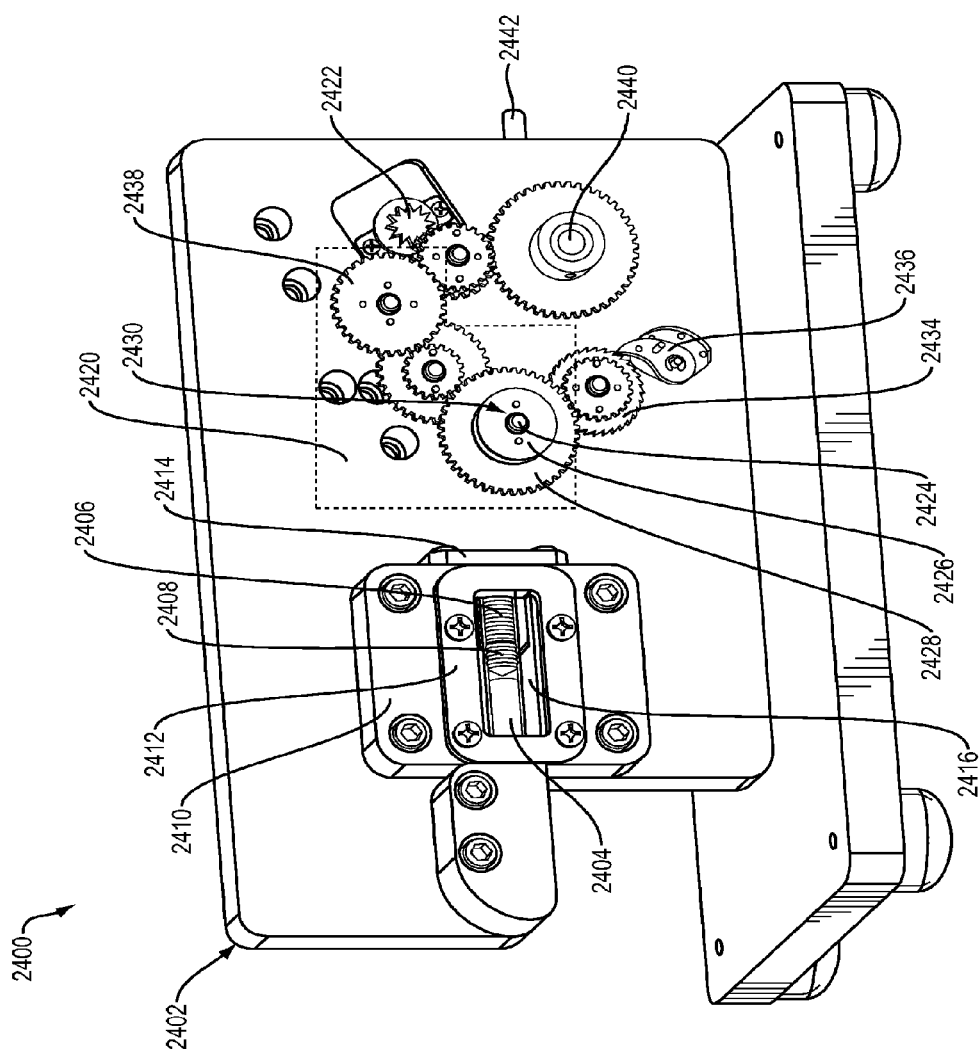
FIG. 24 illustrates a schematic of a portion of an exemplary automatic injection device including a plunger actuation mechanism that employs a fusee and a viscous damping mechanism.

FIG. 24 illustrates a schematic of a portion of an exemplary automatic injection device 2400 including a plunger actuation mechanism that employs a fusee and a viscous damping mechanism. The wearable automatic injection device 2400 includes a housing 2402 having a platform 2410 that is a mechanical structure for holding a syringe or cartridge assembly 2404 in place within the wearable automatic injection device 2400. The syringe or cartridge 2404 includes a barrel portion for holding a dose of a therapeutic agent and a bung 2408 for sealing the dose within the barrel portion. A plunger actuation mechanism 2406 is provided for moving the bung 2408 within the barrel portion for expelling the dose from the barrel portion. A damping mechanism 2422, for example, a viscous damper, is provided to regulate the motion of the bung 2408 so that the therapeutic agent is delivered in a linear fashion, i.e., at a substantially constant flow rate. A gear train 2420 including one or more gears may be provided to couple the plunger actuation mechanism 2406 to the damping mechanism 2422. The gear train 2420 may include any number of suitable gears to provide any suitable gearing ratio.

The platform 2410 of the wearable automatic injection device 2400 may be stationary or moveable. In an exemplary embodiment, the platform 2410 may be a substantially box-shaped or cylindrical structure with an internal space for accommodating the syringe or cartridge 2404. The peripheral walls surrounding the internal space may be configured to hold a syringe or a cartridge assembly 2404 in place. The platform 2410 may include one or more clamping mechanism 2412 for holding the syringe or cartridge 2404 in place. The platform 2410 may also include a flange bearing 2414 provided at the proximal end of the syringe or cartridge 2404. A flange provided at the proximal end of the syringe or cartridge 2404 may slide backward against the flange bearing 2414.

In an exemplary embodiment, the platform 2410 may hold the syringe or cartridge 2404 stationary within and relative to the platform 2410. In another exemplary embodiment, the platform 2410 may allow the syringe or cartridge 2404 to move relative to the platform 2410, for example, toward or away from a fluid transfer mechanism (not pictured). In this exemplary embodiment, the internal space of the platform 2410 may include one or more grooves, tracks or channels for facilitating the movement of the syringe or cartridge 2404 within the platform 2410. In an exemplary embodiment, the platform 2410 may include a window 2416, for example, a cutout or a transparent portion, in order to allow the patient to view the syringe or cartridge 2404.

One or more plunger actuators 2406 may be provided in the vicinity of the syringe or cartridge 2404 for storing energy and providing a force for driving a bung 2408 within the syringe or cartridge 2404 toward the distal end of the syringe or cartridge 2404. In an exemplary embodiment, a plunger actuator 2406, for example, a helical compression spring, may be used to drive the bung 2408. The plunger actuator 2406 may be provided at least partly within the syringe or cartridge 2404. Before an injection in a pre-injection state, the plunger actuator 2406 may be maintained in a compressed state. At the beginning of an injection or during an injection in an injection state, the plunger actuator 2406 may be allowed to expand from the compressed state to a released state. The expansion of the plunger actuator 2406 may push the bung 2408 toward the distal end of the syringe or cartridge 2404, thus expressing the therapeutic agent from the syringe or cartridge 2404. Advantageously, the configuration of the plunger actuator 2406 within the syringe or cartridge 2404 does not add to the length of the housing required to hold the syringe or cartridge 2404. However, in some exemplary embodiments, the plunger actuator 2406 may not provide a constant force to drive the bung 2408.

In another exemplary embodiment, a spiral spring may be used to drive the bung 2408. The spiral spring may be provided outside but alongside the syringe or cartridge 2404 of within the platform 2410, which may add to the space requirement of the housing 2402. Before an injection in a pre-injection state, the spring may be maintained in a compressed state. At the beginning of an injection or during an injection in an injection state, the spring may be allowed to expand from the compressed state to a released state. The expansion of the spring may push the bung 2408 toward the distal end of the syringe or cartridge 2404, thus expressing the therapeutic agent from the syringe or cartridge 2404. Advantageously, the spiral spring may provide a substantially constant force to drive the bung 2408.

One or more damping mechanisms may be provided for regulating the release of energy in the plunger actuator 2406 in order to control the delivery rate and/or the delivery time for delivering the therapeutic agent. In an exemplary embodiment, to achieve a slow and/or controlled delivery, the plunger actuator 2406 is prevented from accelerating without resistance from its compressed state to a released state. The movement of the plunger actuator 2406 may be maintained at a constant speed, for example, by providing linear damping values. Any suitable mechanism may be used to provide resistance against the acceleration of the plunger actuator 2406. In an exemplary embodiment, a rotary viscous damper 2422 may be used to resist the acceleration of the plunger actuator 2406. The viscous damper 2422 may use one or more viscous fluids, for example, silicon grease, to provide resistance. The viscous damper 2422 may include a stationary housing holding a solid rotating element called a "rotor." The outer circumference of the rotor may include a plurality of teeth configured to be engaged by the teeth of a gear in the gear train 2420. The rotor may be surrounded by a thin film of a viscous fluid that is sealed inside the housing. The rotation of the rotor may provide resistance against the acceleration of the plunger actuator 2406 by shearing the viscous fluid. In an exemplary embodiment, the viscous damper 2422 may be replaced with a different viscous damper providing a different level of damping.

The force required to turn the rotary viscous damper 2422 is described with reference to a coordinate system x where x=0 is at the free length of a spring. If m is the inertia of the system, c is the damping coefficient, and k is the spring constant, then:

$$m\ddot{x} + c\dot{x} + kx = 0 \Rightarrow \ddot{x} = \frac{1}{m}[-c\dot{x} - kx] \quad (1)$$

$$\ddot{x} + 2\zeta\omega_0\dot{x} + \omega_0^2 x = 0 \quad (2)$$

where natural frequency:

$$\omega_0 = \sqrt{\frac{k}{m}} \quad (3)$$

and where damping ratio:

$$\zeta = \frac{c}{2\sqrt{mk}} \quad (4)$$

If the damping is driven by a rotary damper, the torque T required to turn the dampener may be assumed to be linearly proportional to the angular velocity by some constant C:

$$T = C_\theta \dot{\theta} \quad (5)$$

If the rotary damper is coupled to the plunger actuator by a gear train of reduction N and a spool of diameter D, then:

$$\dot{x} = \frac{D}{2N}\dot{\theta} \therefore \dot{\theta} = \frac{2N\dot{x}}{D} \text{ and} \quad (6)$$

$$T_{spool} = \frac{F_x D}{2} = NT = NC_\theta\dot{\theta} = \frac{2N^2 C_\theta}{D}\dot{x}$$

$$\therefore F_x = \frac{4N^2 C_\theta}{D^2}\dot{x} \therefore c_x = \frac{4N^2 C_\theta}{D^2}$$

In another exemplary embodiment, an escapement may be used to resist the acceleration of the plunger actuator 2406. The escapement may use a known period of oscillation of a balance wheel and a spiral hairspring to incrementally release the energy of a main spring. An escapement may provide a dependable design and linearity in the release of the energy. In another exemplary embodiment, a runaway escapement may be used to resist the acceleration of the plunger actuator 2406. In another exemplary embodiment, a swiss lever escapement may be used to resist the acceleration of the plunger actuator 2406.

A gear train 2420 may be provided for coupling the plunger actuator 2406 to the regulating device 2422, i.e., the viscous damper or the escapement. The gear train 2420 may include a shaft 2424 may be coupled to the housing 2402 of the wearable automatic injection device 2400 with a close slip fit. In an exemplary embodiment, the shaft 2424 may support a cylindrical structure 2426, for example, a spool or a shaft, and a gear 2428 that is provided below the spool 2426. In an exemplary embodiment, the spool 2426 may be a cam spool or a fusee. One or more snap rings 2430 may be used to retain the spool 2426 and the gear 2428 on the shaft 2424. The spool 2426 and the gear 2428 may be provided around the shaft 2424 such that the centers of rotation of the spool 2426 and the gear 2428 are aligned with each other and with the shaft 2424. The spool 2426 and the gear 2428 may be cooperatively coupled to each other and to the shaft 2424 such that the gear 2428 and the spool 2426 may rotate together on the shaft 2424. In an exemplary embodiment, the spool 2426 and the gear 2428 may be taken off from the shaft 2424 and replaced with a different set of spools and gears. The plunger actuator 2406 may be coupled to the gear train, for example, the spool 2426, using one or more tethers or cables 2442.

In an exemplary embodiment, the spool 2426 may be any suitable rotating mechanism including, but not limited to, a constant diameter spool, a cam spool or fusee. If a cam or fusee is used, the outer diameter of the cam or fusee may vary with linear displacement D. Taking the equation for the linear damping coefficient and holding the gear reduction N and the rotary damping coefficient constant yields:

$$c_x = \frac{4N^2 C_\theta}{D^2} = \frac{a}{D_x^2} \quad (7)$$

where a is constant. Substituting the above into the equation of motion and assuming that the first derivative of $\chi$ is constant, yields:

$$D_x = \sqrt{\frac{-a\dot{x}}{k}} x^{\frac{1}{2}} = C_1 x^{-b} + C_2 \quad (8)$$

where $C_1$, $C_2$ and b are constants that may be varied in order to make the velocity approximately constant. Plugging this variable into the equation of motion and solving for x as a function of time, x may be substituted into equation (8) to determine D as a function of time, $D_t$. The instantaneous velocity may be represented as:

$$\dot{x} = \frac{D_t}{2}\dot{\phi} \Rightarrow \dot{\phi} = \frac{2\dot{x}}{D_t} \Rightarrow \phi_t = \int_0^t \frac{2\dot{x}}{D_t} dt \quad (9)$$

where $\phi$ is the angular position of the cam or fusee. $D_t$ and $\phi_t$ are the polar coordinates of the cam profile.

Exemplary embodiments may couple the plunger actuator 2406 to a bung in the barrel portion of a syringe or cartridge using any suitable mechanism. If a compression spring is used as the plunger actuator 2406, one or more tethers or cables may be used to couple the plunger actuator 2406 to the bung. If a spiral spring is used as the plunger actuator 2406, spur gearing may be used to couple the plunger actuator 2406 to the bung. The torque generated the spiral spring by may be coupled to the bung using a pinion to push a flexible rack around the corner of the syringe or cartridge.

In an exemplary embodiment, the spool 2426 may be in contact with and/or coupled to a ratchet 2434 and pawl 2436. A torsion spring (not pictured) may be provided below the pawl 2436 to preload the pawl 2436 against the ratchet 2434. When the spool 2426 is being wound during assembly of the wearable automatic injection device 2400, the torsion spring may be held in place. After the spool 2426 is wound and before an injection in a pre-injection state, the ratchet 2434 and pawl 2436 may hold the spool 2426 in place and prevent rotational movement of the spool 2426. This holds the tether 2442 in place which, in turn, maintains the plunger actuator 2406 in its compressed state, preventing movement of the plunger. At the beginning of an injection or during an injection in an injection state, the pawl 2436 may be rotated to disengage the ratchet 2434, for example, by a user or automatically upon the pressing of an injection button. This allows the spool 2426 to rotate under the pulling force of the tether 2442 caused by the spring force of the plunger actuator 2406. The spring force of the plunger actuator 2406 pulls the tether 2442 toward the distal end of the syringe or cartridge 2404.

One or more additional gears may be provided in contact with and/or coupled to the gear coupled to the spool 2426, thus forming a gear train 2438. Each gear in the gear train 2438 may be provided on a corresponding shaft coupled to the housing 2402 of the wearable automatic injection device 2400. In an exemplary embodiment, the gears in the gear train 2438 may be taken off from their corresponding shafts and replaced with a different set of gears. One of ordinary skill in the art will recognize that other exemplary devices may include fewer or more gears.

The gear train 2438 may be coupled to the viscous damper 2422 or an escapement that resists acceleration of the bung 2408. That is, the gear train may couple the viscous damper 2422 or an escapement to the tether 2442 holding the bung 2408 so that, when the bung 2408 is moved under the force of the plunger actuator 2406, acceleration of the plunger actuator 2406 is resisted by the viscous damper 2422 or the escapement.

In an exemplary embodiment, the gear train 2438 may be coupled to an encoding device 2440, for example, a rotary encoder, that detects and logs the angular displacement or position of the gear train and the corresponding time. A computing device may be associated with the wearable automatic injection device to determine the position of the syringe plunger based on the data obtained by the encoding device 2440. The computing device may also determine the flow rate of the therapeutic agent from the syringe or cartridge 2404 and the corresponding time based on the data obtained by the encoding device 2440. The computing device may be provided integrally with the encoding device 2440 or separately from the encoding device 2440. During assembly and testing of the wearable automatic injection device, the encoding device 2440 may be used to evaluate different gear trains, viscous dampers and biasing elements, validate mathematical models and account for variables not addressed in the mathematical models. During use of the wearable automatic injection device to perform an injection, the encoding device 2440 may be used to indicate one or more conditions to the user, for example, the flow rate of the therapeutic agent, malfunction of the device (for example, if the flow rate is too high or too low), and the like.

Figure 25:
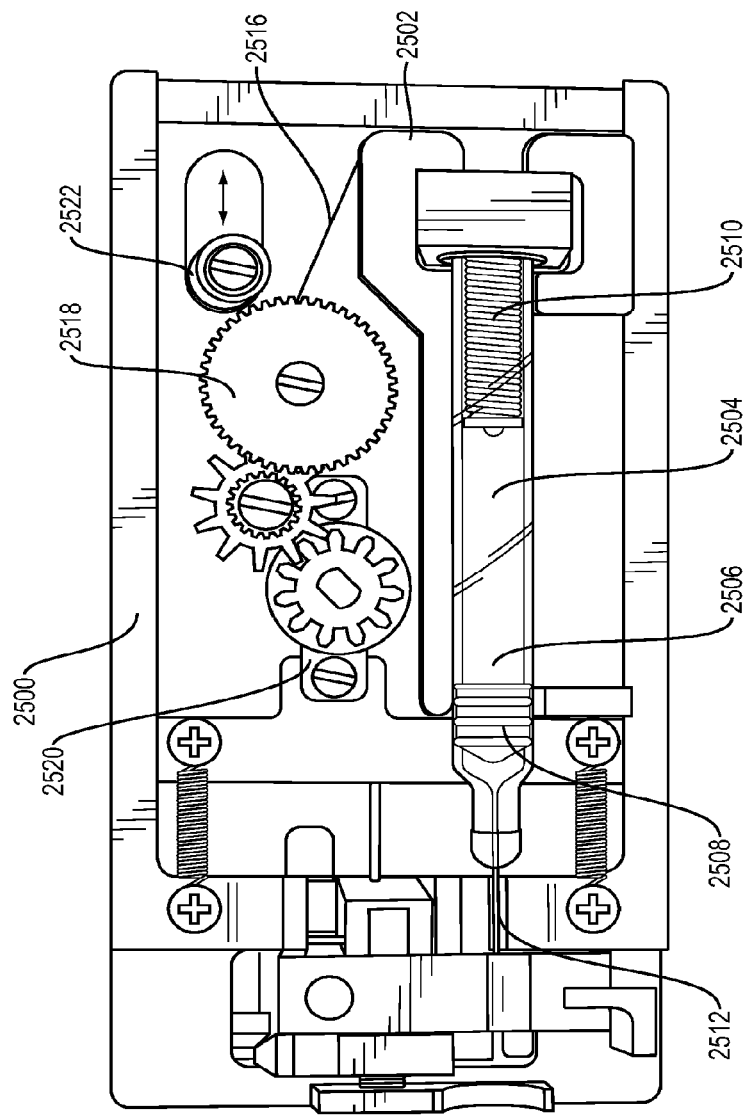
FIG. 25 illustrates a wearable automatic injection device may include a platform, a slideable carriage coupled to the platform, and a cartridge assembly mounted on the slideable carriage.
Figure 26:
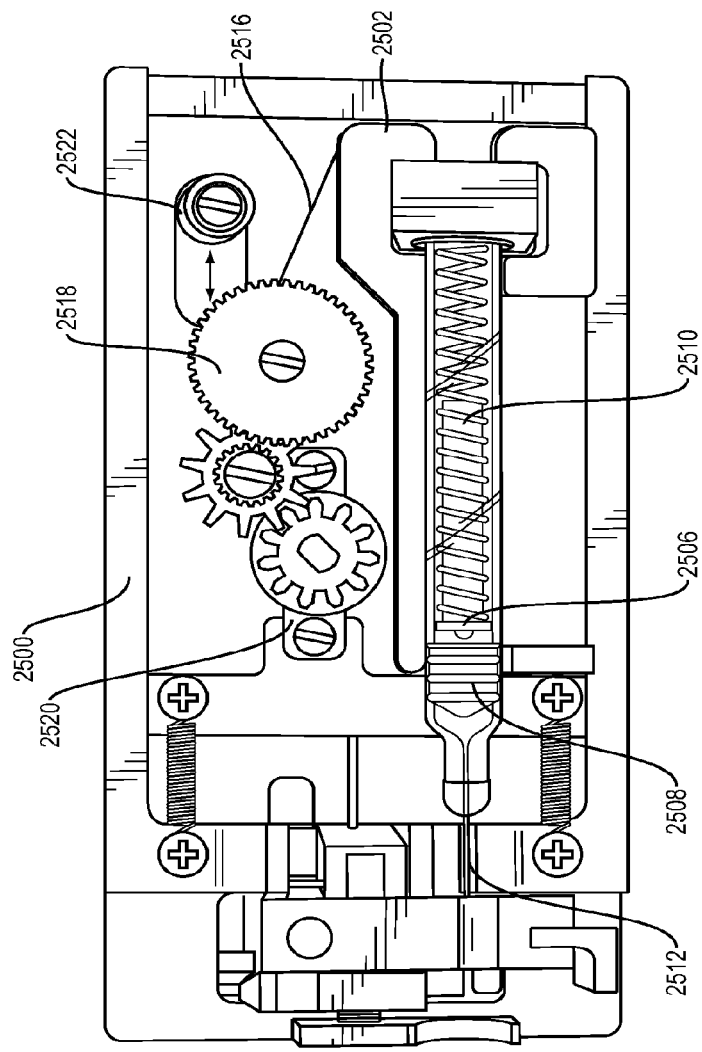
FIG. 26 illustrates a wearable automatic injection device may include a platform, a slideable carriage coupled to the platform, and a cartridge assembly mounted on the slideable carriage.

In an exemplary embodiment illustrated in FIGS. 25 and 26, a wearable automatic injection device may include a syringe assembly moveable relative to a platform in the device. The wearable automatic injection device includes a platform 2500, a slideable carriage 2502 coupled to the platform 2500, and a syringe 2504 mounted on the slideable carriage 2502. A distal end of the syringe 2504 may be coupled to a syringe needle 2512. The syringe 2504 may include a barrel portion 2506 containing a dose of a therapeutic agent sealed by a bung 2508. A plunger actuator 2510 may be provided in the vicinity or in contact with the bung 2508 for moving the bung 2508 forwardly within the barrel portion 2506. In an exemplary embodiment, the plunger actuator 2510 may include a biasing mechanism coupled by a tether to a gear train and thereby to a damping mechanism.

The device may also include an injection button bearing an injection needle (not pictured) and including a pierceable septum that may be pierced by the syringe needle 2512. The septum may be coupled directly or through a conduit to the injection needle such that, when pierced by the syringe needle 2512, the septum establishes fluid communication between the barrel portion 2506 and the injection needle.

In an exemplary embodiment, in a pre-injection state, the syringe needle 2512 may already pierce the septum and be in fluid communication with the injection needle. During an injection in an injection state, the dose of the therapeutic agent may be expelled from the barrel portion 2506 when the plunger actuator 2510 is activated to move the bung 2508 forwardly within the barrel portion 2506. In this embodiment, the carriage 2502 may be stationary on the platform 2500.

In another exemplary embodiment, in a pre-injection state, the syringe needle 2512 may be spaced from the septum and may not be in fluid communication with the injection needle. During an injection in an injection state, the syringe 2504 may be moved forwardly within and relative to the platform 2500 toward the septum in order to pierce the septum with the syringe needle 2512. In this exemplary embodiment, the carriage 2502 may be moveable and may move relative to the platform 2500 toward the septum.

In an exemplary embodiment, a tether 2516 may be used to couple the plunger actuator 2510 to a gear train 2518. The gear train 2518 may in turn be coupled to a damping mechanism 2520 for providing a linear delivery profile of the therapeutic agent. In a pre-injection state, a lockout mechanism 2522 may hold the gear train 2518 in place and prevent rotation of the gears. This causes the tether 2516 to hold the plunger actuator 2510 in place and prevents release of the plunger actuator 2510, thereby preventing movement of the bung 2508. During an injection in an injection state, the lockout mechanism 2522 may be released, for example, manually by a user or automatically, thereby allowing the gears 2518 to rotate under the biasing force of the plunger actuator 2510. This may allow the moveable carriage 2502 to automatically move toward the septum, which results in the syringe needle 2512 piercing the septum. The bung 2508 may also move within the barrel portion 2506 toward the septum under the biasing force of the plunger actuator 2510 to expel the dose through the syringe needle 2512.

Figure 27:
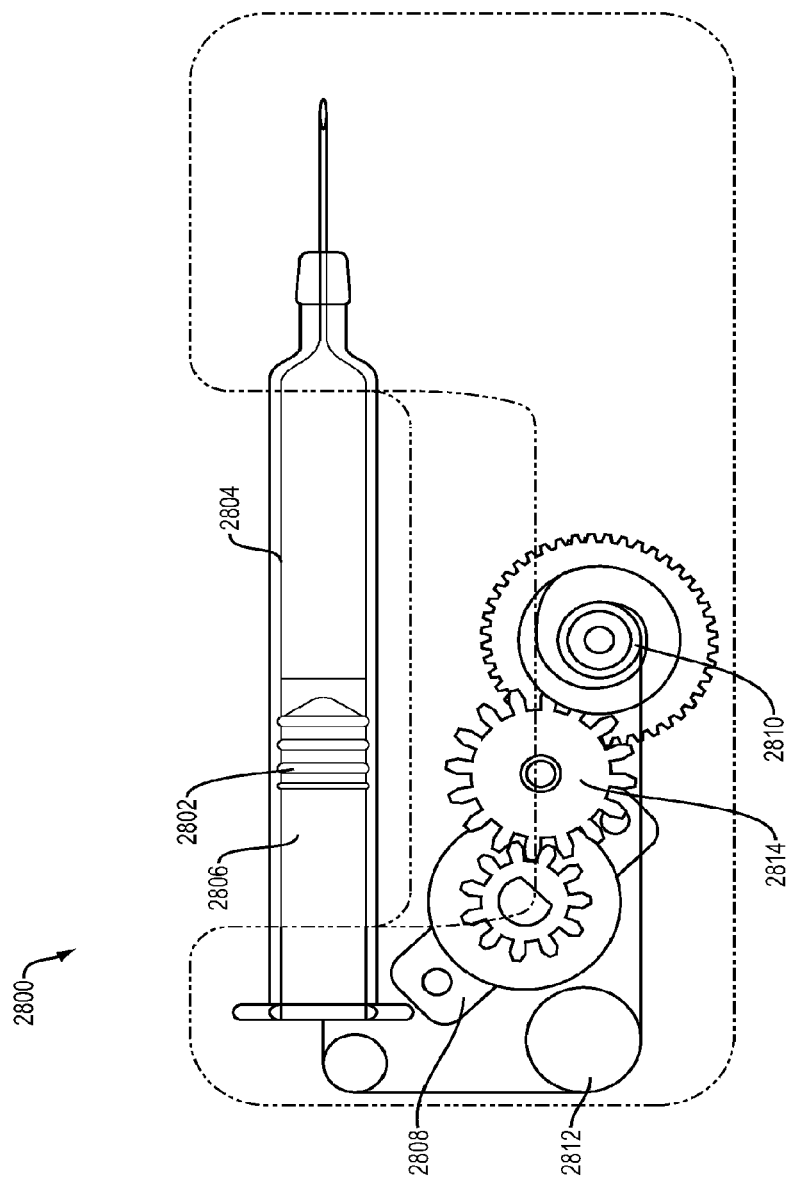
FIG. 27 is a top view through a cover of an exemplary automatic injection device including a plunger actuation mechanism for automatically actuating a bung in a barrel portion.
Figure 28:
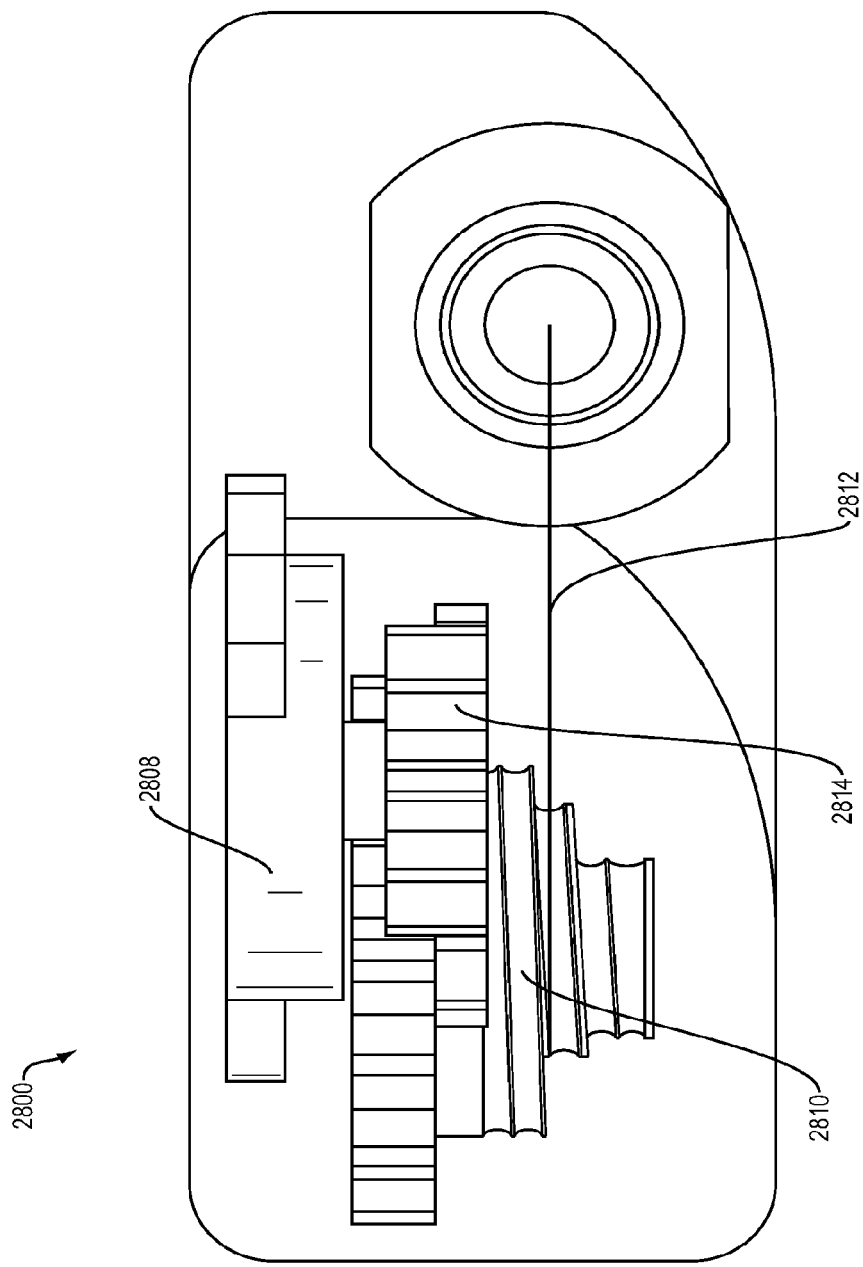
FIG. 28 is a side view of the exemplary automatic injection device of FIG. 27 showing a fusee and a damping mechanism.
Figure 29:
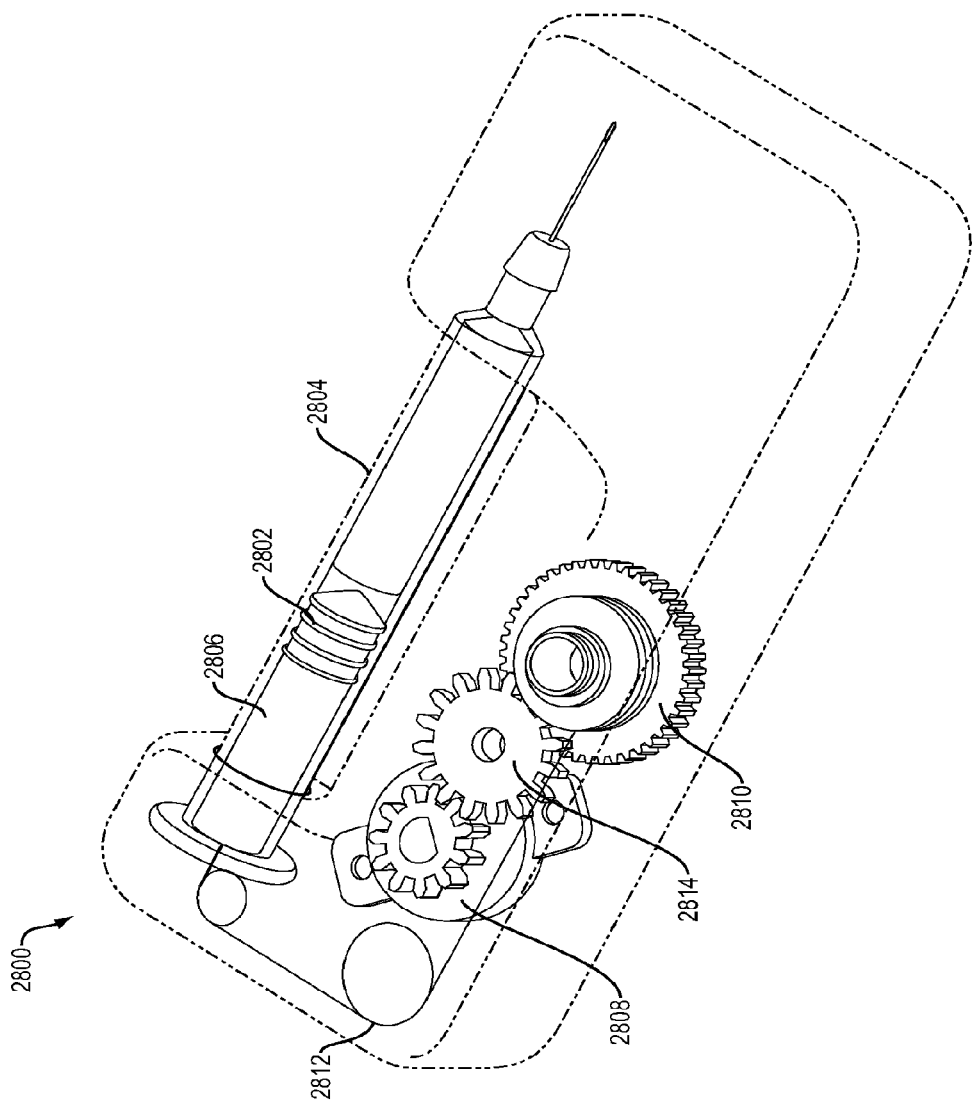
FIG. 29 is a perspective view through a cover of the exemplary automatic injection device of FIG. 27.

FIGS. 27-29 illustrate a schematic of a portion of an exemplary automatic injection device that may include a syringe assembly that is stationary relative to the housing of the device. The wearable automatic injection device 2800 includes a plunger actuation mechanism for automatically actuating a bung 2802 in a barrel portion 2804. FIG. 27 is a top view through a cover of the device 2800. FIG. 28 is a side view of the device 2800. FIG. 29 is a perspective view through a cover of the device 2800.

The plunger actuation mechanism may include a biasing mechanism 2806 that operates as the plunger actuator. In an exemplary embodiment, one or more tethers or cables 2812 may be used to couple the biasing mechanism 2806 to a stage 3 gear 2810, for example a fusee, that unwinds to allow the biasing mechanism 2806 to expand. A stage 1 damper 2808, for example, a viscous damper or an escapement, regulates the movement of the bung 2802 during an injection in an injection state in order to achieve a linear flow rate of the therapeutic agent. One or more stage 2 gears and pinions 2814 may be used to couple the stage 3 gear 2810 and the stage 1 damper 2808.

Table 7 summarizes exemplary features of an exemplary stage 1 damper, an exemplary stage 2 gear, an exemplary stage 2 pinion and an exemplary stage 3 gear that may be used in exemplary automatic injection devices.

TABLE 7

Exemplary features of exemplary plunger actuation components

|  | Stage 3 Gear | Stage 2 Pinion | Stage 2 Gear | Stage 1 Damper |
|---|---|---|---|---|
| Diametral pitch | 72 teeth/in | 72 teeth/in | 31.75 teeth/in | 31.75 teeth/in |
| Number of teeth | 50 teeth | 18 teeth | 16 teeth | 11 teeth |
| Face width | 0.100 in | 0.100 in | 0.050 in | 0.118 in |
| Tooth profile | 14.5 deg | 14.5 deg | 14.5 deg | 14.5 deg |
| Material | Nylon | Nylon | Nylon | Acetal |
| Pitch diameter | 0.694 in | 0.250 in | 0.504 in | 0.346 in |
| Circular pitch | 0.044 in/tooth | 0.044 in/tooth | 0.099 in/tooth | 0.099 in/tooth |
| Yield strength | 11.8 ksi | 11.8 ksi | 11.8 ksi | 10.2 ksi |
| Lewis form factor | 0.346 | 0.270 | 0.255 | 0.192 |
| Torque | 8.5 oz-in | 3.1 oz-in | 3.1 oz-in | 2.1 oz-in |
| Tangential force | 1.53 lbf | 1.53 lbf | 0.76 lbf | 0.76 lbf |
| Radial force | 0.39 lbf | 0.39 lbf | 0.20 lbf | 0.20 lbf |
| Safety factor | 3.71 | 2.90 | 6.25 | 9.62 |
| Total gearing | 4.04 | | | |

Failure analysis was performed on the exemplary plunger actuation mechanism. In an exemplary embodiment, the gear train (including the stage 2 gear) is designed assuming a Lewis bending failure mode which assumes that the gear tooth is a simple cantilever with tooth contact occurring at the tip. The results of the failure analysis summarized in Table 7 indicate that the minimum factor of safety for the gear train is 3 and that the total gear ratio is 4.04.

Figure 30:
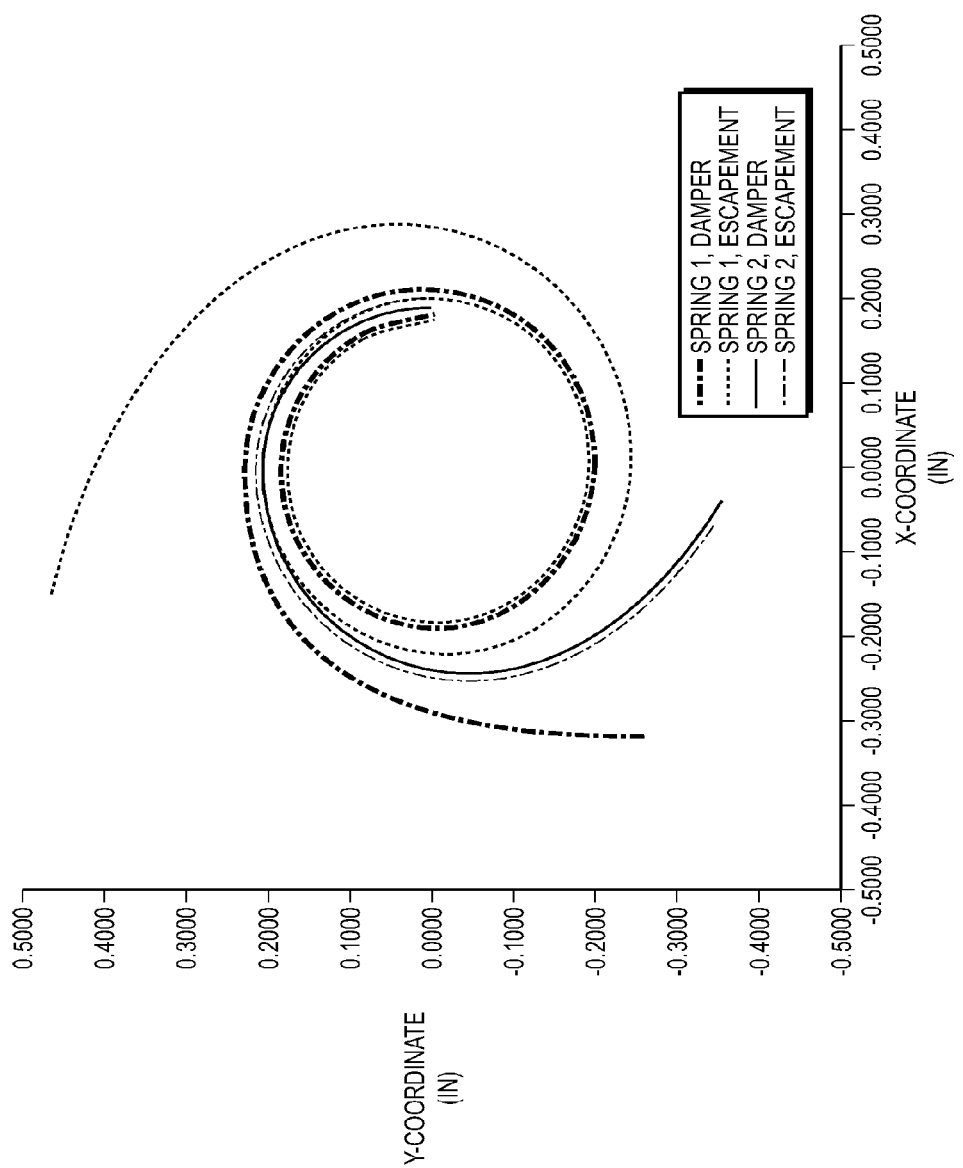
FIG. 30 illustrates x and y coordinates (in inches) of cam profiles for: (i) the combination of spring 1 and a viscous damper, (ii) the combination of spring 1 and an escapement, (iii) the combination of spring 2 and a viscous damper, and (iv) the combination of spring 2 and an escapement.

Different combinations of different types of plunger actuators (spring 1 and spring 2), spools (constant-diameter spool or cam spool), and damping mechanisms (viscous damper or escapement) were tested to determine their effect on the delivery rate of the therapeutic agent. FIG. 30 illustrates x and y coordinates (in inches) of cam profiles for: (i) the combination of spring 1 and a viscous damper, (ii) the combination of spring 1 and an escapement, (iii) the combination of spring 2 and a viscous damper, and (iv) the combination of spring 2 and an escapement.

Figure 31:
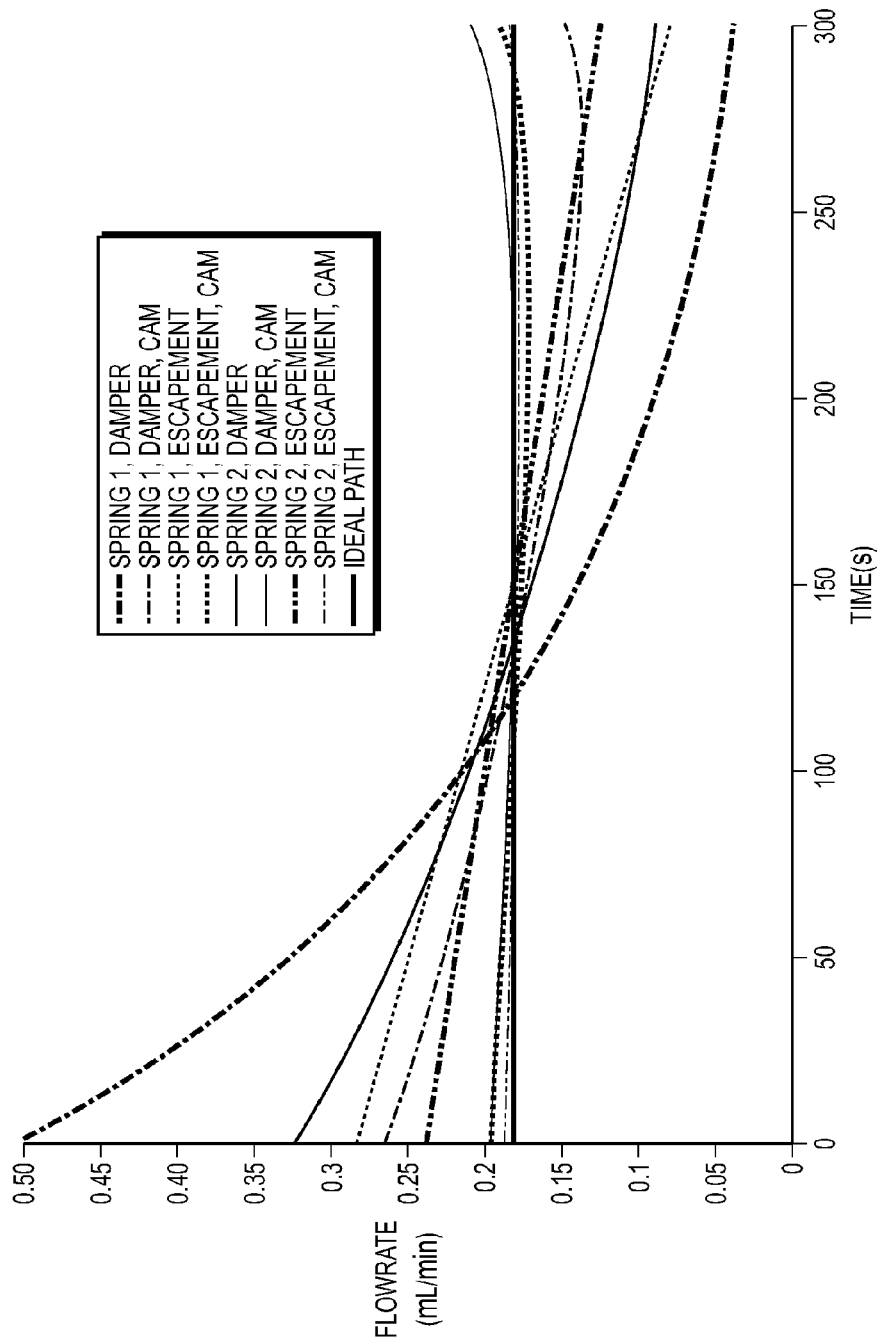
FIG. 31 illustrates a graph of therapeutic agent flow rates (in milliliters per minute) versus time (in seconds) delivered by: (i) the combination of spring 1 and a viscous damper, (ii) the combination of spring 1, a viscous damper and a cam spool, (iii) the combination of spring 1 and an escapement, (iv) the combination of spring 1, an escapement and a cam spool, (v) the combination of spring 2 and a viscous damper, (vi) the combination of spring 2, a viscous damper and a cam spool, (vii) the combination of spring 2 and an escapement, (viii) the combination of spring 2, an escapement and a cam spool, and (ix) and an ideal flow rate in which the therapeutic agent is delivered at a substantially constant rate.
Figure 32:
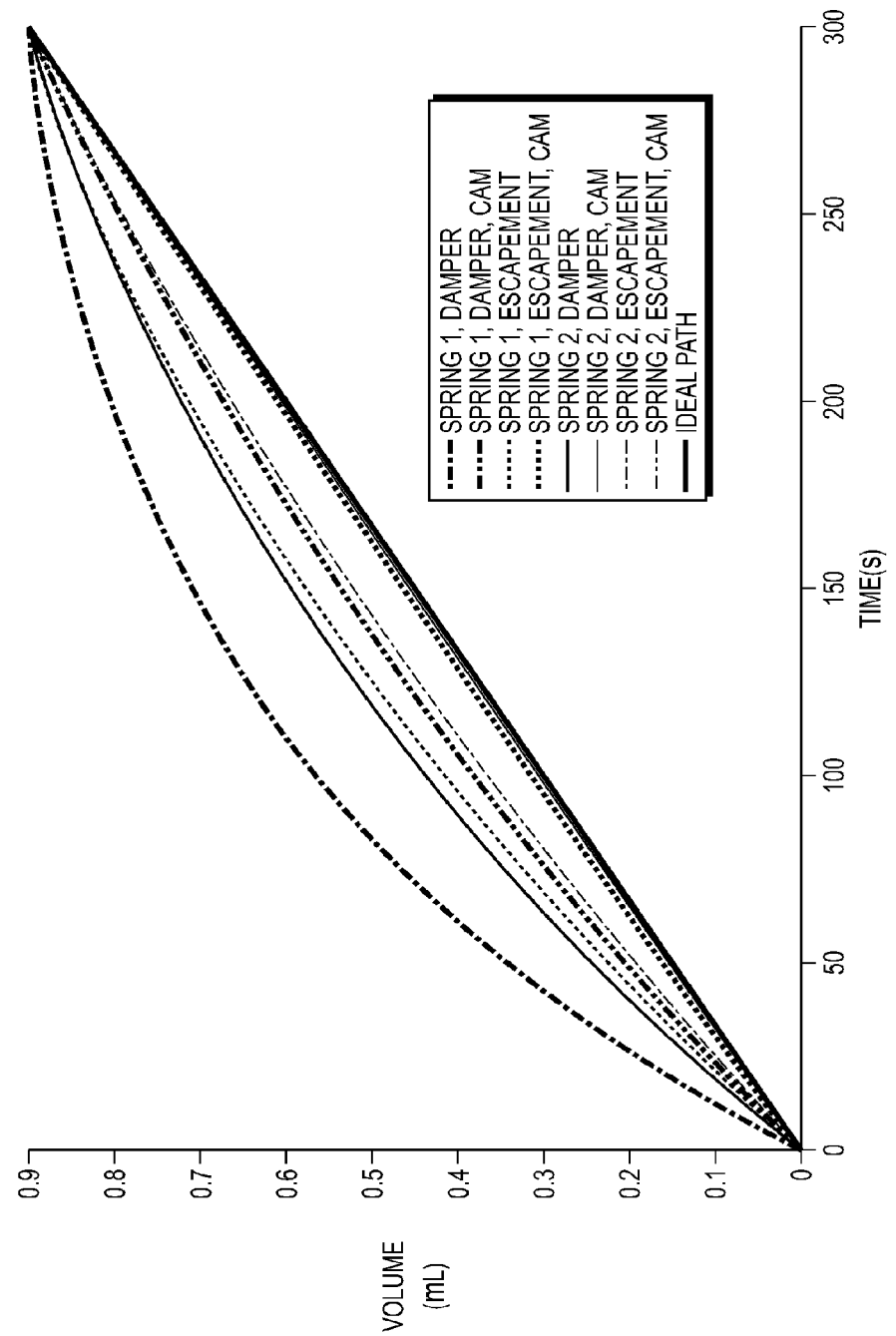
FIG. 32 illustrates a graph of the volume of therapeutic agent (in milliliters) versus time (in seconds) delivered by the combinations of components of FIG. 31.

FIG. 31 illustrates a graph of therapeutic agent flow rates (in milliliters per minute) versus time (in seconds) delivered by: (i) the combination of spring 1 and a viscous damper, (ii) the combination of spring 1, a viscous damper and a cam spool, (iii) the combination of spring 1 and an escapement, (iv) the combination of spring 1, an escapement and a cam spool, (v) the combination of spring 2 and a viscous damper, (vi) the combination of spring 2, a viscous damper and a cam spool, (vii) the combination of spring 2 and an escapement, (viii) the combination of spring 2, an escapement and a cam spool, and (ix) and an ideal flow rate in which the therapeutic agent is delivered at a substantially constant rate. FIG. 32 illustrates a graph of the volume of therapeutic agent (in milliliters) versus time (in seconds) delivered by the combinations of components of FIG. 31.

FIGS. 31 and 32 show that a substantially linear flow rate of the therapeutic agent may be achieved by the use of a cam spool or a fusee. The use of an escapement, versus a viscous damper, may be used to improve the linearity of the flow rate. The total delivery time of the therapeutic agent may be controlled by configuring the gearing ratio.

Figure 33:
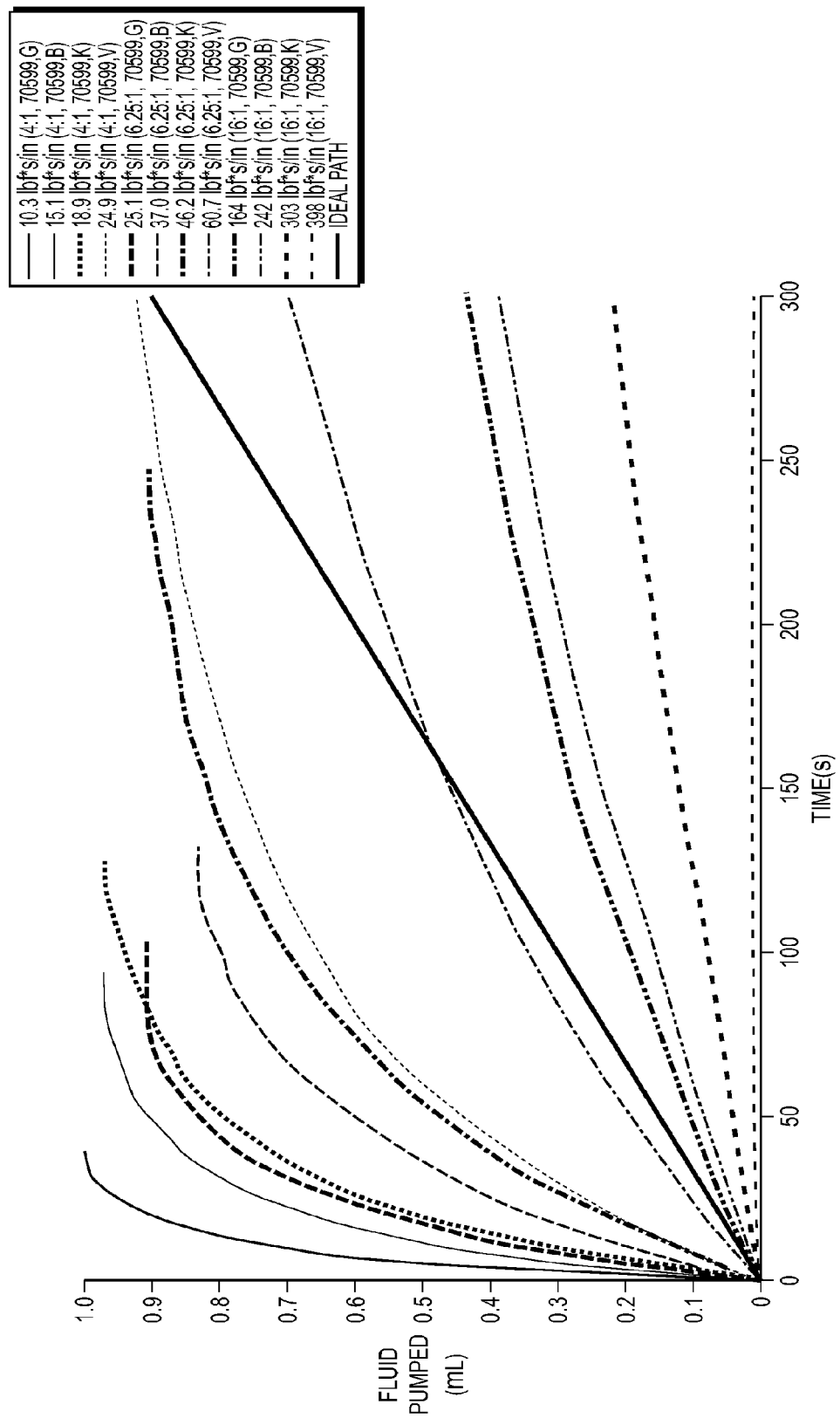
FIG. 33 illustrates a graph of the volume of therapeutic agent (in milliliters) against time (in seconds) delivered using: (i) a G damping mechanism having a damping coefficient of about 10.3 lbf*s/in with a gear ratio of 4:1, (ii) a B damping mechanism having a damping coefficient of about 15.1 lbf*s/in with a gear ratio of 4:1, (iii) a K damping mechanism having a damping coefficient of about 18.9 lbf*s/in with a gear ratio of 4:1, (iv) a V damping mechanism having a damping coefficient of about 24.9 lbf*s/in with a gear ratio of 4:1, (v) a G damping mechanism having a damping coefficient of about 25.1 lbf*s/in with a gear ratio of 6.25:1, (vi) a B damping mechanism having a damping coefficient of about 37.0 lbf*s/in with a gear ratio of 6.25:1, (vii) a K damping mechanism having a damping coefficient of about 46.2 lbf*s/in with a gear ratio of 6.25:1, (viii) a V damping mechanism having a damping coefficient of about 60.7 lbf*s/in with a gear ratio of 6.25:1, (ix) a G damping mechanism having a damping coefficient of about 164 lbf*s/in with a gear ratio of 16:1, (x) a B damping mechanism having a damping coefficient of about 242 lbf*s/in with a gear ratio of 16:1, (xi) a K damping mechanism having a damping coefficient of about 303 lbf*s/in with a gear ratio of 16:1, (xii) a V damping mechanism having a damping coefficient of about 398 lbf*s/in with a gear ratio of 16:1, and (xiii) an ideal flow rate in which the therapeutic agent is delivered at a substantially constant rate.

Different combinations of exemplary dampers and exemplary gear ratios in exemplary plunger actuation mechanisms were tested. The exemplary dampers included: (i) damping mechanism G, (ii) damping mechanism B, (iii) damping mechanism K, and (iv) damping mechanism V. The exemplary gear ratios included: (i) 4:1, (ii) 6.25:1, and (iii) 16:1. FIG. 33 illustrates a graph of the volume of therapeutic agent (in milliliters) against time (in seconds) delivered using: (i) a G damping mechanism having a damping coefficient of about 10.3 lbf*s/in with a gear ratio of 4:1, (ii) a B damping mechanism having a damping coefficient of about 15.1 lbf*s/in with a gear ratio of 4:1, (iii) a K damping mechanism having a damping coefficient of about 18.9 lbf*s/in with a gear ratio of 4:1, (iv) a V damping mechanism having a damping coefficient of about 24.9 lbf*s/in with a gear ratio of 4:1, (v) a G damping mechanism having a damping coefficient of about 25.1 lbf*s/in with a gear ratio of 6.25:1, (vi) a B damping mechanism having a damping coefficient of about 37.0 lbf*s/in with a gear ratio of 6.25:1, (vii) a K damping mechanism having a damping coefficient of about 46.2 lbf*s/in with a gear ratio of 6.25:1, (viii) a V damping mechanism having a damping coefficient of about 60.7 lbf*s/in with a gear ratio of 6.25:1, (ix) a G damping mechanism having a damping coefficient of about 164 lbf*s/in with a gear ratio of 16:1, (x) a B damping mechanism having a damping coefficient of about 242 lbf*s/in with a gear ratio of 16:1, (xi) a K damping mechanism having a damping coefficient of about 303 lbf*s/in with a gear ratio of 16:1, (xii) a V damping mechanism having a damping coefficient of about 398 lbf*s/in with a gear ratio of 16:1, and (xiii) an ideal flow rate in which the therapeutic agent is delivered at a substantially constant rate.

FIG. 33 shows that increasing the damping coefficient for the same gear ratio increases the delivery time of the same volume of therapeutic agent. In some cases, increasing the damping coefficient makes the delivery rate more linear. For example, for the 6:25:1 gear ratio, the highest damping coefficient of about 60.7 lbf*s/in yields linear delivery rate than the lower damping coefficients.

Figure 34:
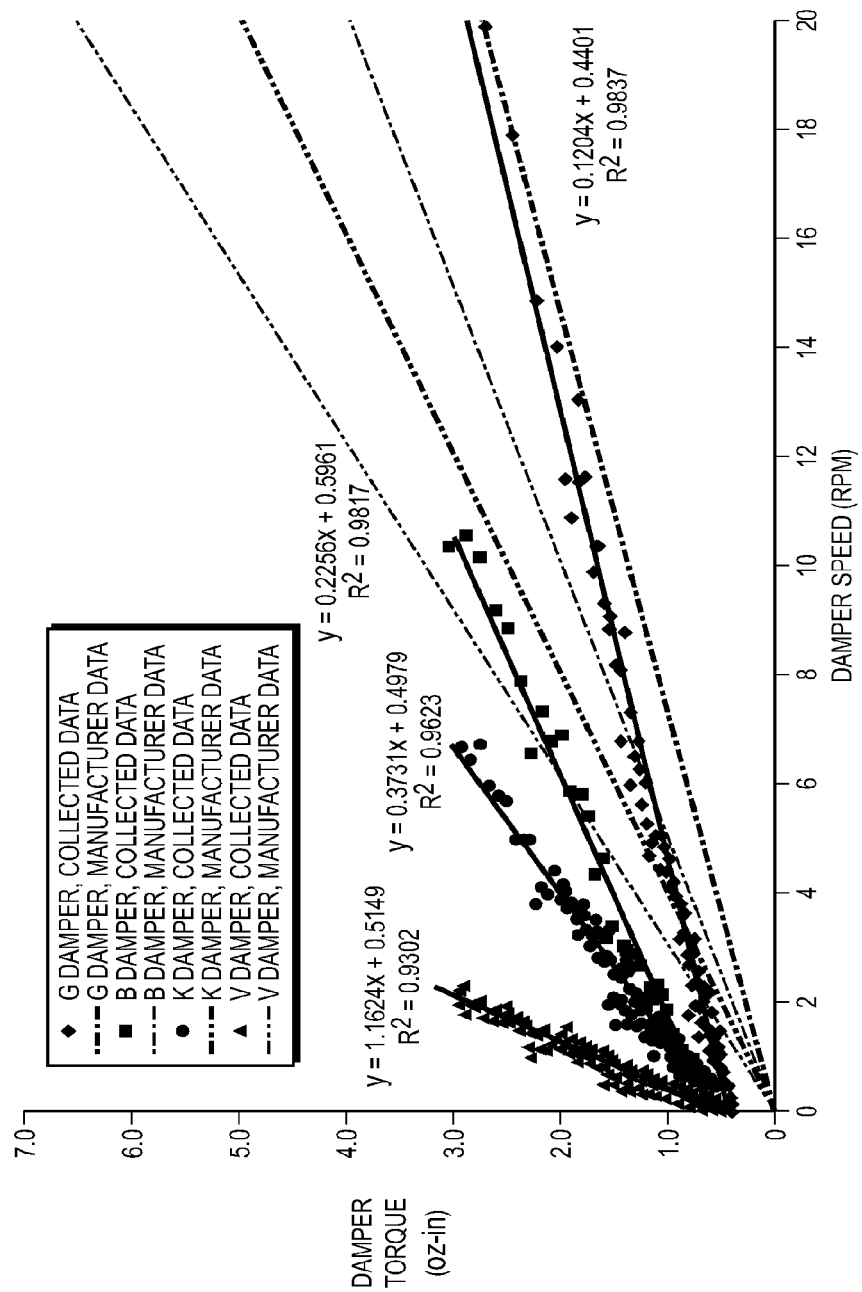
FIG. 34 illustrates a graph of exemplary damper torques (that may be back-calculated from the displacement of the plunger actuator) against damper speeds (in rpm) for G, B, K and V model dampers having increasing damping coefficients.

FIG. 34 illustrates a graph of exemplary damper torques (that may be back-calculated from the displacement of the plunger actuator) against damper speeds (in rpm) for G, B, K and V model dampers having increasing damping coefficients. The dots indicate the actual torque values and the dotted lines indicate the assumed manufacturer damping torque values, which indicates that the manufacturer values were underestimated. The data indicate that the torque values were substantially linear in the range of between 0 and about 20 rpm. This is evidenced by the high correlation coefficient for the linear fit equations shown in the graph. Using the new linear fit equations for the damper torque provided by the linear fit adjusts the damping coefficient and includes a static torque value. Substituting these new values into a computer model allows for a close approximation of the system response.

Figure 35:
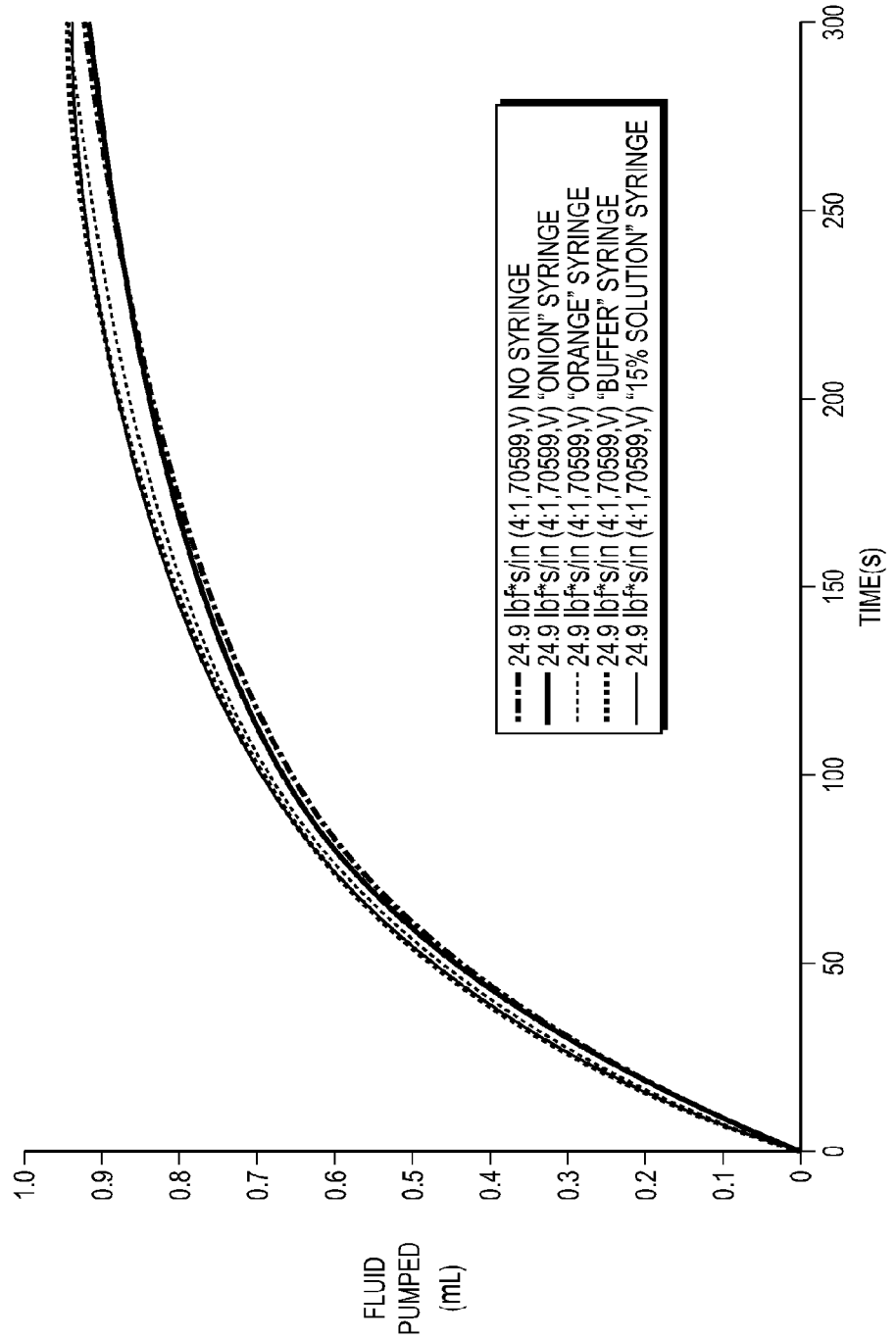
FIG. 35 illustrates a graph of the volume of therapeutic agent (in milliliters) against time (in seconds) delivered by different exemplary syringes using a V model damper having a damping coefficient of about 24.9 lbf*s/in and an exemplary gear ratio of 4:1.

Since the static torque is multiplied by the gear ratio and subtracts directly from the spring force, it may be desirable to choose the highest rate damper and the lowest gearing ratio in an exemplary embodiment, for example, the V model damper and a 4:1 gearing ratio. FIG. 35 illustrates a graph of the volume of therapeutic agent (in milliliters) against time (in seconds) delivered by different exemplary syringes using a V model damper having a damping coefficient of about 24.9 lbf*s/in and an exemplary gear ratio of 4:1.

Figure 36:
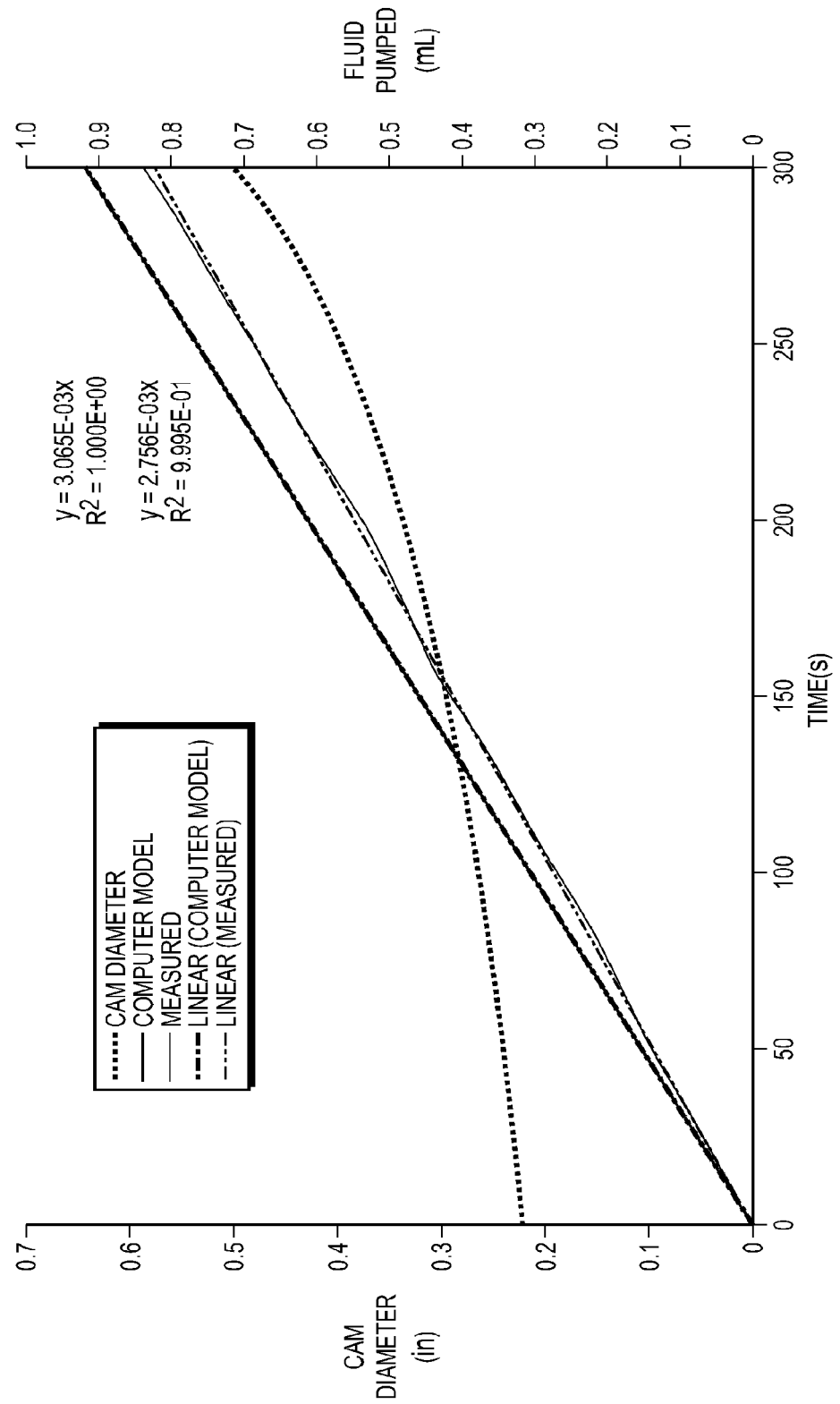
FIG. 36 illustrates a graph of the volume of therapeutic agent (in milliliters) delivered and the diameter of the fusee or cam spool (in inches) versus the time (in seconds).

After adjusting the computer models to reflect the measured damper torque, a fusee was designed to linearize the delivery rate of therapeutic agent. FIG. 36 illustrates a graph of the volume of therapeutic agent (in milliliters) delivered and the diameter of the fusee or cam spool (in inches) versus the time (in seconds). Since the diameter of the fusee changes over the delivery, the angular position data was numerically integrated along the fusee curve to yield the linear position data of the plunger actuator at each data point.

FIG. 36 shows that the actual measured delivery rate is about 10% slower than that predicted by the model but is nearly constant as evidenced by the high correlation coefficient (0.9995). The discrepancy between the measured and predicted data may be explained by inefficiencies in the gearing, for example, areas where the gearing binds may be seen as sharp changes in slope in the graph. The discrepancy may also be explained by the tether coupling the fusee to the plunger actuator not being perfectly in line with the plunger actuator, or the spring rate of the plunger actuator being lower in reality than calculated. Regardless of the source of error, reducing the spring rate of the plunger actuator by about 5% may produce a near perfect correlation (1.0).

Different exemplary damping mechanisms were tested at different temperatures to determine the effect of temperature on the damping effect, i.e., the linearity of the delivery of the therapeutic agent. The viscous rotary damping torque is dependent on the viscosity of the silicon grease inside the rotary damper. The viscosity of the silicon grease depends in part on the temperature of the surrounding environment. Different exemplary damping mechanisms were also tested to determine the effect of manufacturing variability in the damping mechanisms on the damping effect, i.e., the linearity of the delivery of the therapeutic agent. Variations in damper manufacturing may affect the resisting torque provided by the damper.

Figure 37:
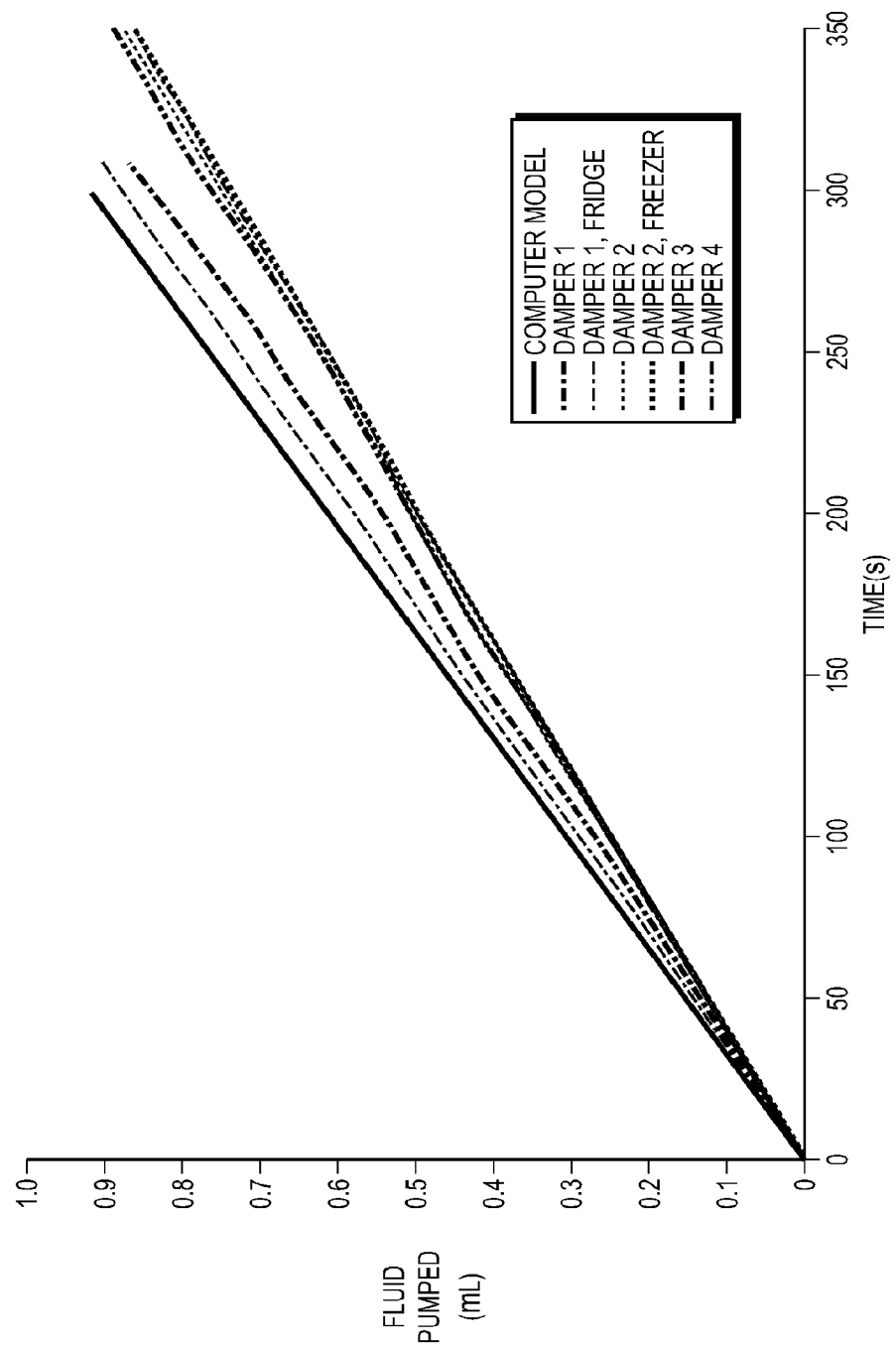
FIG. 37 illustrates a graph of the volume of therapeutic agent (in milliliters) delivered versus time (in seconds) achieved by: (i) a first damper at room temperature, (ii) the first damper at about 40 degrees Fahrenheit (in a refrigerator), (iii) a second damper, (iv) the second damper at about 0 degree Fahrenheit (in a freezer), (v) a third damper having manufacturing variability relative to the first and second dampers, and (vi) a fourth damper having manufacturing variability relative to the first and second dampers.

FIG. 37 illustrates a graph of the volume of therapeutic agent (in milliliters) delivered versus time (in seconds) achieved by: (i) a first damper at room temperature, (ii) the first damper at about 40 degrees Fahrenheit (in a refrigerator), (iii) a second damper, (iv) the second damper at about 0 degree Fahrenheit (in a freezer), (v) a third damper having manufacturing variability relative to the first and second dampers, and (vi) a fourth damper having manufacturing variability relative to the first and second dampers.

FIG. 37 shows that changes in temperature did not substantially affect the damping effect, i.e., the linearity of the delivery of the therapeutic agent. However, the delivery rate was affected in some cases by decreasing the temperature, for example, for the first damper. Similarly, manufacturing variability in the damping mechanisms did not substantially affect the damping effect, i.e., the linearity of the delivery of the therapeutic agent. However, the delivery rate was affected in some cases by manufacturing variability. The damper torque values varied by about 5% in the sample group tested.

Thus, one or more factors may be configured to control the linearity and/or the delivery rate of the therapeutic agent including, but not limited to, the gear ratio, the damping coefficient, manufacturing deviations in the damper, manufacturing deviations in the plunger actuator, and the like. In addition, other characteristics of the plunger actuator may be varied in order to control the linearity and/or the rate of the flow of the therapeutic agent.

Figure 38:
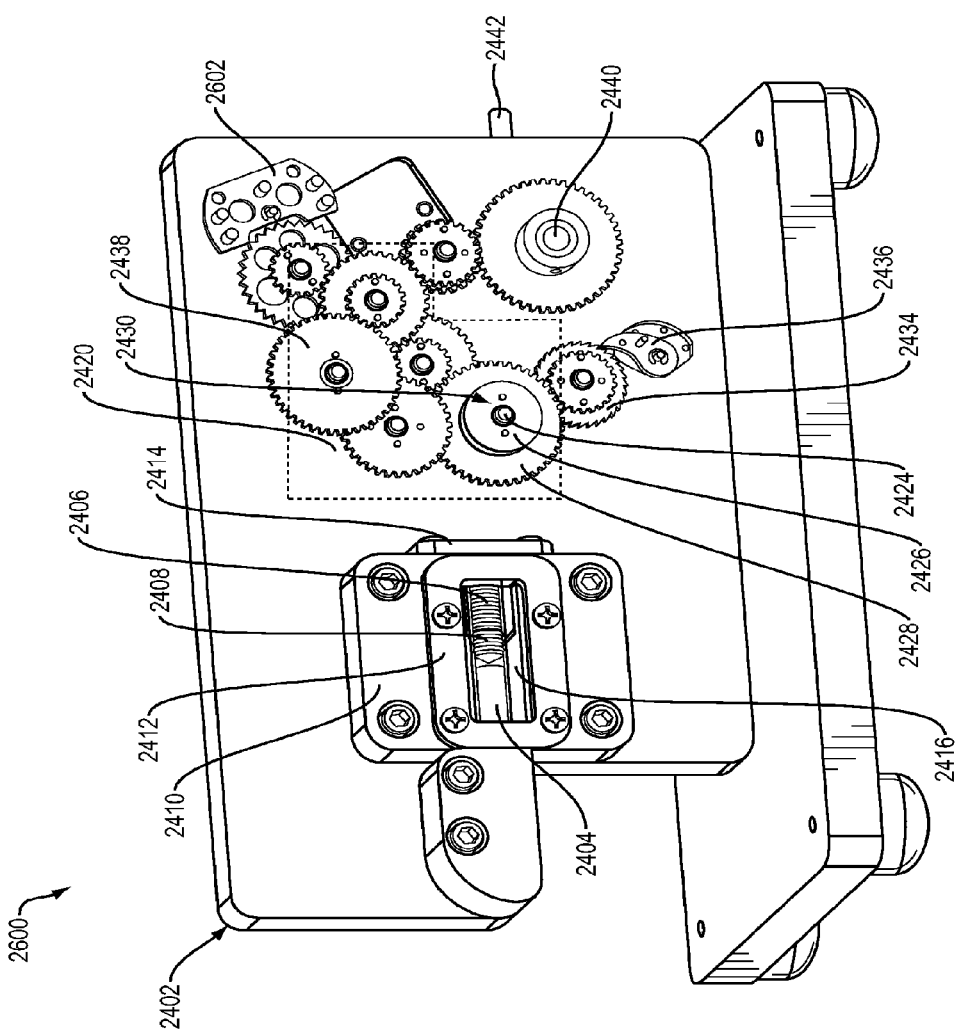
FIG. 38 illustrates a schematic of a portion of an exemplary automatic injection device including a plunger actuation mechanism that employs a fusee and an escapement mechanism.

FIG. 38 illustrates a schematic of a portion of an exemplary automatic injection device 2600 that employs a fusee and an escapement mechanism. The device 2600 includes a plunger actuation mechanism for automatically actuating a bung 2408 contained in a syringe or cartridge 2404. In the exemplary plunger actuation mechanism, a runaway escapement 2602 may be used to resist the acceleration of the plunger actuator 2406 by providing linear damping. In the exemplary runaway escapement 2602, an escape wheel is provided having a plurality of teeth on its circumferential periphery and a pallet is provided in the vicinity of the escape wheel. In an exemplary embodiment, the escape wheel may have 30 teeth, although exemplary escape wheels are not limited to 30 teeth. The escape wheel may be coupled to the spool 2426 via one or more gears forming a gear train. In an exemplary embodiment, a gearing ratio of 50:1 may couple the spool 2426 to the escape wheel, but other exemplary gearing ratios may be used. The pallet may have an adjustable mass moment of inertia by way of pin holes that may be filed with one or more pins, for example, steel dowel pins.

In operation, when torque is applied to the escape wheel, the escape wheel rotates and a tooth of the escape wheel imparts an impulse torque on the pallet such that the kinetic energy of the pallet is reversed. The tooth pushes aside an arm of the pallet. This causes the pallet to oscillate which frees the tooth of the escape wheel, simultaneously bringing the alternate arm of the pallet into interference with a second tooth of the escape wheel. As such, as the escape wheel rotates, its movement is arrested by periodic impact with the pallet, thus allowing the escape wheel to rotate only when the pallet is free to oscillate. As the torque applied to the escape wheel increases, the escape wheel imparts a stronger impulse to the pallet, thus increasing the oscillation speed pallet and therefore allowing the escape wheel to move more rapidly.

Assuming that the collisions between the teeth of the escape wheel and the pallet are perfectly elastic, the pallet absorbs, for each impact:

$$T = J\dot{\phi}^2$$

The power dissipation of the pallet is directly proportion to the frequency of oscillation of the pallet w because two collisions occur between the escape wheel and the pallet for every oscillation of the pallet. Thus:

$$P = 2\omega J\dot{\phi}^2$$

Assuming an impulse time of zero, since the collisions are perfectly elastic, the magnitude of the angular velocity $\dot{\phi}$ may be assumed to be constant and related to $\phi_{max}$, the angular distance between collisions (in radians) may be represented by:

$$\dot{\phi} = 2\omega\phi_{max}$$

Thus, $$P = 8J\omega^3\phi_{max}^2$$

The rotational speed of the escape wheel $\dot{\theta}$ is related to the number of teeth n and the oscillation frequency w and may be represented as:

$$\dot{\theta} = \frac{2\pi\omega}{n} \Rightarrow \omega = \frac{n\dot{\theta}}{2\pi}$$

Thus, $$P = \frac{J\varphi_{max}^2 n^3 \dot{\theta}^3}{\pi^3}$$

Since $P = C_\theta \dot{\theta}^2$ for a viscous rotary damper:

$$C_\theta = \frac{J\varphi_{max}^2 n^3 |\dot{\theta}|}{\pi^3} \Rightarrow F_x = \left(\frac{2nN}{\pi D}\right)^3 J\varphi_{max}^2 |\dot{x}| * \dot{x} = C_x |\dot{x}| * \dot{x}$$

which creates a non-linear differential equation.

In another exemplary plunger actuation mechanism, a swiss lever escapement may be used to resist the acceleration of the plunger actuator. Assuming a coordinate system in which $\theta = 0$ is at the equilibrium of a coil spring attached to a balance wheel. If damping is negligible in this system, then:

$$J\ddot{\theta} + k\theta = 0$$

Where k is the torsional spring constant of the coil spring and J is the mass moment of inertia:

$$J = \int r^2 dm$$

Where r is the distance from the center of rotation and m is mass, the natural frequency of the system is:

$$\omega_0 = \sqrt{\frac{k}{J}}$$

If the escapement wheel has n teeth and a spur gear train of speed reduction N couples the escapement to a spool of diameter D, then the spool rotates at angular velocity:

$$\dot{\phi} = \frac{2\pi\omega_0}{nN}$$

Taking the derivative of the equation relating θ to x:

$$\frac{d}{dt}\left(\phi = \frac{2(x - x_0)}{D}\right)$$

which yields:

$$\dot{\phi} = \frac{2\dot{x}}{D}$$

Thus, $$\dot{x} = \frac{\pi D \omega_0}{nN} = \frac{\pi D}{nN}\sqrt{\frac{k}{J}}$$

The components illustrated in FIG. 38 that are common to FIG. 24 are described with reference to FIG. 24.

Figure 39:
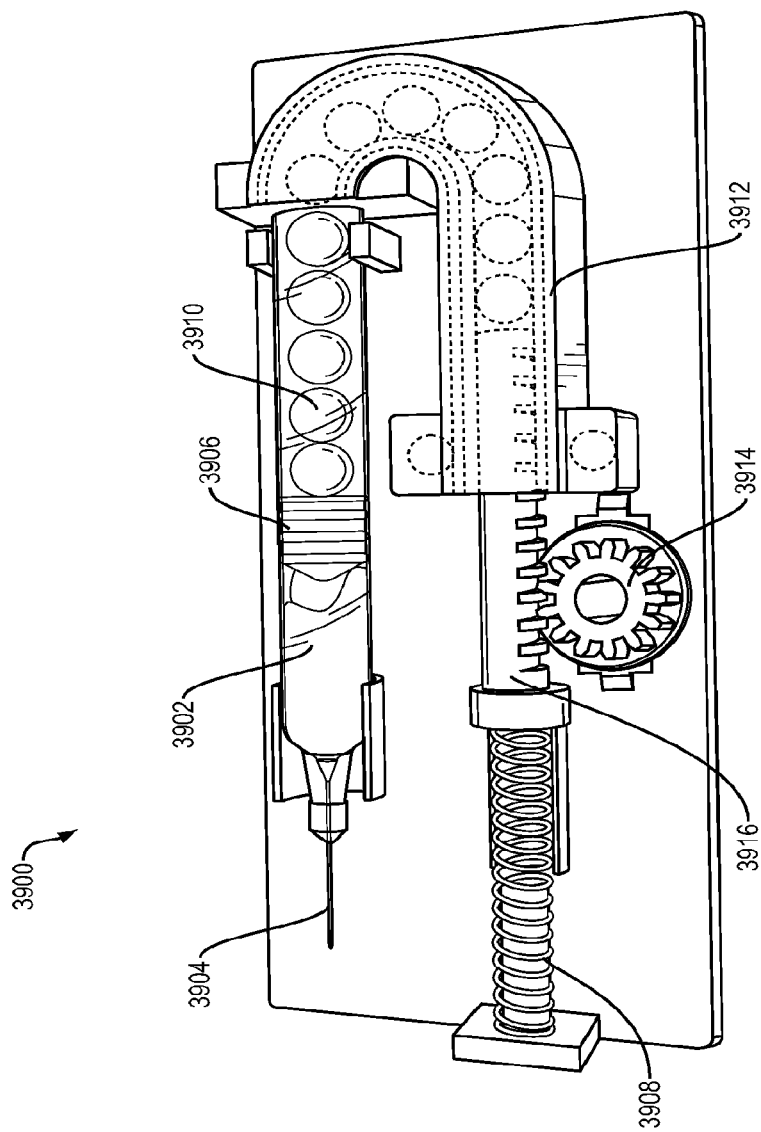
FIG. 39 illustrates an exemplary plunger actuation mechanism that employs one or more linear biasing mechanism to provide a force for expressing a therapeutic agent from the barrel portion of a wearable automatic injection device.

FIG. 39 illustrates an exemplary plunger actuation mechanism 3900 that employs one or more linear biasing mechanisms to provide a force for expressing a therapeutic agent from the barrel portion 3902 of a wearable automatic injection device. The barrel portion 3902 extends longitudinally between a proximal end and a distal end, and is configured to hold a dose of a therapeutic agent. A distal end of the barrel portion 3902 is coupled to a syringe needle 3904. A bung 3906 is provided moveably within the barrel portion 3902 to seal the dose of the therapeutic agent.

One or more linear springs 3908 are provided for providing a biasing force upon the bung 3906 in order to move the bung 3906 within the barrel portion 3902 toward the syringe needle 3904 during an injection in an injection state. A distal end of the linear spring 3908 is in the vicinity of and/or in contact with a plunger 3916 having a plurality of teeth configured for engagement with a damping mechanism. The plunger 3916 may be provided in the vicinity of and/or in contact with a distal end of a force transmission mechanism, for example, one or more ball bearings 3910.

A distal end of the ball bearings 3910 may also be in the vicinity of and/or in contact with the bung 3906 such that the biasing force of the spring 3908 is transmitted to the bung 3906 through the ball bearings 3910. The ball bearings 3910 may be enclosed in an enclosed track 3912 that restricts the lateral or sideway movement of the ball bearings 3910. That is, the biasing force of the spring 3908 causes the plunger 3916 and, in turn, ball bearings 3910 to move substantially in a back or forth manner, i.e., toward or away from the bung 3906. The use of the ball bearings 3910 allows redirection of the biasing force to the bung 3906 and allows minimization of the size of the device. When actuated, the spring 3908 exerts a biasing force in the direction of the bung 3906. The biasing force is transmitted by the plunger 3916 and the ball bearings 3910 to the bung 3906 and causes the bung 3906 to move toward the syringe needle 3904 within the barrel portion 3902. This causes the therapeutic agent to be expressed through the syringe needle 3904 to the exterior of the barrel portion 3902.

A damping mechanism 3914, for example, a rotary viscous damper, may be provided and associated with the spring 3908 and/or the plunger 3916 to regulate the rate of delivery of the therapeutic agent. The damper 3914 may include a hub and a plurality of teeth that extend in a radial manner about the hub. The teeth of the damper 3914 may be configured for engagement with the teeth of the plunger 3916. The damper 3914 may provide a force proportional to the speed of movement of the plunger 3916 in order to regulate the delivery rate. As such, the exemplary system 3900 may be used to provide slow controlled delivery of the therapeutic agent by configuring the force provided by the spring 3908 and/or the properties of the damper 3914.

Figure 40:
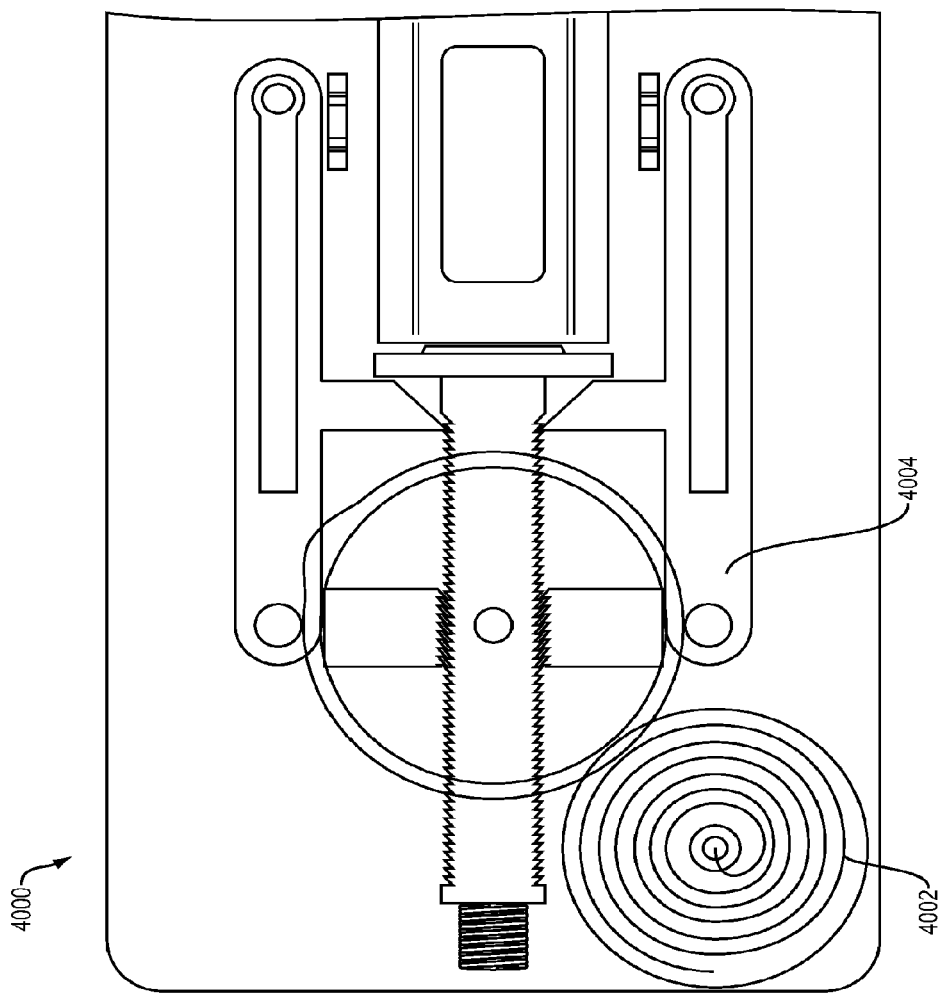
FIG. 40 illustrates an exemplary plunger actuation mechanism that employs one or more clock springs to provide a force for expressing a therapeutic agent from the barrel portion of a wearable automatic injection device.

FIG. 40 illustrates an exemplary plunger actuation mechanism 4000 that employs one or more clock springs to provide a force to a bung in a barrel portion in order to expel a therapeutic agent from the barrel portion. A biasing means 4002 is provided by a compression helical coil spring characterized by spring coils of progressively increasing diameter, such that when the spring is compressed, the coils nest one within the other in the manner of a clock spring, thereby taking up the minimum of space. A portion of the spring 4002 is in the vicinity of and/or in contact with a mechanical escapement mechanism 4004 so that the rotary biasing force of the spring 4002 is converted into a linear displacement of the mechanical escapement mechanism 4004. The mechanical escapement mechanism 4004 may be in the vicinity of and/or in contact with the bung such that the biasing force of the spring 4002 is transmitted as a linear displacement to the bung through the motion of the mechanical escapement mechanism 4004. That is, the biasing force of the spring 4002 causes the mechanical escapement mechanism 4004 to move substantially in a back or forth manner, i.e., toward or away from the bung. The use of the mechanical escapement mechanism 4004 allows redirection of the biasing force to the bung and allows minimization of the size of the device.

When actuated, the spring 4002 exerts a biasing force that is converted to a back and forth force by the mechanical escapement mechanism 4004 in the direction of the bung. The biasing force is transmitted directly or indirectly to the bung and causes the bung to move toward the needle within the barrel portion. This causes the therapeutic agent to be expressed through the needle to the exterior of the barrel portion. As such, the exemplary system 4000 may be used to provide slow controlled delivery of the therapeutic agent by configuring the force provided by the spring 4002 and/or the linear displacement provided by the mechanical escapement mechanism 4004. The mechanical escapement mechanism 4004 may be configured to control, for example, the amount of advance per cycle. The spring 4002 may be sized to predominate over stick-slip forces.

Figure 41:
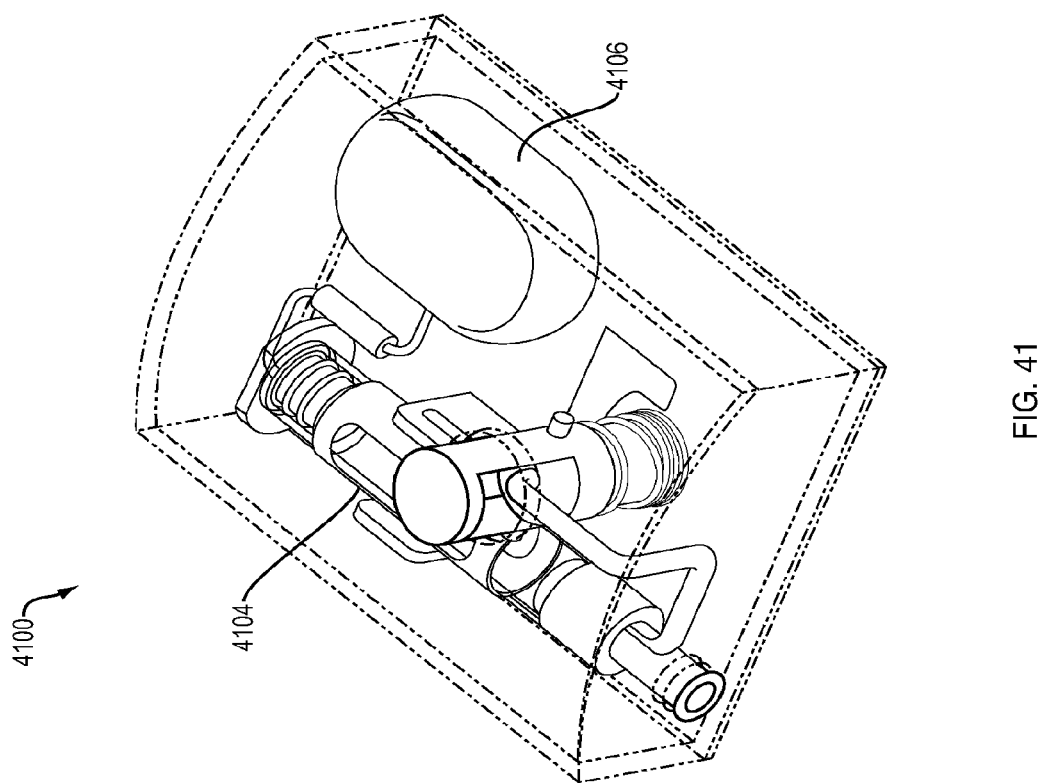
FIG. 41 is a schematic of an exemplary automatic injection device including a plunger actuation mechanism that employs one or more fluid circuits.
Figure 42:
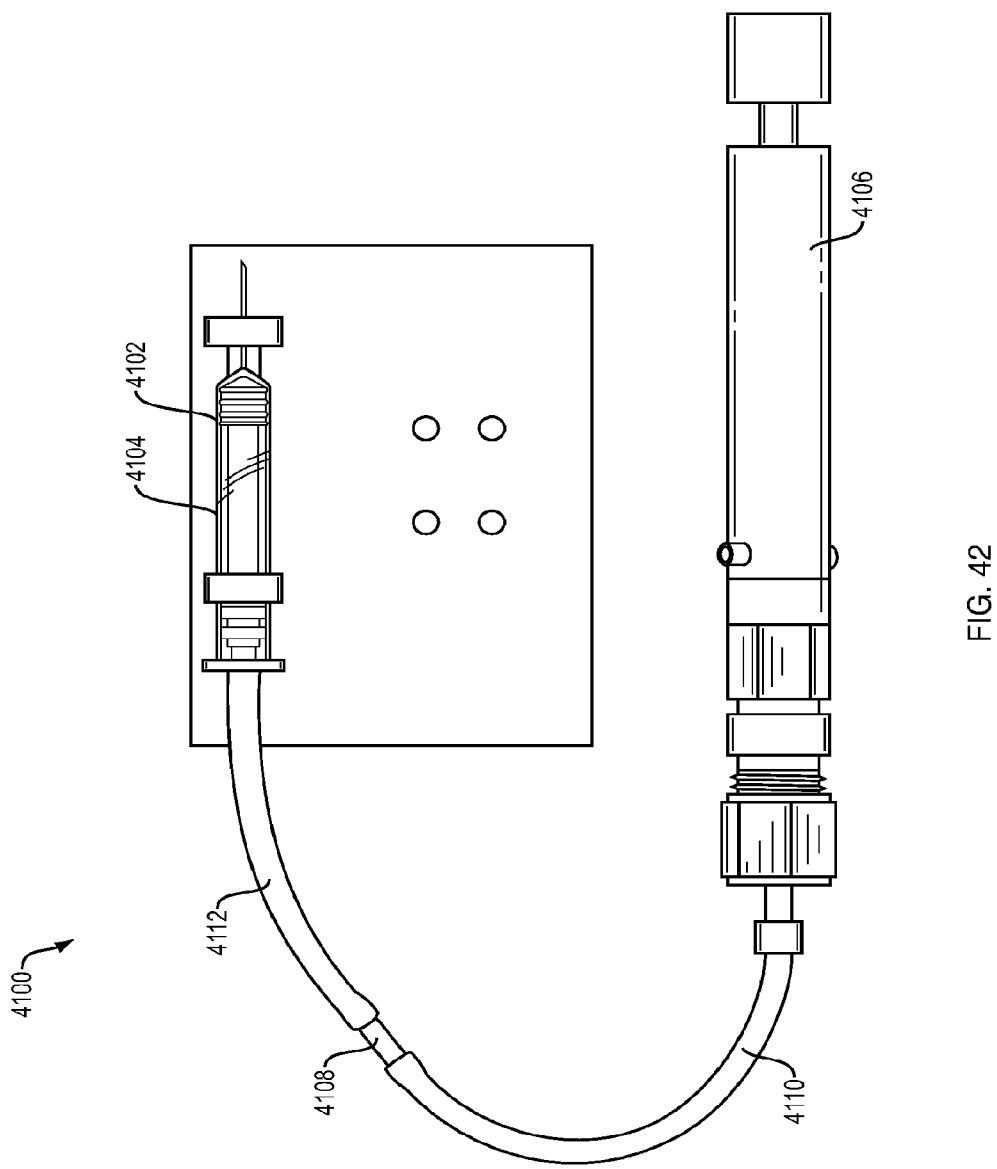
FIG. 42 is an exemplary automatic injection device that employs one or more fluid circuits to perspective view a force to a bung for expressing a dose of a therapeutic agent from a barrel portion.

FIGS. 41 and 42 illustrate an exemplary automatic injection device 4100 that employs a fluid-based plunger actuation mechanism in which the fluid pressure and/or movement of a working fluid is used to move a bung within the barrel portion of a syringe or cartridge. The plunger actuation mechanism includes one or more fluid circuits to provide a force to a bung for expressing a dose of a therapeutic agent from a barrel portion 4104 of a syringe or cartridge. FIG. 41 is a schematic of the exemplary automatic injection device 4100 and FIG. 40 is a perspective view of the exemplary automatic injection device 4100. The wearable automatic injection device 4100 may include a pressure element 4106 that stores an incompressible working fluid that provides a fluid pressure. Exemplary working fluids may include, but are not limited to, water, air, oil, and the like. Exemplary pressure elements 4106 may include, but are not limited to, an elastic bladder, a master cylinder, a spring-loaded syringe, and the like.

The pressure element 4106 may be coupled to a flow restrictor 4108 via a tubing 4110. The flow restrictor 4108 may restrict the flow of the working fluid so that the fluid pressure upstream of the flow restrictor is greater than the fluid pressure downstream of the flow restrictor. The flow restrictor 4108 may include an orifice of diameter ranging from about 0.001 inch to about 0.01 inch, but the diameters of exemplary flow restrictor orifices are not limited to this exemplary range. The orifice of the flow restrictor 4108 may have lengths ranging from about 10 mm to about 50 mm, but the lengths of exemplary flow restrictor orifices are not limited this exemplary range.

Exemplary embodiments may configure a number of characteristics of the delivery system to control the total delivery time of the therapeutic agent. Exemplary embodiments may also configure a number of characteristics of the delivery system based on the viscosity of the working fluid and/or the therapeutic agent. Exemplary characteristics may include, but are not limited to, the diameter of the orifice, the length of the orifice, the viscosity of the working fluid, and the like. For example, the diameter of the orifice of the flow restrictor may be decreased to increase the total delivery time.

The flow restrictor 4108 may also be coupled to the bung via a tubing 4112. When the working fluid is released from the pressure element 4106 via the flow restrictor 4108, the fluid pressure of the working fluid drives the bung forwardly within the barrel portion 4104 in order to expel the dose of the therapeutic agent from the barrel portion 4104.

In an exemplary embodiment, before an injection in a pre-injection state, the working fluid may not be released from the pressure element 4106. In this exemplary embodiment, a delivery trigger (not pictured) may be coupled to the pressure element 4106 so that, upon activation of the delivery trigger, the working fluid is released from the pressure element 4106 into the tubings 4110 and 4112. The fluid pressure of the working fluid advances the bung within the barrel portion 4104, thus injecting the dose into the patient's skin. Thus, the fluid circuit established by the flow of the working fluid and the flow restrictor may provide a regulated force to the bung.

In an exemplary embodiment, the dose is delivered in a linear delivery profile, i.e., at a substantially constant delivery rate. Linearity of the delivery profile may be achieved by the high pressure of the working fluid provided by the pressure element 4106 upstream of the flow restrictor 4108 and the damping effect provided by the flow restrictor 4108. The pressure upstream of the flow restrictor 4108 may be maintained at a high level relative to projected stick-slip forces such that a highly damped system is achieved. For the bung to be moved forward within the barrel portion 4104, the bung would need to pull a vacuum on the working fluid between the flow restrictor 4108 and the barrel portion 4104, which is difficult to achieve to an appreciable extent because the working fluid is essentially incompressible.

Exemplary damped hydraulic delivery circuits allow movement of the bung via volumetric metering, rather than by a direct application of force, thereby minimizing stick-slip phenomena in the delivery profile of the therapeutic agent.

In an exemplary embodiment, an exemplary volume of 0.8 milliliters of therapeutic agent may be delivered at an exemplary delivery pressure of about 16.5 psi within an exemplary duration of about 12 minutes. In another exemplary embodiment, an exemplary volume of 0.8 milliliters of therapeutic agent may be delivered at an exemplary delivery pressure of about 5 psi within an exemplary duration of about 17 minutes.

Figure 43:
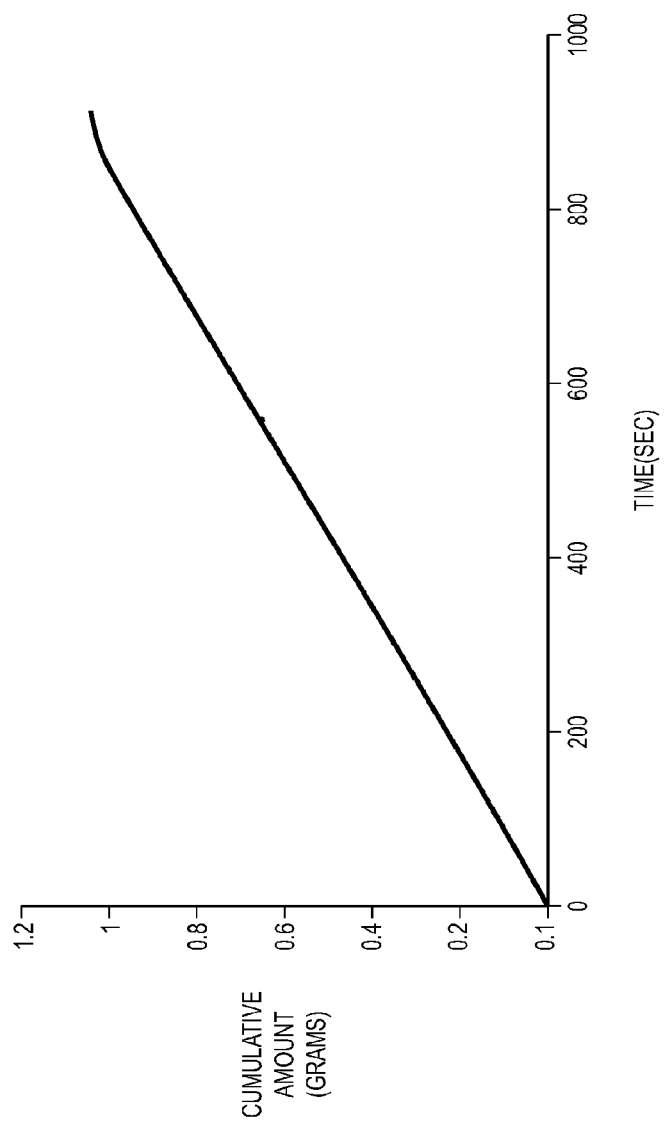
FIG. 43 illustrates a graph of the cumulative amount of therapeutic agent (in grams) against time (in seconds) as delivered by an exemplary delivery system at an exemplary delivery pressure of about 16.5 psi.
Figure 44:
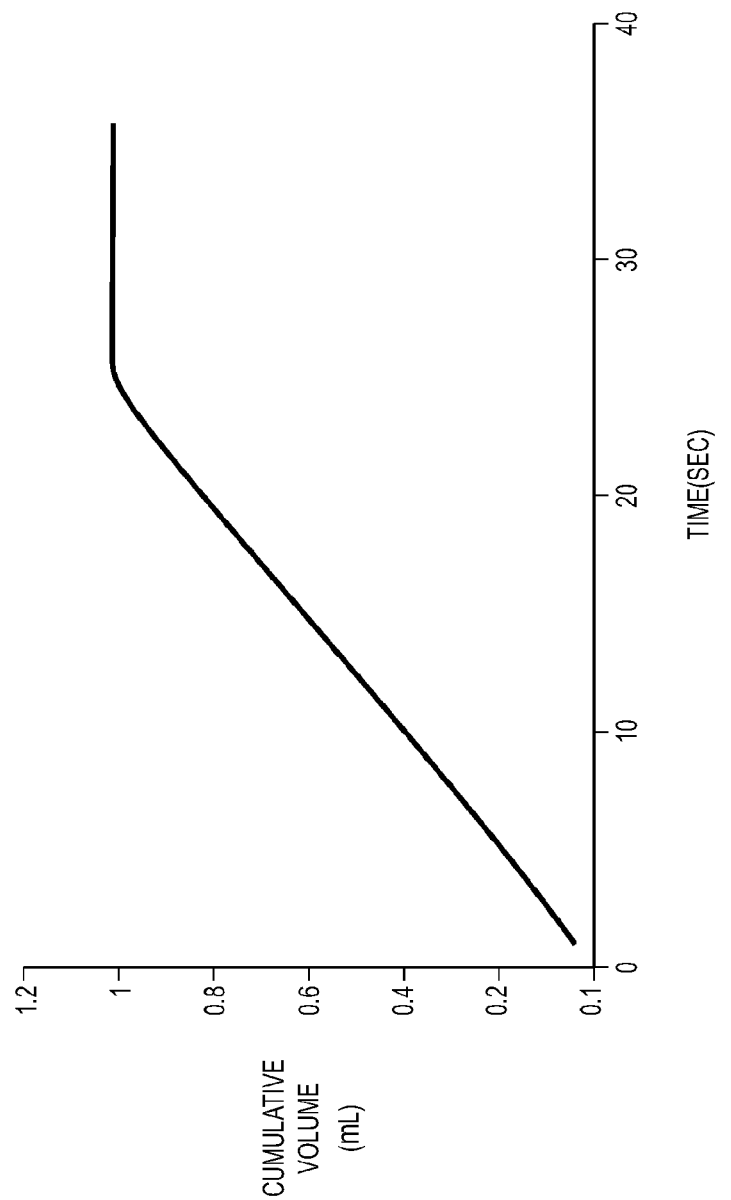
FIG. 44 illustrates a graph of the cumulative volume of therapeutic agent (in milliliters) against time (in seconds) as delivered by an exemplary delivery system including a first flow restrictor.
Figure 45:
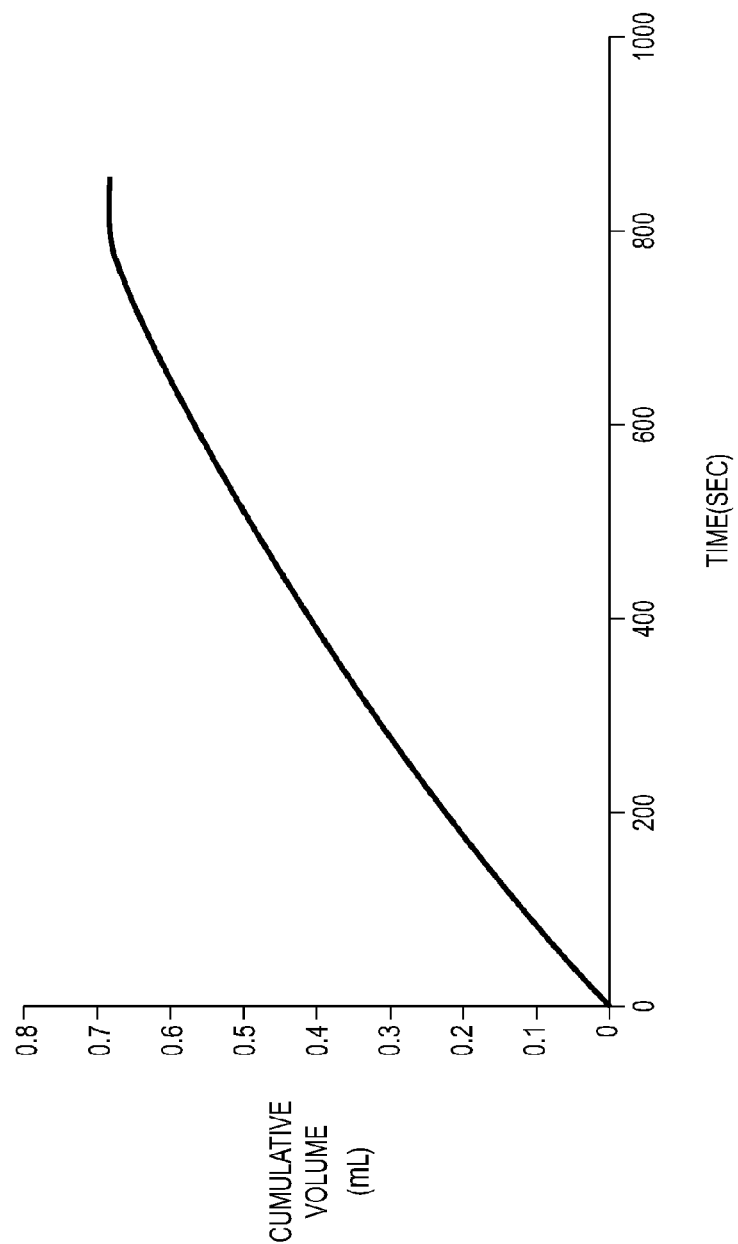
FIG. 45 illustrates a graph of the cumulative volume of therapeutic agent (in milliliters) against time (in seconds) as delivered by an exemplary delivery system including a second flow restrictor.

FIG. 43 illustrates a graph of the cumulative amount of therapeutic agent (in grams) against time (in seconds) as delivered by an exemplary delivery system at an exemplary delivery pressure of about 16.5 psi. FIG. 44 illustrates a graph of the cumulative volume of therapeutic agent (in milliliters) against time (in seconds) as delivered by an exemplary delivery system including a first exemplary flow restrictor having an exemplary diameter of about 0.008 inches and an exemplary length of about 34.3 mm. The total delivery time for delivering about 1 milliliters of a therapeutic agent was about twenty seconds. FIG. 45 illustrates a graph of the cumulative volume of therapeutic agent (in milliliters) against time (in seconds) as delivered by an exemplary delivery system including a second exemplary flow restrictor having an exemplary diameter of about 0.002 inches and an exemplary length of about 34.3 mm. The total delivery time for delivering about 1 milliliters of a therapeutic agent was about 15 minutes. In the illustrative graphs, the delivery profile is substantially linear, i.e., substantially constant over time, and does not display an initial bolus or abrupt changes or inflections representative of inconsistent delivery rates.

Figure 46:
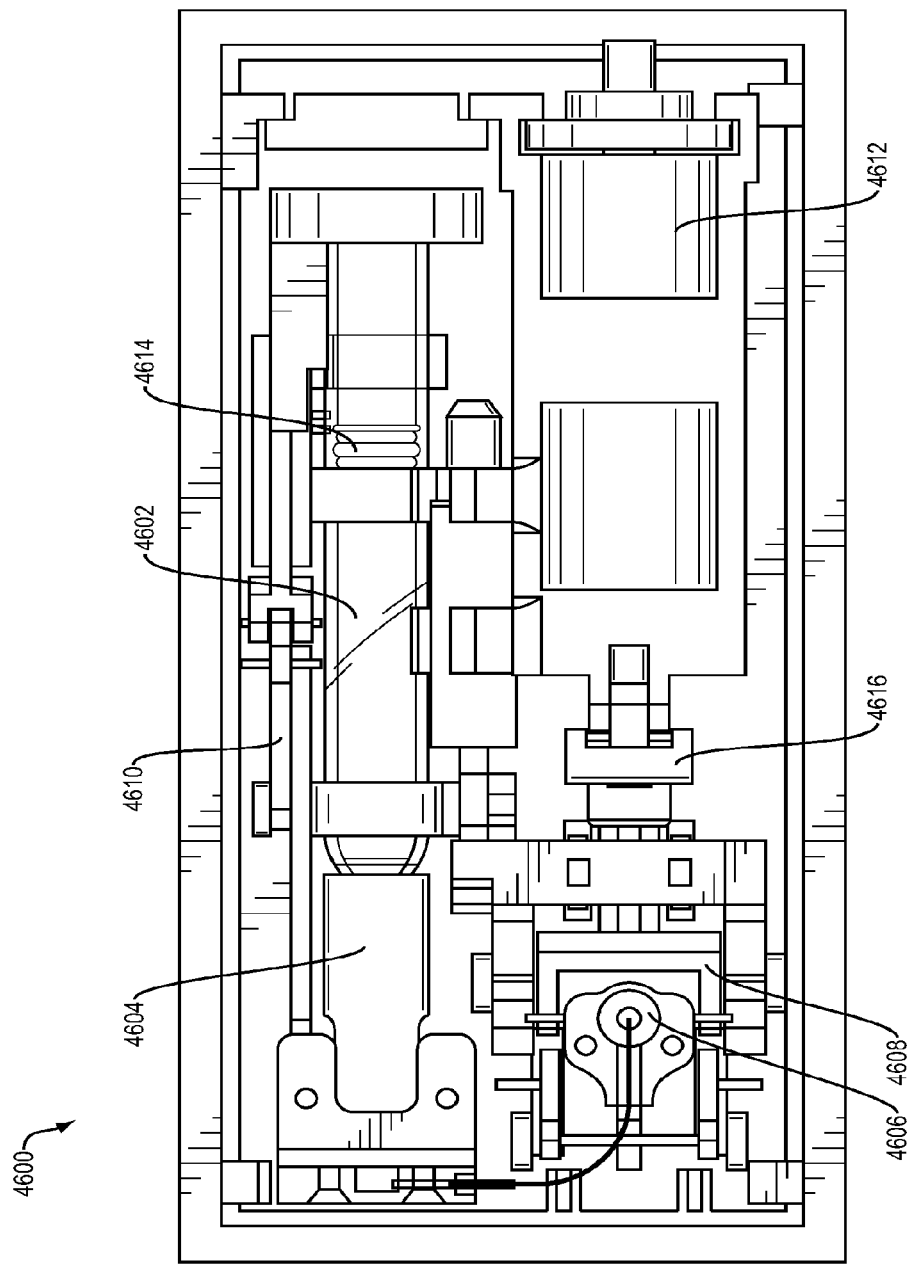
FIG. 46 is a schematic drawing of an exemplary automatic injection device that employs one or more fluid circuits to provide a force for expressing a therapeutic agent from a cartridge assembly.
Figure 47:
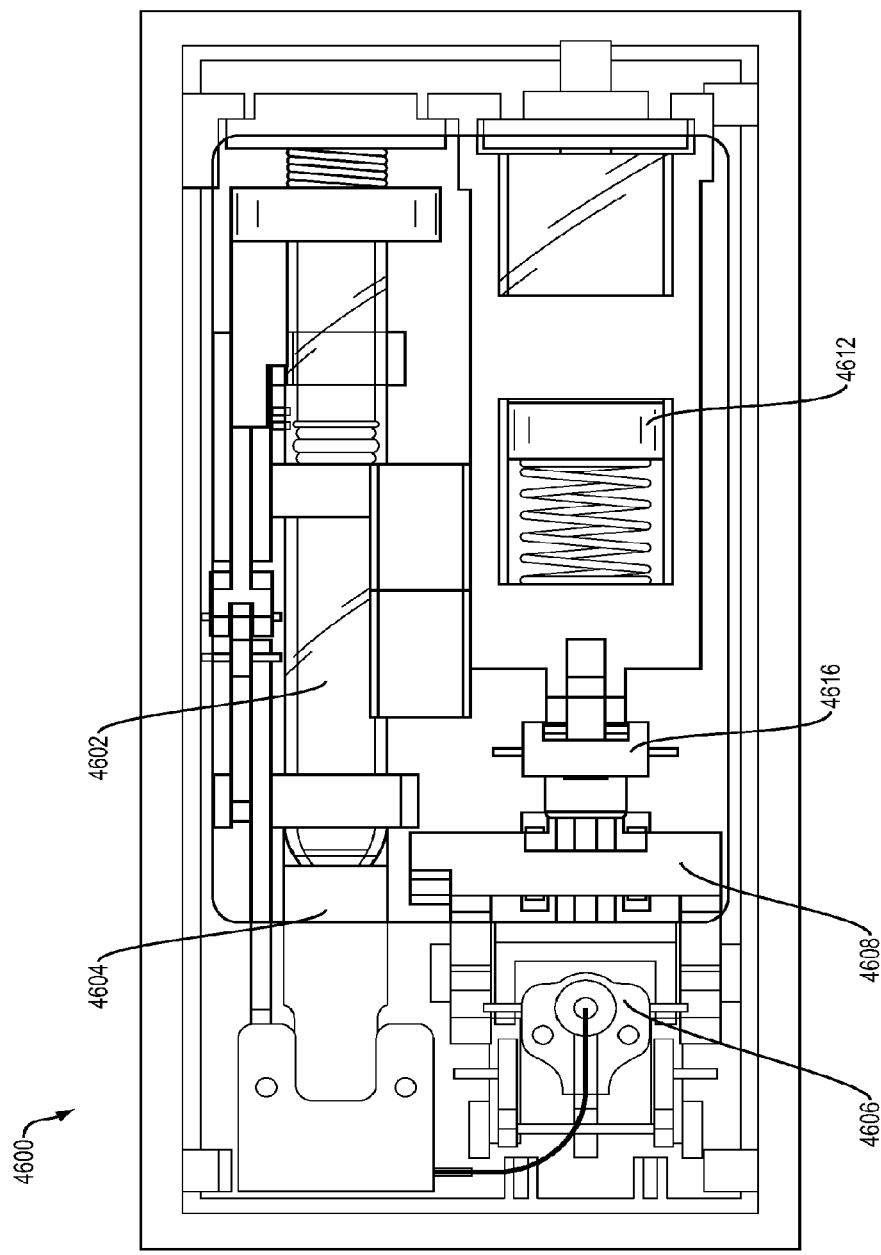
FIG. 47 is a top view of the exemplary device of FIG. 46.

FIG. 46 is a schematic drawing of an exemplary automatic injection device 4600 that employs one or more fluid circuits to provide a force for expressing a therapeutic agent from a cartridge assembly. FIG. 47 is a top view of the exemplary device 4600. The exemplary automatic injection device 4600 includes a barrel portion 4602 containing a dose of a therapeutic agent. A distal end of the barrel portion 4602 is provided in the vicinity of or coupled to a syringe needle (hidden by a needle cover 4604) that is protectively covered by a needle cover 4604. The device 4600 includes an injection button that includes a septum and bears an injection needle (not pictured). In an exemplary embodiment, the device 4600 may include an injection needle carrier 4606 for holding the injection needle. In an exemplary embodiment, the injection needle may be extend substantially orthogonally to the plane of the device as illustrated, and may be held in place by the needle carrier 4606. A needle lock 4608 may be provided for preventing the injection needle from exiting the housing once engaged and may be located in the housing near the injection needle.

In an exemplary embodiment, a syringe or cartridge actuator 4610 may be provided for advancing the barrel portion 4602 within the housing toward the septum. A trigger may be provided for triggering the syringe or cartridge actuator 4610, for example, when the injection button is pressed down or when the needle cover 4604 is removed.

In this exemplary embodiment, a master cylinder 4612 containing a working fluid is provided for providing a fluid pressure to actuate a bung 4614 within the barrel portion 4602. The master cylinder 4612 may be coupled to a delivery trigger 4616 that, when activated, releases the working fluid into fluid communication with the bung 4614 and allows the fluid pressure to advance the bung 4614 within the barrel portion 4602.

Exemplary embodiments also provide needle retraction systems for retracting an injection needle from a vertically lowered position (or an extended or deployed position) outside the housing of the device at the patient contact region to a vertically raised position (or a retracted position) within the housing of the device. The wearable automatic injection device 4600 includes a retraction mechanism that automatically raises the injection button from a vertically depressed position within the housing during an injection in an injection state to a vertically raised position within the housing in a post-injection state after an injection. In an exemplary embodiment, the retraction mechanism may be a telescoping element. The master cylinder 4612 may be coupled to a retraction trigger that, when activated, releases the working fluid into fluid communication with the retraction trigger and allows the fluid pressure to activate the retraction mechanism.

Figure 48:
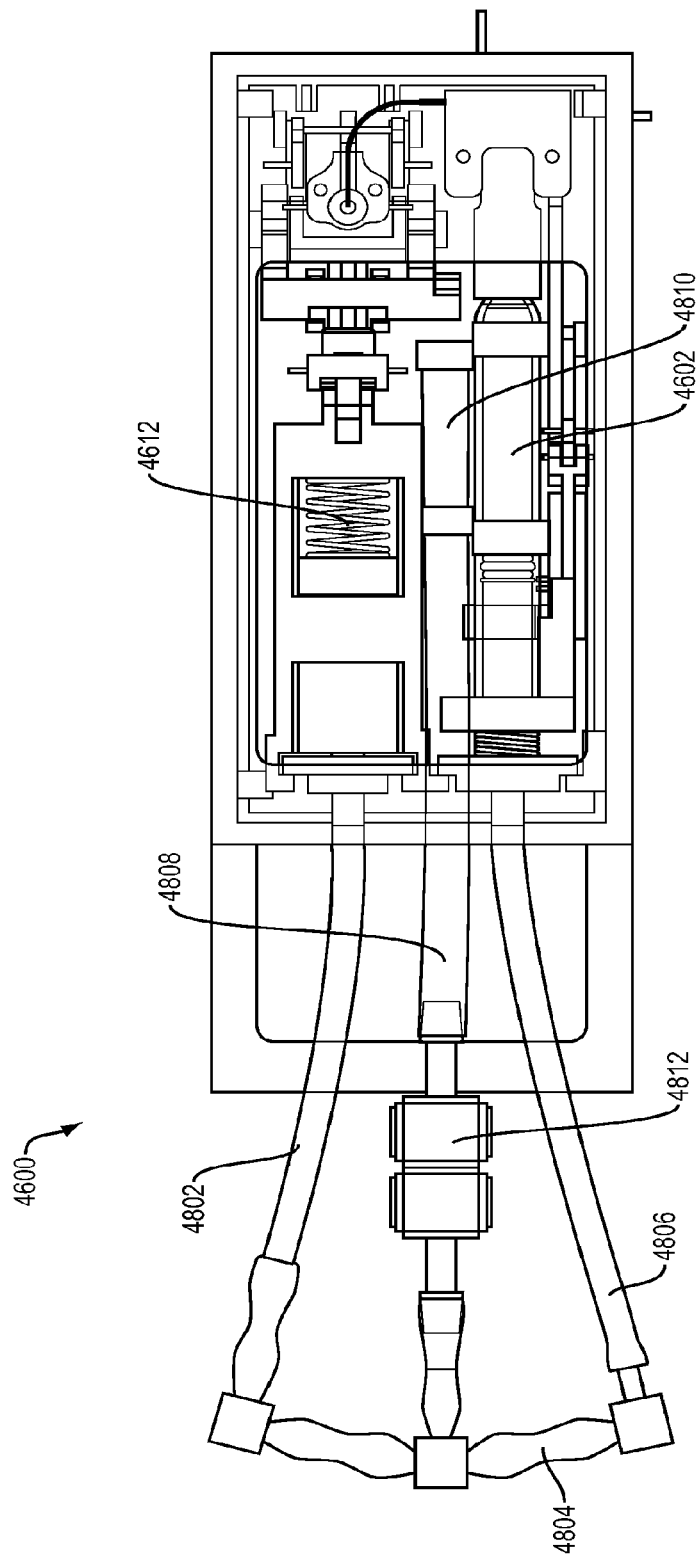
FIG. 48 illustrates a top view of an exemplary automatic injection device which shows a conduit coupling the master cylinder to a flow restrictor, a conduit coupling the flow restrictor to the bung, and a conduit coupling the master cylinder to a retraction mechanism via a valve.
Figure 49:
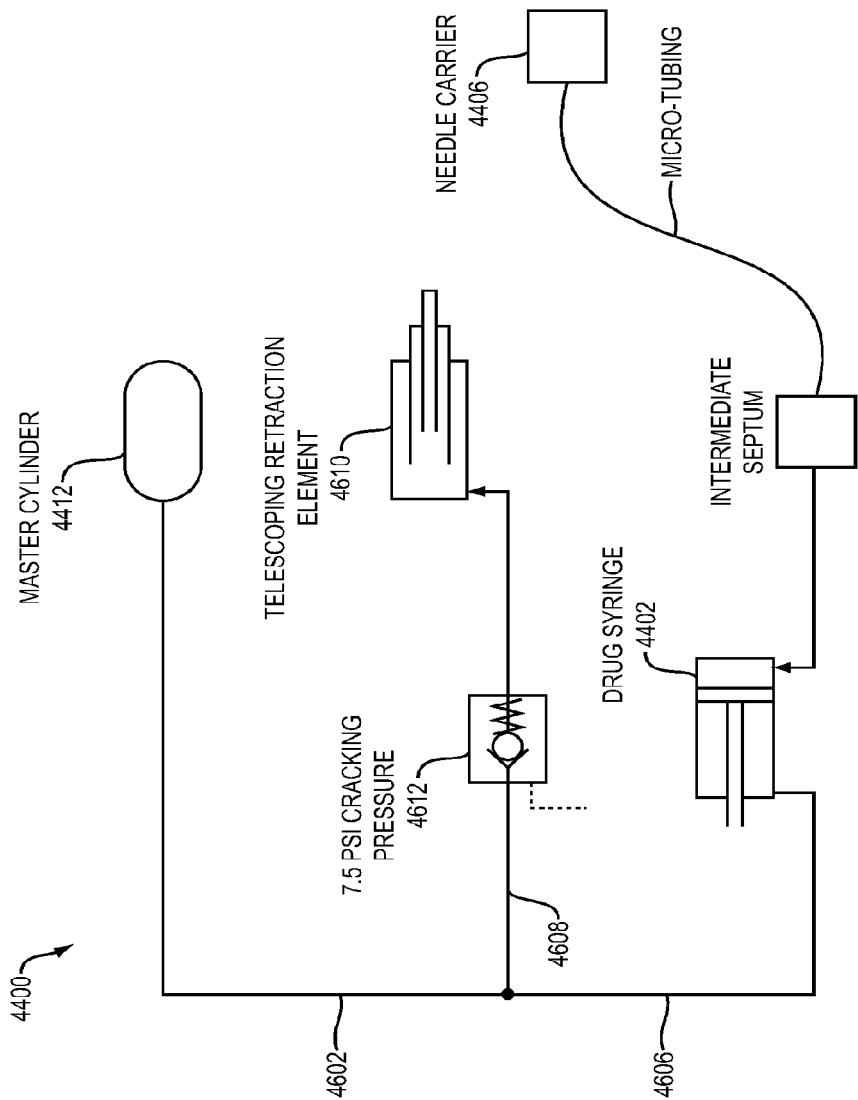
FIG. 49 illustrates a schematic diagram of the device of FIG. 48.

FIG. 48 illustrates a top view of the device 4600 which shows a conduit 4802 coupling the master cylinder 4612 to a flow restrictor 4804, a conduit 4806 coupling the flow restrictor 4804 to the bung in the barrel portion of the device, and a conduit 4808 coupling the master cylinder 4612 to a retraction mechanism 4810 via a valve 4812, for example, a check valve. FIG. 49 illustrates a schematic diagram of the device 4600.

The check valve 4812 may have a suitable cracking pressure at or above which the check valve 4812 allows fluid into the conduit 4808 coupled to the retraction mechanism 4810. In an exemplary embodiment, the cracking pressure is higher than the maximum fluid pressure in the conduit 4806 required to drive the bung during an injection in an injection state. Otherwise, undesirably, the needle retraction process may begin during or even before the injection. In an exemplary embodiment, the pressure in the conduit 4806 at the end of the movement of the bung during an injection in an injection state is higher than the cracking pressure. Otherwise, at the end of the movement of the bung, the pressure in the conduit 4808 may be insufficient to activate the retraction mechanism 4810. The volume of the working fluid in the master cylinder 4612 is sufficient to deliver the entire dose of the therapeutic agent and to activate the retraction mechanism 4810.

In an exemplary embodiment, the retraction mechanism 4810 and the check valve 4812 may be provided separately. In another exemplary embodiment, the retraction mechanism 4810 and the check valve 4812 may be provided as a single element, for example, as an inverting diaphragm.

Figure 50:
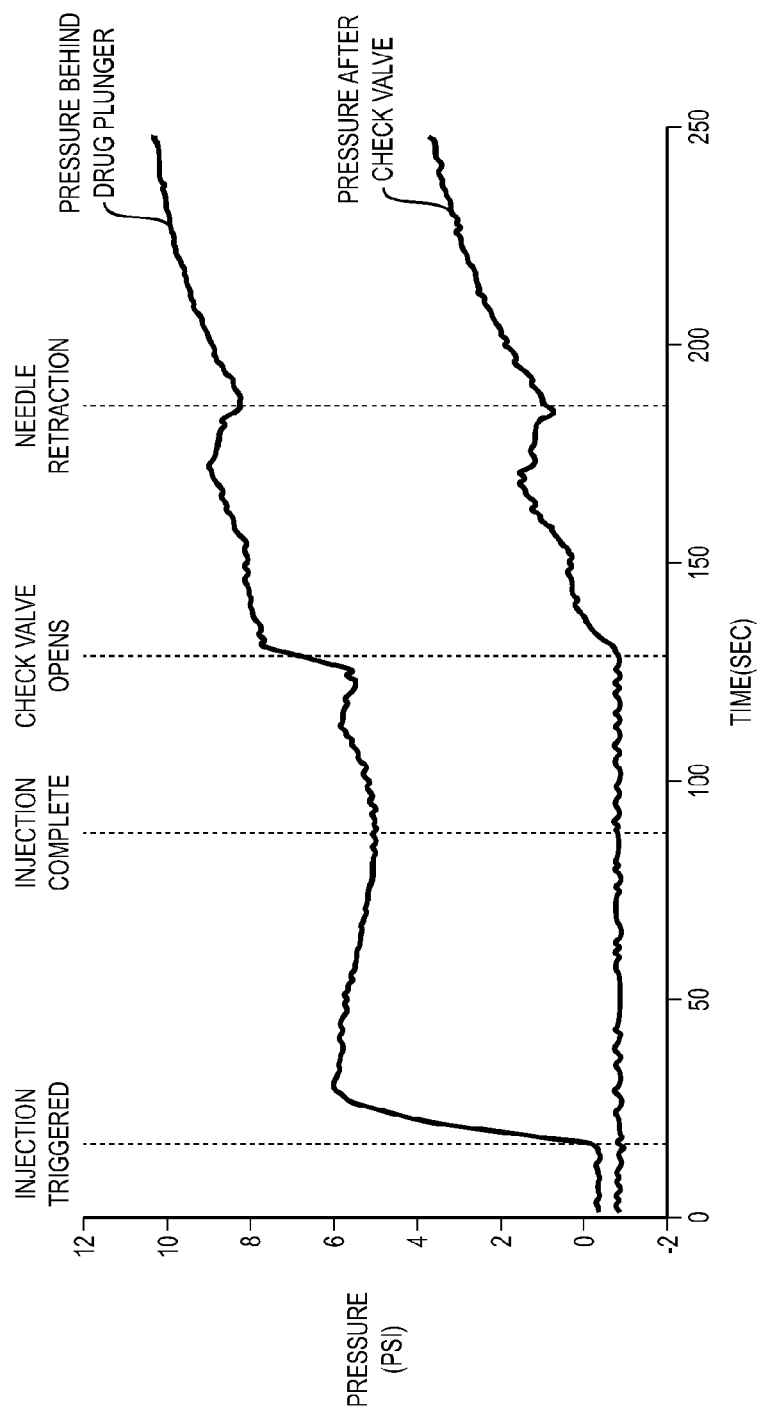
FIG. 50 illustrates a graph of the pressure after a check valve and behind a bung (in psi) versus time (in seconds) in an exemplary embodiment.

FIG. 50 illustrates a graph of the pressure after the check valve and behind the bung (in psi) versus time (in seconds) in an exemplary embodiment. In an exemplary embodiment, the cracking pressure of the check valve may be about 7.5 psi and the diameter of the flow restrictor orifice may be about 0.008 inches.

During an injection in an injection state, the flow restrictor 4804 may cause the pressure in the conduit 4802 to be about 10 to about 15 psi, while the pressure in the conduit 4806 may be about 5 to about 6 psi. The check valve 4812 thus prevents any flow of the working fluid from entering the conduit 4808 while the bung is moving during the injection. Once the bung stops moving at the end of the injection, i.e., when the dose has been completely expelled from the barrel portion, the pressure in the conduit 4806 increases beyond 7.5 psi. This causes the check valve 4812 to open, allowing the working fluid to flow into the conduit 4808 which activates the retraction mechanism 4810. The retraction mechanism 4810 in turn unlocks the needle lock and retracts the injection button/carrier 4606 bearing the injection needle. Because it is based on pressure equalization in the hydraulic circuit, the needle retraction process ensures that the entire dose is delivered before the injection needle is retracted, maximizes utilization of the therapeutic agent, and minimizes the overfill required in the barrel portion 4602.

Any suitable trigger mechanism may be used to trigger the needle retraction systems. In an exemplary embodiment, the trigger mechanism may automatically trigger the needle retraction system when the wearable automatic injection device moves from an injection state to a post-injection state. In an exemplary embodiment, completion of the delivery of a therapeutically effective dose of the therapeutic agent may trigger the needle retraction system. In another exemplary embodiment, the removal of the device from the patient before completion of the delivery of a therapeutically effective dose of the therapeutic agent may trigger the needle retraction system. In another exemplary embodiment, the needle retraction system may be manually triggered by a user.

Figure 51:
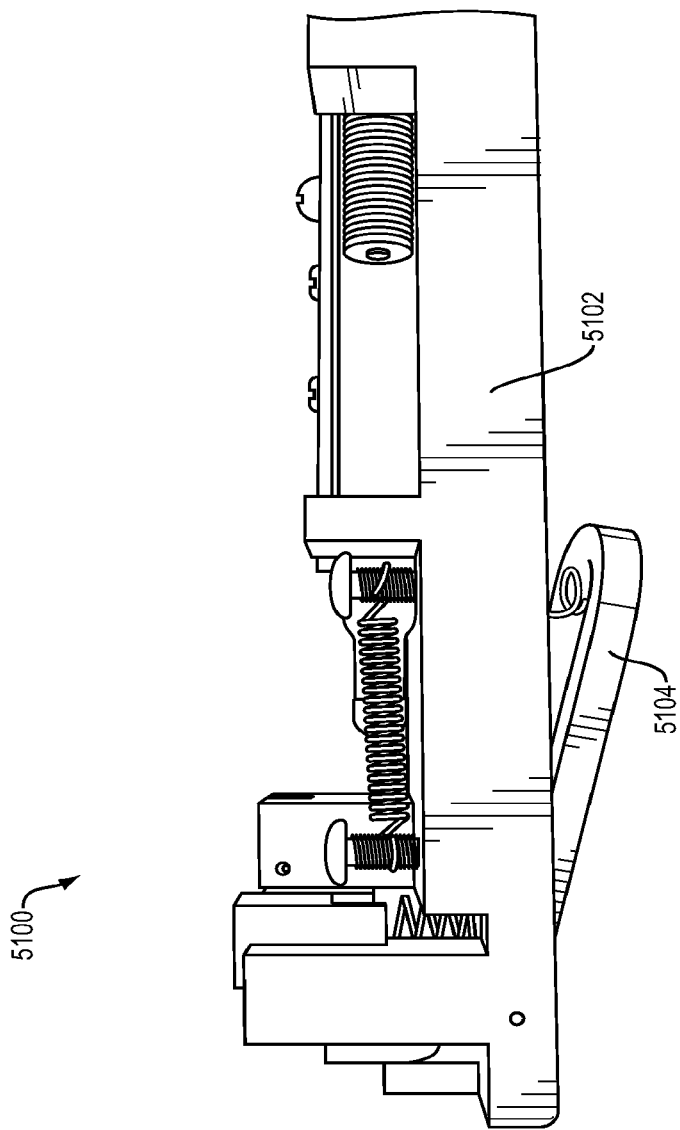
FIG. 51 illustrates a side view of an exemplary automatic injection device in which the housing of the wearable automatic injection device includes a skin sensor foot.

FIG. 51 illustrates a side view of an exemplary automatic injection device 5100 in which the housing 5102 of the wearable automatic injection device 5100 includes a skin sensor foot 5104, which is a structure in an exemplary embodiment housed under or in the portion of the housing 5102 proximal to the injection site. In an exemplary embodiment, prior to injection of the therapeutic agent and during injection, the skin sensor foot 5104 is retained within or forms a portion of the underside of the housing 5102. When the wearable automatic injection device 5100 is attached to the injection site and activated, the skin sensor foot 5104 may be free to move but may be constrained by the injection site. In an exemplary embodiment, when the wearable automatic injection device 5100 is removed from the injection site, regardless of whether the drug delivery was completed, the skin sensor foot 5104 is no longer constrained, and extends and projects outside the periphery of the housing 5102. This, in turn, trips a retraction trigger. When the retraction trigger is activated, a retraction mechanism retracts the injection needle which may also raise the injection button from the vertically lowered position to the vertically raised position, so that the injection button protrudes from the top of the housing 5102 and the injection needle is retracted within the housing 5102.

V. EXEMPLARY NEEDLE PROTECTION SYSTEMS

Exemplary embodiments provide different exemplary needle protection systems for maintaining the injection needle within the wearable automatic injection device in a post-injection state after an injection. Protection of the needle prevents accidental needle sticks from injuring the patient or any other humans in the vicinity of the wearable automatic injection device.

FIGS. 52A and 52B illustrate an exemplary needle protection system 5200 that maintains an injection needle 5202 in a retracted position within a housing 5204 of an automatic injection system. The injection needle 5202 is movable relative to the housing 5204 away from or toward the patient's skin. When the needle 5202 is in a position within the housing 5204 farther from the patient's skin, the needle 5202 is in a retracted position and does not protrude outside the housing 5204. When the needle 5202 is in a position within the housing 5204 closer to the patient's skin, the needle 5202 is in an inserted or deployed position and protrudes fully or partly from the housing 5204. The housing 5204 may be provided with an aperture 5206 through which the needle 5202 may protrude outside the housing 5204.

The needle protection system 5200 employs a barrier mechanism 5208 which prevents the needle 5202 from protruding from the housing 5204 in a pre-injection state before an injection and in a post-injection state after an injection when the needle 5202 is in the retracted position. FIG. 52A illustrates the system 5200 in which the needle 5202 is in an inserted or deployed position and protrudes fully or partly through the aperture 5206 outside the housing 5204, for example, during an injection in an injection state. In this case, the barrier mechanism 5208 is displaced away from the aperture 5206 so that the aperture 5206 is open to the outside of the housing 5204, and the needle 5202 is free to protrude through the aperture 5206 to the outside of the housing 5204. FIG. 52B illustrates the system 5200 in which the needle 5202 is in a retracted position and does not protrude from the housing 5204, for example, in a pre-injection state and a post-injection state. In this case, the barrier mechanism 5208 is aligned with and covers the aperture 5206 so that the aperture 5206 is no longer open to the outside of the housing 5204, and the needle 5202 is not free to protrude through the aperture 5206 to the outside of the housing 5204. In an exemplary embodiment, the barrier mechanism 5208 may be moved rotatably above a point of rotation between a first position in which it exposes the aperture 5206 (in FIG. 52A) to a second position in which it covers the aperture 5206 (in FIG. 52B).

FIGS. 53A and 53B illustrate another exemplary needle protection system 5300 provided in the housing 5302 of an automatic injection system. The automatic injection system includes an injection needle 5304 that is movable relative to the housing 5302 away from or toward the patient's skin. When the needle 5304 is in a position within the housing 5302 farther from the patient's skin, the needle 5304 is in a retracted position and does not protrude outside the housing 5302. When the needle 5304 is in a position within the housing 5302 closer to the patient's skin, the needle 5304 is in an inserted or deployed position and protrudes fully or partly from the housing 5302.

The needle protection system 5300 includes a needle lock-out sleeve 5306 provided in the vicinity of the injection needle 5304 for locking the injection needle in the retracted position in a pre-injection state and a post-injection state. The needle lockout sleeve 5306 may be coupled to a pin 5308 disposed in a slot 5310. The pin 5308 may be in a first position (illustrated in FIG. 53A) relative to the slot 5310 in which the needle lockout sleeve 5306 locks the injection needle 5304 in the retracted position within the housing 5302. The pin 5308 may be in a second position (illustrated in FIG. 53B) relative to the slot 5310 in which the needle lockout sleeve 5306 allows the injection needle 5304 to protrude outside the housing 5302.

In an exemplary embodiment, an early-removal retraction trigger 5312 that, when tripped, triggers a retraction mechanism that retracts the injection needle 5304 into the housing 5302. The early-removal retraction trigger 5312 may be tripped when the wearable automatic injection device 5300 is removed from the injection site before the therapeutically effective dose of therapeutic agent is completely delivered. In an exemplary embodiment, the early-removal retraction trigger 5312 may include a latch 5314, e.g., a flexible plastic hook, that is released upon removal of the wearable automatic injection device 5300 from the injection site. FIG. 53A shows the early-removal retraction trigger 5312 in which the latch 5314 is engaged to a portion of the lockout sleeve 5306 when the wearable injection device is coupled to the injection site. FIG. 53B shows the early-removal retraction trigger 5312 in which the latch 5314 is released from the portion of the lockout sleeve 5306 when the wearable injection device is removed from the injection device. Release of the latch 5314 from the portion of the lockout sleeve 5306 triggers the retraction mechanism. An exemplary retraction mechanism may be responsive to an end-of-dose retraction trigger and responsive to the early-removal retraction trigger 5310 to automatically retract the injection needle 5304 from the injection site.

Figure 54:
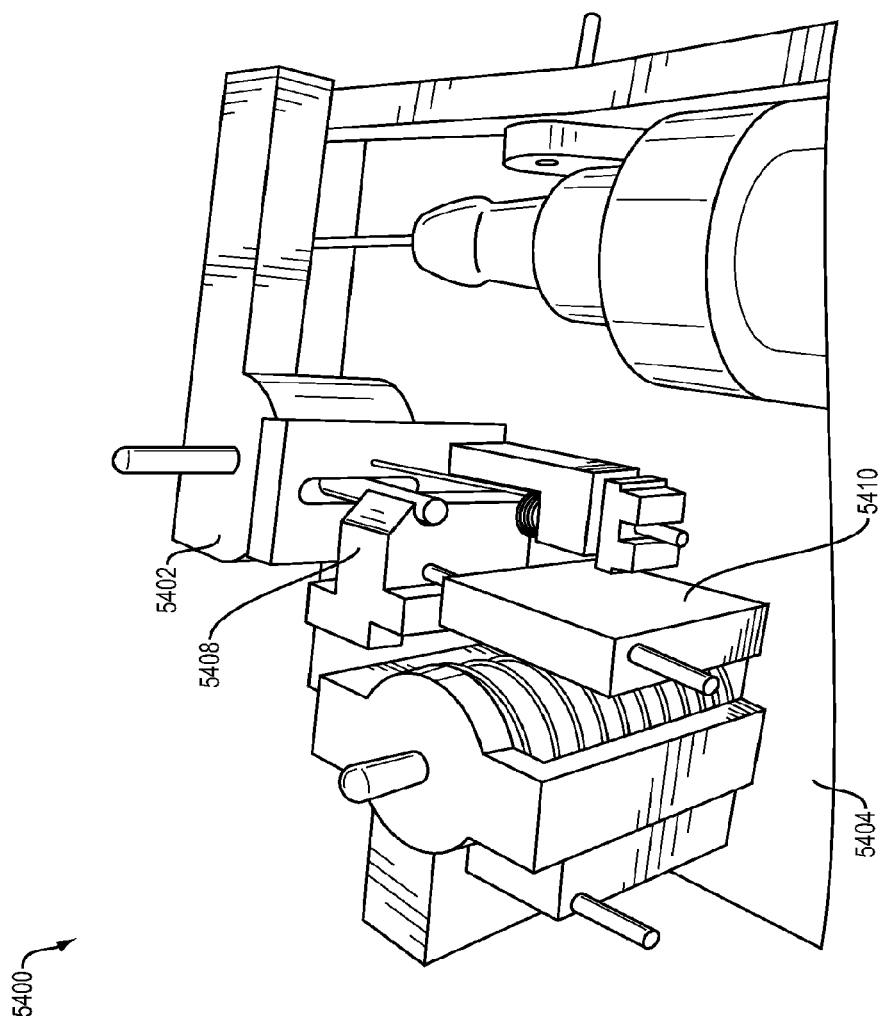
FIG. 54 illustrates another exemplary needle protection system provided in of an exemplary automatic injection system.

FIG. 54 illustrates an exemplary needle protection system 5400 that maintains an injection needle held by an injection carrier 5402 in a retracted position within a housing 5404 of an automatic injection system. The injection needle is movable relative to the housing 5404 away from or toward the patient's skin. When the injection needle is in a position within the housing 5404 farther from the patient's skin, the needle is in a retracted position and does not protrude outside the housing 5404. When the needle is in a position within the housing 5404 closer to the patient's skin, the needle is in an inserted or deployed position and protrudes fully or partly from the housing 5404. The housing 5404 may be provided with an aperture through which the needle may protrude outside the housing 5404.

The needle protection system 5400 includes a needle lock 5408 provided in the vicinity of or in contact with the needle carrier 5402. In an exemplary embodiment, the needle lock 5408 may be a pivoting or rotating member that may pivot or rotate about a pivoting point or interface. A needle lock release mechanism 5410 may be provided in the vicinity of or in contact with the needle lock 5408. The needle lock release mechanism 5410 may be in a first position when the injection needle is in a vertically lowered position and protrudes outside the housing 5404 (in an injection state), and in a second position when the injection needle is in a vertically raised or retracted position within the housing 5404 (in a pre-injection state or a post-injection state)

When the needle lock release mechanism 5410 is in the first position (that is, when the injection needle is in a vertically lowered injection position), the needle lock 5408 may be in an unlocked position in which it does not lock the injection needle in the vertically raised position in the housing 5404. Alternatively, the needle lock 5408 may in a locked position in which it locks the injection needle 5408 in the vertically lowered position in the housing 5404. In an exemplary embodiment (that is, when the injection needle is in a vertically lowered injection position), retraction of the injection needle and/or the needle carrier 5402 to the vertically raised position within the housing 5404 may trigger the needle lock release mechanism 5410, i.e., move the release mechanism from the first position to the second position. When the needle lock release mechanism 5410 is moved to the second position, the needle lock 5408 may pivot or rotate, thereby locking the injection needle and/or the needle carrier 5402 in the vertically raised position in the housing 5404.

Figure 55:
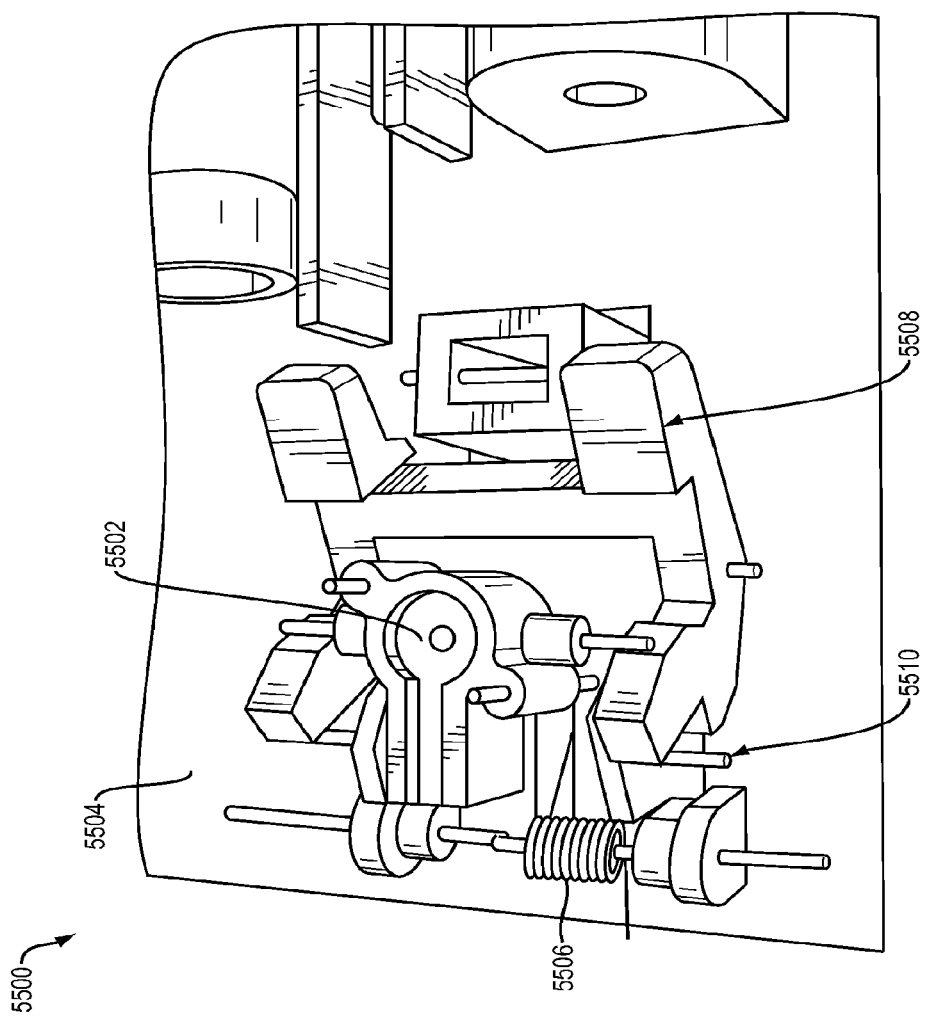
FIG. 55 illustrates another exemplary needle protection system provided in an exemplary automatic injection system.

FIG. 55 illustrates an exemplary needle protection system 5500 that maintains an injection needle held by an injection carrier 5502 in a retracted position within a housing 5504 of an automatic injection system. The injection needle is movable relative to the housing 5504 away from or toward the patient's skin. When the injection needle is in a position within the housing 5504 farther from the patient's skin, the needle is in a retracted position and does not protrude outside the housing 5504. When the needle is in a position within the housing 5504 closer to the patient's skin, the needle is in an inserted or deployed position and protrudes fully or partly from the housing 5504. The housing 5504 may be provided with an aperture through which the needle may protrude outside the housing 5504.

The needle protection system 5500 includes a needle lock 5508 provided in the vicinity of or in contact with the needle carrier 5502. In an exemplary embodiment, the needle lock 5508 may be a pivoting or rotating member that may pivot or rotate about a pivoting point or interface. The needle lock 5508 may include a biasing mechanism 5506 that applies a rotational spring force to the needle carrier 5502 about a longitudinal axis of the biasing mechanism. In an exemplary embodiment, the needle lock 5508 may be provided in a symmetrical manner about the needle carrier 5502 such that the rotational force is applied by the biasing mechanism 5506 substantially symmetrically about the needle carrier 5502.

A needle lock release mechanism 5510 may be provided in the vicinity of or in contact with the needle lock 5508. The needle lock release mechanism 5510 may be in a first position when the injection needle is in a vertically lowered position and protrudes outside the housing 5504 (in an injection state), and in a second position when the injection needle is in a vertically raised or retracted position within the housing 5504 (in a pre-injection state or a post-injection state)

When the needle lock release mechanism 5510 is in the first position (that is, when the injection needle is in a vertically lowered injection position), the biasing mechanism 5506 may apply a spring force to the needle carrier 5502 in the clockwise direction toward the patient's body such that the needle carrier 5502 is held in the vertically lowered position. When the needle lock release mechanism 5510 is in the second position (that is, when the injection needle is in a vertically raised pre or post-injection state), the biasing mechanism 5506 may apply a spring force to the needle carrier 5502 in the counter-clockwise direction away from the patient's body such that the needle carrier 5502 is raised to and held in the vertically raised position.

In an exemplary embodiment, retraction of the injection needle and/or the needle carrier 5502 to the vertically raised position within the housing 5504 may trigger the needle lock release mechanism 5510, i.e., move the release mechanism from the first position to the second position. When the needle lock release mechanism 5510 is moved to the second position, the needle lock 5508 may pivot or rotate under the force of the biasing member 5506 in the counter-clockwise direction away from the patient's body, thereby locking the injection needle and/or the needle carrier 5502 in the vertically raised position in the housing 5504.

VI. THERAPEUTIC AGENTS FOR USE IN EXEMPLARY AUTOMATIC INJECTION DEVICES

Exemplary automatic injection devices may be used to administer essentially any substance or therapeutic agent that is suitable for administration by injection. Typically, the substance or therapeutic agent will be in a fluid, e.g., liquid form, although medications in other forms such as gels or semi-solids, slurries, particulate solutions, etc. also may suitable for use if the wearable automatic injection device is designed to permit the administration of such forms of the medication.

Preferred medications are biological agents, such as antibodies, cytokines, vaccines, fusion proteins and growth factors. Methods of making antibodies are described above.

Non-limiting examples of other biological agents that can be used as the medication in the automatic injection device include but are not limited to antibodies to or antagonists of human cytokines or growth factors, for example, TNF, LT, IL-1, IL-2, IL-3, IL-4, IL-5, IL-6, IL-7, IL-8, IL-15, IL-16, IL-18, IL-21, IL-23, interferons, EMAP-II, GM-CSF, FGF, and PDGF; antibodies to cell surface molecules such as CD2, CD3, CD4, CD8, CD25, CD28, CD30, CD40, CD45, CD69, CD80 (B7.1), CD86 (B7.2), CD90, CTLA or their ligands including CD154 (gp39 or CD40L); TNFα converting enzyme (TACE) inhibitors; IL-1 inhibitors (Interleukin-1-converting enzyme inhibitors, IL-1RA etc.); Interleukin 11; IL-18 antagonists including IL-18 antibodies or soluble IL-18 receptors, or IL-18 binding proteins; non-depleting anti-CD4 inhibitors; antagonists of the co-stimulatory pathway CD80 (B7.1) or CD86 (B7.2) including antibodies, soluble receptors or antagonistic ligands; agents which interfere with signaling by proinflammatory cytokines such as TNFα or IL-1 (e.g. IRAK, NIK, IKK, p38 or MAP kinase inhibitors); IL-1 converting enzyme (ICE) inhibitors; T-cell signaling inhibitors such as kinase inhibitors; metalloproteinase inhibitors; angiotensin converting enzyme inhibitors; soluble cytokine receptors and derivatives thereof (e.g. soluble p55 or p75 TNF receptors and the derivatives p75TNFRIgG (Enbrel™ and p55TNFRIgG (Lenercept)), sIL-1RI, sIL-1RII, sIL-6R); antiinflammatory cytokines (e.g. IL-4, IL-10, IL-11, IL-13 and TGF-beta); Rituximab; IL-1 TRAP; MRA; CTLA4-Ig; IL-18 BP; anti-IL-18; anti-IL15; IDEC-CE9.1/SB 210396 (non-depleting primatized anti-CD4 antibody; IDEC/Smith-Kline; see e.g., Arthritis & Rheumatism (1995) Vol. 38; S185); DAB 486-IL-2 and/or DAB 389-IL-2 (IL-2 fusion proteins; Seragen; see e.g., Arthritis & Rheumatism (1993) Vol. 36; 1223); Anti-Tac (humanized anti-IL-2Ra; Protein Design Labs/Roche); IL-4 (anti-inflammatory cytokine; DNAX/Schering); IL-10 (SCH 52000; recombinant IL-10, anti-inflammatory cytokine; DNAX/Schering); IL-10 and/or IL-4 agonists (e.g., agonist antibodies); IL-1RA (IL-1 receptor antagonist; Synergen/Amgen); anakinra (Kineret®/Amgen); TNF-bp/s-TNF (soluble TNF binding protein; see e.g., Arthritis & Rheumatism (1996) 39(9, supplement); S284; Amer. J. Physiol.—Heart and Circulatory Physiology (1995) 268:37-42); R973401 (phosphodiesterase Type IV inhibitor; see e.g., Arthritis & Rheumatism (1996) 39(9, supplement); S282); MK-966 (COX-2 Inhibitor; see e.g., Arthritis & Rheumatism (1996) 39(9, supplement); S81); Iloprost (see e.g., Arthritis & Rheumatism (1996) 39(9, supplement); S82); zap-70 and/or lck inhibitor (inhibitor of the tyrosine kinase zap-70 or lck); VEGF inhibitor and/or VEGF-R inhibitor (inhibitors of vascular endothelial cell growth factor or vascular endothelial cell growth factor receptor; inhibitors of angiogenesis); TNF-convertase inhibitors; anti-IL-12 antibodies; anti-IL-18 antibodies; interleukin-11 (see e.g., Arthritis & Rheumatism (1996) 39(9, supplement), S296); interleukin-13 (see e.g., Arthritis & Rheumatism (1996) 39(9, supplement), S308); interleukin-17 inhibitors (see e.g., Arthritis & Rheumatism (1996) 39(9, supplement), S120); anti-thymocyte globulin; anti-CD4 antibodies; CD5-toxins; ICAM-1 antisense phosphorothioate oligo-deoxynucleotides (ISIS 2302; Isis Pharmaceuticals, Inc.); soluble complement receptor 1 (TP10; T Cell Sciences, Inc.); and anti-IL2R antibodies.

VII. TNFα INHIBITORS FOR USE IN EXEMPLARY AUTOMATIC INJECTION DEVICES

According to one embodiment of the invention, the illustrative automatic injection device may be used to deliver a dose of a TNF inhibitor used to treat arthritis and other diseases. In one embodiment, the solution contained in the syringe contains 40 or 80 milligrams of drug product (TNFα blocker or inhibitor)/1 mL, for example, 40 or 80 mg adalimumab, 4.93 mg sodium chloride, 0.69 mg monobasic sodium phosphate dehydrate, 1.22 mg dibasic sodium phosphate dehydrate, 0.24 mg sodium citrate, 1.04 mg citric acid monohydrate, 9.6 mg mannitol, 0.8 mg polysorbate 50 and water for injection, with USP sodium hydroxide added as necessary to adjust pH to be about 5.2.

The present invention can be used to administer a dose of a substance, such as a liquid drug, e.g., a TNFα inhibitor, to a patient. In one embodiment, the dose delivered by the automatic injection device of the invention comprises a human TNFα antibody, or antigen-binding portion thereof.

In one embodiment, the TNF inhibitor used in the methods and compositions of the invention includes isolated human antibodies, or antigen-binding portions thereof, that bind to human TNFα with high affinity and a low off rate, and have a high neutralizing capacity. Preferably, the human antibodies of the invention are recombinant, neutralizing human anti-hTNFα antibodies, such as, e.g., the recombinant, neutralizing antibody referred to as D2E7, also referred to as HUMIRA or adalimumab (Abbott Laboratories; the amino acid sequence of the D2E7 VL region is shown in SEQ ID NO: 1 of U.S. Pat. No. 6,090,382 the amino acid sequence of the D2E7 VH region is shown in SEQ ID NO: 2 of U.S. Pat. No. 6,090,382). Properties of D2E7 have been described in Salfeld et al., U.S. Pat. Nos. 6,090,382, 6,258,562, and 6,509,015. Other examples of TNFα inhibitors include chimeric and humanized murine anti-hTNFα antibodies that have undergone clinical testing for treatment of rheumatoid arthritis (see e.g., Elliott et al. (1994) Lancet 344:1125-1127; Elliot et al. (1994) Lancet 344:1105-1110; and Rankin et al. (1995) Br. J. Rheumatol. 34:334-342).

An anti-TNFα antibody (also referred to herein as a TNFα antibody), or an antigen-binding fragment thereof, includes chimeric, humanized, and human antibodies. Examples of TNFα antibodies that may be used in the invention include, but not limited to, infliximab (Remicade®, Johnson and Johnson; described in U.S. Pat. No. 5,656,272, incorporated by reference herein), CDP571 (a humanized monoclonal anti-TNF-alpha IgG4 antibody), CDP 870 (a humanized monoclonal anti-TNF-alpha antibody fragment), an anti-TNF dAb (Peptech), and CNTO 148 (golimumab; Medarex and Centocor, see WO 02/12502). Additional TNF antibodies that may be used in the invention are described in U.S. Pat. Nos. 6,593,458; 6,498,237; 6,451,983; and 6,448,380.

Other examples of TNFα inhibitors which may be used in the methods and compositions of the invention include etanercept (Enbrel, described in WO 91/03553 and WO 09/406, 476), soluble TNF receptor Type I, a pegylated soluble TNF receptor Type I (PEGs TNF-R1), p55TNFR1gG (Lenercept), and recombinant TNF binding protein (r-TBP-I) (Serono).

In one embodiment, exemplary embodiments provide improved uses and compositions for treating a disorder in which TNFα is detrimental, e.g., rheumatoid arthritis, with a TNFα inhibitor, e.g., a human TNFα antibody, or an antigen-binding portion thereof, through a wearable automatic injection device.

A TNFα inhibitor includes any agent (or substance) that interferes with TNFα activity. In a preferred embodiment, the TNFα inhibitor can neutralize TNFα activity, particularly detrimental TNFα activity which is associated with disorders in which TNFα activity is detrimental, including, but not limited to, rheumatoid arthritis, juvenile rheumatoid arthritis, ankylosing spondylitis, Crohn's disease, psoriasis, and psoriatic arthritis.

VIII. PHARMACEUTICAL COMPOSITIONS FOR USE IN EXEMPLARY AUTOMATIC INJECTION DEVICES

Pharmaceutical compositions may be loaded into the automatic injection device of the invention for delivery to a patient. In one embodiment, antibodies, antibody-portions, as well as other TNFα inhibitors, can be incorporated into pharmaceutical compositions suitable for administration to a patient using the device of the invention. Typically, the pharmaceutical composition comprises an antibody, antibody portion, or other TNFα inhibitor, and a pharmaceutically acceptable carrier. "Pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it is preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody, antibody portion, or other TNFα inhibitor.

The compositions for use in the methods and compositions of the invention may be in a variety of forms in accordance with administration via the device of the invention, including, for example, liquid solutions (e.g., injectable and infusible solutions), dispersions or suspensions. In a preferred embodiment, the antibody or other TNFα inhibitor is administered by subcutaneous injection using the device of the invention. In one embodiment, the patient administers the TNFα inhibitor, including, but not limited to, TNFα antibody, or antigen-binding portion thereof, to himself/herself using the device of the invention.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody, antibody portion, or other TNFα inhibitor) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In one embodiment, exemplary embodiments provide a wearable automatic injection device, e.g., autoinjector pen, comprising an effective TNFα inhibitor and a pharmaceutically acceptable carrier. Thus, the invention provides a pre-fillable and/or pre-filled automatic injection device comprising a TNFα inhibitor.

In one embodiment, the antibody or antibody portion for use in the methods of the invention is incorporated into a pharmaceutical formulation as described in PCT/IB03/04502 and U.S. Patent Publication No. 2004/0033228. This formulation includes a concentration 50 mg/ml of the antibody D2E7 (adalimumab), wherein a wearable automatic injection device contains 40 mg of antibody for subcutaneous injection. In one embodiment, the automatic injection device of the invention (or more specifically the syringe of the device) comprises a formulation of adalimumab having the following formula: adalimumab, sodium chloride, monobasic sodium phosphate dihydrate, dibasic sodium phosphate dihydrate, sodium citrate, citric acid monohydrate, mannitol, polysorbate 80 and water, e.g., water for injection. In another embodiment, the automatic injection device comprises a volume of adalimumab including 40 mg adalimumab, 4.93 mg sodium chloride, 0.69 mg monobasic sodium phosphate dihydrate, 1.22 mg dibasic sodium phosphate dihydrate, 0.24 mg sodium citrate, 1.04 mg citric acid monohydrate, 9.6 mg mannitol, 0.8 mg polysorbate 80 and water, e.g., water for injection. In one embodiment, sodium hydroxide is added as necessary to adjust pH.

The dose amount of TNFα inhibitor in the automatic injection device may vary according to the disorder for which the TNFα inhibitor is being used to treat. In one embodiment, the invention includes a wearable automatic injection device comprising a dose of adalimumab of about 20 mg of adalimumab; 40 mg of adalimumab; 80 mg of adalimumab; and 160 mg of adalimumab. It should be noted that for all ranges described herein, including the dose ranges, all numbers intermediary to the recited values are included in the invention, e.g., 36 mg of adalimumab, 48 mg of adalimumab, etc. In addition ranges recited using said numbers are also included, e.g. 40 to 80 mg of adalimumab. The numbers recited herein are not intended to limit the scope of the invention.

The TNFα antibodies and inhibitors used in the invention may also be administered in the form of protein crystal formulations that include a combination of protein crystals encapsulated within a polymeric carrier to form coated particles. The coated particles of the protein crystal formulation may have a spherical morphology and be microspheres of up to 500 micro meters in diameter or they may have some other morphology and be microparticulates. The enhanced concentration of protein crystals allows the antibody of the invention to be delivered subcutaneously. In one embodiment, the TNFα antibodies of the invention are delivered via a protein delivery system, wherein one or more of a protein crystal formulation or composition, is administered to a patient with a TNFα-related disorder. Compositions and methods of preparing stabilized formulations of whole antibody crystals or antibody fragment crystals are also described in WO 02/072636, which is incorporated by reference herein. In one embodiment, a formulation comprising the crystallized antibody fragments described in International Patent Application No. PCT/IB03/04502 and U.S. Patent Publication No. 2004/0033228 is used to treat rheumatoid arthritis using the methods of the invention.

Supplementary active compounds can also be incorporated into the compositions. In certain embodiments, an antibody or antibody portion for use in the methods of the invention is co-formulated with and/or co-administered with one or more additional therapeutic agents, including a rheumatoid arthritis inhibitor or antagonist. For example, an anti-hTNFα antibody or antibody portion may be co-formulated and/or co-administered with one or more additional antibodies that bind other targets associated with TNFα related disorders (e.g., antibodies that bind other cytokines or that bind cell surface molecules), one or more cytokines, soluble TNFα receptor (see e.g., PCT Publication No. WO 94/06476) and/or one or more chemical agents that inhibit hTNFα production or activity (such as cyclohexane-ylidene derivatives as described in PCT Publication No. WO 93/19751) or any combination thereof. Furthermore, one or more antibodies of the invention may be used in combination with two or more of the foregoing therapeutic agents. Such combination therapies may advantageously utilize lower dosages of the administered therapeutic agents, thus avoiding possible side effects, complications or low level of response by the patient associated with the various monotherapies. Additional agents that may be used in combination with a TNFα antibody or antibody portion are described in U.S. patent application Ser. No. 11/800,531, which is expressly incorporated herein by reference in its entirety.

IX. INCORPORATION BY REFERENCE

The contents of all references, including patents and patent applications, cited throughout this application are hereby incorporated herein by reference in their entirety. The appropriate components and methods of those references may be selected for the invention and embodiments thereof. Still further, the components and methods identified in the Background section are integral to this disclosure and can be used in conjunction with or substituted for components and methods described elsewhere in the disclosure within the scope of the invention.

X. EQUIVALENTS

In describing exemplary embodiments, specific terminology is used for the sake of clarity. For purposes of description, each specific term is intended to at least include all technical and functional equivalents that operate in a similar manner to accomplish a similar purpose. Additionally, in some instances where a particular exemplary embodiment includes a plurality of system elements or method steps, those elements or steps may be replaced with a single element or step. Likewise, a single element or step may be replaced with a plurality of elements or steps that serve the same purpose. Further, where parameters for various properties are specified herein for exemplary embodiments, those parameters may be adjusted up or down by 1/20th, 1/10th, 1/5th, 1/3rd, 1/2, etc., or by rounded-off approximations thereof, unless otherwise specified. Moreover, while exemplary embodiments have been shown and described with references to particular embodiments thereof, those of ordinary skill in the art will understand that various substitutions and alterations in form and details may be made therein without departing from the scope of the invention. Further still, other aspects, functions and advantages are also within the scope of the invention.

Exemplary flowcharts are provided herein for illustrative purposes and are non-limiting examples of methods. One of ordinary skill in the art will recognize that exemplary methods may include more or fewer steps than those illustrated in the exemplary flowcharts, and that the steps in the exemplary flowcharts may be performed in a different order than shown.

What is claimed is:

1. A wearable automatic injection device free of a battery for providing a subcutaneous injection of a therapeutic agent into a patient, the wearable automatic injection device comprising:

a housing comprising a patient contact portion securable to the patient;

an injection assembly moveably disposed in the housing holding a hypodermic injection needle for insertion into the patient, the injection assembly moveable between a retracted position in which the injection needle does not protrude outside the housing and an extended position in which the injection needle protrudes outside the housing;

a vessel provided in the housing for holding the therapeutic agent;

a plunger moveably disposed in the vessel for ejecting the therapeutic agent from the vessel into the injection assembly;

a plunger actuation mechanism for actuating the plunger using a mechanical or hydraulic mechanism within the vessel;

a retraction trigger responsive to a change of state of the wearable automatic injection device from an injection state to a post-injection state, wherein the wearable automatic injection device enters the post-injection state upon completion of delivery of a therapeutically effective dose of the therapeutic agent and enters the post-injection state upon removal of the wearable automatic injection device from the patient prior to completion of delivery of the therapeutically effective dose of the therapeutic agent; and a retraction mechanism for automatically retracting the injection assembly from the extended position in the injection state to the retracted position in the post-injection state upon triggering by the retraction trigger.

2. The wearable automatic injection device of claim 1, wherein the housing further comprises:

an interior portion defined by a plurality of walls and defining at least one open end opposing the patient contact portion.

3. The wearable automatic injection device of claim 1, further comprising:

a cover portion covering the open end of the housing.

4. The wearable automatic injection device of claim 1, wherein the housing is provided as a unitary cover coupled to a base that forms the patient contact portion.

5. The wearable automatic injective device of claim 1, wherein the housing is provided as a plurality of walls defining at least one open end opposing the patient contact portion.

6. The wearable automatic injection device of claim 1, further comprising:

an adhesive layer provided on the patient contact portion of the housing for attaching the housing to the patient.

7. The wearable automatic injection device of claim 1, further comprising:

an inspection window disposed in the housing that allows the user to inspect the therapeutic agent held by the vessel from outside the housing.

8. The wearable automatic injection device of claim 1, wherein the vessel comprises a syringe.

9. The wearable automatic injection device of claim 8, wherein the syringe comprises:

a barrel portion for holding the therapeutic agent; and a syringe needle coupled to a distal end of the barrel portion for establishing fluid communication between the barrel portion of the syringe and the injection needle.

10. The wearable automatic injection device of claim 9, wherein the injection assembly comprises:

a septum that is pierceable by the syringe needle of the syringe; and a fluid conduit extending between the injection needle and the septum, wherein piercing of the septum by the syringe needle of the syringe couples the barrel portion of the syringe and the injection needle.

11. The wearable automatic injection device of claim 10, wherein the syringe needle of the syringe is spaced from the septum when the device is in a pre-injection state, and wherein the syringe needle pierces the septum when the device is in the injection state.

12. The wearable automatic injection device of claim 1, wherein the vessel comprises a cartridge.

13. The wearable automatic injection device of claim 12, wherein the cartridge comprises:

a barrel portion for holding the therapeutic agent; and a septum that is pierceable by a piercing needle.

14. The wearable automatic injection device of claim 13, wherein the injection assembly comprises:

the piercing needle for establishing fluid communication between the barrel portion of the cartridge and the injection needle; and a fluid conduit provided between the injection needle and the piercing needle for establishing fluid communication between the injection needle and the barrel portion of the cartridge.

15. The wearable automatic injection device of claim 14, wherein piercing of the septum by the piercing needle of the injection assembly establishes fluid communication between the barrel portion of the cartridge and the injection needle.

16. The wearable automatic injection device of claim 15, wherein the septum of the cartridge is spaced from the piercing needle of the injection assembly when the device is in a pre-injection state, and wherein the piercing needle pierces the septum when the device is in the injection state.

17. The wearable automatic injection device of claim 1, wherein the vessel is moveably disposed within the housing.

18. The wearable automatic injection device of claim 17, wherein the vessel is moveable between a first position in a pre-injection state and a second position in the injection state.

19. The wearable automatic injection device of claim 18, further comprising:

a vessel actuator for automatically actuating the vessel from the first position to the second position.

20. The wearable automatic injection device of claim 19, wherein a fluid pathway is established between the injection needle and the vessel when the injection assembly is in the extended position and the vessel is in the second position in the injection state.

21. The wearable automatic injection device of claim 1, wherein the plunger actuation mechanism ejects the therapeutic agent into the patient at a controlled rate.

22. The wearable automatic injection device of claim 1, wherein the plunger actuation mechanism comprises a biasing mechanism.

23. The wearable automatic injection device of claim 22, wherein the plunger actuation mechanism further comprises:

a fusee; and a tether coupling the biasing mechanism to the fusee and the plunger.

24. The wearable automatic injection device of claim 23, wherein the plunger actuation mechanism further comprises:

a damping mechanism coupled to the fusee for regulating the movement of the fusee; and a gear train including one or more gears for coupling the fusee to the damping mechanism.

25. The wearable automatic injection device of claim 24, wherein the damping mechanism comprises a viscous damper.

26. The wearable automatic injection device of claim 24, wherein the damping mechanism comprises an escapement mechanism.

27. The wearable automatic injection device of claim 26, wherein the escapement mechanism is a swiss lever escapement.

28. The wearable automatic injection device of claim 26, wherein the escapement mechanism is a runaway escapement.

29. The wearable automatic injection device of claim 22, wherein the plunger actuation mechanism further comprises:

one or more ball bearings for coupling the biasing mechanism to the plunger.

30. The wearable automatic injection device of claim 29, wherein the plunger actuation mechanism further comprises:

a damping mechanism coupled to the biasing mechanism and the ball bearings for regulating the movement of the ball bearings.

31. The wearable automatic injection device of claim 30, wherein the damping mechanism comprises a viscous damper.

32. The wearable automatic injection device of claim 1, wherein the plunger actuation mechanism further comprises:

a source of a working fluid for providing a hydraulic pressure to eject the therapeutic agent from the vessel; and a fluid conduit provided between the source of the working fluid and the plunger.

33. The wearable automatic injection device of claim 32, wherein the plunger actuation mechanism further comprises:

a damping mechanism coupled to the vessel and the source of the working fluid to regulate the ejection of the therapeutic agent from the vessel.

34. The wearable automatic injection device of claim 33, wherein the damping mechanism comprises a flow restrictor for maintaining the hydraulic pressure downstream of the flow restrictor toward the vessel at a lower pressure that the hydraulic pressure upstream of the flow restrictor toward the source of the working fluid.

35. The wearable automatic injection device of claim 34, wherein the flow restrictor is coupled to the retraction trigger and wherein delivery of the therapeutic agent in the vessel causes the flow restrictor to activate the retraction trigger.

36. The wearable automatic injection device of claim 1, further comprising:

a needle locking mechanism for automatically locking the injection needle in the retracted position within the housing in the post-injection state.

37. The wearable automatic injection device of claim 36, wherein the needle locking mechanism comprises:

a barrier mechanism moveably disposed over an injection needle aperture in the housing;

wherein the injection needle aperture is open and allows the injection needle to protrude outside the housing when the barrier mechanism is in a first position; and wherein the injection needle aperture is closed and prevents the injection needle from protruding outside the housing when the barrier mechanism is in a second position.

38. The wearable automatic injection device of claim 36, wherein the needle locking mechanism comprises:
- a needle lock release mechanism responsive to retraction of the injection assembly from the extended position in the injection state to the retraction position in the post-injection state; and
- a pivoting member coupled to the injection needle and to the needle lock release mechanism;
- wherein activation of the needle lock release mechanism causes the pivoting member to pivot the injection needle away from an injection needle aperture in the housing.

39. The wearable automatic injection device of claim 1, wherein the post-injection state comprises completion of delivery of a therapeutically effective dose of the therapeutic agent and removal of the wearable automatic injection device from the patient prior to completion of delivery of a therapeutically effective dose of the therapeutic agent.

40. The wearable automatic injection device of claim 1, wherein the therapeutic agent comprises a protein in a solution.

41. The wearable automatic injection device of claim 40, wherein the protein comprises any of a fusion protein, an enzyme, an antibody, or an antigen-binding fragment thereof in a solution.

42. The wearable automatic injection device of claim 41, wherein the antibody is a dual specificity antibody.

43. The wearable automatic injection device of claim 1, wherein the injection state comprises one or more states of the wearable automatic injection device during the delivery of the therapeutic agent.

* * * * *